United States Patent
Holtzman et al.

(10) Patent No.: US 9,187,470 B2
(45) Date of Patent: Nov. 17, 2015

(54) ANTI-MUCUS DRUGS AND USES THEREFOR

(71) Applicant: Washington University, Saint Louis, MO (US)

(72) Inventors: Michael Holtzman, St. Loius, MO (US); Arthur Romero, Chesterfield, MO (US); Yael Alevy, St. Louis, MO (US); Anand Patel, Saint Louis, MO (US); Thomas Brett, Saint Louis, MO (US); Dhara Patel, Saint Louis, MO (US)

(73) Assignee: Washington University, Saint Louis, MO (US)

(*) Notice: Subject to any disclaimer, the term of this patent is extended or adjusted under 35 U.S.C. 154(b) by 0 days.

(21) Appl. No.: 14/599,427

(22) Filed: Jan. 16, 2015

(65) Prior Publication Data

US 2015/0183777 A1    Jul. 2, 2015

Related U.S. Application Data

(63) Continuation-in-part of application No. PCT/US2013/050921, filed on Jul. 17, 2013.

(60) Provisional application No. 61/672,378, filed on Jul. 17, 2012.

(51) Int. Cl.
| | |
|---|---|
| *C07D 417/14* | (2006.01) |
| *C07D 401/12* | (2006.01) |
| *C07D 405/14* | (2006.01) |
| *C07D 409/14* | (2006.01) |
| *C07D 417/12* | (2006.01) |
| *C07D 471/04* | (2006.01) |
| *C07D 491/048* | (2006.01) |

(52) U.S. Cl.
CPC ............ *C07D 417/14* (2013.01); *C07D 401/12* (2013.01); *C07D 405/14* (2013.01); *C07D 409/14* (2013.01); *C07D 417/12* (2013.01); *C07D 471/04* (2013.01); *C07D 491/048* (2013.01)

(58) Field of Classification Search
CPC .. C07D 417/14; C07D 401/12; C07D 405/14; C07D 409/14; C07D 417/12; C07D 471/04; C07D 491/048
See application file for complete search history.

(56) References Cited

U.S. PATENT DOCUMENTS

| | | | |
|---|---|---|---|
| 7,321,040 B2 | 1/2008 | Braganza et al. | |
| 8,017,641 B2 | 9/2011 | Munson et al. | |
| 2004/0053958 A1 | 3/2004 | Dombroski et al. | |
| 2008/0261965 A1* | 10/2008 | Flynn .................. | C07D 401/14 514/230.5 |
| 2009/0012079 A1 | 1/2009 | Lewthwaite et al. | |
| 2009/0018141 A1 | 1/2009 | Shoemaker et al. | |
| 2011/0251216 A1 | 10/2011 | Chinnaiyan et al. | |

FOREIGN PATENT DOCUMENTS

| | | |
|---|---|---|
| WO | 99/32106 A1 | 7/1999 |
| WO | 2007/064872 A2 | 6/2007 |
| WO | 2010/094956 A1 | 8/2010 |
| WO | 2011/121366 A1 | 10/2011 |
| WO | 2012/019015 A2 | 2/2012 |

OTHER PUBLICATIONS

Getlik, Matthaus et al. "Structure based design, syntheis and ibological evaluation of N-pyrazole, N-thiazole urea inhibitors of MAP ki8nase p38-alpha"; European Journal of Medicinal Chemistry, 48, Feb. 2012, pp. 1-15.
Kuma Y. et al. "BIRB796 inhibits all p38 MAPK isoforms in vitro and in vivo" J Biol Chem. May 20, 2005;280 (20):19472-9. Baltimore, MD, USA.
Pargellis C. et al. "Inhibition of p38 MAP kinase by utilizing a novel allosteric binding site." Nat Struct Biol. Apr. 2002;9(4):268-72. New York, NY, USA.
Kuglstatter A. et al. "X-ray crystal structure of JNK2 complexed with the p38alpha inhibitor BIRB796: insights into the rational design of DFG-out binding MAP kinase inhibitors.". Bioorg Med Chem Lett. Sep. 1, 2010;20(17):5217-20. Oxford, England and New York, USA.
Dumas J et al. "Synthesis and pharmacological characterization of a potent, orally active p38 kinase inhibitor." Bioorg Med Chem Lett. Jun. 17, 2002;12(12):1559-62. Oxford, England and New York, USA.
Alevy, Y. G., et al. IL-13-induced airway mucus production is attenuated by MAPK13 inhibition. (2012) J. Clin. Invest. 122:4555-4568. PMCID: PMC3533556.
Tyner, JW. et al. "Blocking airway mucous cell metaplasia by inhibiting EGFR antiapoptosis and IL-13 transdifferentiation signals." J Clin Invest. Feb. 2006;116(2):309-21. USA.
Kim, EY. et al. "Persistent activation of an innate immune response translates respiratory viral infection into chronic lung disease." Nat Med. Jun. 2008;14(6):633-40 New York, NY USA.
Patel, AC. "Genetic segregation of airway disease traits despite redundancy of calcium-activated chloride channel family members." Physiol Genomics. May 16, 2006;25(3):502-13. Bethesda, MD.
Patel, AC et al. "The role of CLCA proteins in inflammatory airway disease." Annu Rev Physiol. 2009;71:425-49. Palo Alto, CA.
Agapov E. et al. "Macrophage chitinase 1 stratifies chronic obstructive lung disease." Am J Respir Cell Mol Biol. Oct. 2009;41(4):379-84. New York, NY, USA.
"Drug screening—higher throughput, quicker and more effective thanks to automation." http://www.bio-pro.de/magazin/thema/00138/index.html?lang=en&print_style=yes&prin=, BioPro Baden Wurttemberg GmbH Sep. 25, 2008, Germany. Retrieved from the Internet Feb. 3, 2015.

(Continued)

*Primary Examiner* — Rebecca Anderson
(74) *Attorney, Agent, or Firm* — Saul L. Zackson; Zackson Law LLC

(57) ABSTRACT

Disclosed are methods of identifying, generating and synthesizing compounds that inhibit MAPK13 activity. In various embodiments, compounds, salts thereof and prodrugs thereof of the present teachings can be useful for the treatment of diseases and disorders that involve excess mucus production.

15 Claims, 17 Drawing Sheets

(56) References Cited

OTHER PUBLICATIONS

Atsushi Nakanishi et al. Role of gob-5 in mucus overproduction and airway hyperresponsiveness in asthma, PNAS, Apr. 24, 2001, v. 98, No. 9, pp. 5175-5180, USA.

Clontech., Vector Information, pTRE-Tight Vector Informatoin, Cat. No. 631059, Jul. 28, 2010 [online] http://www.clontech.com/US/Products/Inducible_Systems/Tetracycline-Inducible_Expression/ibcGetAttachment.jsp?cItemId=17960&fileId=5878245&itex=10020:22372:US Retrieved from the internet Feb. 3, 2015.

TET Systems, 2008 [online] Retrieved from the Internet: <URL: htpp ://www. tetsystems .com/science-technology /principles-components// Retrieved from the internet Aug. 25, 2015.

* cited by examiner

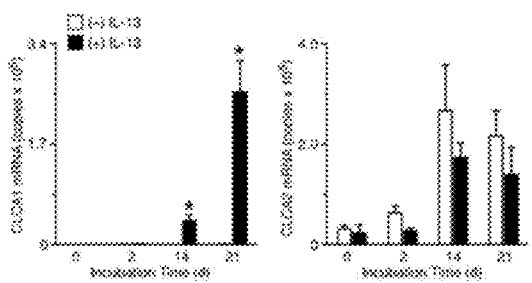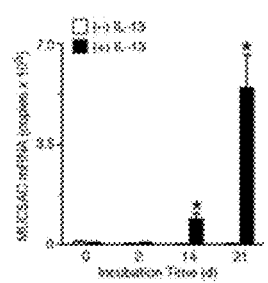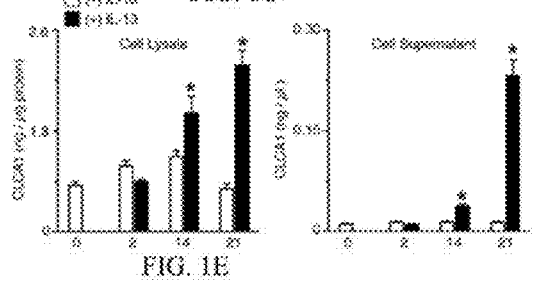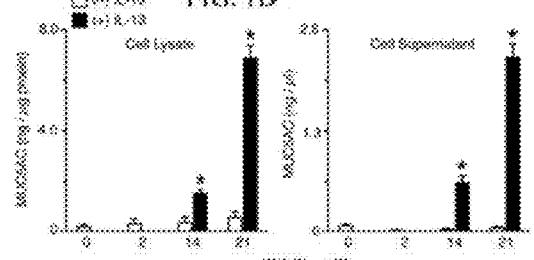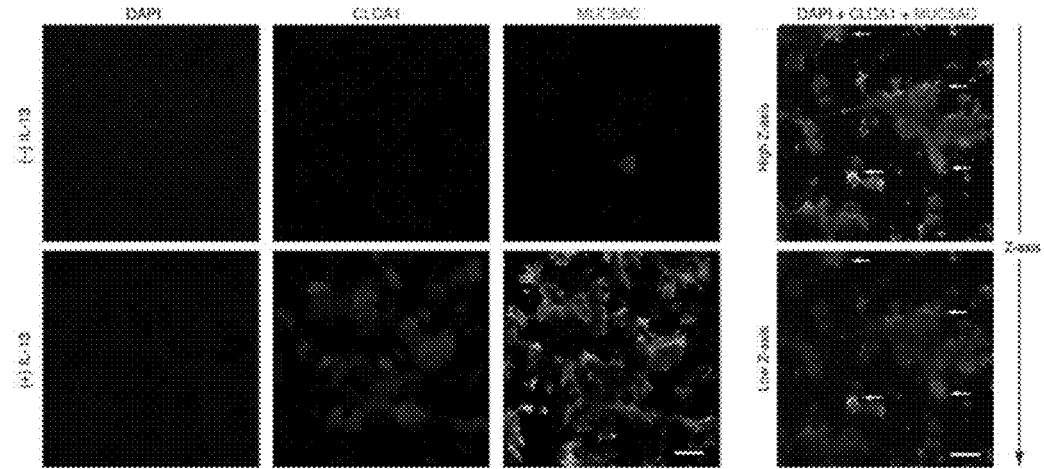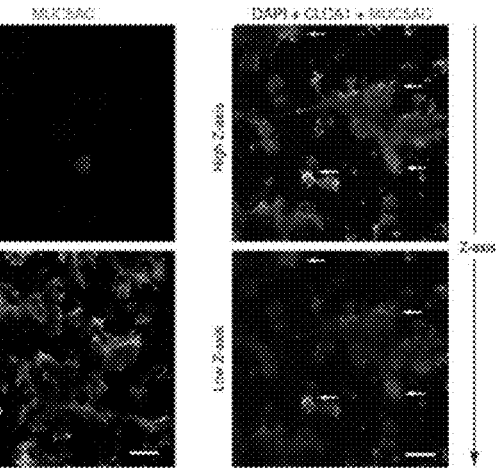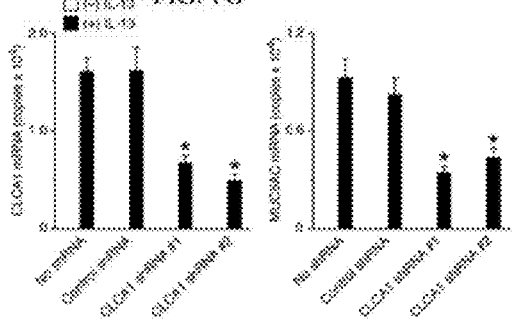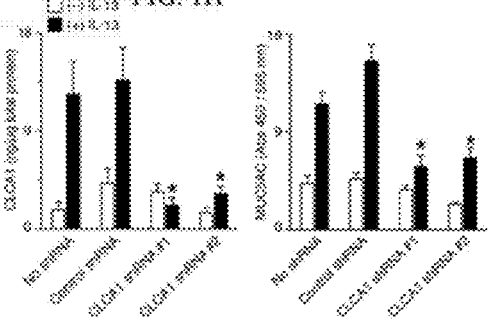

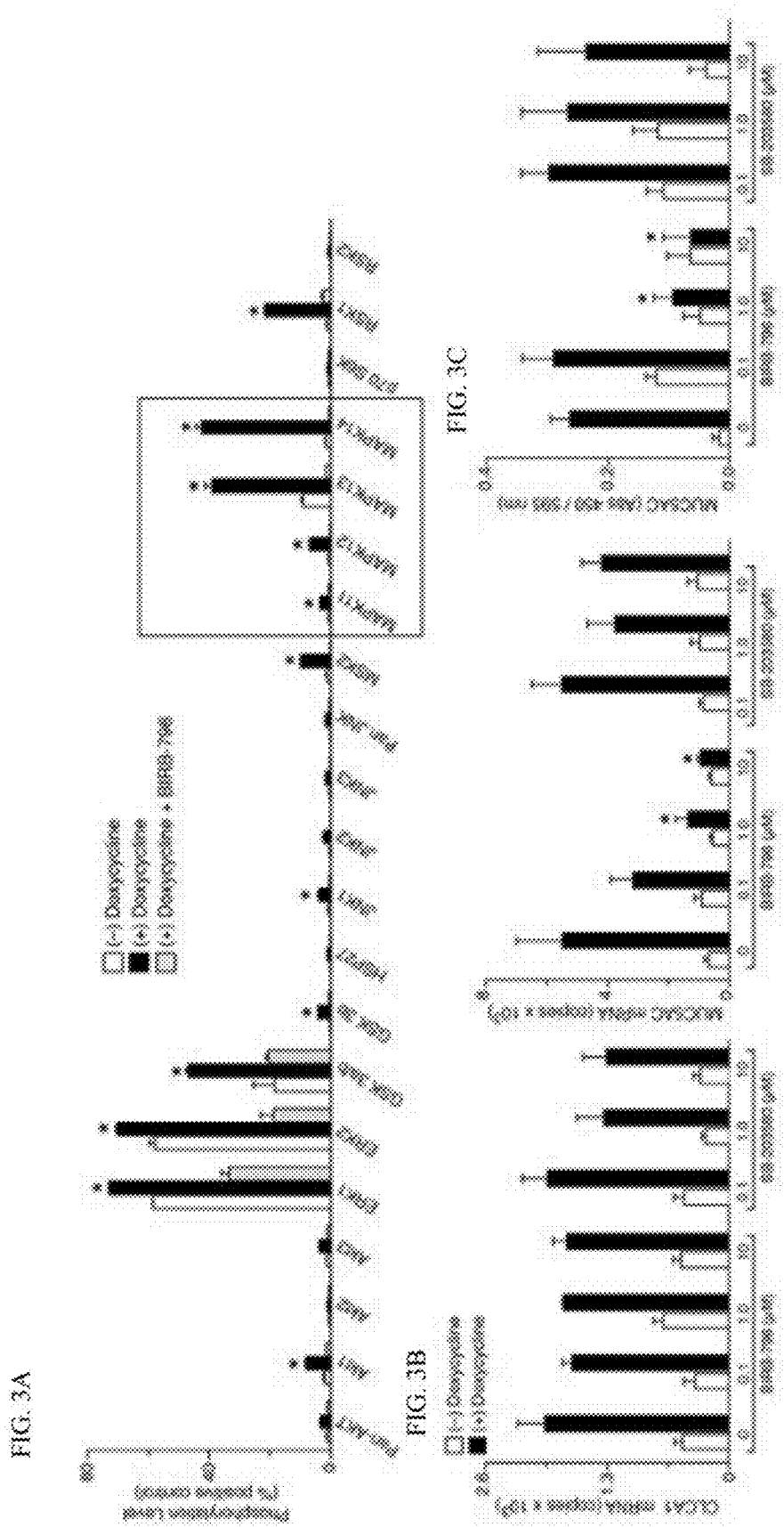

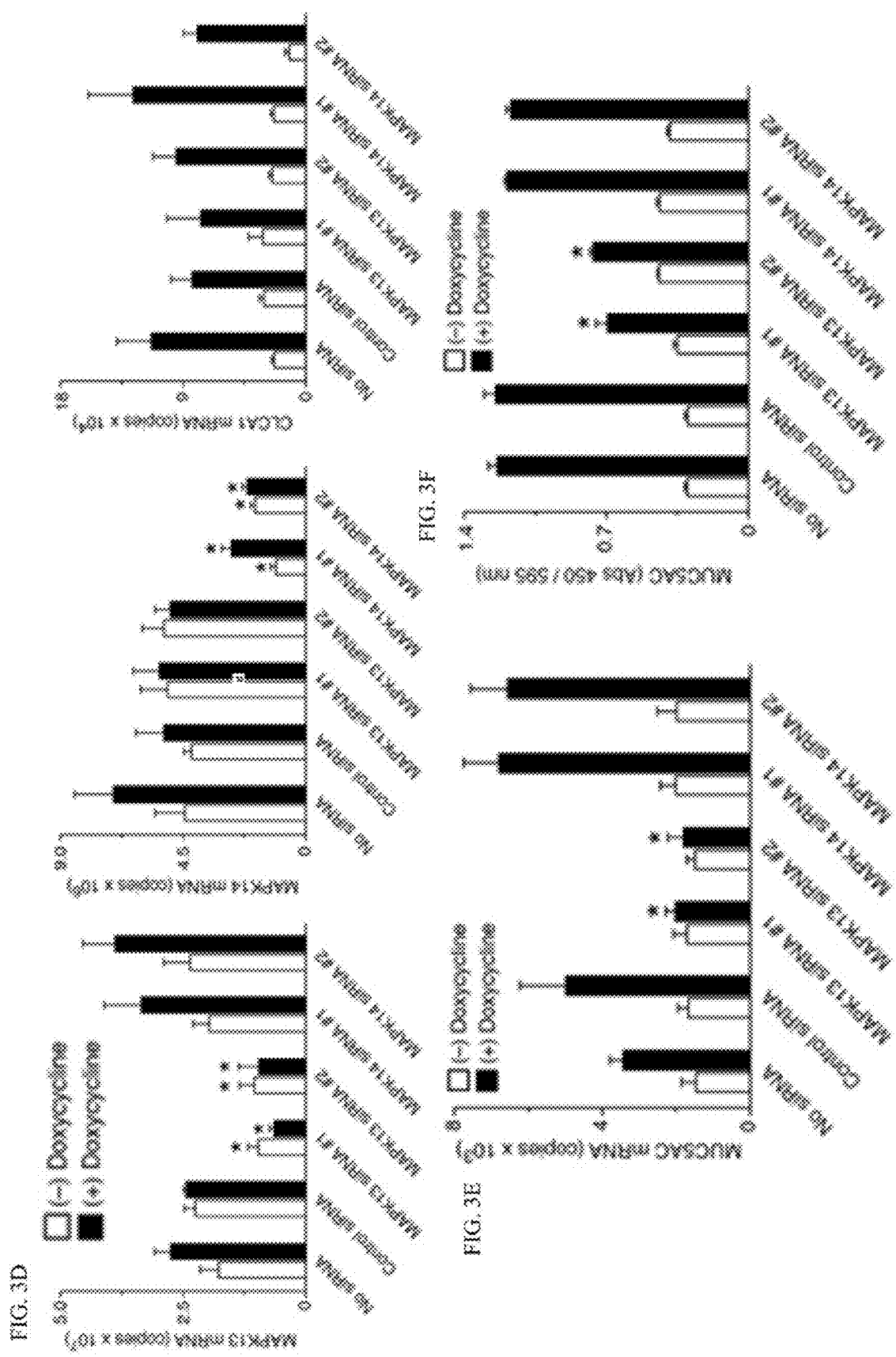

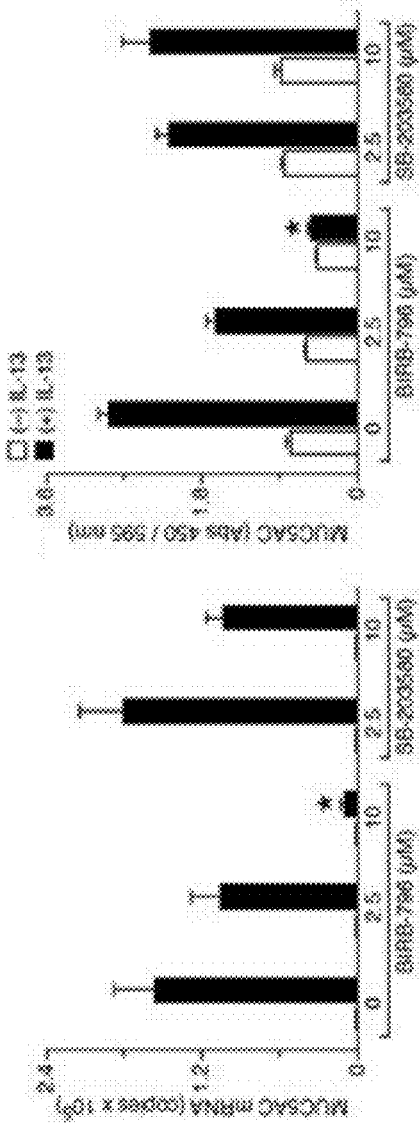
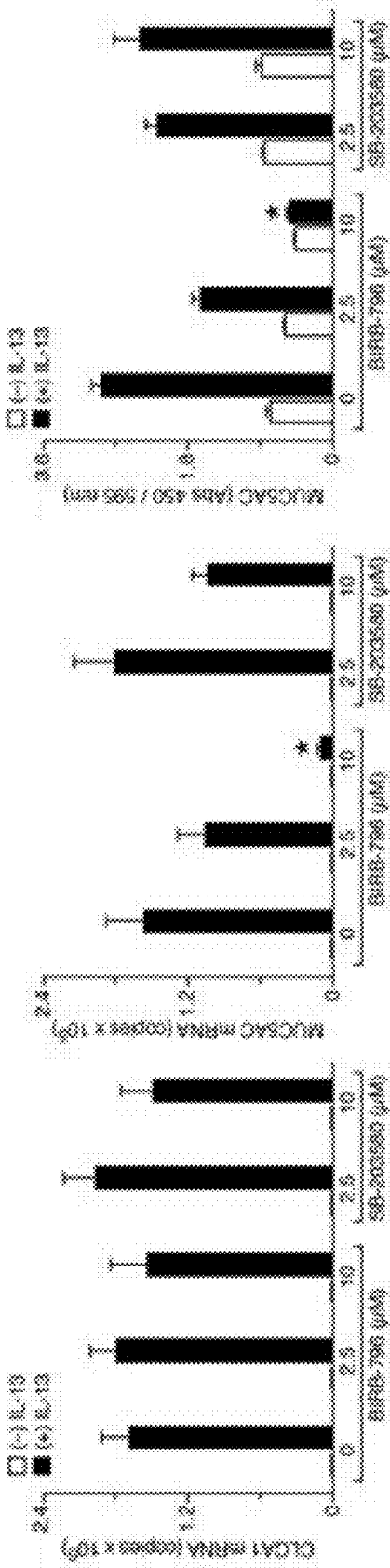
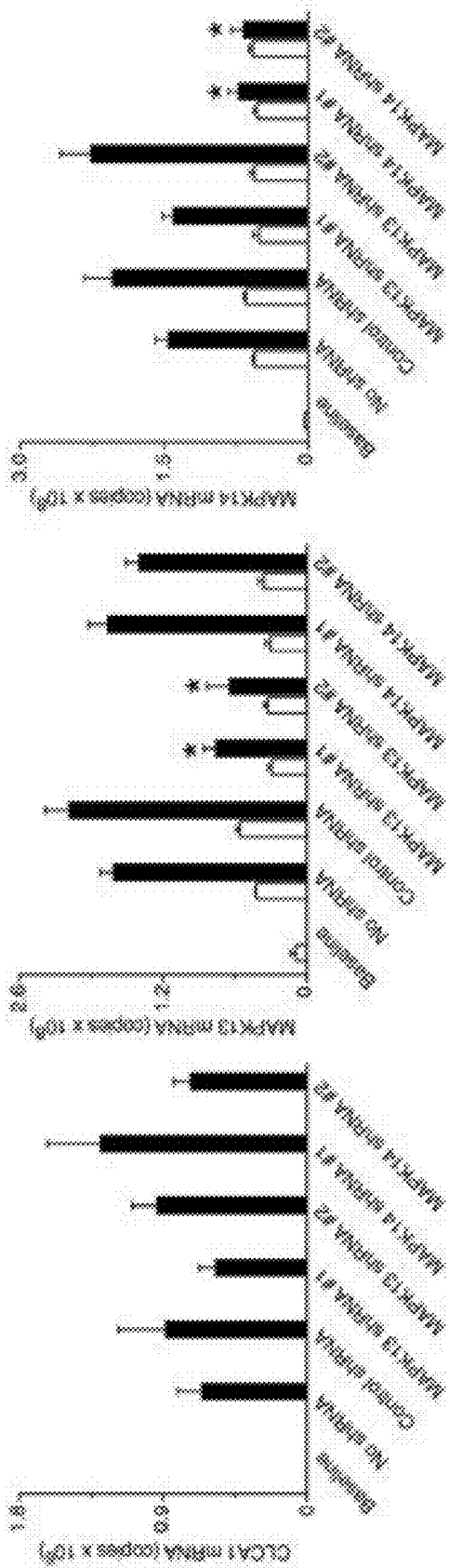

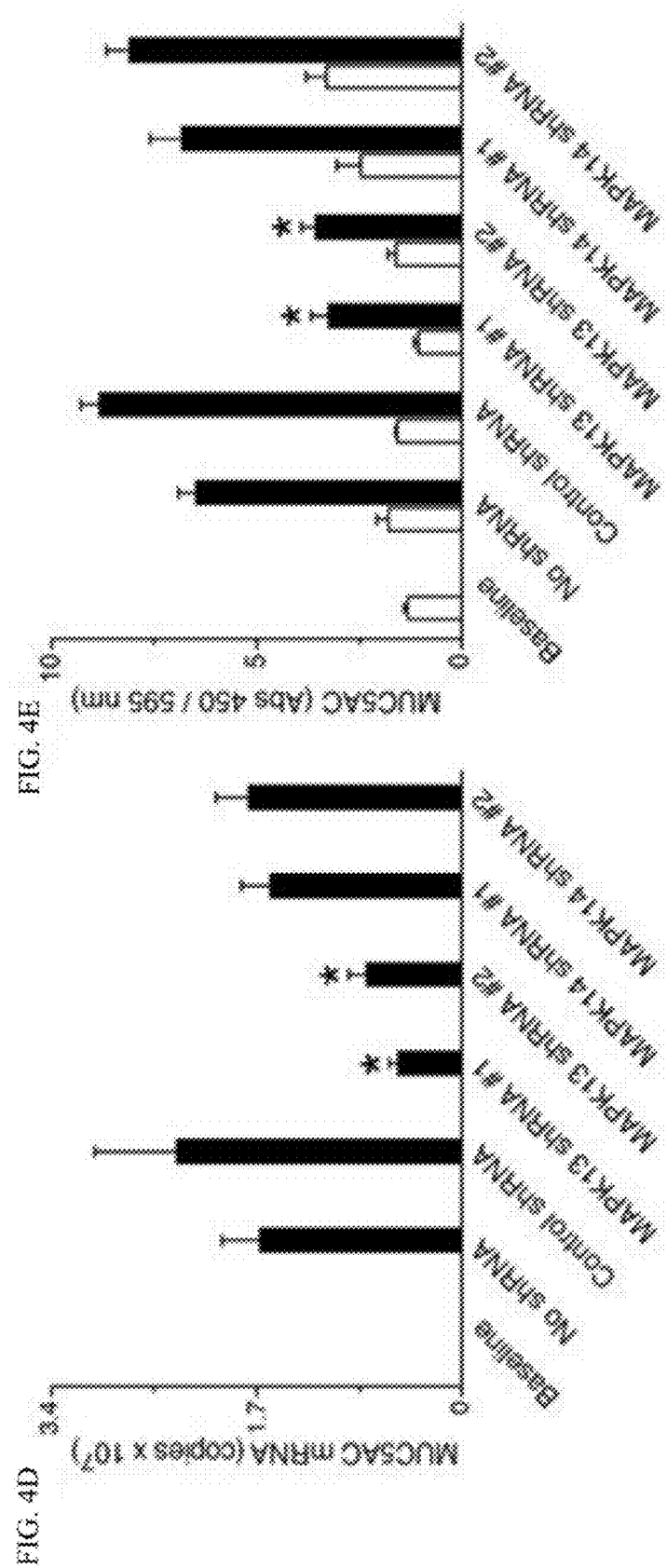

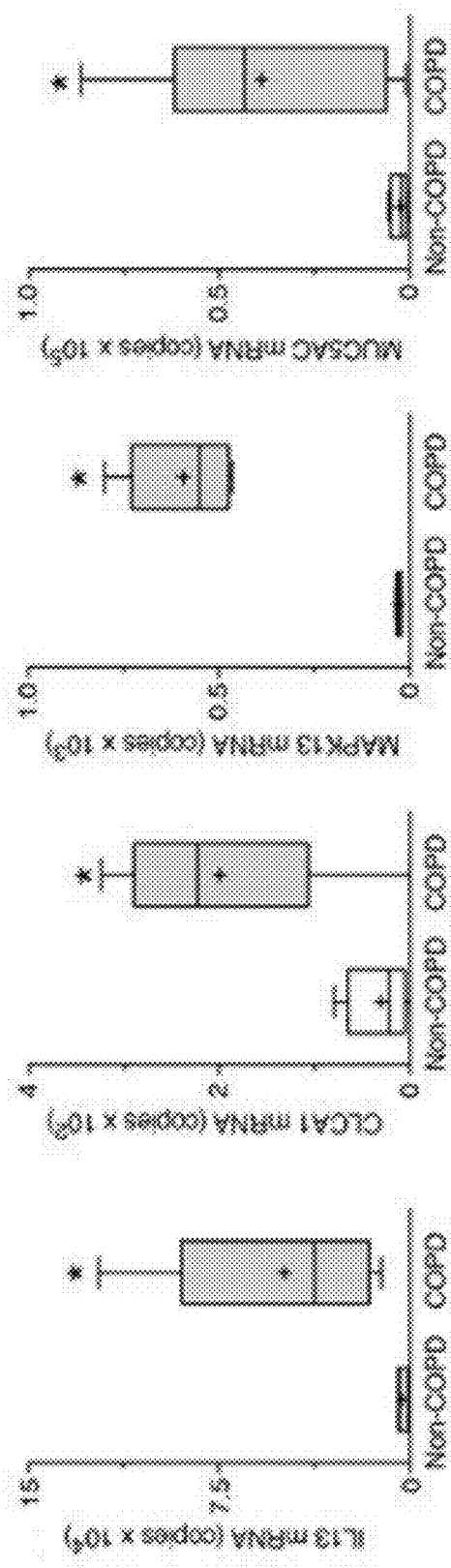
FIG. 5A
FIG. 5B
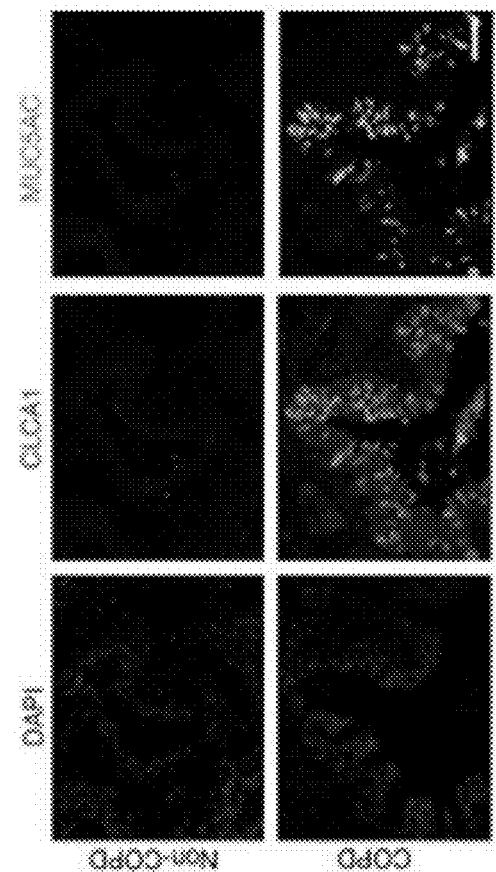
FIG. 5C
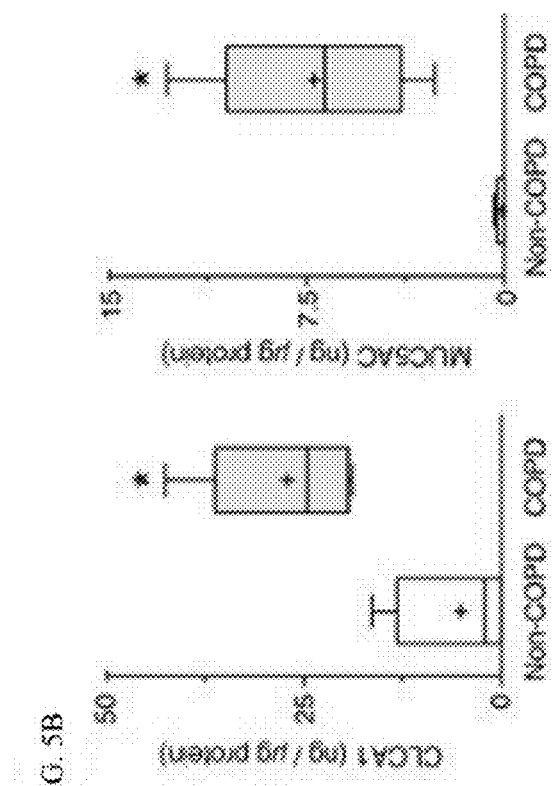

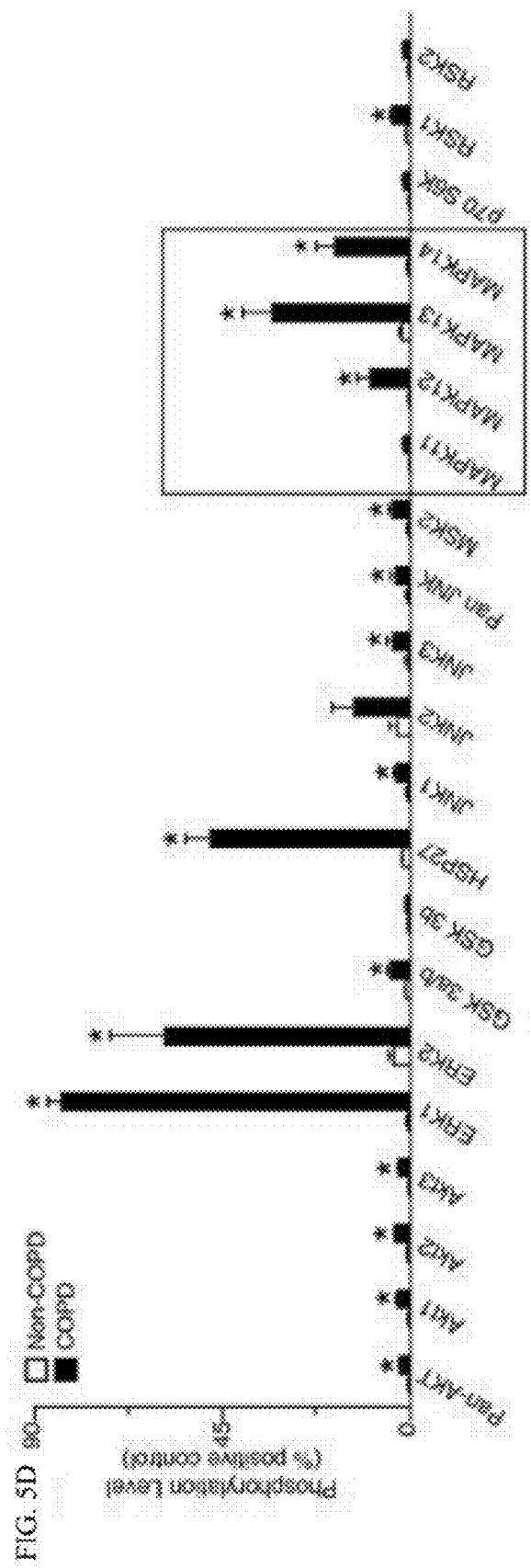

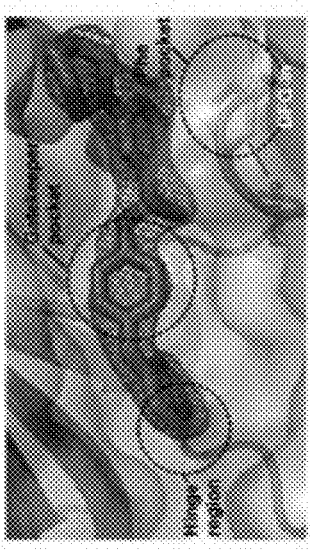
FIG. 6A SB3 706-MAPK13 mode
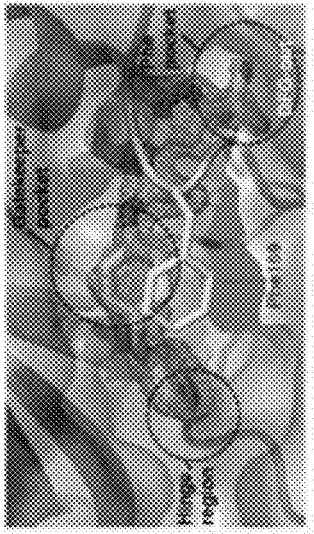
FIG. 6B Compound 61-MAPK13
FIG. 6C Compound 124-MAPK13
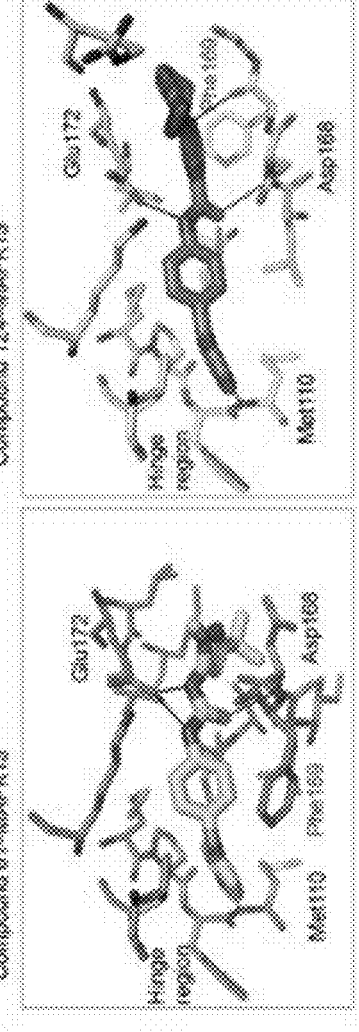
FIG. 6D
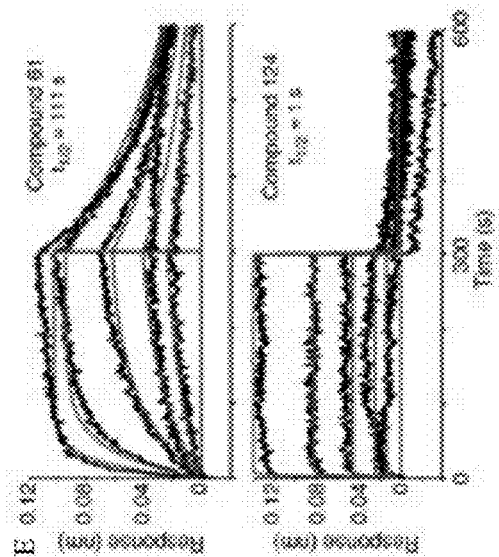
FIG. 6E

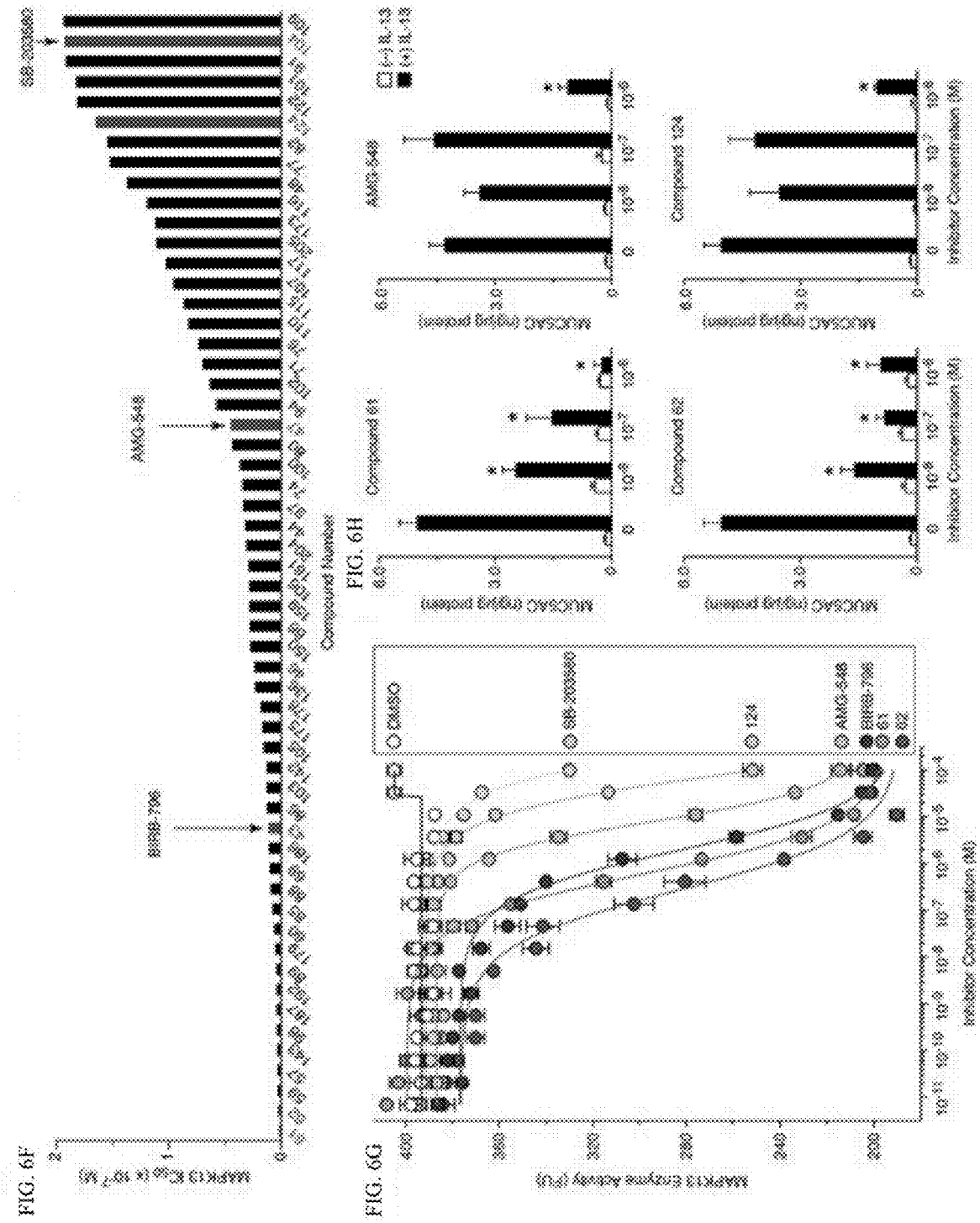

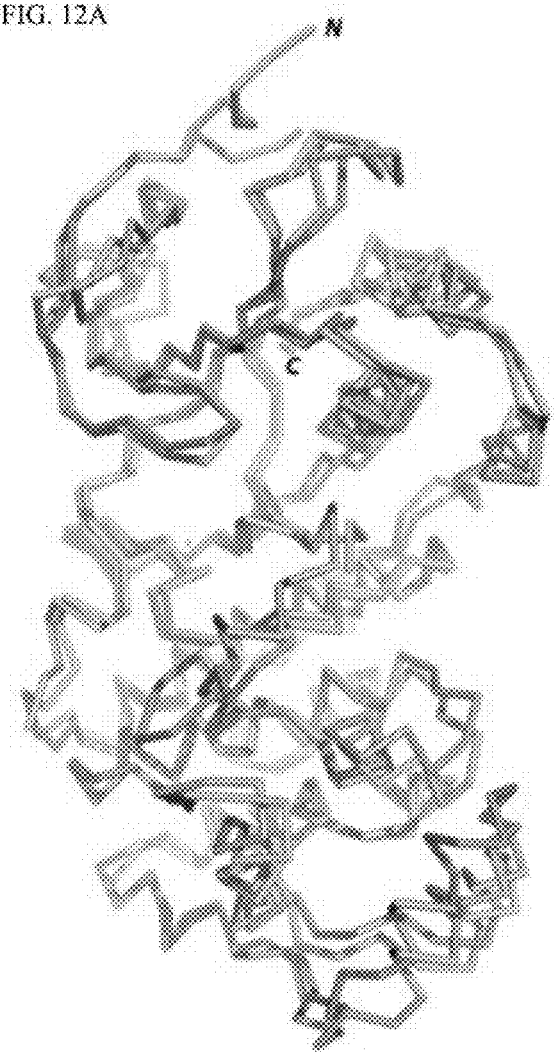 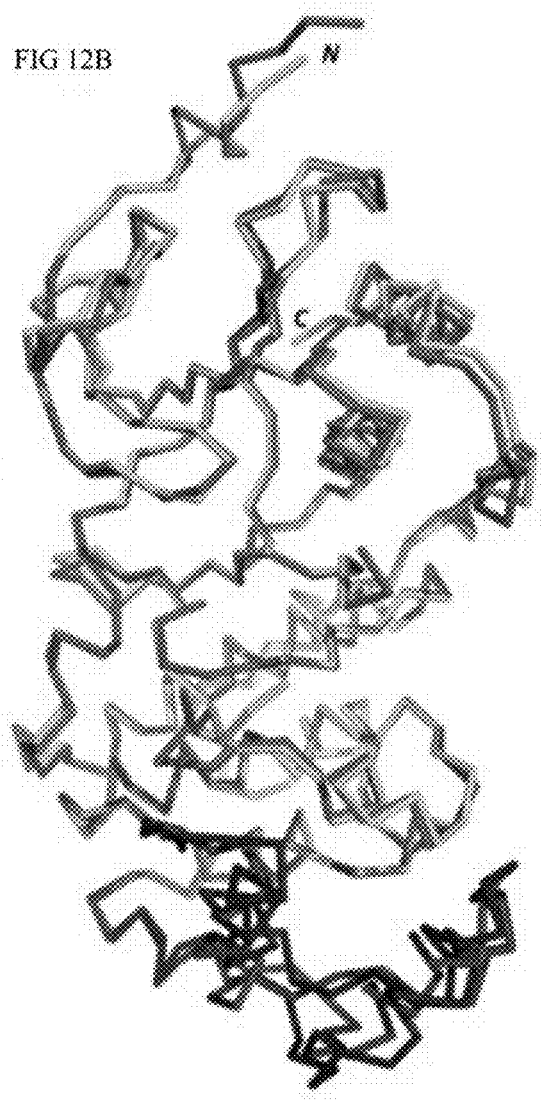

ANTI-MUCUS DRUGS AND USES THEREFOR

RELATED APPLICATIONS

This application is a continuation-in-part of PCT/US2013/050921 filed on Jul. 17, 2013 and claims priority to U.S. Provisional Patent Application 61/672,378 filed 17 Jul. 2012. These applications are incorporated by reference each in its entirety.

GOVERNMENT RIGHTS

This invention was made with the support of Grant NHLBI RO1 HL073159 from the National Institutes of Health. The government of the United States of America may have certain rights in this work.

REFERENCE TO A SEQUENCE LISTING

The Sequence Listing, which is a part of the present disclosure, includes a text file comprising primer nucleotide and/or amino acid sequences of the present invention. The subject matter of the Sequence Listing is incorporated herein by reference in its entirety. The information recorded in computer readable form is identical to the written sequence listing.

INTRODUCTION

An excess of airway mucous secretions is one of the most common maladies of mankind. The condition is a feature of acute respiratory illnesses and a characteristic feature of chronic lung diseases such as asthma and chronic obstructive pulmonary disease (COPD). Mucus overproduction is responsible for much of the morbidity and mortality associated with these conditions. In the case of asthma, reports of mucus plugging and inspissation are typical of autopsies of asthmatic patients (Kuyper, L. M., et al. Am. J. Med. 115:6-11, 2003). Similarly, much of the distress of COPD patients may depend on disease of small airways that are grossly overpopulated with mucous cells (Hogg, J. C., et al. N. Eng. J. Med. 350:2645-53, 2004). Moreover, mucus production may be an early sign of progressive disease (Brito-Mutunayagam, R., et al. Chest 138:605-13, 2010). At present, however, there is no specific and effective treatment for overproduction of mucus.

One of the chief reasons for the lack of effective therapeutics for excess mucus production is that the underlying cellular and molecular mechanism for this process is poorly understood. It has been shown that initial stimuli, such as allergens, viruses, and cigarette smoking, will lead to immune cell production of IL-13 as the critical driver for mucous cell metaplasia (Wills-Karp, M., et al. Science. 282:2258-61, 1998; Tyner, J. W., et al. J. Clin. Invest. 116:309-21, 2006; Grayson, M. H., et al. J. Exp. Med. 204:2759-69, 2007; Kim, E. Y., et al. Nat. Med. 14:633-40, 2008). Subsequent downstream events for IL-13 signaling in mucous precursor cells likely involves up-regulation and activation of the IL-13 receptor and associated STAT6 transcription factor (Kim, E. Y., et al. Nat. Med. 14:633-40, 2008; Kuperman, D. A., et al. Nat. Med. 8:885-9, 2002). However, the next step between these events and downstream mucin gene expression still needed to be defined. The lack of identifiable STAT6 binding sites in the mucin gene promoter indicates that intermediate steps are required to convert the IL-13 signal to mucin gene expression (Li, D., et al. J. Biol. Chem. 273:6812-20, 1998; Hewson, C. A., et al. J. Mol. Biol. 344:683-95, 2004). Other studies of cultured human airway epithelial cells have suggested that activation of MEK1/2, PI3K, SPhk1, and MAPK14 (p38α-MAPK) are necessary for IL-13-induced mucous cell formation (Atherton. H. C., et al. Am. J. Physiol. Lung Cell Mol. Physiol. 285:L730-9, 2003; Pulm. Pharmacol. Ther. 23:36-42, 2010). However, it remains uncertain whether these signaling events were associated with mucous cell metaplasia and mucus overproduction in humans with lung disease.

In this context, the present inventors previously provided evidence that calcium-activated chloride channel (CLCA) genes may fulfill a critical role for the development of mucous cell metaplasia. For example, gene transfer with vectors encoding mouse Clca3, Clca5, or Clca6 is sufficient for mucous cell metaplasia in mice (Patel, A. C., et al. Physiol. Genomics. 25:502-13, 2006; Patel, A. C., et al. Am. J. Respir. Crit. Care Med. 175:A499, 2007). Furthermore, both the mouse Clca and human CLCA gene promoter regions contain consensus STAT6-binding sites that could mediate direct responsiveness to IL-13 stimulation (Patel, A. C., et al. Annu. Rev. Physiol. 71:425-49, 2009). In addition, CLCA proteins undergo extracellular secretion and cleavage suggesting that they might function as signaling molecules rather than ion channels (Gibson, A., et al. J. Biol. Chem. 280:27205-12, 2005; Mundhenk, L., et al. J. Biol. Chem. 281:30072-80, 2006).

SUMMARY

The present inventors disclose compounds that inhibit airway mucous production.

In various embodiments of the present teachings, the present inventors have developed compounds that block IL-13-stimulated mucus production in human airway epithelial cells. Accordingly, in various embodiments, the present teachings include compounds that can be administered in amounts effective for blocking IL-13-stimulated mucus production in airway epithelial cells. In various embodiments, a compound of the present teachings can have activity as an inhibitor of MAPK13 activity. In various embodiments, a compound of the present teachings can have activity as an inhibitor of MAPK13 activity preferential to activity as a MAPK14 inhibitor.

In various embodiments, methods are disclosed for treating hypersecretory diseases of the pulmonary airways and other sites as well, such as, without limitation, asthma and COPD. These methods comprise administering to a subject in need thereof one or more compounds of the present teachings, in a dose effective for reducing mucus production. In some configurations, the methods can include administering a pharmaceutical composition comprising a compound, a salt thereof, or a prodrug thereof of the present teachings.

In some embodiments, the present inventors disclose methods for designing candidate inhibitors of MAPK13. Such inhibitors can be effective for reducing mucus production stimulated through a MAPK13-dependent pathway. In some configuration, these methods can include a ligand-hopping strategy which can be used to identify candidate kinase inhibitors that may preferentially inhibit MAPK13 activity compared to MAPK14 activity.

In various embodiments, the present inventors disclose compounds having structures of Formula I or Formula II, pharmaceutically acceptable salts thereof, and prodrugs thereof of structures

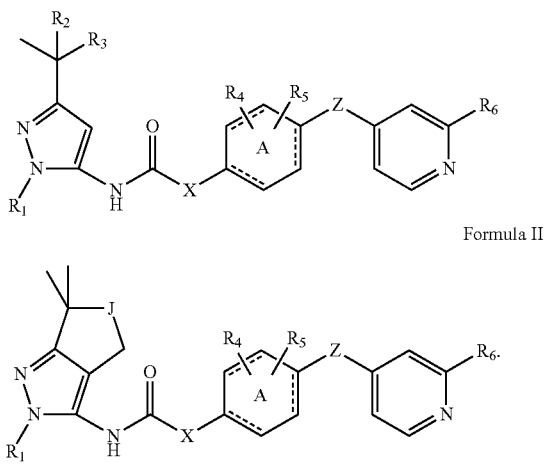

Formula I

Formula II

In various configurations, $R_1$ can be selected from the group consisting of H, lower alkyl and aryl selected from the group consisting of phenyl and pyridinyl. In some configurations, the aryl can comprise 0, 1 or 2 substituents each independently selected from the group consisting of a halogen, a hydroxyl, an ether, a thioether, a lower alkyl, an ester, a carbamate, an amide, and a urea. In various configurations, $R_2$ and $R_3$ in Formula I together can comprise a 4-6 member aliphatic, carbocyclic or aliphatic heterocyclic ring comprising 0, 1 or 2 heteroatoms selected from the group consisting of N, O and S. In some configurations, J in Formula II can be selected from the group consisting of $CH_2$, O and S. In various configurations, X can be selected from the group consisting of $CH_2$, NH (preferred), O and S. In some configurations, Ring A can be aliphatic, aromatic (preferably benzene), heteroaromatic, or a trans-substituted cyclohexane ring. In various configurations, if ring A is aromatic (preferably benzene) or heteroaromatic wherein a heteroatom can be, without limitation, N, O or S. In some embodiments, each $R_4$ and $R_5$ can be independently selected from the group consisting of H, a first halogen (preferably $R_4$ is an F), lower alkyl, $-CF_3$, $-OR_8$ and $-SR_9$, with the proviso that $R_4$ and $R_5$ do not together comprise a ring. In various embodiments, each of $R_8$ and $R_9$ can be independently selected from the group consisting of H, lower alkyl, cycloalkyl, cycloalkylalkyl, heterocyclyl, heterocycloalkyl, aryl, and arylaklyl. In some configurations, Z can be selected from the group consisting of $CH_2$, NH, O and S (O and S preferred). In various configurations, $R_6$ can be selected from the group consisting of H, amine, lower alkyl, cycloalkyl, cycloalkylalkyl, heterocyclyl, heterocyloalkyl, aryl, arylalkyl, heteroaryl, heteroarylalkyl, $-OR_{12}$, $-SR_{13}$, $-NR_{14}R_{15}$, $-C(O)NR_{16}R_{17}$, $-NR_{18}C(O)R_{19}$, $-C(O)OR_{20}$, $-NR_{21}C(O)OR_{22}$, $-NR_{23}C(O)NR_{24}R_{25}$. In various configurations, when $R_6$ is lower alkyl, cycloalkyl, cycloalkylalkyl, heterocyclyl, heterocyloalkyl, aryl, arylalkyl, heteroaryl, or heteroarylalkyl, then $R_6$ can be optionally substituted with 1-2 radicals each independently selected from the group consisting of halogen, hydroxyl, ether, $-CF_3$, thioether, amide, carbamate, urea, and ester. In various configurations, each of $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ and $R_{25}$ can be independently selected from the group consisting of H, lower alkyl, cycloalkyl, cycloalkylalkyl, heterocyclyl, heterocycloalkyl, aryl, and arylaklyl. Lower alkyl can be $C_1$-$C_{10}$ linear alkyl, $C_3$-$C_{10}$ branched alkyl, or $C_3$-$C_{10}$ cyclic alkyl and 0, 1, 2 or 3 carbons of a lower alkyl can be replaced with a heteroatom, each heteroatom selected from the group consisting of N, O, and S. In some configurations, if $R_8$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ or $R_{25}$ is not H, $R_8$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ or $R_{25}$ can be further substituted with 1-2 groups selected from the group consisting of halogen, hydroxyl, ether, $-CF_3$, thioether, amide, carbamate, urea, and ester. In some configurations where a nitrogen is substituted with two $R_8$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ or $R_{25}$ groups, the $R_8$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ or $R_{25}$ groups can optionally be taken together to form a 5-7 membered ring. In various configurations, "lower alkyl" can include $C_1$-$C_{10}$ linear alkyl, $C_3$-$C_{10}$ branched alkyl and $C_3$-$C_{10}$ cyclic alkyl.

In various embodiments, the present inventors disclose compounds having structures of Formula III or Formula IV, pharmaceutically acceptable salts thereof, and prodrugs thereof of structures

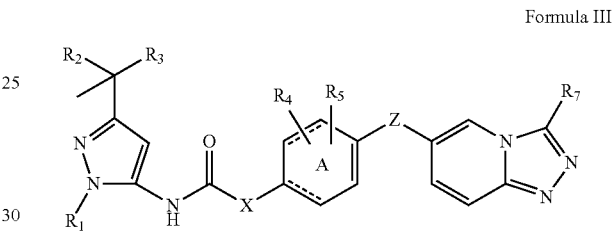

Formula III

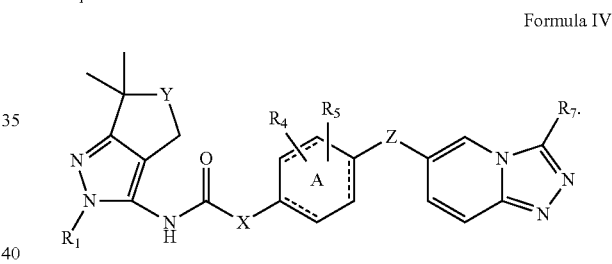

Formula IV

In various configurations, $R_1$ can be selected from the group consisting of H, lower alkyl and aryl selected from the group consisting of phenyl and pyridinyl. In some configurations, the aryl can comprise 1-2 substituents each independently selected from the group consisting of a halogen, a hydroxyl, an ether, a thioether, a lower alkyl, an ester, a carbamate, an amide, and a urea. In various configurations, $R_2$ and $R_3$ in Formula III together can comprise a 4-6 member aliphatic carbocyclic or aliphatic heterocyclic ring comprising 0, 1 or 2 heteroatoms selected from the group consisting of N, O and S. In various configurations. Y in Formula IV can be selected from the group consisting of $CH_2$, O and S. In some configurations, X can be selected from the group consisting of $CH_2$, NH (preferred), O and S. In various configurations, Ring A can be an aromatic (preferably benzene), heteroaromatic or a trans-substituted cyclohexane ring. In some configurations, if ring A is aromatic (preferably benzene) or heteroaromatic, each $R_4$ and $R_5$ can be independently selected from the group consisting of H, a halogen (preferably $R_4$ is an F), lower alkyl, $-CF_3$, $-OR_8$, and $-SR_8$, with the proviso that $R_4$ and $R_5$ do not together comprise a ring. In various configurations, Z can be selected from the group consisting of $CH_2$, NH, O, or S. In various configurations, $R_7$ can be selected from the group consisting of H, lower alkyl, arylalkyl, heterocyloalkyl, cycloalkyl, cycloalkylalkyl aryl, heteroaryl, heterocyclo. In some configurations, if $R_7$ is not H, $R_7$ can be substituted with 0-3 groups independently selected from the group consisting of halogen, —OH, —OR$_8$, —CF$_3$, —SR$_8$, —NR$_8$R$_8$, —CONR$_8$R$_8$, —NR$_8$COR$_8$, —CO$_2$R$_8$, —NR$_8$C(O)OR$_8$ and —NR$_8$C(O)NR$_8$R$_8$. In various configurations, R$_8$ can be selected from the group consisting of H, lower alkyl, cycloalkyl, cycloalkylalkyl, heterocyclyl, heterocycloalkyl, aryl, arylalkyl, heteroaryl and heteroarylalkyl. In some configurations, if R$_8$ is not H, R$_8$ can be further substituted with 0-2 groups selected from the group consisting of halogen, hydroxyl, ether, —CF$_3$, thioether, amide, carbamate, urea and ester. In some configurations, where a nitrogen is substituted by two R$_8$ groups, the R$_8$ groups can optionally be taken together to form a 5-7 membered ring. In various configurations, "lower alkyl" can include C$_1$-C$_{10}$ linear alkyl, C$_3$-C$_{10}$ branched alkyl and C$_3$-C$_{10}$ cyclic alkyl. In some embodiments, lower alkyl can be C$_1$-C$_{10}$ linear alkyl, C$_3$-C$_{10}$ branched alkyl, or C$_3$-C$_{10}$ cyclic alkyl and 0, 1, 2 or 3 carbons of a lower alkyl are replaced with a heteroatom, each heteroatom selected from the group consisting of N, O, and S.

In various embodiments, the present inventors disclose compounds having structures of Formula V, pharmaceutically acceptable salts thereof, and prodrugs thereof of structures Formula V

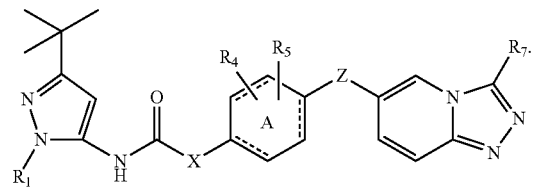

In various configurations, R$_1$ can be selected from the group consisting of H, lower alkyl and aryl selected from the group consisting of phenyl and pyridinyl. In some configurations, the aryl optionally can comprise 1-2 substituents each independently selected from the group consisting of a halogen, a hydroxyl, an ether, a thioether, a lower alkyl, an ester, a carbamate, an amide and a urea. In various configurations, X can be selected from the group consisting of CH$_2$, NH (preferred), O, or and S. In various configurations, Ring A can be a benzene, pyridine or trans-substituted cyclohexane ring. In some configurations, if ring A is benzene or pyridine, R$_4$ and R$_5$ can be independently selected from the group consisting of H, halogen (preferred is R$_4$ is fluorine), lower alkyl, —CF$_3$, ether, and thioether, with the proviso that R$_4$ and R$_5$ together do not comprise a ring. In various configurations, Z can be selected from the group consisting of CH$_2$, NH, O and S (O and S are preferred). In various configurations, R$_7$ can be a 4-7 membered heterocyclic ring containing 1-2 ring atoms independently selected from the group consisting of N, O and S. In some configurations, the heterocyclic ring in R$_7$ can be optionally substituted with 0-3 substituents independently selected from the group consisting of H, halogen, hydroxyl, lower alkyl, —OR$_8$, —SR$_8$, —NR$_8$R$_8$, —CONR$_8$R$_8$, —NR$_8$COR$_8$, —CO$_2$R$_8$, —NR$_8$C(O)OR$_8$, —NR$_8$C(O)NR$_8$R$_8$. In various configurations, when the heterocyclic ring in R$_7$ is substituted by an alkyl, the alkyl can optionally be further substituted by 0-2 substituents independently selected from the group consisting of halogen, hydroxyl, —OR$_8$, —SR$_8$, —NR$_8$R$_8$, —CONR$_8$R$_8$, —NR$_8$COR$_8$, —CO$_2$R$_8$, —NR$_8$C(O)OR$_8$, —NR$_8$C(O)NR$_8$R$_8$. In various configurations, each R$_8$ is independently selected from the group consisting of H, lower alkyl, cycloalkyl, cycloalkylalkyl, heterocyclyl, heterocycloalkyl, aryl, arylalkyl, heteroaryl and heteroarylalkyl. In some configurations, if R$_7$ is not H, R$_7$ can be optionally further substituted with 0-2 groups independently selected from the group consisting of halogen, hydroxyl, ether, —CF$_3$, thioether, amide, carbonate, urea and ester. In various configurations, when a nitrogen is substituted by two R$_8$ groups, the R$_8$ groups can optionally comprise a 5-7 membered ring. In various configurations, "lower alkyl" can include C$_1$-C$_{10}$ linear alkyl, C$_3$-C$_{10}$ branched alkyl and C$_3$-C$_{10}$ cyclic alkyl.

In various embodiments, the present inventors disclose compounds having structures of Formula VI or Formula VII, pharmaceutically acceptable salts thereof, and prodrugs thereof of structures Formula VI

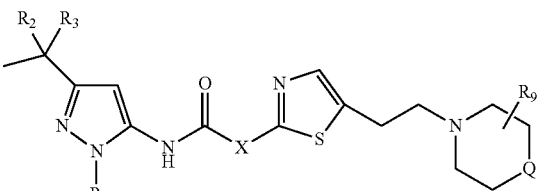

Formula VII

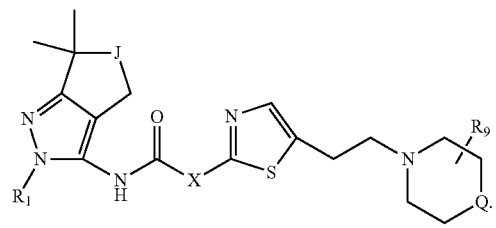

In various configurations R$_1$ can be selected from the group consisting of H, lower alkyl and aryl selected from the group consisting of phenyl and pyridinyl. In some configurations, the aryl can optionally comprise 0-2 substituents each independently selected from the group consisting of a halogen, a hydroxyl, an ether, a thioether a lower alkyl, an ester, a carbamate, an amide, and a urea. In various configurations, R$_2$ and R$_3$ in Formula VI together can be each independently selected from the group consisting of H or lower alkyl or together can comprise a 4-6 member aliphatic, carbocyclic, heterocyclic or aliphatic heterocyclic ring comprising 0, 1 or 2 heteroatoms, each selected from the group consisting of N, O and S. In various configurations, J in Formula VII can be selected from the group consisting of CH$_2$, O and S. In various configurations. Q can be selected from the group consisting of O and S (O is preferred). In some configurations, R$_9$ can be selected from the group consisting H, lower alkyl, cycloalkyl, cycloalkylalkyl, heteroaryl, heteroarylalkyl, heterocyclyl, heterocyloalkyl, heterocycylalkyl, hydroxylalkyl, alkloxyalkyl, aminoalkyl, carboxamido, carboxamidoalkyl, aryl, arylalkyl, —NHC(O)R$_8$, —NHC(O)NR$_{10}$R$_{11}$, —CH$_2$NHC(O)R$_{12}$, —CH$_2$NHC(O)NR$_{13}$R$_{14}$, —C(O)NR$_{15}$R$_{16}$, —C(O)OR$_{17}$, —C(O)NR$_{18}$R$_{19}$, and —C(O)OR$_{20}$. Each of R$_8$, R$_{10}$, R$_{11}$, R$_{12}$, R$_{13}$, R$_{14}$, R$_{15}$, R$_{16}$, R$_{17}$, R$_{18}$, R$_{19}$ and R$_{20}$ can be independently selected from the group consisting of H, lower alkyl, cycloalkyl, cycloalkylalkyl, heterocyclyl, heterocycloalkyl, aryl, and arylalkyl. Lower alkyl can be C$_1$-C$_{10}$ linear alkyl, C$_3$-C$_{10}$ branched alkyl, or C$_3$-C$_{10}$ cyclic alkyl and 0, 1, 2 or 3 carbons of a lower alkyl can be replaced with a heteroatom, each heteroatom can be selected from the group consisting of N, O, and S. In some configurations, "lower alkyl" can include $C_1$-$C_{10}$ linear alkyl, $C_3$-$C_{10}$ branched alkyl and $C_3$-$C_{10}$ cyclic alkyl.
In various embodiments of the present teachings, the present inventors disclose compounds, pharmaceutically acceptable salts thereof, and prodrugs thereof having structures such as
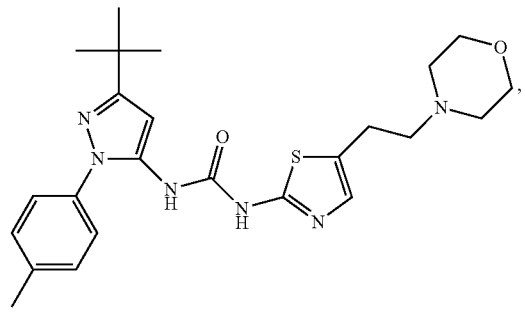
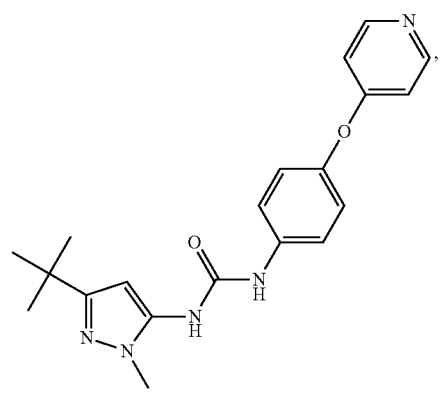
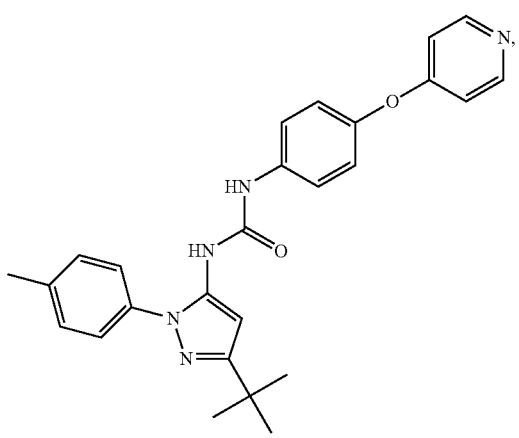
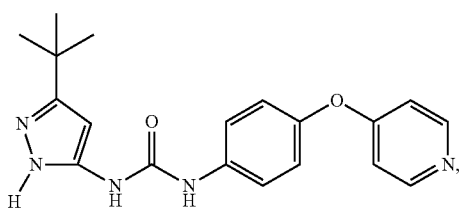
-continued
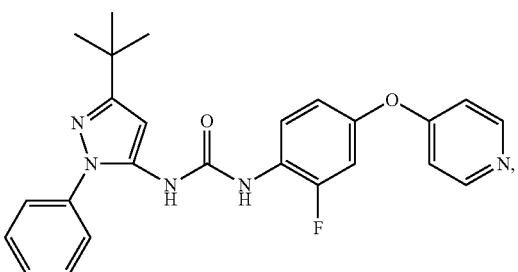
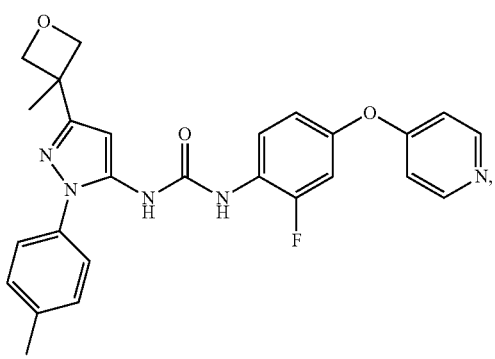
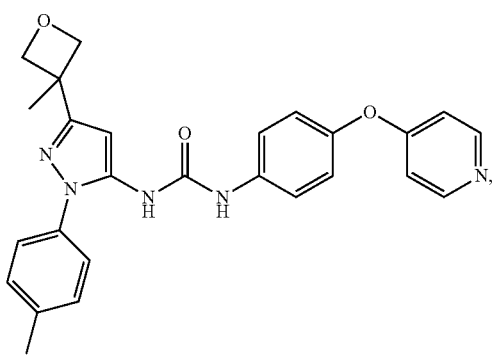
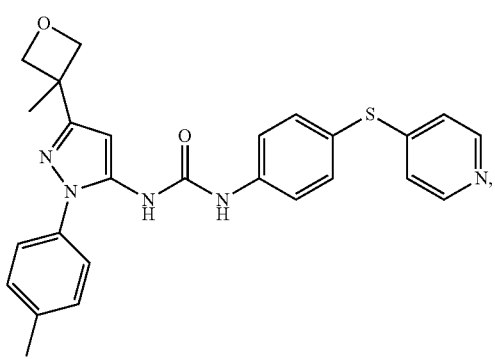

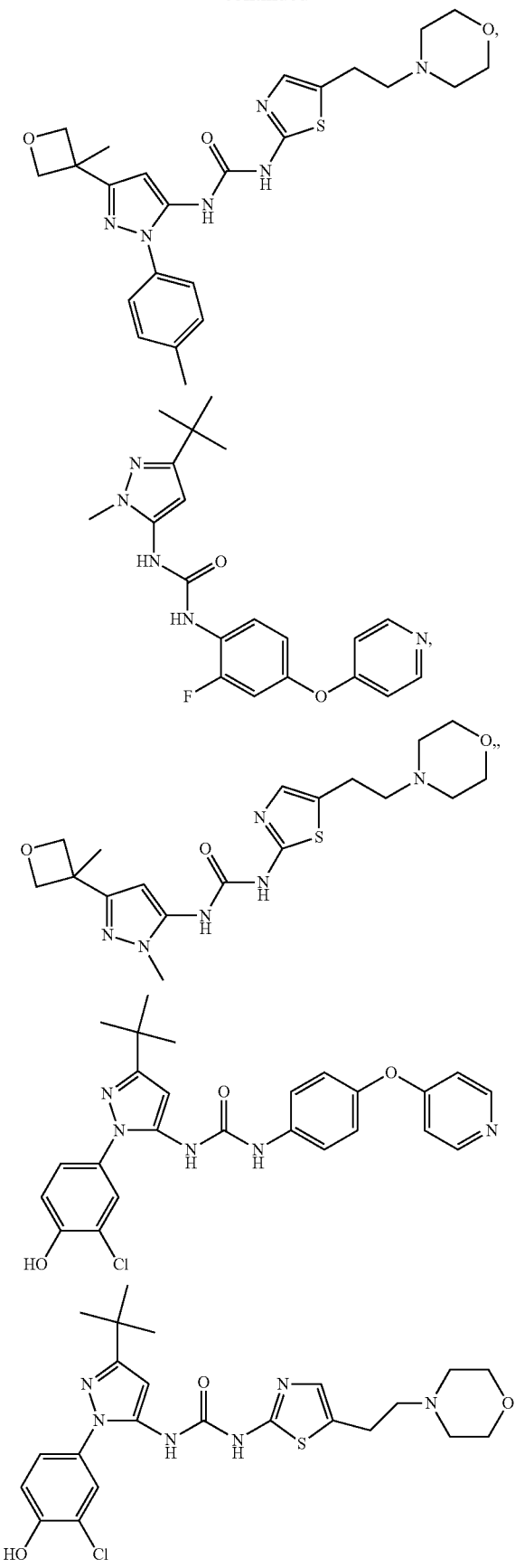
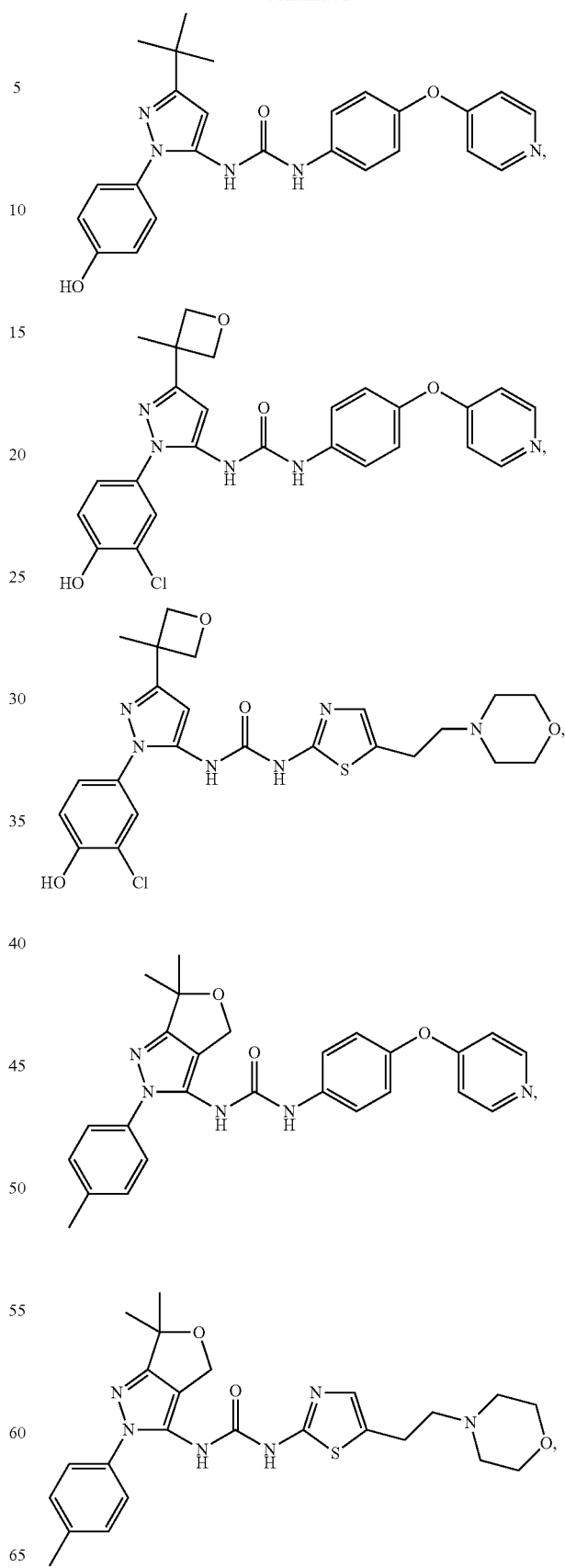

11
-continued
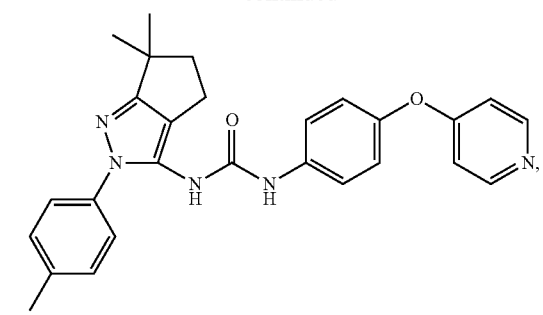
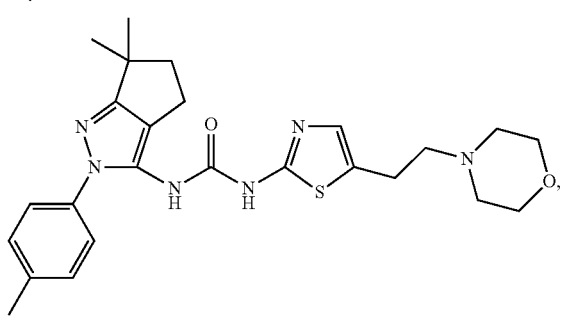
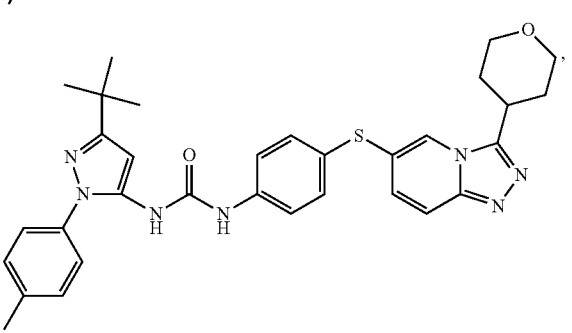
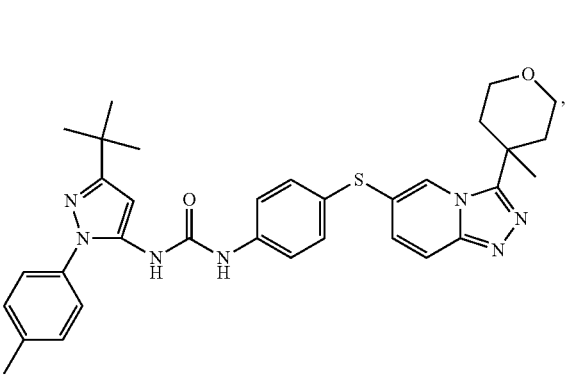
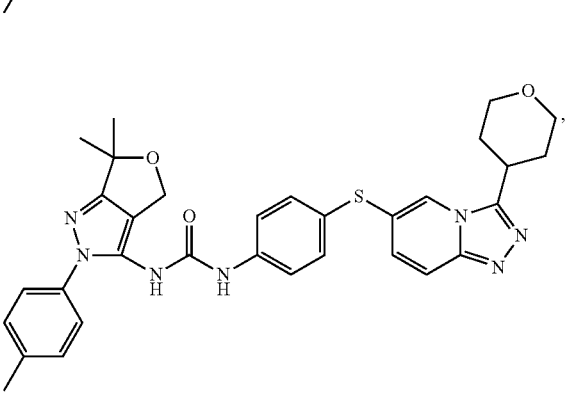
12
-continued
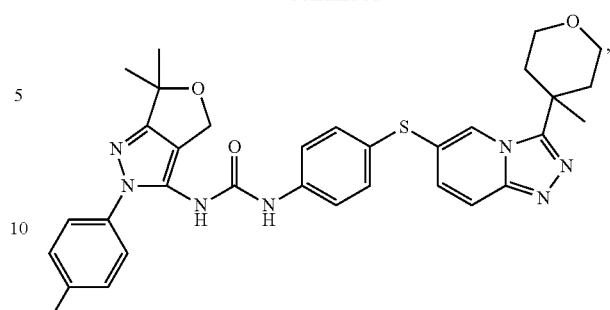
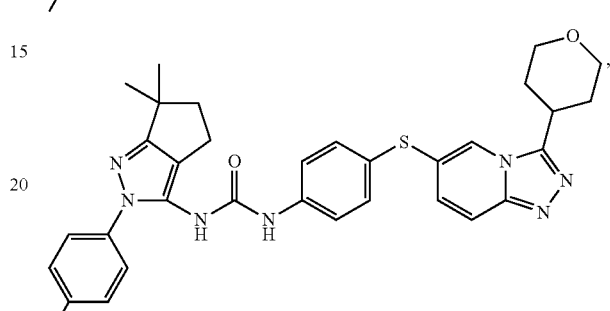
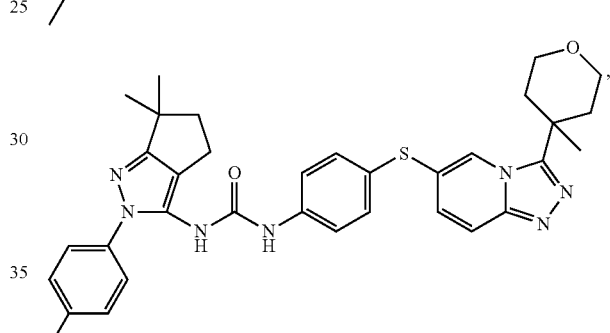
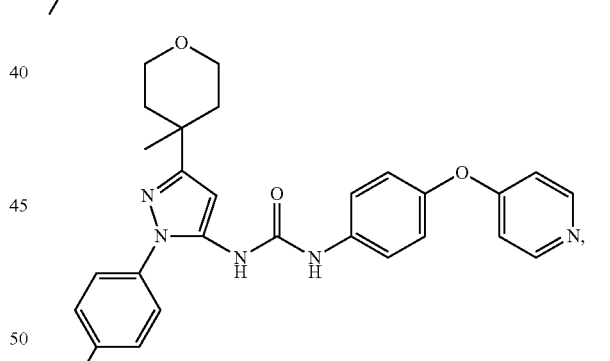
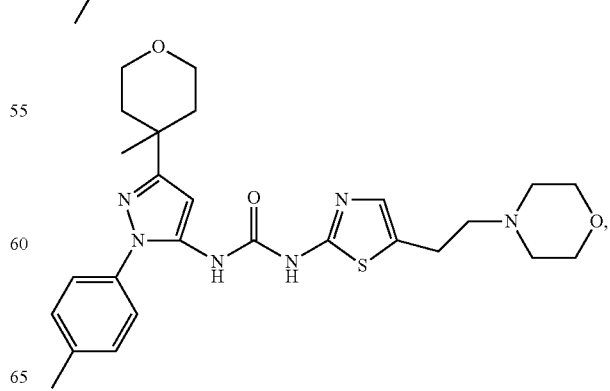

-continued
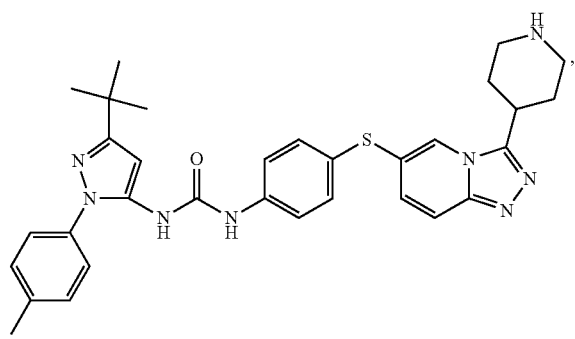
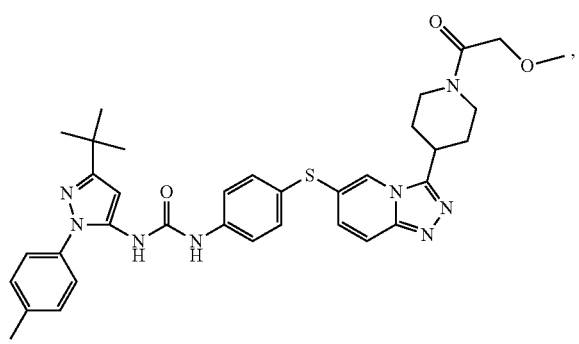
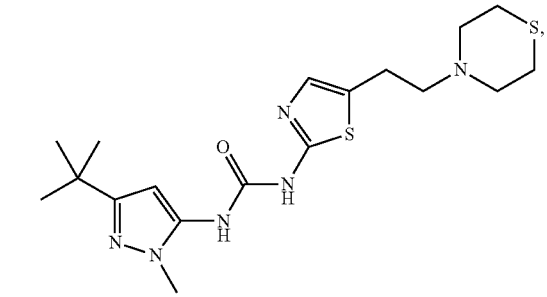
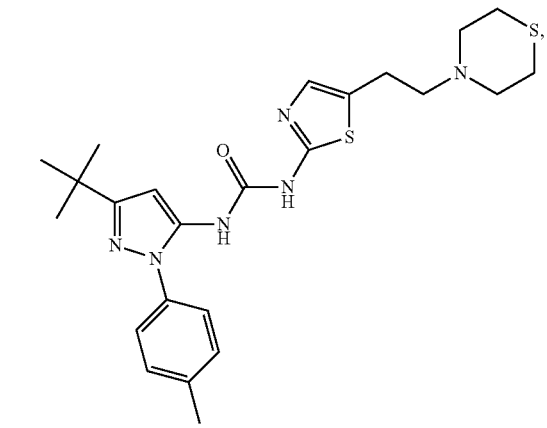
-continued
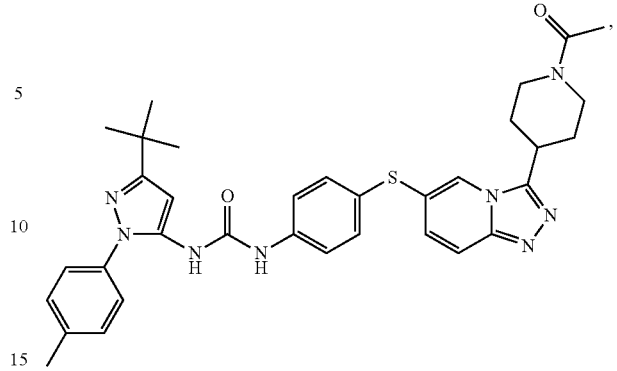
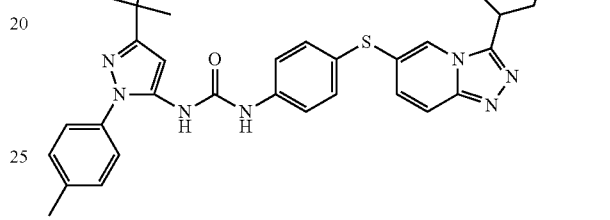
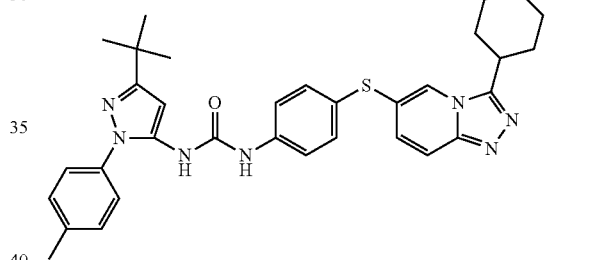
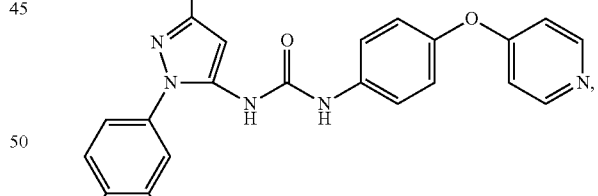
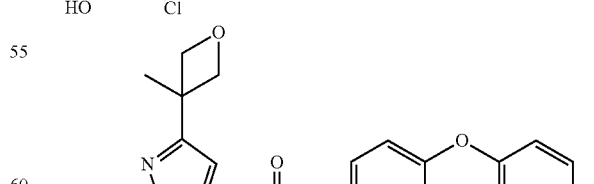
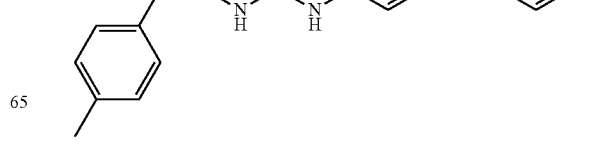

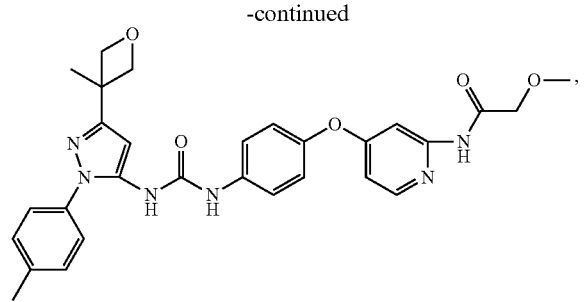
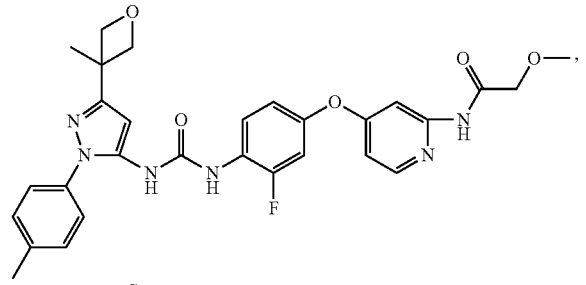
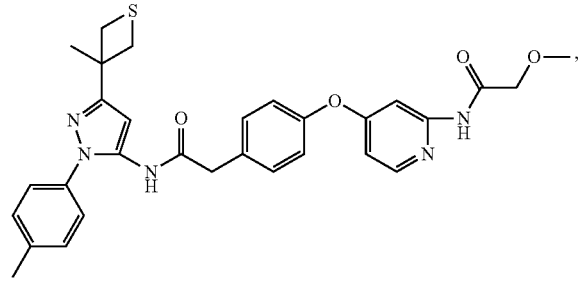
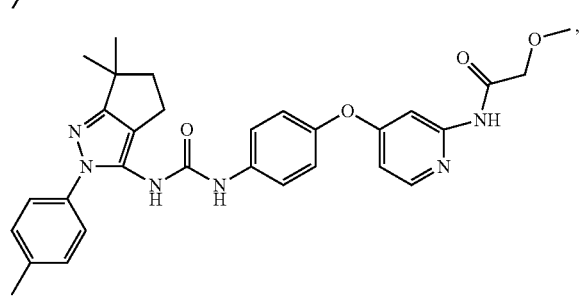
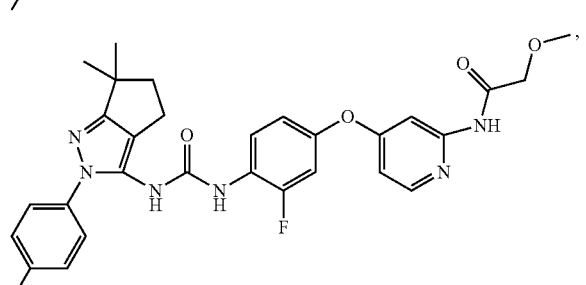
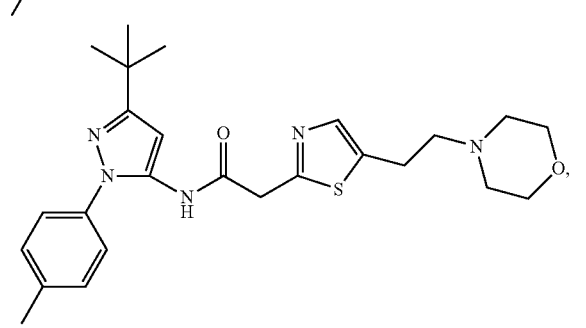

In some embodiments of the present teachings, the inventors disclose compounds comprising a 3-(3-methyloxetan-3-yl)-1H-pyrazole or derivatives thereof such as wherein $R^1$ comprises a bond and $R^2$ comprises a bond, or a salt or prodrug thereof. In some configurations, $R^1$ can comprise one or more atoms and $R^2$ can comprise one or more atoms. In some configurations, $R^1$ can be selected from the group consisting of methyl, methylbenzene, chlorobenzene and fluorobenzene. In some configurations, $R^2$ can b selected from the group consisting of

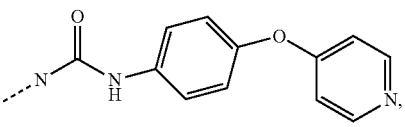

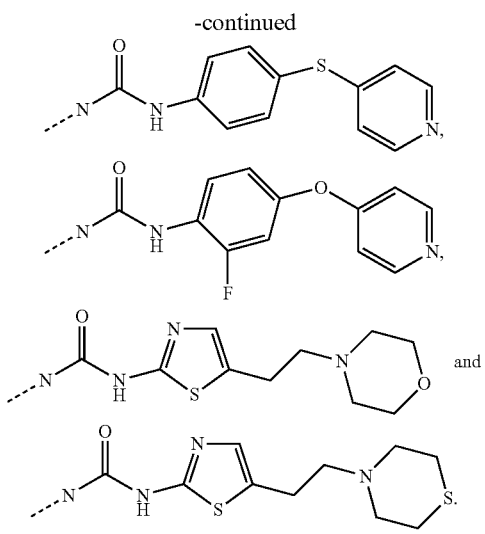

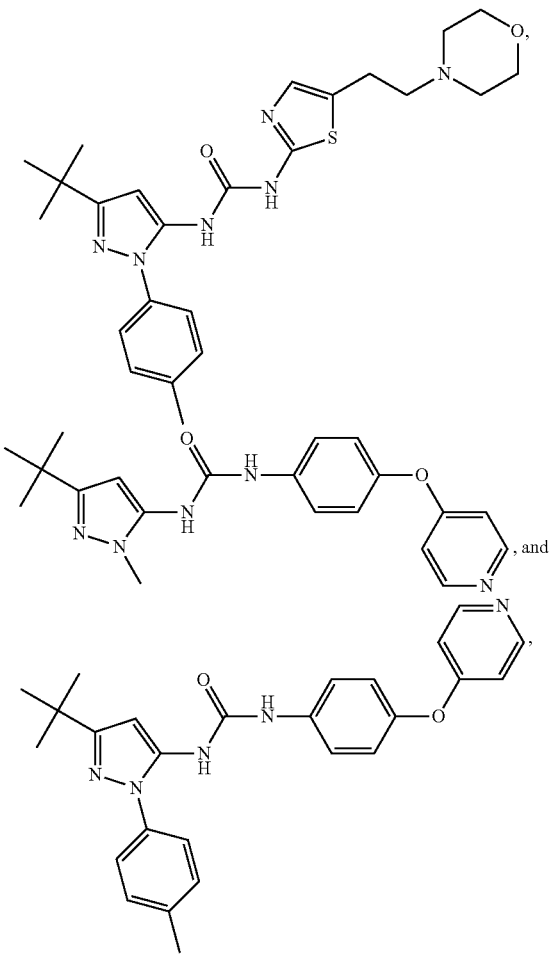

In various configurations, a compound comprising such structures can have activity as an inhibitor of a MAPK kinase, such as MAPK13 and/or MAPK14.

The present teachings include methods of identifying one or more inhibitors of MAPK13. In some embodiments, these methods can comprise providing, on a digital computer, a molecular model comprising a complex of binding pocket domains of MAPK13; docking a chemical database to the molecular model; scoring the compounds comprised by the database; and identifying one or more high-scoring compounds.

In various embodiments, the present teachings include methods of inhibiting MAPK13 activity. In some configurations, these methods can comprise contacting MAPK13 with at least one compound of Formula I-VII or a pharmaceutically acceptable salt thereof. In some embodiments, a compound can exhibit slow-off binding kinetics. Without being limited by theory, a compound exhibiting slow off binding kinetics can bind MAPK13 by a DFG-out binding mode. In some embodiments, a compound that exhibits slow off binding kinetics against MAPK13, when administered to a subject in need, can remain on-target (for example, after administration directly to a lung) for a longer duration (compared to other MAPK inhibitors), and thereby can provide a sustained effect. In some configurations, a compound that exhibits slow off binding kinetics against MAPK13 can reduce the need for repeated dosing and can also allow for a smaller doses compared to other MAPK inhibitors.

In various embodiments, the present teachings include cell lines. In some embodiments, a cell line can include NCI-H292 cells comprising a nucleic acid encoding tTA with pTRE-tight-hCLCA1 whereby the cell expresses hCLCA1 after doxycycline withdrawal.

In various embodiments, the present teachings include methods of treating an inflammatory airway disease in a subject in need thereof. In various configurations, a method of these embodiments can comprise administering to a subject in need thereof a compound, a pharmaceutically acceptable salt thereof, or a prodrug thereof of the present teachings. In some embodiments, a compound can be selected from the group consisting of Formulae I-VII. In some configurations, the compound can be selected from the group consisting of or any other MAPK13-inhibiting compound, prodrug or salt thereof described herein.

In various embodiments, the present teachings include methods of delivering a MAPK13 blocking drug directly to a region of the lung affected by inflammatory airway disease. In some configurations, these methods can comprise administering the drug by an inhalation route. In some configurations, these methods can comprise administering the drug by an inhalation route to treat COPD. In some configurations, these methods can comprise administering the drug by an inhalation route to treat asthma.

The present teachings include methods of treating an inflammatory airway disease such as an inflammatory airway disease in a subject in need thereof. In various configurations, these methods can comprise administering a therapeutically effective amount of a pharmaceutical composition comprising a compound, prodrug or salt thereof of any of Formulas I-VII, or a combination thereof, directly to the lung by utilizing an inhalation route of administration. In various configurations these methods can comprise administering a therapeutically effective amount of a pharmaceutical composition comprising a compound, prodrug or salt thereof of any of Formulas I-VII, or a combination thereof, directly to the lung by utilizing an inhalation route of administration wherein the composition is mixed with a carrier. In various configurations the carrier can be lactose.

The present teachings include the following aspects, without limitation.

1. A compound, a pharmaceutically acceptable salt thereof, or a prodrug thereof, of Formula I or Formula II

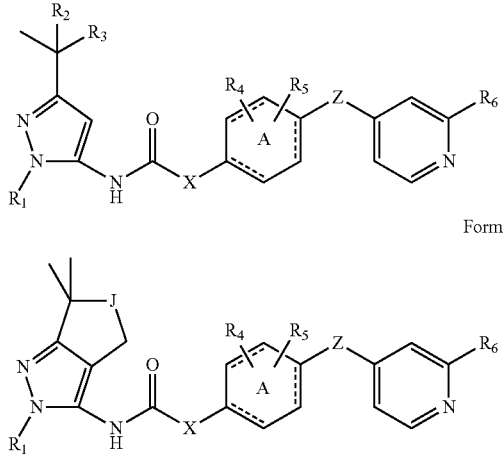

wherein $R_1$ is selected from the group consisting of H, lower alkyl, and aryl (phenyl and pyridinyl preferred; phenyl most preferred), wherein the aryl can be optionally substituted with 0-2 radicals each independently selected from the group consisting of halogen, hydroxyl, —$OR_{26}$, —$SR_{27}$, lower alkyl, —$C(O)OR_{28}$, —$OC(O)R_{29}$, —$NR_{30}C(O)R_{31}$, —$C(O)NR_{32}$, —$NR_{33}C(O)NR_{34}R_{35}$, —$OC(O)NR_{36}R_{37}$, —$NR_{38}C(O)OR_{39}$, imidazolyl;

$R_2$ and $R_3$ in Formula I together can comprise a 4-6 member aliphatic, carbocyclic or heterocyclic ring comprising 0, 1 or 2 heteroatoms selected from the group consisting of N, O and S;

J in Formula II can be selected from the group consisting of $CH_2$, O and S;

X can be selected from the group consisting of $CH_2$, NH (preferred), O and S;

Ring A can be a 6-membered aliphatic, aromatic or heteroaromatic ring selected from the group consisting of benzene (benzene preferred), pyridine, or pyrimidine, or a trans-substituted cyclohexane ring, wherein if ring A is aromatic or heteroaromatic, each $R_4$ and $R_5$ can be independently selected from the group consisting of H, a first halogen (preferably $R_4$ is fluorine), lower alkyl, —$CF_3$, —$OR_8$ and —$SR_9$, with the proviso that $R_4$ and $R_5$ do not together comprise a ring, and wherein if ring A is cyclohexane, R4 and R5 are H;

Z can be selected from the group consisting of $CH_2$, NH, O and S (O and S preferred);

$R_6$ can be selected from the group consisting of H, amine, lower alkyl, cycloalkyl, cycloalkylalkyl, heterocyclyl, heterocyloalkyl, aryl, arylalkyl, —$OR_{12}$, —$SR_{13}$, —$NR_{14}R_{15}$, —$C(O)NR_{16}R_{17}$, —$NR_{18}C(O)R_{19}$, —$C(O)OR_{20}$, —$NR_{21}C(O)OR_{22}$, —$NR_{23}C(O)NR_{24}R_{25}$; and, when $R_6$ is lower alkyl, cycloalkyl, cycloalkylalkyl, heterocyclyl, heterocyloalkyl, aryl, arylalkyl, then $R_6$ can be optionally further substituted with 0-2 radicals selected from the group consisting of halogen, hydroxyl, —$NR_{40}R_{41}$, —$OR_{42}$, —$SR_{43}$, —$CF_3$, —$C(O)NR_{44}R_{45}$, —$NR_{46}C(O)R_{47}$, —$NR_{48}C(O)NR_{49}R_{50}$, —$OC(O)NR_{51}R_{51}$, —$NC(O)R_{53}$, —$C(O)OR_{54}$;

$R_8$ and $R_9$, if present, can each be independently selected from the group consisting of H, lower alkyl, cycloalkyl, cycloalkylalkyl, heterocyclyl, heterocyloalkyl, aryl, and arylaklyl, and, if $R_8$ or $R_9$ is not H, $R_8$ or $R_9$ can be optionally further substituted with 0-2 radicals selected from the group consisting of halogen, hydroxyl, —$NR_{40}R_{41}$, —$OR_{42}$, —$SR_{43}$, —$CF_3$, —$C(O)NR_{44}R_{45}$, —$NR_{46}C(O)R_{47}$, —$NR_{48}C(O)NR_{49}R_{50}$, —$OC(O)NR_{51}R_{52}$, —$NC(O)OR_{53}$, —$C(O)OR_{54}$; additionally, in cases where a nitrogen is substituted with two $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, or $R_{25}$ groups, the two $R_{12}$, $R_{13}$, $R_{14}$, $R_{15}$, $R_{16}$, $R_{17}$, $R_{16}$, $R_{17}$, $R_{18}$, $R_{19}$, $R_{20}$, $R_{21}$, $R_{22}$, $R_{23}$, $R_{24}$ or $R_{25}$ groups can optionally be taken together to form a 5-6 membered ring; $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, or $R_{54}$, if present, can be selected from the group consisting of H, methyl, ethyl, propyl, isopropyl, and cyclopropylmethyl, and, in cases where a nitrogen is substituted with two $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$ or $R_{54}$ groups, the $R_{40}$, $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$ or $R_{54}$ groups can optionally be taken together to form a 5-6 membered ring;

$R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$ or $R_{39}$, if present, can be selected from the group consisting of H, methyl, ethyl, propyl, isopropyl, and cyclopropylmethyl, and, in cases where a nitrogen is substituted with two $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$ or $R_{39}$ groups, the $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, or $R_{39}$ groups can optionally be taken together to comprise or consist of a 5-6 membered ring;

if present, each of $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ and $R_{25}$ can be independently selected from the group consisting of H, lower alkyl, cycloalkyl, cycloalkylalkyl, heterocyclyl, heterocycloalkyl, aryl, and arylaklyl; and wherein lower alkyl is $C_1$-$C_{10}$ linear alkyl, $C_3$-$C_{10}$ branched alkyl, or $C_3$-$C_{10}$ cyclic alkyl and 0, 1, 2 or 3 carbons of a lower alkyl are replaced with a heteroatom, each heteroatom selected from the group consisting of N, O, and S;

"lower alkyl" includes $C_1$-$C_{10}$ linear alkyl and $C_3$-$C_{10}$ branched alkyl, wherein 0-3 alkyl chain carbons optionally can be replaced with one or more heteroatoms independently selected from the group consisting of N, O, and S; "cycloalkyl" includes 3-7 membered carbocyclic rings, and includes or can be selected from the group consisting of cyclopropyl, cyclobutyl, cyclopentyl, cyclohexyl and cycloheptyl; "cycloalkylalkyl" includes cycloalkyl rings attached through a divalent lower alkyl group, and includes, but is not limited to, cyclopropylmethyl, cyclopropylethyl, cyclobutylmethyl, cyclobutylethyl, cyclopentylmethyl, and cyclohexylmethyl; "heterocycyl" includes or consists of 4-7 membered aliphatic rings containing 1-2 heteroatoms selected from the group consisting of O, N, and S, and includes or consists of 4-7 membered aliphatic rings containing 1-2 heteroatoms wherein the ring can be selected from the group consisting of oxetane, tetrahydrofuran, dihydropyran, azetidine, pyrroldine, piperidine, thietane, thiolane, tetrahydrothiopyran, 1,2-dioxane and piperazine; "heterocycylalkyl" includes or consists of a 4-7 membered aliphatic ring containing 1-2 heteroatoms selected from the group consisting of O, N, and S, attached through a divalent lower alkyl group, and includes, but is not limited to, oxetanylmethyl, oxetanylethyl, tetrahydrofuranylmethyl, tetrahydrofuranylethyl, tetrahydropyranylmethyl, tetrahydropyranylethyl, dioxanylmethyl, azetidinylmethyl, azetidinylethyl, pyrrolidinylmethyl, pyrrolidinylethyl, piperidinylmethyl, piperidinylethyl, piperazinylmethyl, piperazinylethyl, thietanylmethyl, thietanylethyl, tetrahydrothiophenylmethyl, tetrahydrothiopyranylmethyl, and tetrahydrothiopyranylethyl; "aryl" includes phenyl, a 5-6 membered heteroaromatic ring containing 1-2 nitrogens, or a fused bicyclic ring wherein at least one of the rings is aromatic and the fused ring system contains 1-3 heteroatoms selected from the group consisting of O, N, and S, and includes, but is not limited to, pyridinyl, pyrimidinyl, pyrazinyl, pyridazinyl, furyl, oxazolyl, isoxazolyl, thiophenyl, thiazolyl, thiadiazolyl, benzothiophenyl, indolyl, quinolinyl, isoquinolinyl, indolinyl, isoindolinyl, tetrahydroquinolinyl, dihydrobenzofuryl, chromanyl, isochromanyl, dihydrobenzothiophenyl, thiochromanyl, and isothiochromanyl; "arylalkyl" includes an aryl ring attached through a divalent lower alkyl group, and includes, but is not limited to, benzyl, phenylethyl, pyridinylmethyl, pyridinylethyl, pyrimidylmethyl, pyridinylethyl, pyridazinylmethyl, pyrazinylmethyl, indolylmethyl, quinolinylmethyl, indolinylmethyl, isoindolinylmethyl, and thiochromanylmethyl.

2. A compound, a pharmaceutically acceptable salt thereof, or a prodrug thereof, of Formula III or Formula IV

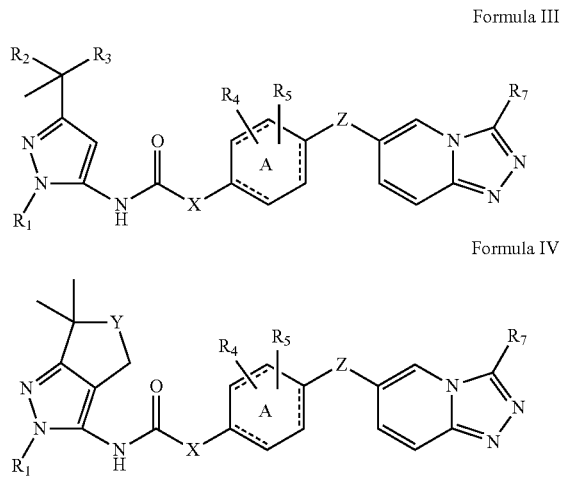

Formula III

Formula IV wherein $R_1$ is selected from the group consisting of H, lower alkyl, and aryl (phenyl and pyridinyl preferred; phenyl most preferred), wherein the aryl can be optionally substituted with 0-2 radicals each independently selected from the group consisting of halogen, hydroxyl, —$OR_{11}$, —$SR_{11}$, lower alkyl, —$CO_2R_{11}$, —$OC(O)R_{11}$, —$NR_{10}COR_{11}$, —$CONR_{11}$, —$NR_{11}C(O)NR_{11}R_{11}$, —$OC(O)NR_{11}R_{11}$, —$NR_{11}C(O)OR_{11}$, and imidazolyl; $R_2$ and $R_3$ in Formula III together can comprise a 4-6 member aliphatic carbocyclic or heterocyclic ring comprising 0, 1 or 2 heteroatoms selected from the group consisting of N, O and S; Y in Formula IV can be selected from the group consisting of $CH_2$, O and S; X can be selected from the group consisting of $CH_2$, NH (preferred), O and S; Ring A can be an aromatic or heteroaromatic ring selected from the group consisting of benzene (benzene preferred), pyridine, or pyrimidine, or a trans-substituted cyclohexane ring, wherein if ring A is aromatic or heteroaromatic, each $R_4$ and $R_5$ can be independently selected from the group consisting of H, a halogen (preferably $R_4$ is fluorine), lower alkyl, —$CF_3$, —$OR_8$ and —$SR_8$, with the proviso that $R_4$ and $R_5$ do not together comprise a ring, and wherein if ring A is cyclohexane, $R_4$ and $R_5$ are H; Z can be selected from the group consisting of $CH_2$, NH, O and S (O and S preferred); $R_7$ can be selected from the group consisting of H, amine, lower alkyl, cycloalkyl, cycloalkylalkyl, heterocyclyl, heterocyloalkyl, aryl, arylalkyl, —$OR_8$, —$SR_8$, —$NR_8R_8$, —$CONR_8R_8$, —$NR_8COR_8$, —$CO_2R_8$, —$NR_8C(O)OR_8$, —$NR_8C(O)NR_8R_8$; and, when $R_7$ is lower alkyl, cycloalkyl, cycloalkylalkyl, heterocyclyl, heterocyloalkyl, aryl, or arylalkyl, then $R_7$ optionally can be further substituted with 0-2 groups selected from the group consisting of halogen, hydroxyl, —$NR_{10}R_{10}$, —$OR_{10}$, —$SR_{10}$, —$CF_3$, —$CONR_{10}R_{10}$, —$NR_{10}C(O)R_{10}$, —$NR_{10}C(O)NR_{10}R_{10}$, —$OC(O)NR_{10}R_{10}$, —$NC(O)OR_{10}$, —$CO_2R_{10}$; $R_8$, if present, can be selected from the group consisting of H, lower alkyl, cycloalkyl, cycloalkylalkyl, heterocyclyl, heterocycloalkyl, aryl, and arylaklyl, and, if $R_8$ is not H, $R_8$ can be optionally further substituted with 0-2 radicals selected from the group consisting of halogen, hydroxyl, —$NR_{10}R_{10}$, —$OR_{10}$, —$SR_{10}$, —$CF_3$, —$CONR_{10}R_{10}$, —$NR_{10}C(O)R_{10}$, —$NR_{10}C(O)NR_{10}R_{10}$, —$OC(O)NR_{10}R_{10}$, —$NC(O)OR_{10}$, —$CO_2R_{10}$; additionally, in cases in which a nitrogen is substituted with two $R_8$ groups, the $R_8$ groups can optionally be taken together to form a 5-6 membered ring; $R_{10}$, if present, can be selected from the group consisting of H, methyl, ethyl, propyl, isopropyl, and cyclopropylmethyl, and, in cases where a nitrogen is substituted with two $R_{10}$ groups, the $R_{10}$ groups can optionally be taken together to form a 5-6 membered ring; $R_{11}$, if present, can be selected from the group consisting of H, methyl, ethyl, propyl, isopropyl, and cyclopropylmethyl, and, in cases where a nitrogen is substituted with two $R_{11}$ groups, the $R_{11}$ groups can optionally be taken together to form a 5-6 membered ring; "lower alkyl" includes C1-C10 linear alkyl and C3-C10 branched alkyl, wherein 0-3 alkyl chain carbons which optionally can be replaced with heteroatoms independently selected from the group consisting of N, O, or S "cycloalkyl" includes 3-7 membered carbocyclic rings, which can include cyclopropyl, cyclobutyl, cyclopentyl, cyclohexyl, and cycloheptyl; "cycloalkylalkyl" includes cycloalkyl rings attached through a divalent lower alkyl group, and can include, but is not limited to, cyclopropylmethyl, cyclopropylethyl, cyclobutylmethyl, cyclobutylethyl, cyclopentylmethyl and cyclohexylmethyl; "heterocycyl" includes 4-7 membered aliphatic rings containing 1-2 heteroatoms selected from the group consisting of O, N, and S, and can include or can be selected from the group consisting of oxetane, tetrahydrofuran, dihydropyran, azetidine, pyrroldine, piperidine, thietane, thiolane, tetrahydrothiopyran, 1,2-dioxane and piperazine; "heterocycylalkyl" includes a 4-7 membered aliphatic ring containing 1-2 heteroatoms selected from the group consisting of O, N, and S, attached through a divalent lower alkyl group, and can include, but is not limited to, oxetanylmethyl, oxetanylethyl, tetrahydrofuranylmethyl, tetrahydrofuranylethyl, tetrahydropyranylmethyl, tetrahydropyranylethyl, dioxanylmethyl, azetidinylmethyl, azetidinylethyl, pyrrolidinylmethyl, pyrrolidinylethyl, piperidinylmethyl, piperidinylethyl, piperazinylmethyl, piperazinylethyl, thietanylmethyl, thietanylethyl, tetrahydrothiophenylmethyl, tetrahydrothiopyranylmethyl, and tetrahydrothiopyranylethyl; "aryl" includes phenyl, a 5-6 membered heteroaromatic ring containing 1-2 nitrogens, or a fused bicyclic ring wherein at least one of the rings is aromatic and the fused ring system contains 1-3 heteroatoms selected from the group consisting of O, N, and S, and can include, but is not limited to, pyridinyl, pyrimidinyl, pyrazinyl, pyridazinyl, furyl, oxazolyl, isoxazolyl, thiophenyl, thiazolyl, thiadiazolyl, benzothiophenyl, indolyl, quinolinyl, isoquinolinyl, indolinyl, isoindolinyl, tetrahydroquinolinyl, dihydrobenzofuryl, chromanyl, isochromanyl, dihydrobenzothiophenyl, thiochromanyl, and isothiochromanyl; "arylalkyl" includes an aryl ring attached through a divalent lower alkyl group, and can include, but is not limited to, benzyl, phenylethyl, pyridinylmethyl, pyridinylethyl, pyrimidylmethyl, pyridinylethyl, pyridazinylmethyl, pyrazinylmethyl, indolylmethyl, quinolinylmethyl, indolinylmethyl, isoindolinylmethyl, and thiochromanylmethyl.

3. A compound, a pharmaceutically acceptable salt thereof, or a prodrug thereof, of Formula V:

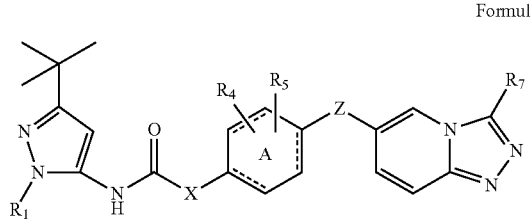

Formula V wherein $R_1$ is selected from the group consisting of H, lower alkyl, and aryl (phenyl and pyridinyl preferred, (phenyl most preferred), wherein the aryl can be optionally substituted with 0-2 radicals each independently selected from the group consisting of halogen, hydroxyl, —$OR_{11}$, —$SR_{11}$, lower alkyl, —$COR_{11}$, —$OC(O)R_{11}$, —$NR_{10}COR_{11}$, —$CONR_{11}$, —$NR_{11}C(O)NR_{11}R_{11}$, —$OC(O)NR_{11}R_{11}$, —$NR_{11}C(O)OR_{11}$, and imidazolyl; X can be selected from the group consisting of $CH_2$, NH (preferred), O and S; Ring A can be an aromatic or heteroaromatic ring selected from the group consisting of benzene (benzene preferred), pyridine, and pyrimidine, or a trans-substituted cyclohexane ring, wherein if ring A is aromatic or heteroaromatic, each $R_4$ and $R_5$ can be independently selected from the group consisting of H, a halogen (preferably $R_4$ is fluorine), lower alkyl, —$CF_3$, —$OR_8$ and —$SR_8$, with the proviso that $R_4$ and $R_5$ do not together comprise a ring, and wherein if ring A is cyclohexane, $R_4$ and $R_5$ are H; Z is selected from the group consisting of $CH_2$, NH, O and S (O and S preferred); $R_7$ is a 4-7 membered heterocyclic ring containing 1-2 ring atoms independently selected from the group consisting of N, O and S; wherein the heterocyclic ring can be optionally substituted with 0-3 substituents independently selected from the group consisting of H, halogen, hydroxyl, lower alkyl, —$OR_8$, —$SR_8$, —$NR_8R_8$, —$CONR_8R_8$, —$NR_8COR_8$, —$CO_2R_8$, —$NR_8C(O)OR_8$ and —$NR_8C(O)NR_8R_8$; and, in cases where the heterocyclic ring is substituted by lower alkyl, the alkyl optionally can be further substituted by 0-2 substituents independently selected from the group consisting of halogen, hydroxyl, —$OR_8$, —$SR_8$, —$NR_8R_8$, —$CONR_8R_8$, —$NR_8COR_8$, —$CO_2R_8$, —$NR_8C(O)OR_8$ and —$NR_8C(O)NR_8R_8$; $R_8$, if present, can be selected from the group consisting of H, lower alkyl, cycloalkyl, cycloalkylalkyl, heterocyclyl, heterocycloalkyl, aryl and arylaklyl, and if $R_8$ is not H, $R_8$ can be optionally further substituted with 0-2 radicals selected from the group consisting of halogen, hydroxyl, —$NR_{10}R_{10}$, —$OR_{10}$, —$SR_{10}$, —$CF_3$, —$CONR_{10}R_{10}$, —$NR_{10}C(O)R_{10}$, —$NR_{10}C(O)NR_{10}R_{10}$, —$OC(O)NR_{10}R_{10}$, —$NC(O)OR_{10}$ and —$CO_2R_{10}$; additionally, in cases where a nitrogen is substituted with two $R_8$ groups, the $R_8$ groups can optionally be taken together to form a 5-6 membered ring; $R_{10}$, if present, can be selected from the group consisting of H, methyl, ethyl, propyl, isopropyl and cyclopropylmethyl, and in cases where a nitrogen is substituted with two $R_{10}$ groups, the $R_{10}$ groups optionally can be taken together to form a 5-6 membered ring; $R_{11}$, if present, can be selected from the group consisting of H, methyl, ethyl, propyl, isopropyl and cyclopropylmethyl, and, in cases where a nitrogen is substituted with two $R_{11}$ groups, the $R_{11}$ groups optionally can be taken together to form a 5-6 membered ring; "lower alkyl" includes C1-C10 linear alkyl and C3-C10 branched alkyl, wherein 0-3 alkyl chain carbons optionally can be replaced with one or more heteroatoms independently selected from the group consisting of N, O, or S; "cycloalkyl" can include or can be selected from the group consisting of 3-7 membered carbocyclic rings, and includes cyclopropyl, cyclobutyl, cyclopentyl, cyclohexyl, and cycloheptyl; "cycloalkylalkyl" includes cycloalkyl rings attached through a divalent lower alkyl group, and includes, but is not limited to, cyclopropylmethyl, cyclopropylethyl, cyclobutylmethyl, cyclobutylethyl, cyclopentylmethyl, and cyclohexylmethyl; "heterocycyl" includes 4-7 membered aliphatic rings containing 1-2 heteroatoms selected from the group consisting of O, N, and S, and includes oxetane, tetrahydrofuran, dihydropyran, azetidine, pyrroldine, piperidine, thietane, thiolane, tetrahydrothiopyran, 1,2-dioxane, and piperazine; "heterocyylalkyl" includes a 4-7 membered aliphatic ring containing 1-2 heteroatoms selected from the group consisting of O, N, and S, attached through a divalent lower alkyl group, and includes, but is not limited to, oxetanylmethyl, oxetanylethyl, tetrahydrofuranylmethyl, tetrahydrofuranylethyl, tetrahydropyranylmethyl, tetrahydropyranylethyl, dioxanylmethyl, azetidinylmethyl, azetidinylethyl, pyrrolidinylmethyl, pyrrolidinylethyl, piperidinylmethyl, piperidinylethyl, piperazinylmethyl, piperazinylethyl, thietanylmethyl, thietanylethyl, tetrahydrothiophenylmethyl, tetrahydrothiopyranylmethyl, and tetrahydrothiopyranylethyl; "aryl" includes phenyl, a 5-6 membered heteroaromatic ring containing 1-2 nitrogens, or a fused bicyclic ring wherein at least one of the rings is aromatic and the fused ring system contains 1-3 heteroatoms selected from the group consisting of O, N, and S, and includes, but is not limited to, pyridinyl, pyrimidinyl, pyrazinyl, pyridazinyl, furyl, oxazolyl, isoxazolyl, thiophenyl, thiazolyl, thiadiazolyl, benzothiophenyl, indolyl, quinolinyl, isoquinolinyl, indolinyl, isoindolinyl, tetrahydroquinolinyl, dihydrobenzofuryl, chromanyl, isochromanyl, dihydrobenzothiophenyl, thiochromanyl, and isothiochromanyl; "arylalkyl" includes an aryl ring attached through a divalent lower alkyl group, and includes, but is not limited to, benzyl, phenylethyl, pyridinylmethyl, pyridinylethyl, pyrimidylmethyl, pyridinylethyl, pyridazinylmethyl, pyrazinylmethyl, indolylmethyl, quinolinylmethyl, indolinylmethyl, isoindolinylmethyl, and thiochromanylmethyl.

4. A compound, a pharmaceutically acceptable salt thereof, or a prodrug thereof, of Formula VI or Formula VII

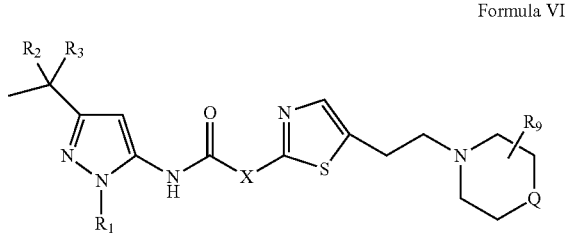

Formula VI

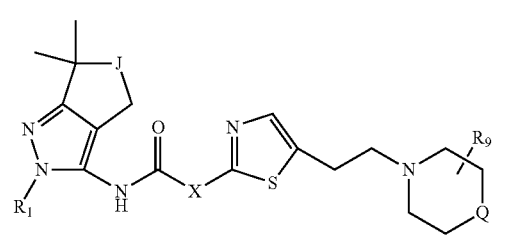

Formula VII wherein $R_1$ is selected from the group consisting of H, lower alkyl, and aryl (phenyl and pyridinyl preferred; phenyl most preferred);

wherein the aryl is optionally substituted with 0-2 radicals each independently selected from the group consisting of halogen, hydroxyl, —OR$_{18}$, —SR$_{19}$, lower alkyl, —C(O)OR$_{20}$, —C(O)R$_{21}$, —NR$_{22}$C(O)R$_{23}$, —C(O)NR$_{24}$, —NR$_{25}$C(O)NR$_{26}$R$_{27}$, —OC(O)NR$_{28}$R$_{29}$, —NR$_{30}$C(O)OR$_{31}$, and imidazolyl;

R$_2$ and R$_3$ in Formula VI are each independently selected from the group consisting of H or lower alkyl, or together comprise a 4-6 member aliphatic carbocyclic or heterocyclic ring comprising 0, 1 or 2 heteroatoms, each heteroatom selected from the group consisting of N, O and S:

J in Formula VII is selected from the group consisting of CH$_2$, O and S;

Q is selected from the group consisting of O and S (O is preferred);

X is selected from the group consisting of CH$_2$ and NH;

R$_9$ is selected from the group consisting of H, lower alkyl, cycloalkyl, cycloalkylalkyl, heterocycyl, heterocycylalkyl, aryl, arylalkyl, —NHC(O)R$_8$, —NHC(O)NR$_{10}$R$_{11}$, CH$_2$NHC(O)R$_{12}$, —CH$_2$NHC(O)NR$_{11}$R$_{14}$, —C(O)NR$_{15}$R$_{16}$, and —CO(O)OR$_{17}$, and, when R$_9$ is lower alkyl, cycloalkyl, cycloalkylalkyl, heterocycyl, heterocycylalkyl, aryl, and arylalkyl, R$_9$ can optionally be further substituted with 0-3 groups selected from the group consisting of halogen, hydroxyl, amine, lower alkyl, cycloalkyl, cycloalkylalkyl, heterocyclyl, heterocyloalkyl, aryl, arylalkyl, —OR$_{32}$, —SR$_{33}$—NR$_{34}$R$_{35}$, —C(O)NR$_{36}$R$_{37}$, —NR$_{38}$C(O)R$_{39}$, —C(O)OR$_{40}$, —NR$_{41}$C(O)OR$_{42}$, and —NR$_{43}$C(O)NR$_{44}$R$_{45}$; and wherein lower alkyl is C$_1$-C$_{10}$ linear alkyl, C$_3$-C$_{10}$ branched alkyl, or C$_3$-C$_{10}$ cyclic alkyl and 0, 1, 2 or 3 carbons of a lower alkyl are replaced with a heteroatom, each heteroatom selected from the group consisting of N, O, and S.

each of R$_8$, R$_{10}$, R$_{11}$, R$_{12}$, R$_{13}$, R$_{14}$, R$_{15}$, R$_{16}$ or R$_{17}$ can be selected from the group consisting of H, lower alkyl, cycloalkyl, cycloalkylalkyl, heterocyclyl, heterocycloalkyl, aryl, and arylaklyl; and, if R$_{32}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$ or R$_{45}$ is not H, R$_{32}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$ or R$_{45}$ can be optionally further substituted with 0-2 groups selected from the group consisting of halogen, hydroxyl, —NR$_{46}$R$_{47}$, —OR$_{48}$, —SR$_{49}$, —CF$_3$, —CONR$_{50}$R$_{51}$, —NR$_{52}$C(O)R$_{53}$, —NR$_{54}$C(O)NR$_{55}$R$_{56}$, —OC(O)NR$_{57}$R$_{58}$, —NC(O)OR$_{59}$, —C(O)OR$_{60}$; additionally, in cases where a nitrogen is substituted with two R$_{32}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$ or R$_{45}$ groups, the R$_{12}$, R$_{32}$, R$_{33}$, R$_{34}$, R$_{35}$, R$_{36}$, R$_{37}$, R$_{38}$, R$_{39}$, R$_{40}$, R$_{41}$, R$_{42}$, R$_{43}$, R$_{44}$ or R$_{45}$ groups can optionally be taken together to form a 5-6 membered ring;

R$_{46}$, R$_{47}$, R$_{48}$, R$_{49}$, R$_{50}$, R$_{51}$, R$_{52}$, R$_{53}$, R$_{54}$, R$_{55}$, R$_{56}$, R$_{57}$, R$_{58}$, R$_{59}$ or R$_{60}$, if present, can be selected from the group consisting of H, methyl, ethyl, propyl, isopropyl, and cyclopropylmethyl, and, in cases where a nitrogen is substituted with two R$_{46}$, R$_{47}$, R$_{48}$, R$_{49}$, R$_{50}$, R$_{51}$, R$_{52}$, R$_{53}$, R$_{54}$, R$_{55}$, R$_{56}$, R$_{57}$, R$_{58}$, R$_{59}$ or R$_{60}$ groups, the R$_{46}$, R$_{47}$, R$_{48}$, R$_{49}$, R$_{50}$, R$_{51}$, R$_{52}$, R$_{53}$, R$_{54}$, R$_{55}$, R$_{56}$, R$_{57}$, R$_{58}$, R$_{59}$ or R$_{60}$ groups can optionally be taken together to form a 5-6 membered ring;

R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$ or R$_{31}$, if present, can be selected from the group consisting of H, methyl, ethyl, propyl, isopropyl, and cyclopropylmethyl, and, in cases where a nitrogen is substituted with two R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$ or R$_{31}$ groups, the R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$ or R$_{31}$ groups can optionally be taken together to comprise or consist of a 5-6 membered ring;

"lower alkyl" includes C1-C10 linear alkyl and C3-C10 branched alkyl, wherein 0-3 alkyl chain carbons may be optionally replaced with heteroatoms separately selected from the group consisting of N, O, or S; "cycloalkyl" includes 3-7 membered carbocyclic rings, and includes cyclopropyl, cyclobutyl, cyclopentyl, cyclohexyl, and cycloheptyl;

"cycloalkylalkyl" includes cycloalkyl rings attached through a divalent lower alkyl group, and includes, but is not limited to, cyclopropylmethyl, cyclopropylethyl, cyclobutylmethyl, cyclobutylethyl, cyclopentylmethyl, and cyclohexylmethyl; "heterocycyl" includes 4-7 membered aliphatic rings containing 1-2 heteroatoms selected from the group consisting of O, N, and S, and includes oxetane, tetrahydrofuran, dihydropyran, azetidine, pyrroldine, piperidine, thietane, thiolane, tetrahydrothiopyran, 1,2-dioxane, and piperazine; "heterocycylalkyl" includes a 4-7 membered aliphatic ring containing 1-2 heteroatoms selected from the group consisting of O, N, and S, attached through a divalent lower alkyl group, and includes, but is not limited to, oxetanylmethyl, oxetanylethyl, tetrahydrofuranylmethyl, tetrahydrofuranylethyl, tetrahydropyranylmethyl, tetrahydropyranylethyl, dioxanylmethyl, azetidinylmethyl, azetidinylethyl, pyrrolidinylmethyl, pyrrolidinylethyl, piperidinylmethyl, piperidinylethyl, piperazinylmethyl, piperazinylethyl, thietanylmethyl, thietanylethyl, tetrahydrothiophenylmethyl, tetrahydrothiopyranylmethyl, and tetrahydrothiopyranylethyl; "aryl" includes phenyl, a 5-6 membered heteroaromatic ring containing 1-2 nitrogens, or a fused bicyclic ring wherein at least one of the rings is aromatic and the fused ring system contains 1-3 heteroatoms selected from the group consisting of O, N, and S, and includes, but is not limited to, pyridinyl, pyrimidinyl, pyrazinyl, pyridazinyl, furyl, oxazolyl, isoxazolyl, thiophenyl, thiazolyl, thiadiazolyl, benzothiophenyl, indolyl, quinolinyl, isoquinolinyl, indolinyl, isoindolinyl, tetrahydroquinolinyl, dihydrobenzofuryl, chromanyl, isochromanyl, dihydrobenzothiophenyl, thiochromanyl, and isothiochromanyl; "arylalkyl" includes an aryl ring attached through a divalent lower alkyl group, and includes, but is not limited to, benzyl, phenylethyl, pyridinylmethyl, pyridinylethyl, pyrimidylmethyl, pyridinylethyl, pyridazinylmethyl, pyrazinylmethyl, indolylmethyl, quinolinylmethyl, indolinylmethyl, isoindolinylmethyl, and thiochromanylmethyl.

5. A compound (compound 89)

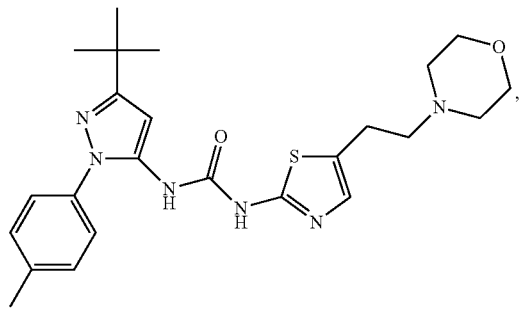

a pharmaceutically acceptable salt thereof, or a prodrug thereof.

6. A compound (compound 61)

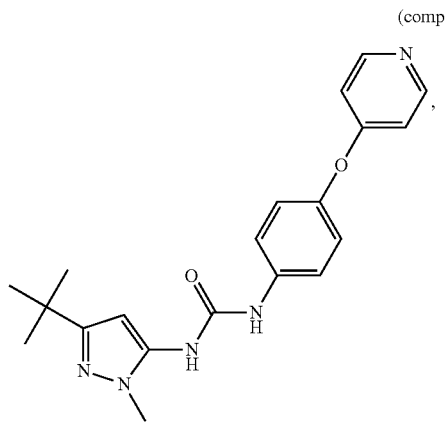

a pharmaceutically acceptable salt thereof, or a prodrug thereof.

7. A compound (compound 179)

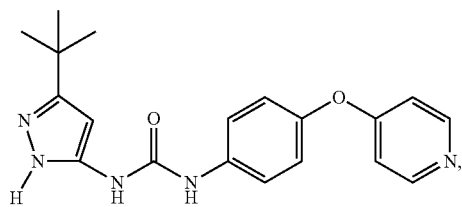

a pharmaceutically acceptable salt thereof, or a prodrug thereof.

8. A compound (compound 62)

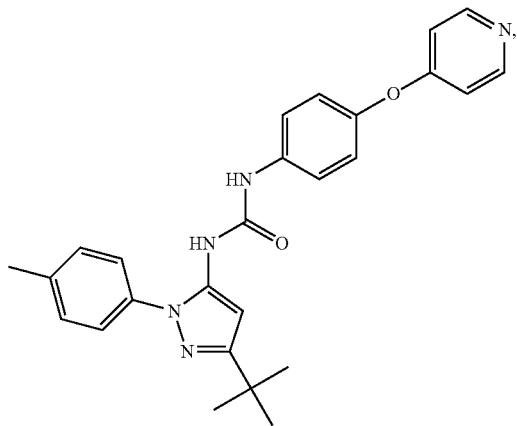

a pharmaceutically acceptable salt thereof, or a prodrug thereof.

9. A compound (compound 193)

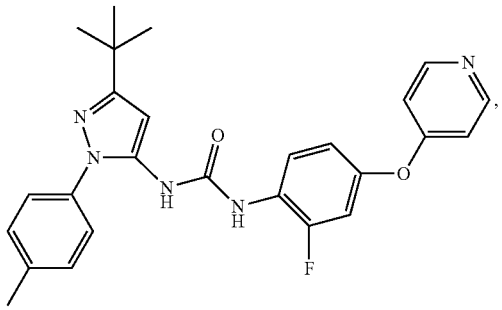

a pharmaceutically acceptable salt thereof, or a prodrug thereof.

10. A compound (compound 194)

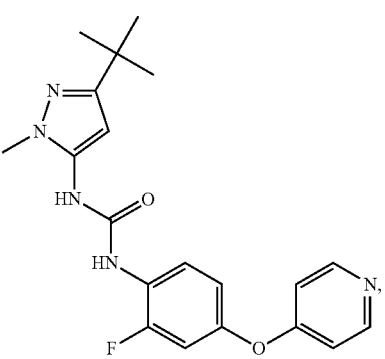

a pharmaceutically acceptable salt thereof, or a prodrug thereof.

11. A compound (compound 192)

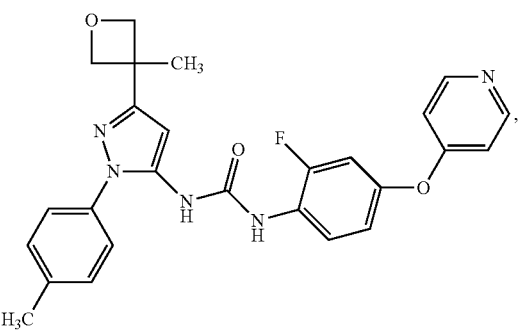

a pharmaceutically acceptable salt thereof, or a prodrug thereof.

12. A compound

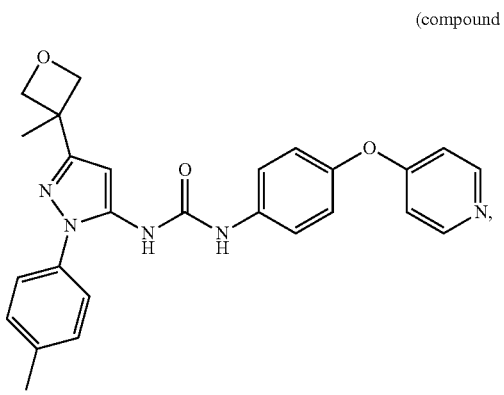
(compound 186)

a pharmaceutically acceptable salt thereof, or a prodrug thereof.

13. A compound

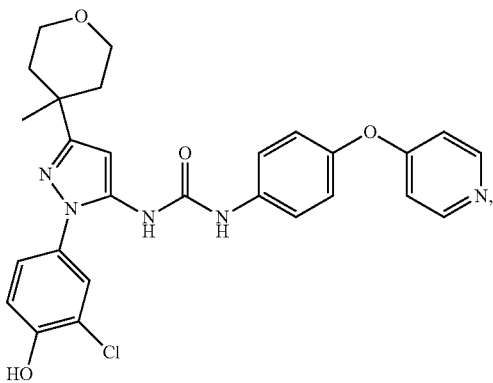
(compound 226)

a pharmaceutically acceptable salt thereof, or a prodrug thereof.

14. A compound

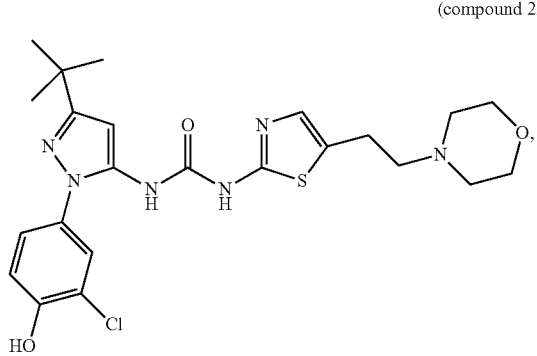
(compound 227)

a pharmaceutically acceptable salt thereof, or a prodrug thereof.

15. A compound

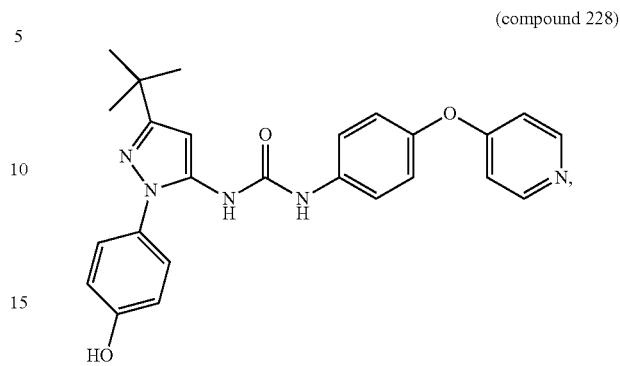
(compound 228)

a pharmaceutically acceptable salt thereof, or a prodrug thereof.

16. A compound

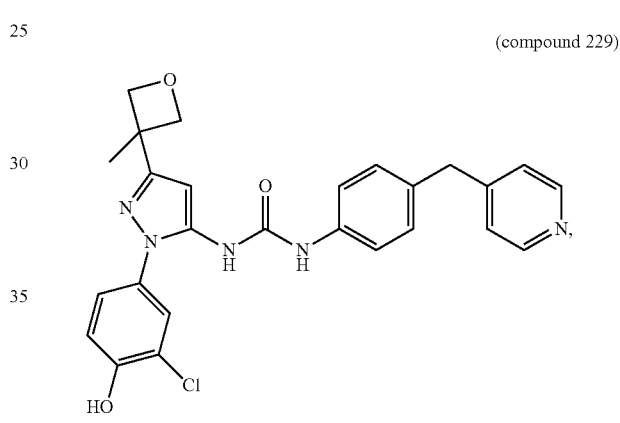
(compound 229)

a pharmaceutically acceptable salt thereof, or a prodrug thereof.

17. A compound

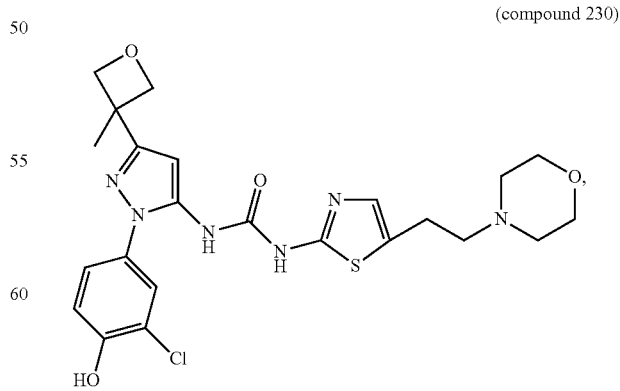
(compound 230)

a pharmaceutically acceptable salt thereof, or a prodrug thereof.

18. A compound

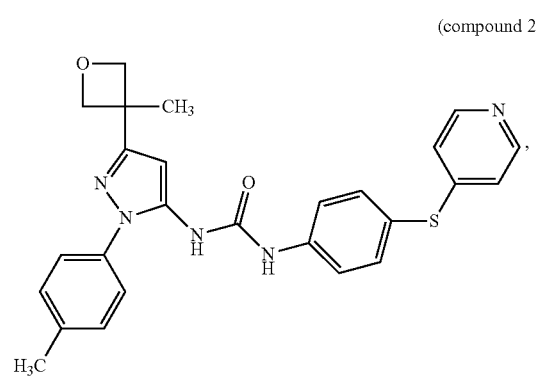
(compound 204)

a pharmaceutically acceptable salt thereof, or a prodrug thereof.

19. A compound

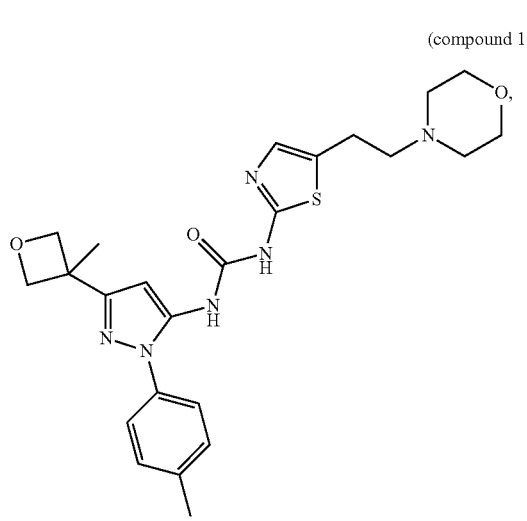
(compound 187)

a pharmaceutically acceptable salt thereof, or a prodrug thereof.

20. A compound

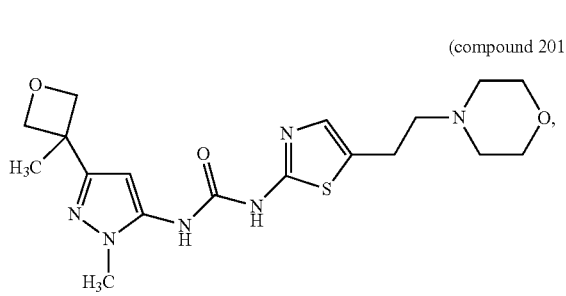
(compound 201)

a pharmaceutically acceptable salt thereof, or a prodrug thereof.

21. A compound

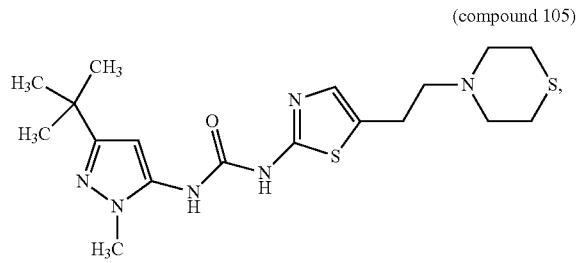 [SMILES: Cn1nc(C(C)(C)C)cc1NC(=O)Nc1ncc(CCN2CCSCC2)s1]
(compound 105)

a pharmaceutically acceptable salt thereof, or a prodrug thereof.

22. A compound

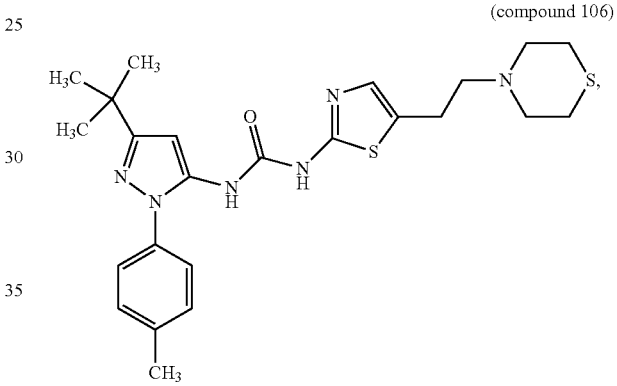
(compound 106)

a pharmaceutically acceptable salt thereof, or a prodrug thereof.

23. A compound

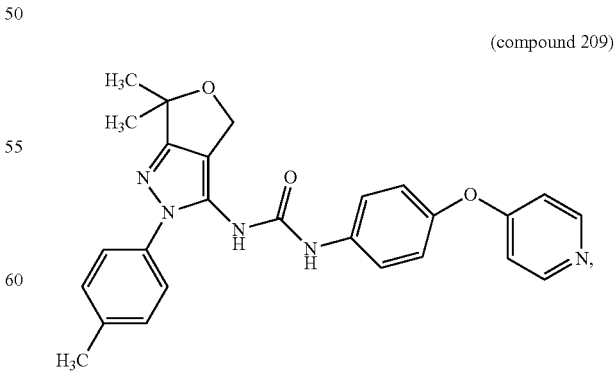
(compound 209)

a pharmaceutically acceptable sat thereof or a prodrug thereof.

24. A compound

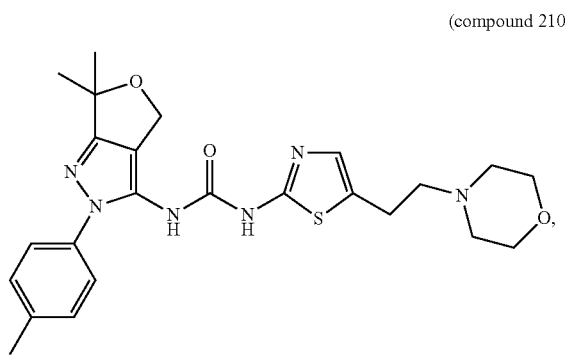 [SMILES: Cc1ccc(-n2nc3c(c2NC(=O)Nc2ncc(CCN4CCOCC4)s2)COC3(C)C)cc1]
(compound 210)

or a pharmaceutically acceptable salt thereof.

25. A compound

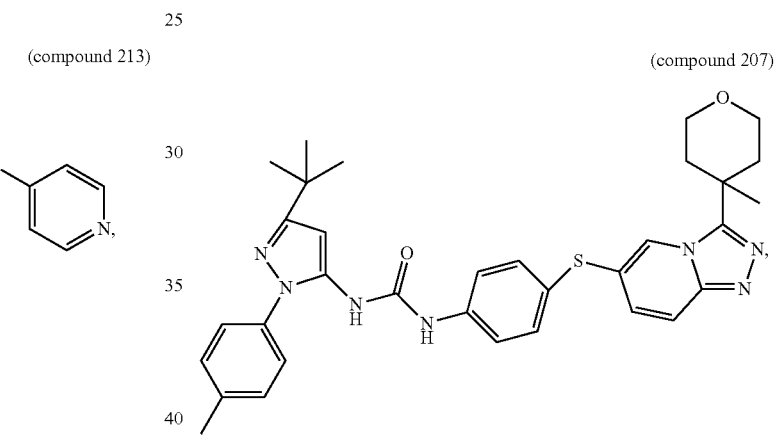
(compound 213)

pharmaceutically acceptable salt thereof, or a prodrug thereof.

26. A compound

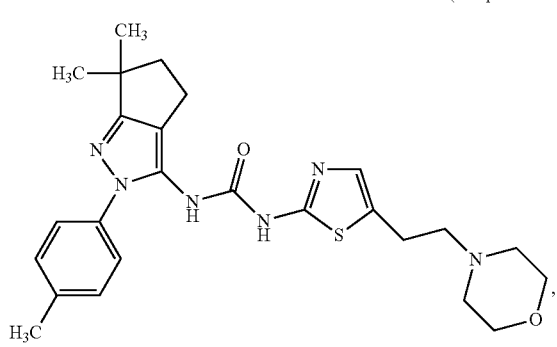
(compound 214)

a pharmaceutically acceptable salt thereof, or a prodrug thereof.

27. A compound

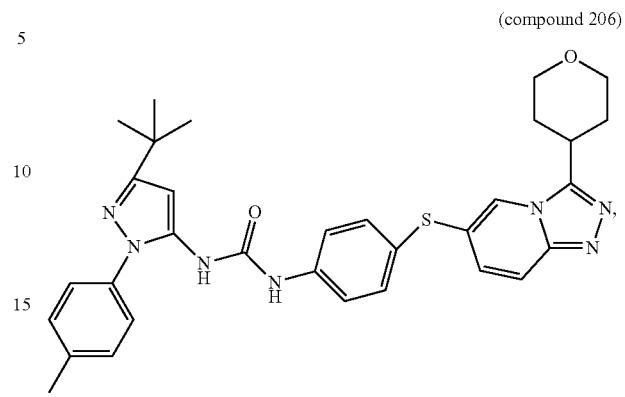
(compound 206)

a pharmaceutically acceptable salt thereof, or a prodrug thereof.

28. A compound

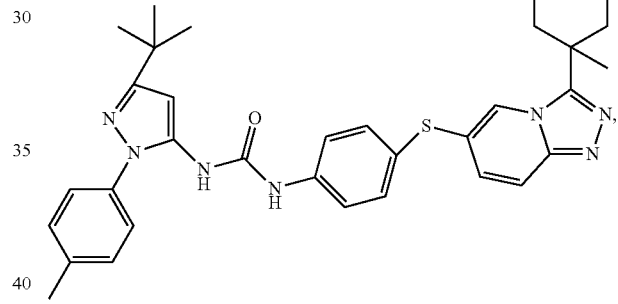
(compound 207)

pharmaceutically acceptable salt thereof, or a prodrug thereof.

29. A compound

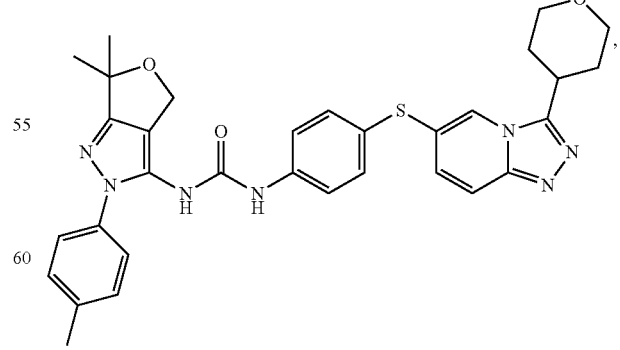
(compound 211)

a pharmaceutically acceptable salt thereof, or a prodrug thereof.

30. A compound

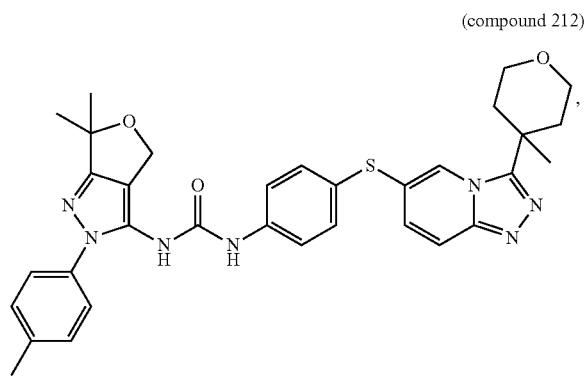 [SMILES: Cc1ccc(-n2nc3c(c2NC(=O)Nc2ccc(Sc4ccc5nnc(C6(C)CCOCC6)n5c4)cc2)COC3(C)C)cc1]

(compound 212)

a pharmaceutically acceptable salt thereof, or a prodrug thereof.

31. A compound

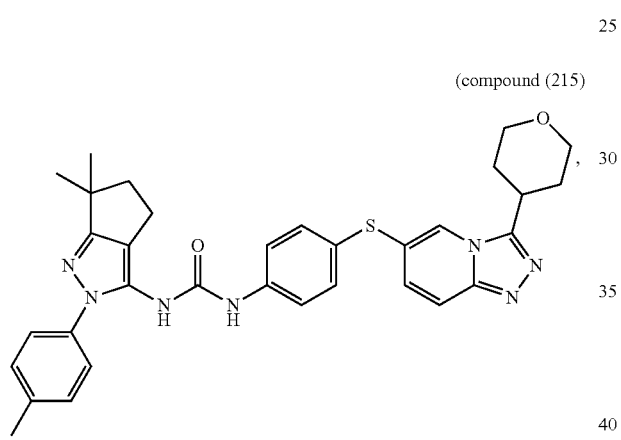

(compound (215))

a pharmaceutically acceptable salt thereof, or a prodrug thereof.

32. A compound

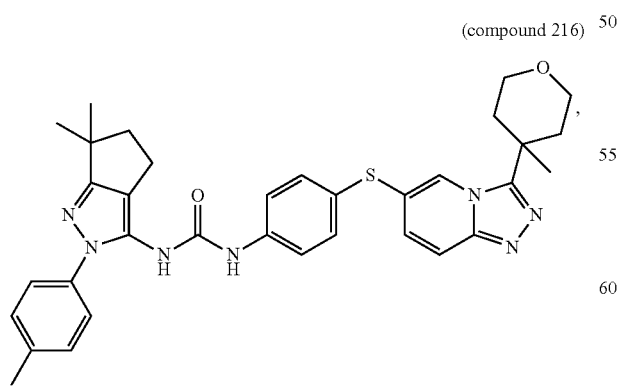

(compound 216)

a pharmaceutically acceptable salt thereof, or a prodrug thereof.

33. A compound

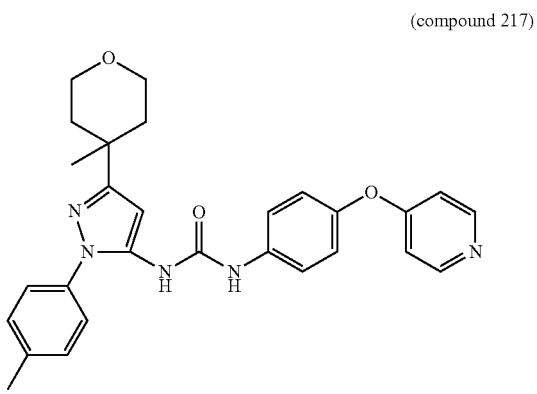 [SMILES: Cc1ccc(-n2nc(C3(C)CCOCC3)cc2NC(=O)Nc2ccc(Oc3ccncc3)cc2)cc1]

(compound 217)

or a pharmaceutically acceptable salt thereof.

34. A compound

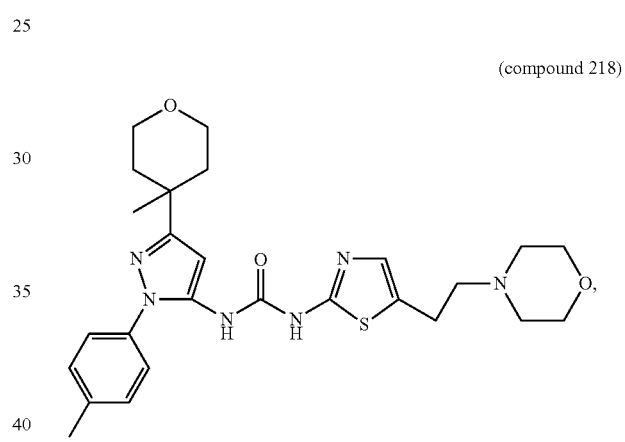

(compound 218)

a pharmaceutically acceptable salt thereof, or a prodrug thereof.

35. A compound

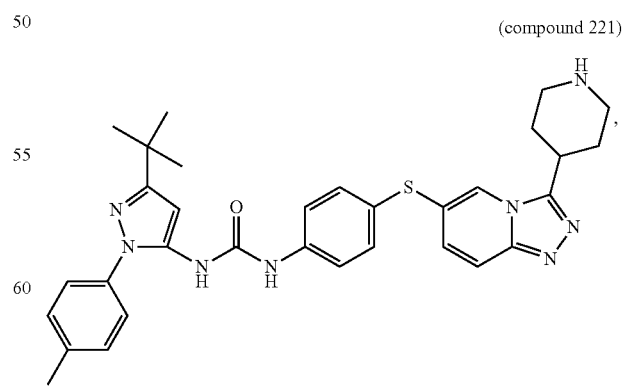

(compound 221)

a pharmaceutically acceptable salt thereof, or a prodrug thereof.

36. A compound (compound 222)

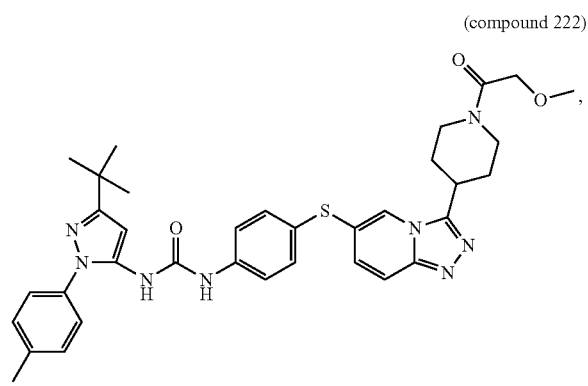 [SMILES: COCC(=O)N1CCC(c2nnc3ccc(Sc4ccc(NC(=O)Nc5cc(C(C)(C)C)nn5-c5ccc(C)cc5)cc4)cn23)CC1]

a pharmaceutically acceptable salt thereof, or a prodrug thereof.

37. A compound (compound 223)

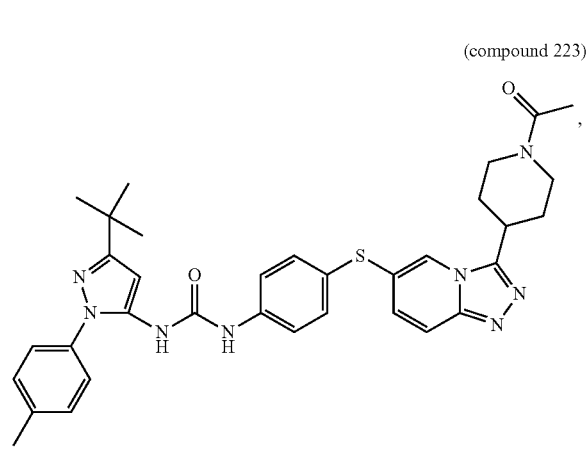 [SMILES: CC(=O)N1CCC(c2nnc3ccc(Sc4ccc(NC(=O)Nc5cc(C(C)(C)C)nn5-c5ccc(C)cc5)cc4)cn23)CC1]

a pharmaceutically acceptable salt thereof, or a prodrug thereof.

38. A compound (compound 224)

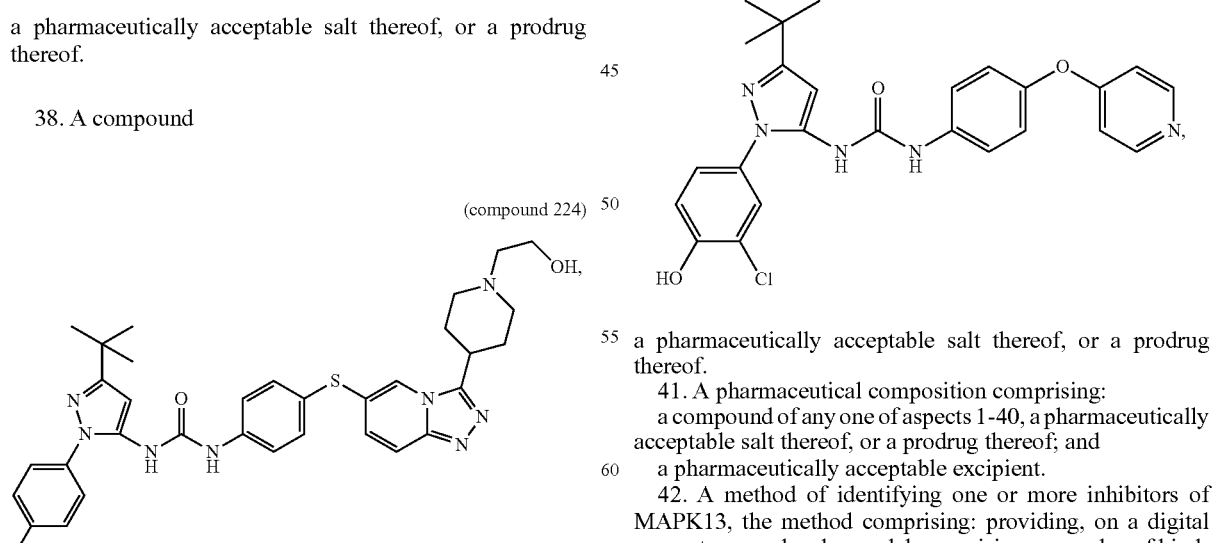

a pharmaceutically acceptable salt thereof, or a prodrug thereof.

39. A compound (compound 225)

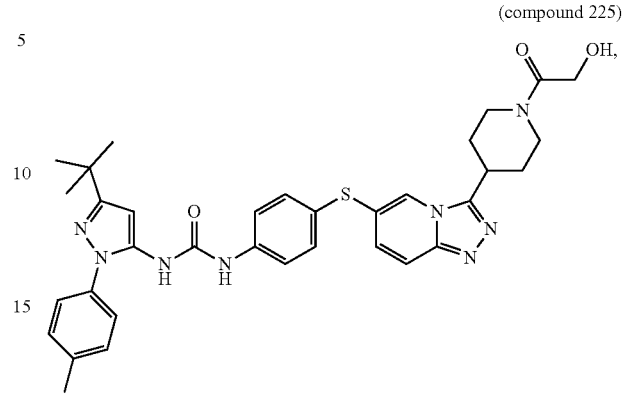

a pharmaceutically acceptable salt thereof, or a prodrug thereof.

40. A compound

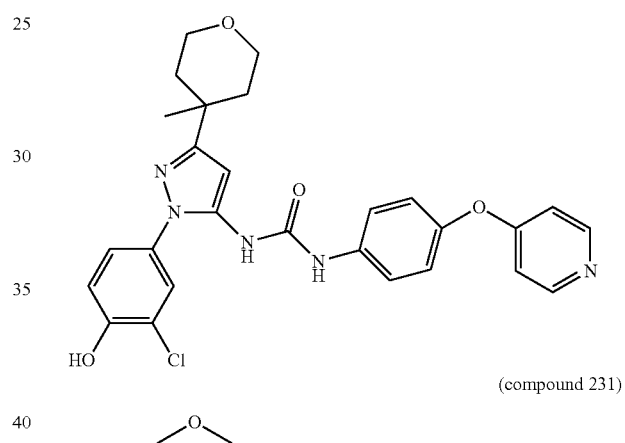

a pharmaceutically acceptable salt thereof, or a prodrug thereof.

41. A pharmaceutical composition comprising:
a compound of any one of aspects 1-40, a pharmaceutically acceptable salt thereof, or a prodrug thereof; and
a pharmaceutically acceptable excipient.

42. A method of identifying one or more inhibitors of MAPK13, the method comprising: providing, on a digital computer, a molecular model comprising a complex of binding pocket domains of MAPK13; docking a chemical database to the molecular model; scoring the compounds comprised by the database; and identifying one or more high-scoring compounds.

43. A method of inhibiting MAPK13 activity, the method comprising of blocking the enzyme's function by contacting MAPK13 with a compound of Formula I-VII or a pharmaceutically acceptable salt thereof.

44. A cell line comprising NCI-H292 cells, a plasmid encoding tTA with pTRE-tight-hCLCA1 wherein the cell expresses hCLCA1 after doxycycline withdrawal.

45. A method of treating an inflammatory airway disease in a subject in need thereof, the method comprising of administering to the subject a compound, a pharmaceutically acceptable salt thereof, or a prodrug thereof, wherein the compound is selected from the group consisting of Formulae I-VII in a therapeutically effective amount.

46. A method of treating an inflammatory airway disease in a subject in need thereof, the method comprising of administering to the subject a compound, a pharmaceutically acceptable salt thereof, or a prodrug thereof, wherein the compound is selected from the group consisting of

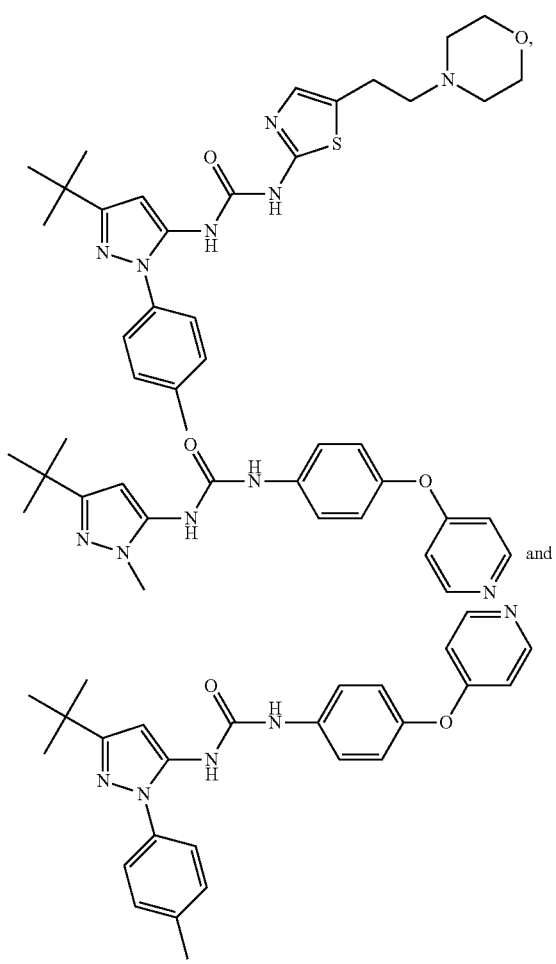

in a therapeutically effective amount.

47. A method of delivering a MAPK13 blocking drug directly to the region of the lung affected by the disease, comprising administering the drug by an inhalation route.

48. A method of treating an inflammatory airway disease in a subject in need thereof, the method comprising administering a pharmaceutical composition comprising a compound of Formula I-VII directly to the lung in a therapeutically effective amount by utilizing an inhalation route of administration.

49. A method of treating an inflammatory airway disease in a subject in need thereof, the method comprising of administering a drug represented by Formula I-VII by an oral route of administration in a therapeutically effective amount.

BRIEF DESCRIPTION OF THE DRAWINGS

FIG. 1A-H illustrates IL-13-induced mucus production depends on hCLCA1 in human epithelial cells.

FIG. 3A-F illustrates the effect of MAPK inhibition or knockdown on hCLCA1-driven mucus production in lung epithelial cells.

FIG. 4A-E illustrates the effect of MAPK inhibition or knockdown on IL-13 mucus production in human airway epithelial cells.

FIG. 5A-D illustrates evidence of an IL-13 to hCLCA1 to MAPK13 to mucin gene signaling pathway in COPD.

FIG. 6A-H illustrates discovery and validation of a potent MAPK13 inhibitor.

FIG. 12A-B illustrates superposition of MAPK13 inactivated apo structure with MAPK14 and a previously deposited MAPK13 structure.

DETAILED DESCRIPTION

Figure 2A:
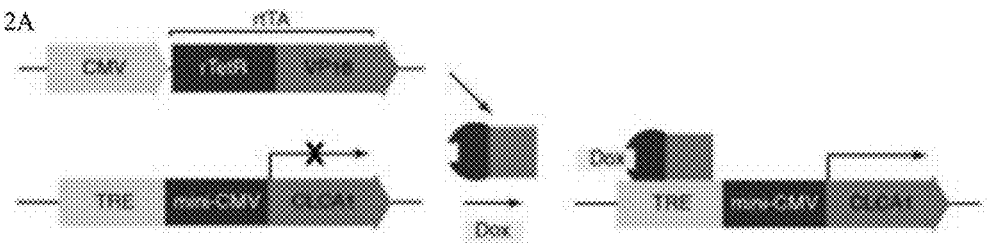
FIG. 2A-F illustrates the effect of hCLCA1 expression on mucus production in lung epithelial cells.

In the present teachings, a signal transduction basis for mucous cell metaplasia is shown. The present inventors have found that human CLCA1 can activate MAPK3 (also known as p38δ-MAPK), which in turn can convey a signal to stimulate mucin gene expression. The same signaling pathway can be active in humans with COPD.

In the present teachings, a signaling pathway for IL-13 driven mucus production that proceeds via CLCA1 and MAPK13 activation to MUC5AC gene expression is disclosed. The inventors have identified a signaling pathway that proceeds from hCLCA1 to MAPK13 to MUC5AC mucin gene expression. Furthermore, to interrupt this pathway, the inventors have designed and synthesized small molecular weight compounds to inhibit MAPK13 activation. Interruption of this pathway can interfere with mucus overproduction and thereby provide treatment methods for diseases and conditions that involve excess mucus production.

In various embodiments, this pathway can be critical for the development of mucus production and the manifestation of mucous cell metaplasia in airway diseases such as COPD. The present teachings assign a new function for MAPK13 in controlling mucus production and validate MAPK13 blockade as a therapeutic strategy to correct overproduction of mucus, for example in inflammatory disease.

Without being limited by theory, in the DFG-out binding mode (See Example 3, infra), the kinase is believed to undergo a large conformational change in the activation loop which evacuates a deep pocket for inhibitor binding and can result in locking the kinase into an inactive conformation that can be incompatible with phosphate transfer, and therefore demonstrates slow-off binding kinetics. In various embodiments of the present teachings, compounds 61 and 117 can demonstrate the DFG-out and DFG-in binding modes, respectively. The DFG-out binding mode displayed for compound 61 corresponds to a 40-fold increase in complex half-life (FIG. 6E) which can also be reflected in a greater potency in the cellular assay (infra). Without being limited by theory, both compound 61 and 117 display similar contacts with MAPK13 and can form hydrogen bonds with the same residues (FIG. 6D). In addition, without being limited by theory, molecular modeling indicates that the MAPK13 Phe169 pocket can accommodate the moiety of compound 117. Without being limited by theory, the structural reason for 117 displaying DFG-in binding appears to be steric fit. Achieving slow-off binding kinetics (i.e. DFG-out binding mode) can ensure that drug administered directly to the lungs can remain on-target for a long duration, providing a sustained effect and thus minimizing the need for repeated dosing, while also allowing for a smaller dose.

In various embodiments, a pharmaceutically acceptable salt of the present teachings can include acid addition salts, base addition salts, and the salts of quaternary amines and pyridiniums. An acid addition salts can be formed from a compound of the present teachings and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums can include, for example, chloride, bromide, iodide, sulfate, phosphate, methansulfonate, citrate, acetate, malonate, fumarate, sulfamate, or tartrate. A base addition salts can include but are not limited to salts such as sodium, potassium, calcium, lithium, magnesium, ammonium and alkylammonium. Also, basic nitrogen-containing groups can be quaternised with such agents as lower alkyl halides, such as methyl, ethyl, propyl, and butyl chlorides, bromides and iodides; dialkyl sulfates like dimethyl and diethyl sulfate; and others. A salt of the present teachings can be made by methods well-known to skilled artisans for example by treating the compound with an appropriate acid or base in the presence of a suitable solvent.

In some embodiments, a compound of the present teachings can be in crystalline form and or as a solvate (e.g. hydrate). The term "solvate" as used herein refers to a complex of variable stoichiometry formed by a solute (such as a compound of the present teachings) and a solvent that does not interfere with the biological activity of the solute. Solvents can be, for example, water, ethanol or acetic acid. Methods of solvation are generally known within the art.

In various embodiments, a compound of the present teachings can be used in the treatment of skin cancer and sepsis.

The term "prodrug" is used in its broadest sense and encompasses compounds that are convened in vivo to the compounds of the present teachings. Such prodrug compounds include, for example, compounds comprising an ester in place of a free hydroxy group, or an N-oxide in place of ring Nitrogen. Examples of ester prodrugs include alkyl esters, phosphate esters and esters formed from amino acids, such as valine.

The term "pharmaceutically acceptable ester" includes biologically acceptable esters of compound of the invention such as sulphonic, phosphonic and carboxylic acid derivatives.

Any compound that is a prodrug of a compound disclosed herein is within the scope and spirit of the invention.

The present teachings include pharmaceutical compositions. In some embodiments, a pharmaceutical composition can comprise any of the compounds, pharmaceutically acceptable salts thereof or prodrugs thereof described herein, and a pharmaceutically acceptable excipient. An excipient of the present teachings can be any excipient known to skilled artisans, such as, without limitation, an excipient described in Rowe, R. C., et al., Handbook of Pharmaceutical Excipients, Fourth Edition, Pharmaceutical Press, 2003. Pharmaceutical compositions of the present teachings can be prepared by procedures known in the art. For example, the compounds can be formulated into tablets, capsules, powders, suspensions, solutions for parenteral administration including intravenous, intramuscular, and subcutaneous administration, and into solutions for application onto patches for transdermal application with common and conventional carriers, binders, diluents, and excipients. In various configurations, powder particle size can be within the range of 0.1-50 microns. In various configurations, powder particle size can be 1-5 microns. In various configurations, a powder composition can be administered directly to the lung. In various configurations, a composition can be administered using a dry powder inhaler (DPI) apparatus.

Inert pharmaceutically acceptable carriers useful to form pharmaceutical formulations in accordance with the present teachings include starch, mannitol, calcium sulfate, dicalcium phosphate, magnesium stearate, silicic derivatives, and/or sugars such as sucrose, lactose, and glucose. Binding agents can include carboxymethyl cellulose and other cellulose derivatives, gelatin, natural and synthetic gums including alginates such as sodium alginate, polyethylene glycol, waxes and the like. Diluents useful in the present teachings can include a suitable oil, saline, sugar solutions such as aqueous dextrose or aqueous glucose, and glycols such as polyethylene or polypropylene glycol. Other excipients can include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents can also be added to a pharmaceutical formulation.

TABLE 1

Compounds of the present teachings.

| Analog # | Compound name | MAPK13 Inhibition Biochemical Potency | Analytical LC-MS (retention time) |
|---|---|---|---|
| 89 | 1-[5-tert-butyl-2-(p-tolyl)pyrazol-3-yl]-3-[5-(2-morpholinoethyl)thiazol-2-yl]urea | +++ | 3.70 min |
| 186 | 1-[5-(3-methyloxetan-3-yl)-2-(p-tolyl)pyrazol-3-yl]-3-[4-(4-pyridyloxy)phenyl]urea | +++ | 3.34 min |
| 187 | 1-[5-(3-methyloxetan-3-yl)-2-(p-tolyl)pyrazol-3-yl]-3-[5-(2-morpholinoethyl)thiazol-2-yl]urea | ++ | 3.14 min |
| 192 | 1-[2-fluoro-4-(4-pyridyloxy)phenyl]-3-[5-(3-methyloxetan-3-yl)-2-(p-tolyl)pyrazol-3-yl]urea | +++ | 3.40 min |
| 204 | 1-[5-(3-methyloxetan-3-yl)-2-(p-tolyl)pyrazol-3-yl]-3-[4-(4-pyridylsulfanyl)phenyl]urea | ++ | 3.50 min |

TABLE 1-continued

Compounds of the present teachings.

| Analog # | Compound name | MAPK13 Inhibition Biochemical Potency | Analytical LC-MS (retention time) |
|---|---|---|---|
| 209 | 1-[6,6-dimethyl-2-(p-tolyl)-4H-furo[3,4-c]pyrazol-3-yl]-3-[4-(4-pyridyloxy)phenyl]urea | + | 3.40 min |
| 213 | 1-[6,6-dimethyl-2-(p-tolyl)-4,5-dihydrocyclopenta[c]pyrazol-3-yl]-3-[4-(4-pyridyloxy)phenyl]urea | ++ | 3.68 min |
| 214 | 1-[6,6-dimethyl-2-(p-tolyl)-4,5-dihydrocyclopenta[c]pyrazol-3-yl-3-[5-(2-morpholinoethyl)thiazol-2-yl]urea | + | 3.49 min |
| 229 | 1-[2-(3-chloro-4-hydroxy-phenyl)-5-(3-methyloxetan-3-yl)pyrazol-3-yl]-3-[4-(4-pyridyloxy)phenyl]urea | ++ | 3.17 min |
| 234 | 1-[2-(3-chloro-4-hydroxy-phenyl)-6,6-dimethyl-4,5-dihydrocyclopenta[c]pyrazol-3-yl]-3-[2-fluoro-4-(4-pyridyloxy)phenyl]urea | | 3.61 min |
| 235 | 1-[2-fluoro-4-(4-pyridyloxy)phenyl]-3-[2-(4-hydroxyphenyl)-6,6-dimethyl-4,5-dihydrocyclopenta[c]pyrazol-3-yl]urea | | 3.36 min |
| 236 | N-[5-tert-butyl-2-(4-hydroxyphenyl)pyrazol-3-yl]-2-[4-(4-pyridyloxy)phenyl]acetamide | | 4.86 min |
| 240 | N-[5-tert-butyl-2-(p-tolyl)pyrazol-3-yl]-2-[4-(4-pyridyloxy)phenyl]acetamide | | |
| 241 | N-[5-tert-butyl-2-(p-tolyl)pyrazol-3-yl]-2-[2-fluoro-4-(4-pyridyloxy)phenyl]acetamide | | |
| 242 | N-(5-tert-butyl-2-(p-tolyl)pyrazol-3-yl]-2-[3-fluoro-4-(4-pyridyloxy)phenyl]acetamide | | |
| 244 | N-[5-tert-butyl-2-(p-tolyl)pyrazol-3-yl]-2-[3-chloro-4-[(2-chloro-4-pyridyl)oxy]phenyl]acetamide | | 5.73 min |
| 245 | N-(5-(3-methylthietan-3-yl)-2-(p-tolyl)pyrazol-3-yl]-2-[4-(4-pyridyloxy)phenyl]acetamide | | 3.80 min |
| 246 | 2-[2-fluoro-4-(4-pyridyloxy)phenyl]-N-[5-(3-methylthietan-3-yl)-2-(p-tolyl)pyrazol-3-yl]acetamide | | 3.83 min |
| 247 | 2-[3-fluoro-4-(4-pyridyloxy)phenyl]-N-[5-(3-methylthietan-3-yl)-2-(p-tolyl)pyrazol-3-yl]acetamide | | 3.81 min |
| 249 | 2-[3-chloro-4-[(2-chloro-4-pyridyl)oxy]phenyl]-N-(5-(3-methylthietan-3-yl)-2-(p-tolyl)pyrazol-3-yl]acetamide | | 5.70 min |
| 250 | 1-[5-(3-methylthietan-3-yl)-2-(p-tolyl)pyrazol-3-yl]-3-[4-(4-pyridylsulfanyl)phenyl]urea | | 4.07 min |
| 251 | 1-[2-fluoro-4-(4-pyridylsulfanyl))phenyl]-3-[5-(3-methylthietan-3-yl)-2-(p-tolyl)pyrazol-3-yl]urea | | 4.24 min |
| 252 | 1-[5-(3-methylthietan-3-yl)-2-(p-tolyl)pyrazol-3-yl]-3-[4-(4-pyridyloxy)phenyl]urea | | 3.96 min |
| 253 | 1-2-fluoro-4-(4-pyridyloxy)phenyl]-3-[5-(3-methylthietan-3-yl)-2-(p-tolyl)pyrazol-3-yl]urea | | 3.99 min |
| 254 | 1-[5-(3-methylthietan-3-yl)-2-(p-tolyl)pyrazol-3-yl-3-[5-(2-morpholinoethyl)thiazol-2-yl]urea | | |
| 243 | N-(5-tert-butyl-2-(p-tolyl)pyrazol-3-yl]-2-[3-chloro-4-(4-pyridyloxy)phenyl]acetamide | | |
| 248 | 2-[3-chloro-4-(4-pyridyloxy)phenyl]-N-[5-(3-methylthietan-3-yl)-2-(p-tolyl)pyrazol-3-yl]acetamide | | |
| 106 | 1-[5-tert-butyl-2-(p-tolyl)pyrazol-3-yl]-3-[5-(2-thiomorpholinoethyl)thiazol-2-yl]urea | ++ | |
| 107 | 1-5-tert-butyl-2-(p-tolyl)pyrazol-3-yl]-3-[4-(2-morpholioethyl)thiazol-2-yl]urea | + | |
| 115 | 1-[5-tert-butyl-2-(p-tolyl)pyrazol-3-yl]-3-[2-(tetrahydropyran-4-carbonyl)isoindolin-5-yl]urea | + | |
| 116 | 1-5-tert-butyl-2-(p-tolyl)pyrazol-3-yl]-3-[2-(pyridine-4-carbonyl)isoindolin-5-yl]urea | ~ | |
| 117 | 3-(4-methylimidazol-1-yl)-N-[4-(4-pyridyloxy)phenyl]benzamide | ~ | |
| 122 | N-[4-(4-pyridyloxy)phenyl]-2-pyrrolidin-1-yl-pyridine-4-carboxamide | ~ | |
| 124 | 2-morpholino-N-[4-(4-pyridyloxy)phenyl]pyridine-4-carboxamide | ~ | |
| 180 | 1-[5-tert-butyl-2-(4-tert-butylphenyl)pyrazol-3-yl]-3-[5-(2-morpholinoethyl)thiazol-2-yl]urea | | |
| 201 | 1-[2-methyl-5-(3-methyloxetan-3-yl)pyrazol-3-yl]-3-[5-(2-morpholinoethyl)thiazol-2-yl]urea | + | |
| 202 | 1-[2-methyl-5-(3-methyloxetan-3-yl)pyrazol-3-yl]-3-[4-(4-pyridyloxy)phenyl]urea | + | |
| 203 | 1-[2-fluoro-4-(4-pyridloxy)phenyl]-3-[2-methyl-5-(3-methyloxetan-3-yl)pyrazol-3-yl]urea | + | |
| 205 | 1-[2-methyl-5-(3-methyloxetan-3-yl)pyrazol-3-yl]-3-[4-(4-pyridylsulfanyl)phenyl]urea | | |
| 210 | 1-(6,6-dimethyyl-2-(p-tolyl)-4H-furo[3,4-c]pyrazol-3-yl]-3-[5-(2-morpholinoethyl)thiazol-2-yl]urea | ~ | |
| 211 | 1-[6,6-dimethyl-2-(p-tolyl)-4H-furo[3,4-c]pyrazol-3-yl]-3-[4-[(3-tetrahydropyran-4-yl-[1,2,4]triazolo[4,3-a]pyridin-6-yl]sulfanyl]phenyl]urea | + | |
| 212 | 1-[6,6-dimethyl-2-(p-tolyl)-4H-furo[3,4-c]pyrazol-3-yl]-3-[4-[[3-(4-methyltetrahydropyran-4-yl)-[1,2,4]triazolo[4,3-a]pyridin-6-yl]sulfanyl]phenyl]urea | + | |
| 215 | 1-[6,6-dimethyl-2-(p-tolyl])-4,5-dihydrocyclopenta[c]pyrazol-3-yl-3-[4-[(3-tetrahydropyran-4-yl-[1,2,4]triazolo[4,3-a]pyridin-6-yl]sulfanyl]phenyl[urea | + | |
| 216 | 1-[6,6-dimethyl-2-(p-tolyl)-4,5-dihydrocyclopenta[c]pyrazol-3-yl]-3-[4-[[3-(4-methyltetrahydropyran-4-yl)-[1,2,4]triazolo[4,3-a]pyridin-6-yl]sulfanyl]phenyl]urea | + | |
| 217 | 1-[5-(4-methyltetrahydropyran-4-yl)-2-(p-tolyl)pyrazol-3-yl]-3-[4-(4-pyridyloxy)phenyl]urea | + | |
| 218 | 1-[5-(4-methyltetrahydropyran-4-yl)-2-(p-tolyl)pyrazol-3-yl]-3-[5-(2-morpholinoethyl)thiazol-2-yl]urea | + | |

TABLE 1-continued

Compounds of the present teachings.

| Analog # | Compound name | MAPK13 Inhibition Biochemical Potency | Analytical LC-MS (retention time) |
|---|---|---|---|
| 219 | 1-5-(4-methyltetrahydropyran-4-yl)-2-(p-tolyl)pyrazol-3-yl]-3-4-[(3-tetrahydropyran-4-yl-[1,2,4]triazolo[4,3-a]pyridin-6-yl)sulfanyl]phenyl]urea | + | |
| 220 | 1-[5-(4-methyltetrahydropyran-4-yl)-2-(p-tolyl)pyrazol-3-yl]-3-[4-[[3-(4-methyltetrahydropyran-4-yl)-[1,2,4]triazolo[4,3-a]pyridin-6-yl]sulfanyl]phenyl]urea | + | |
| 227 | 1-[5-tert-butyl-2-(3-chloro-4-hydroxy-phenyl)pyraxol-3-yl]-3-[5-(2-morpholinoethyl)thiazol-2-yl]urea | ++ | |
| 230 | 1-[2-(3-chloro-4-hydroxy-phenyl)-5-(3-methyloxetan-3-yl)pyrazol-3-yl]-3-[5-(2-morpholinoethyl)thiazol-2-yl]urea | + | |
| 231 | 1-[2-(3-chloro-4-hydroxy-phenyl)-5-(4-methyltetrahydropyran-4-yl]pyrazol-3-yl]-3-[4-(4-pyridyloxy)phenyl]urea | + | |
| 232 | 1-[2-(3-chloro-4-hyxdroxy-phenyl)-5-(4-methyltetrahydropyran-4-yl)pyrazol-3-yl]-3-[5-(2-morphoinoethyl)thiazol-2-yl]urea | + | |
| 233 | 1-[2-(4-hydroxyphenyl)-5-(4-methyltetrahydropyran-4-yl)pyrazol-3-yl]-3-[4-(4-pyridyloxy)phenyl]urea | ++ | |
| 237 | N-[5-tert-butyl-2-(4-hydroxyphenyl)pyrazol-3-yl]-2-[2-fluoro-4-(4-pyridyloxy)phenyl]acetamide | | |
| 238 | N-[5-tert-butyl-2-(4-hydroxyphenyl)pyrazol-3-yl]-2-[3-fluoro-4-(4-pyridyloxy)phenyl]acetamide | | |
| 239 | N-[5-tert-butyl-2-(4-hydroxyphenyl)pyrazol-3-yl]-2-[3-chloro-4-(4-pyridyloxy)phenyl]acetamide | | |
| 109 | N-[4-(4-pyridyloxy)phenyl-2-pyrrolidin-1-yl-pyridine-4-carboxamide | ~ | |
| 110 | N-[4-(4-pyridyloxy)phenyl]-3-pyrrolidin-1-yl-benzamide | ~ | |

TABLE II

Compounds of the present teachings.

| Analog # | Compound name | Structure |
|---|---|---|
| 89 | 1-[5-tert-butyl-2-(p-tolyl)pyrazol-3-yl]-3-[5-(2-morpholinoethyl)thiazol-2-yl]urea | 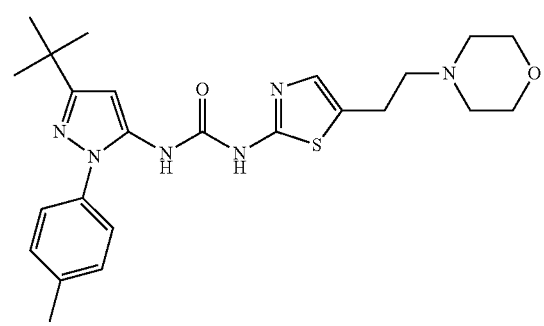 [SMILES: Cc1ccc(-n2nc(C(C)(C)C)cc2NC(=O)Nc2ncc(CCN3CCOCC3)s2)cc1] |
| 186 | 1-[5-(3-methyloxetan-3-yl)-2-(p-tolyl)pyrazol-3-yl]-3-[4-(4-pyridyloxy)phenyl]urea | 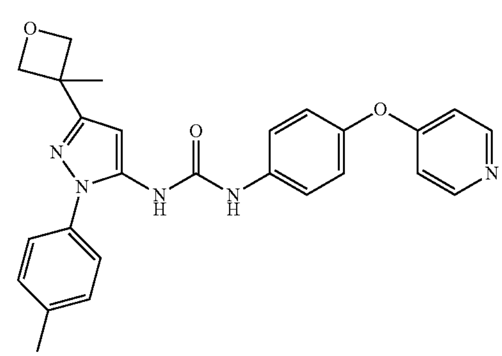 [SMILES: Cc1ccc(-n2nc(C3(C)COC3)cc2NC(=O)Nc2ccc(Oc3ccncc3)cc2)cc1] |

TABLE II-continued

Compounds of the present teachings.

| Analog # | Compound name | Structure |
|---|---|---|
| 187 | 1-[5-(3-methyloxetan-3-yl)-2-(p-tolyl)pyrazol-3-yl]-3-[5-(2-morpholinoethyl)thiazol-2-yl]urea | 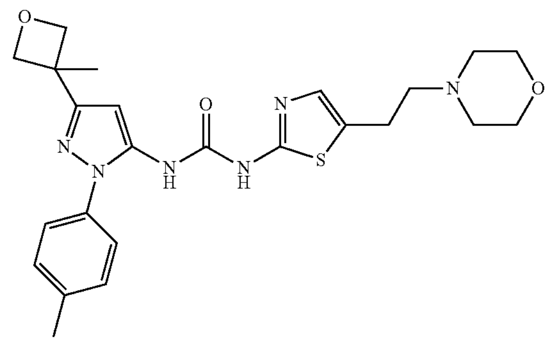 [SMILES: Cc1ccc(-n2nc(C3(C)COC3)cc2NC(=O)Nc2ncc(CCN3CCOCC3)s2)cc1] |
| 192 | 1-[2-fluoro-4-(4-pyridyloxy)phenyl]-3-[5-(3-methyloxetan-3-yl)-2-(p-tolyl)pyrazol-3-yl]urea | 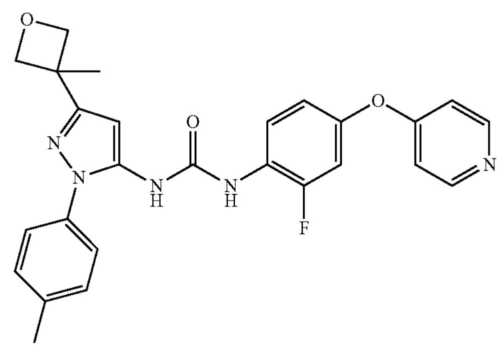 [SMILES: Cc1ccc(-n2nc(C3(C)COC3)cc2NC(=O)Nc2ccc(Oc3ccncc3)cc2F)cc1] |
| 204 | 1-[5-(3-methyloxetan-3-yl)-2-(p-tolyl)pyrazol-3-yl]-3-[4-(4-pyridylsulfanyl)phenyl]urea | 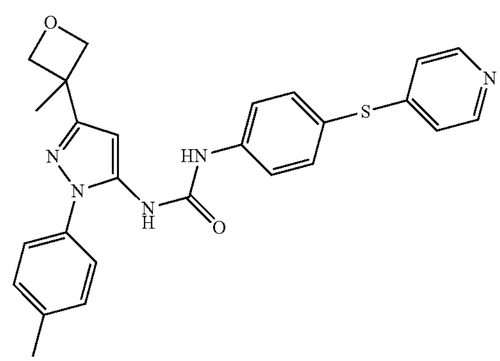 [SMILES: Cc1ccc(-n2nc(C3(C)COC3)cc2NC(=O)Nc2ccc(Sc3ccncc3)cc2)cc1] |
| 209 | 1-[6,6-dimethyl-2-(p-tolyl)-4H-furo[3,4-c]pyrazol-3-yl]-3-[4-(4-pyridyloxy)phenyl]urea | 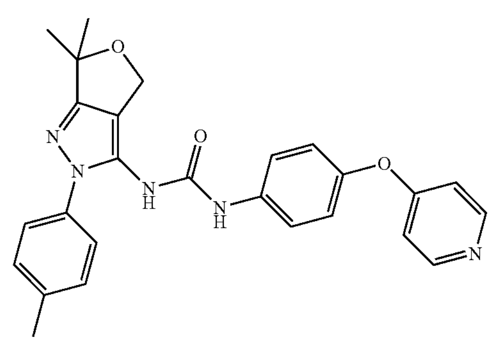 [SMILES: Cc1ccc(-n2nc3c(c2NC(=O)Nc2ccc(Oc4ccncc4)cc2)COC3(C)C)cc1] |

TABLE II-continued

Compounds of the present teachings.

| Analog # | Compound name | Structure |
|---|---|---|
| 213 | 1-[6,6-dimethyl-2-(p-tolyl)-4,5-dihydro-cyclopenta[c]pyrazol-3-yl]-3-[4-(4-pyridyloxy)phenyl]urea | 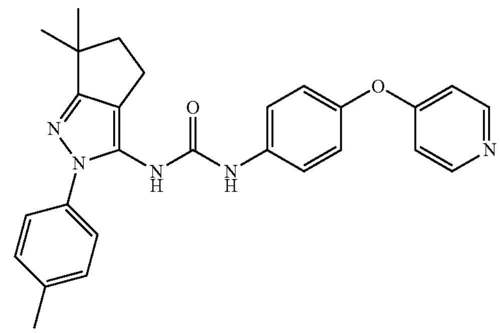 [SMILES: Cc1ccc(-n2nc3c(c2NC(=O)Nc2ccc(Oc4ccncc4)cc2)CCC3(C)C)cc1] |
| 214 | 1-[6,6-dimethyl-2-(p-tolyl)-4,5-dihydro-cyclopenta[c]pyrazol-3-yl]-3-[5-(2-morpholinoethyl)thiazol-2-yl]urea | 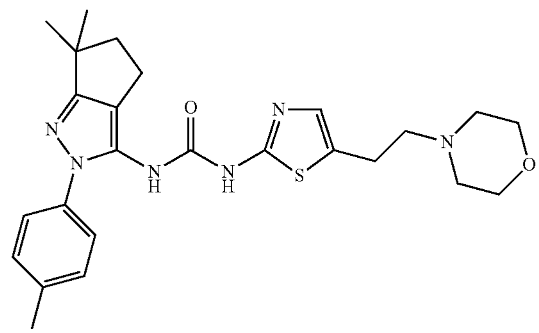 [SMILES: Cc1ccc(-n2nc3c(c2NC(=O)Nc2ncc(CCN4CCOCC4)s2)CCC3(C)C)cc1] |
| 229 | 1-[2-(3-chloro-4-hydroxy-phenyl)-5-(3-methyloxetan-3-yl)pyrazol-3-yl]-3-[4-(4-pyridyloxy)phenyl]urea | 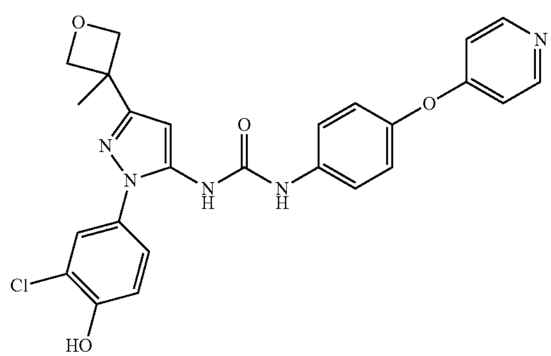 [SMILES: CC1(c2cc(NC(=O)Nc3ccc(Oc4ccncc4)cc3)n(-c3ccc(O)c(Cl)c3)n2)COC1] |
| 234 | 1-[2-(3-chloro-4-hydroxy-phenyl)-6,6-dimethyl-4,5-dihydrocyclopenta[c]pyrazol-3-yl]-3-[2-fluoro-4-(4-pyridyloxy)phenyl]urea | 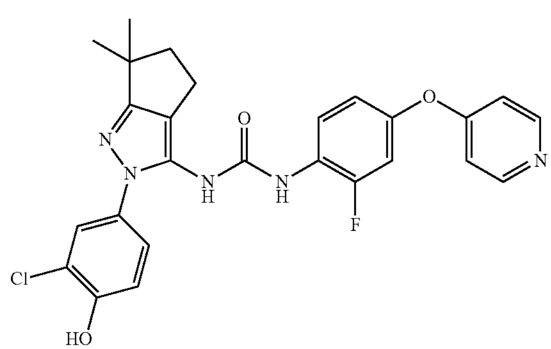 [SMILES: CC1(C)CCc2c1nn(-c1ccc(O)c(Cl)c1)c2NC(=O)Nc1ccc(Oc2ccncc2)cc1F] |

TABLE II-continued

Compounds of the present teachings.

| Analog # | Compound name | Structure |
|---|---|---|
| 235 | 1-[2-fluoro-4-(4-pyridyloxy)phenyl]-3-[2-(4-hydroxyphenyl)-6,6-dimethyl-4,5-dihydrocyclopenta[c]pyrazol-3-yl]urea | 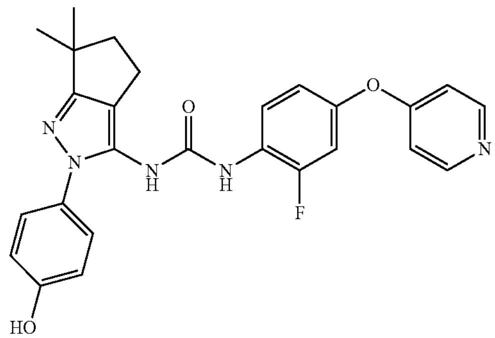 [SMILES: CC1(C)CCc2c1nn(-c1ccc(O)cc1)c2NC(=O)Nc1ccc(Oc2ccncc2)cc1F] |
| 236 | N-[5-tert-butyl-2-(4-hydroxyphenyl)pyrazol-3-yl]-2-[4-(4-pyridyloxy)phenyl]acetamide | 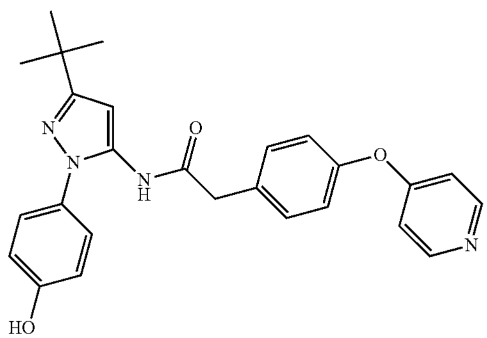 [SMILES: CC(C)(C)c1cc(NC(=O)Cc2ccc(Oc3ccncc3)cc2)n(-c2ccc(O)cc2)n1] |
| 240 | N-[5-tert-butyl-2-(p-tolyl)pyrazol-3-yl]-2-[4-(4-pyridyloxy)phenyl]acetamide | 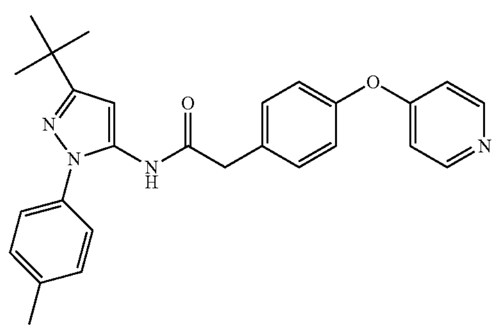 [SMILES: Cc1ccc(-n2nc(C(C)(C)C)cc2NC(=O)Cc2ccc(Oc3ccncc3)cc2)cc1] |
| 241 | N-[5-tert-butyl-2-(p-tolyl)pyrazol-3-yl]-2-[2-fluoro-4-(4-pyridyloxy)phenyl]acetamide | 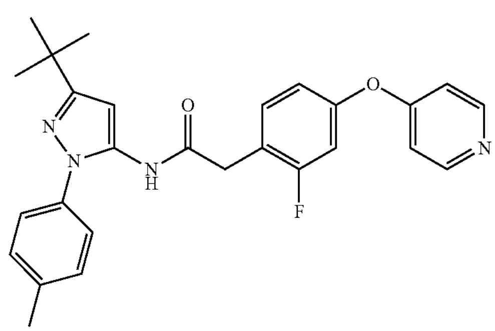 [SMILES: Cc1ccc(-n2nc(C(C)(C)C)cc2NC(=O)Cc2ccc(Oc3ccncc3)cc2F)cc1] |

TABLE II-continued

Compounds of the present teachings.

| Analog # | Compound name | Structure |
|---|---|---|
| 242 | N-[5-tert-butyl-2-(p-tolyl)pyrazol-3-yl]-2-[3-fluoro-4-(4-pyridyloxy)phenyl]acetamide | 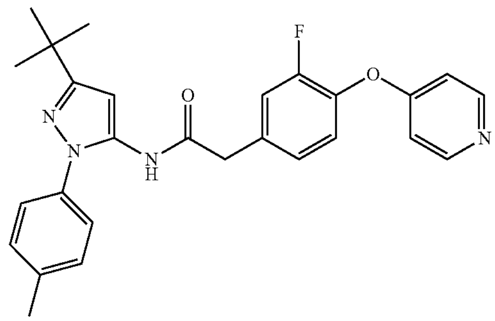 [SMILES: Cc1ccc(-n2nc(C(C)(C)C)cc2NC(=O)Cc2ccc(Oc3ccncc3)c(F)c2)cc1] |
| 244 | N-[5-tert-butyl-2-(p-tolyl)pyrazol-3-yl]-2-[3-chloro-4-[(2-chloro-4-pyridyl)oxy]phenyl]acetamide | 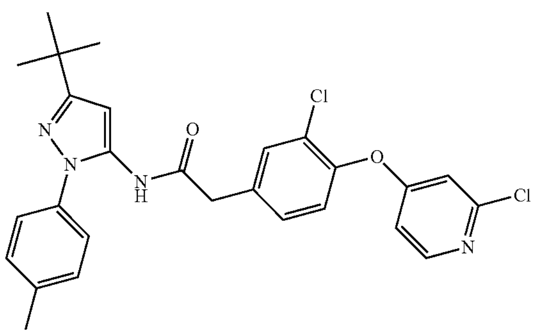 [SMILES: Cc1ccc(-n2nc(C(C)(C)C)cc2NC(=O)Cc2ccc(Oc3ccnc(Cl)c3)c(Cl)c2)cc1] |
| 245 | N-[5-(3-methylthietan-3-yl)-2-(p-tolyl)pyrazol-3-yl]-2-[4-(4-pyridyloxy)phenyl]acetamide | 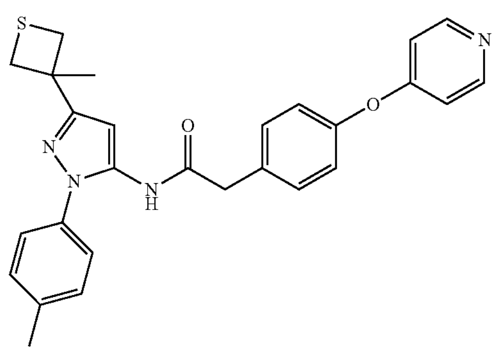 [SMILES: Cc1ccc(-n2nc(C3(C)CSC3)cc2NC(=O)Cc2ccc(Oc3ccncc3)cc2)cc1] |
| 246 | 2-[2-fluoro-4-(4-pyridyloxy)phenyl]-N-[5-(3-methylthietan-3-yl)-2-(p-tolyl)pyrazol-3-yl]acetamide | 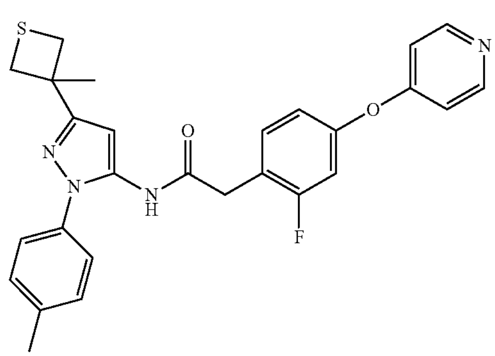 [SMILES: Cc1ccc(-n2nc(C3(C)CSC3)cc2NC(=O)Cc2ccc(Oc3ccncc3)cc2F)cc1] |

TABLE II-continued

Compounds of the present teachings.

| Analog # | Compound name | Structure |
|---|---|---|
| 247 | 2-[3-fluoro-4-(4-pyridyloxy)phenyl]-N-[5-(3-methylthietan-3-yl)-2-(p-tolyl)pyrazol-3-yl]acetamide | 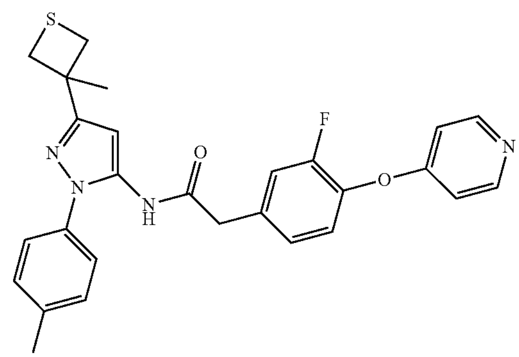 [SMILES: Cc1ccc(-n2nc(C3(C)CSC3)cc2NC(=O)Cc2ccc(Oc3ccncc3)c(F)c2)cc1] |
| 249 | 2-[3-chloro-4-[(2-chloro-4-pyridyl)oxy]phenyl]-N-[5-(3-methylthietan-3-yl)-2-(p-tolyl)pyrazol-3-yl]acetamide | 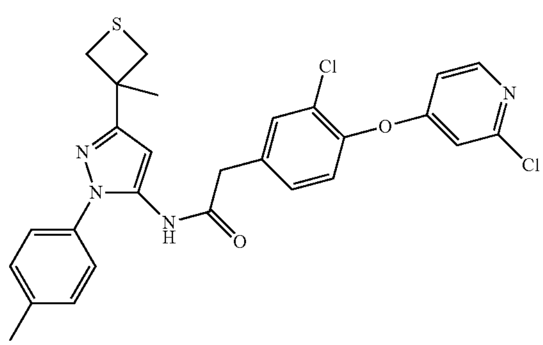 [SMILES: Cc1ccc(-n2nc(C3(C)CSC3)cc2NC(=O)Cc2ccc(Oc3ccnc(Cl)c3)c(Cl)c2)cc1] |
| 250 | 1-[5-(3-methylthietan-3-yl)-2-(p-tolyl)pyrazol-3-yl]-3-[4-(4-pyridylsulfanyl)phenyl]urea | 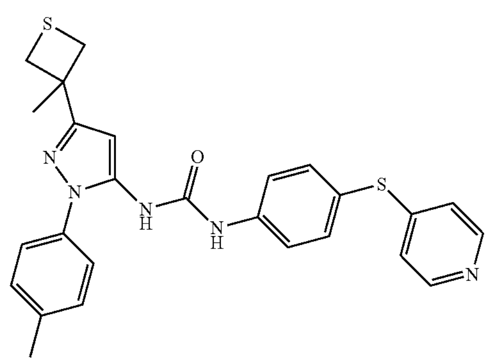 [SMILES: Cc1ccc(-n2nc(C3(C)CSC3)cc2NC(=O)Nc2ccc(Sc3ccncc3)cc2)cc1] |
| 251 | 1-[2-fluoro-4-(4-pyridylsulfanyl)phenyl]-3-[5-(3-methylthietan-3-yl)-2-(p-tolyl)pyrazol-3-yl]urea | 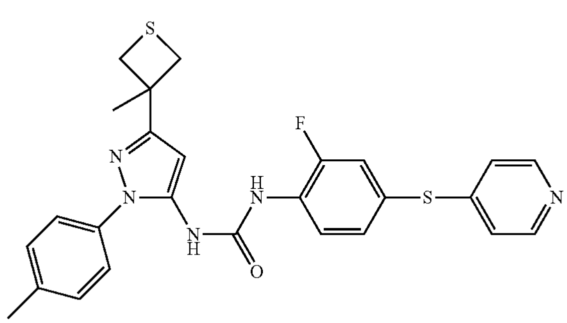 [SMILES: Cc1ccc(-n2nc(C3(C)CSC3)cc2NC(=O)Nc2ccc(Sc3ccncc3)cc2F)cc1] |

TABLE II-continued

Compounds of the present teachings.

| Analog # | Compound name | Structure |
|---|---|---|
| 252 | 1-[5-(3-methylthietan-3-yl)-2-(p-tolyl)pyrazol-3-yl]-3-[4-(4-pyridyloxy)phenyl]urea | 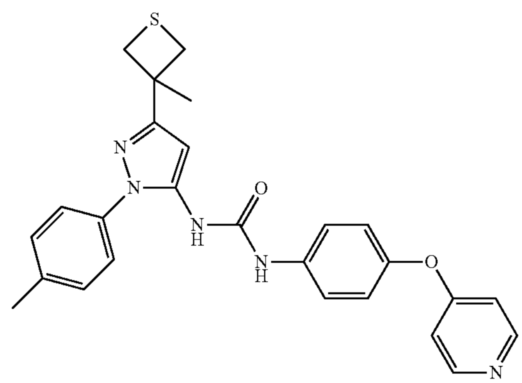 [SMILES: Cc1ccc(-n2nc(C3(C)CSC3)cc2NC(=O)Nc2ccc(Oc3ccncc3)cc2)cc1] |
| 253 | 1-[2-fluoro-4-(4-pyridyloxy)phenyl]-3-[5-(3-methylthietan-3-yl)-2-(p-tolyl)pyrazol-3-yl]urea | 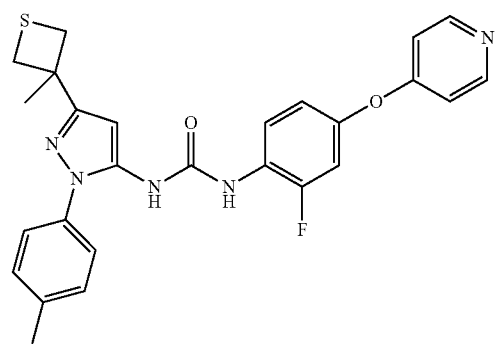 [SMILES: Cc1ccc(-n2nc(C3(C)CSC3)cc2NC(=O)Nc2ccc(Oc3ccncc3)cc2F)cc1] |
| 254 | 1-[5-(3-methylthietan-3-yl)-2-(p-tolyl)pyrazol-3-yl]-3-[5-(2-morpholinoethyl)thiazol-2-yl]urea | 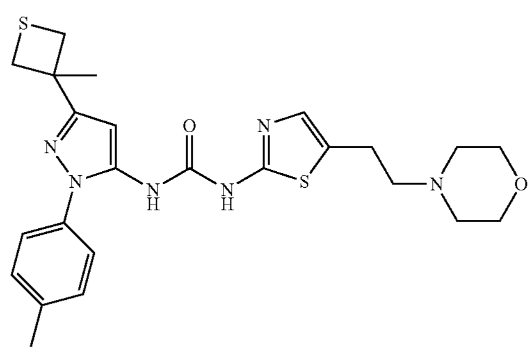 [SMILES: Cc1ccc(-n2nc(C3(C)CSC3)cc2NC(=O)Nc2ncc(CCN3CCOCC3)s2)cc1] |
| 243 | N-[5-tert-butyl-2-(p-tolyl)pyrazol-3-yl]-2-[3-chloro-4-(4-pyridyloxy)phenyl]acetamide | 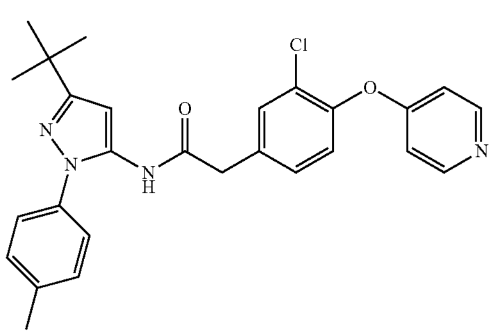 [SMILES: Cc1ccc(-n2nc(C(C)(C)C)cc2NC(=O)Cc2ccc(Oc3ccncc3)c(Cl)c2)cc1] |

TABLE II-continued

Compounds of the present teachings.

| Analog # | Compound name | Structure |
|---|---|---|
| 248 | 2-[3-chloro-4-(4-pyridyloxy)phenyl]-N-[5-(3-methylthietan-3-yl)-2-(p-tolyl)pyrazol-3-yl]acetamide | 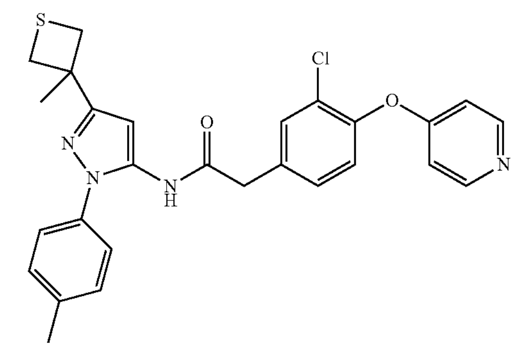 [SMILES: Cc1ccc(-n2nc(C3(C)CSC3)cc2NC(=O)Cc2ccc(Oc3ccncc3)c(Cl)c2)cc1] |
| 106 | 1-[5-tert-butyl-2-(p-tolyl)pyrazol-3-yl]-3-[5-(2-thiomorpholinoethyl)thiazol-2-yl]urea | 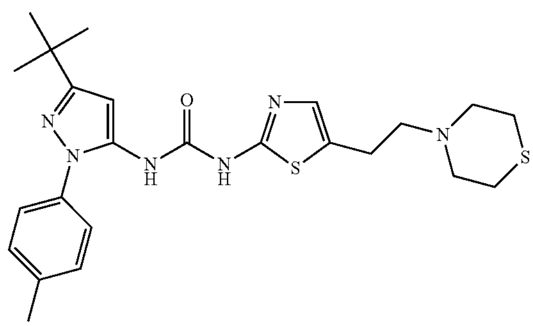 [SMILES: Cc1ccc(-n2nc(C(C)(C)C)cc2NC(=O)Nc2ncc(CCN3CCSCC3)s2)cc1] |
| 107 | 1-[5-tert-butyl-2-(p-tolyl)pyrazol-3-yl]-3-[4-(2-morpholinoethyl)thiazol-2-yl]urea | 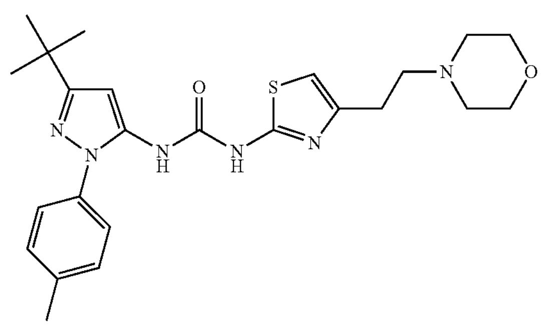 [SMILES: Cc1ccc(-n2nc(C(C)(C)C)cc2NC(=O)Nc2nc(CCN3CCOCC3)cs2)cc1] |
| 115 | 1-[5-tert-butyl-2-(p-tolyl)pyrazol-3-yl]-3-[2-(tetrahydropyran-4-carbonyl)isoindolin-5-yl]urea | 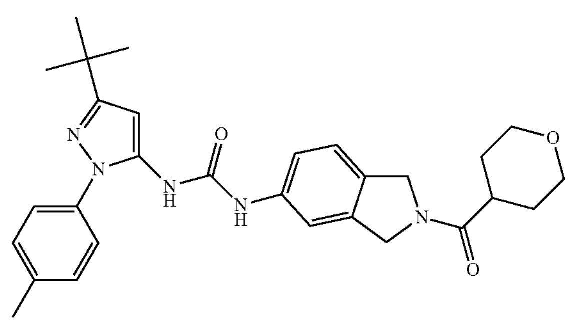 [SMILES: Cc1ccc(-n2nc(C(C)(C)C)cc2NC(=O)Nc2ccc3c(c2)CN(C(=O)C2CCOCC2)C3)cc1] |

TABLE II-continued

Compounds of the present teachings.

| Analog # | Compound name | Structure |
|---|---|---|
| 116 | 1-[5-tert-butyl-2-(p-tolyl)pyrazol-3-yl]-3-[2-(pyridine-4-carbonyl)isoindolin-5-yl]urea | 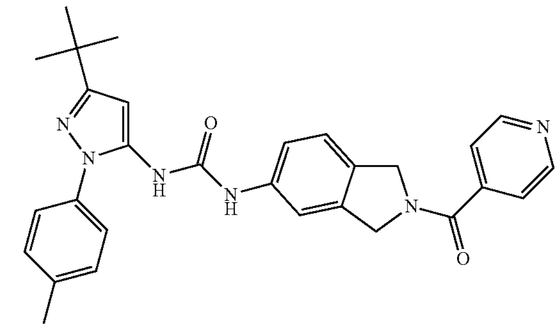 [SMILES: Cc1ccc(-n2nc(C(C)(C)C)cc2NC(=O)Nc2ccc3c(c2)CN(C(=O)c2ccncc2)C3)cc1] |
| 117 | 3-(4-methylimidazol-1-yl)-N-[4-(4-pyridyloxy)phenyl]benzamide | 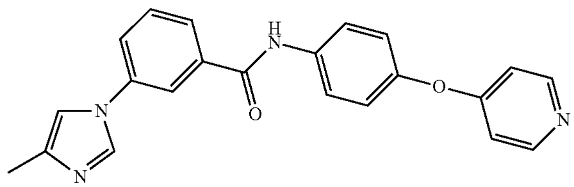 [SMILES: Cc1cn(-c2cccc(C(=O)Nc3ccc(Oc4ccncc4)cc3)c2)cn1] |
| 122 | N-[4-(4-pyridyloxy)phenyl]-2-pyrrolidin-1-yl-pyridine-4-carboxamide | 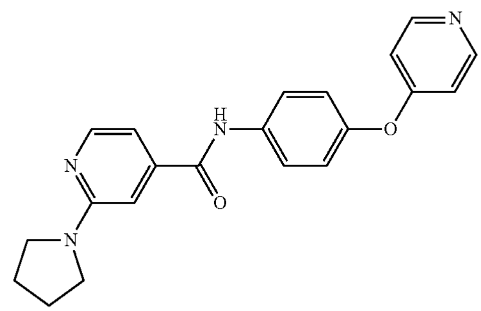 [SMILES: O=C(Nc1ccc(Oc2ccncc2)cc1)c1ccnc(N2CCCC2)c1] |
| 124 | 2-morpholino-N-[4-(4-pyridyloxy)phenyl]pyridine-4-carboxamide | 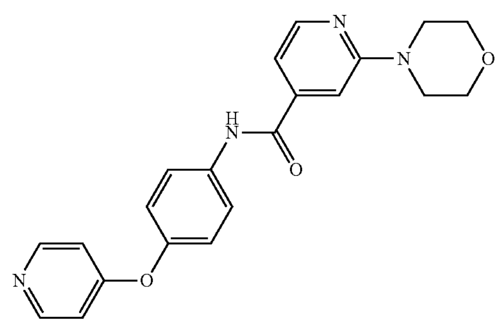 [SMILES: O=C(Nc1ccc(Oc2ccncc2)cc1)c1ccnc(N2CCOCC2)c1] |
| 180 | 1-[5-tert-butyl-2-(4-tert-butylphenyl)pyrazol-3-yl]-3-[5-(2-morpholino-ethyl)thiazol-2-yl]urea | 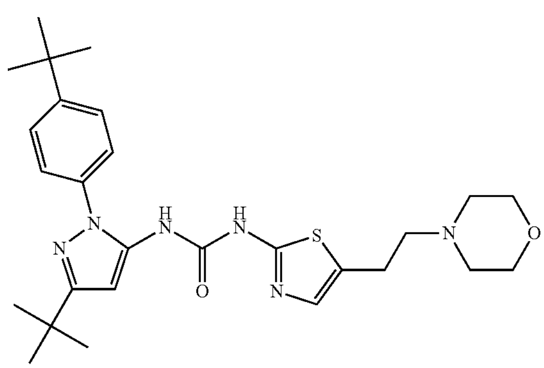 [SMILES: CC(C)(C)c1ccc(-n2nc(C(C)(C)C)cc2NC(=O)Nc2ncc(CCN3CCOCC3)s2)cc1] |

TABLE II-continued

Compounds of the present teachings.

| Analog # | Compound name | Structure |
|---|---|---|
| 201 | 1-[2-methyl-5-(3-methyloxetan-3-yl)pyrazol-3-yl]-3-[5-(2-morpholinoethyl)thiazol-2-yl]urea | 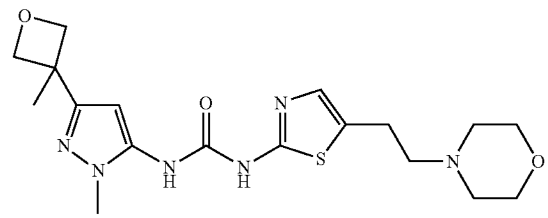 [SMILES: Cn1nc(C2(C)COC2)cc1NC(=O)Nc1ncc(CCN2CCOCC2)s1] |
| 202 | 1-[2-methyl-5-(3-methyloxetan-3-yl)pyrazol-3-yl]-3-[4-(4-pyridyloxy)phenyl]urea | 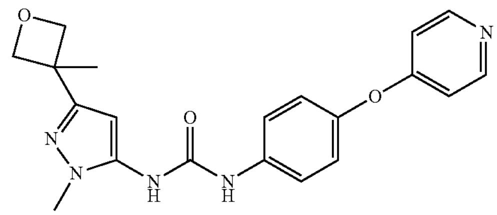 [SMILES: Cn1nc(C2(C)COC2)cc1NC(=O)Nc1ccc(Oc2ccncc2)cc1] |
| 203 | 1-[2-fluoro-4-(4-pyridyloxy)phenyl]-3-[2-methyl-5-(3-methyloxetan-3-yl)pyrazol-3-yl]urea | 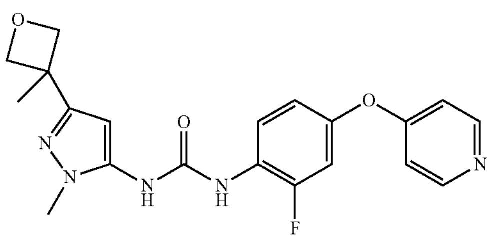 [SMILES: Cn1nc(C2(C)COC2)cc1NC(=O)Nc1ccc(Oc2ccncc2)cc1F] |
| 205 | 1-[2-methyl-5-(3-methyloxetan-3-yl)pyrazol-3-yl]-3-[4-(4-pyridylsulfanyl)phenyl]urea | 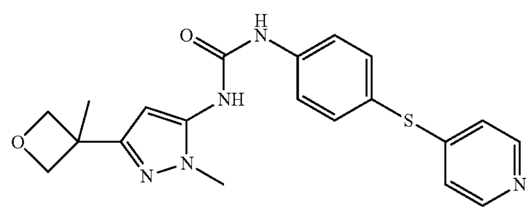 [SMILES: Cn1nc(C2(C)COC2)cc1NC(=O)Nc1ccc(Sc2ccncc2)cc1] |
| 210 | 1-[6,6-dimethyl-2-(p-tolyl)-4H-furo[3,4-c]pyrazol-3-yl]-3-[5-(2-morpholinoethyl)thiazol-2-yl]urea | 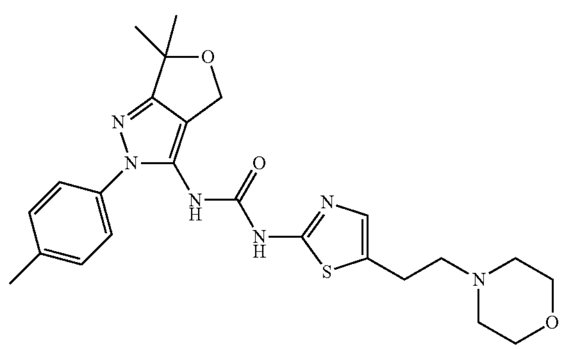 [SMILES: Cc1ccc(-n2nc3c(c2NC(=O)Nc2ncc(CCN4CCOCC4)s2)COC3(C)C)cc1] |
| 211 | 1-[6,6-dimethyl-2-(p-tolyl)-4H-furo[3,4-c]pyrazol-3-yl]-3-[4-[(3-tetrahydropyran-4-yl-[1,2,4]triazolo[4,3-a]pyridin-6-yl)sulfanyl]phenyl]urea | 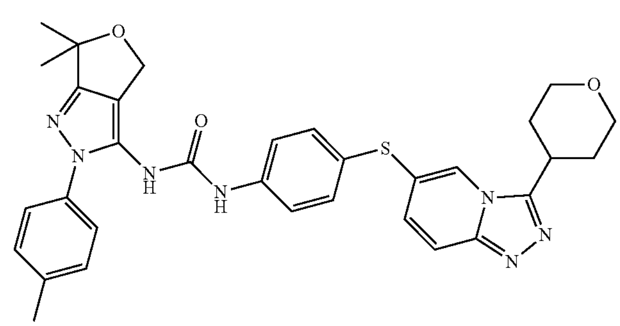 [SMILES: Cc1ccc(-n2nc3c(c2NC(=O)Nc2ccc(Sc4ccc5nnc(C6CCOCC6)n5c4)cc2)COC3(C)C)cc1] |

TABLE II-continued

Compounds of the present teachings.

| Analog # | Compound name | Structure |
|---|---|---|
| 212 | 1-[6,6-dimethyl-2-(p-tolyl)-4H-furo[3,4-c]pyrazol-3-yl]-3-[4-[[3-(4-methyltetrahydropyran-4-yl)-[1,2,4]triazolo[4,3-a]pyridin-6-yl]sulfanyl]phenyl]urea | 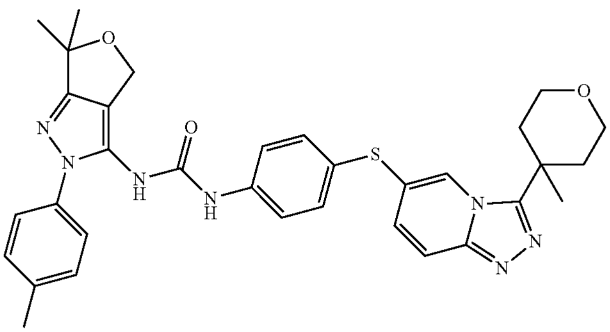 [SMILES: Cc1ccc(-n2nc3c(c2NC(=O)Nc2ccc(Sc4ccc5nnc(C6(C)CCOCC6)n5c4)cc2)COC3(C)C)cc1] |
| 215 | 1-[6,6-dimethyl-2-(p-tolyl)-4,5-dihydro-cyclopenta[c]pyrazol-3-yl]-3-[4-[(3-tetrahydropyran-4-yl-[1,2,4]triazolo[4,3-a]pyridin-6-yl)sulfanyl]phenyl]urea | 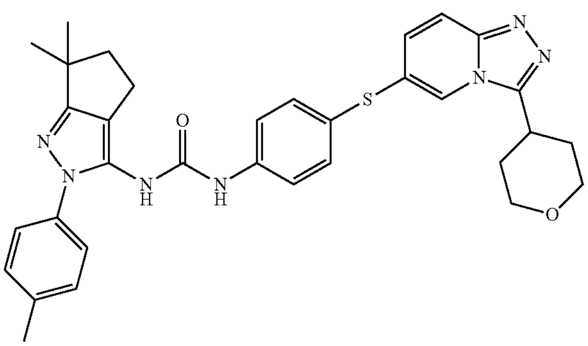 [SMILES: Cc1ccc(-n2nc3c(c2NC(=O)Nc2ccc(Sc4ccc5nnc(C6CCOCC6)n5c4)cc2)CCC3(C)C)cc1] |
| 216 | 1-[6,6-dimethyl-2-(p-tolyl)-4,5-dihydro-cyclopenta[c]pyrazol-3-yl]-3-[4-[[3-(4-methyltetrahydropyran-4-yl)-[1,2,4]triazolo[4,3-a]pyridin-6-yl)sulfanyl]phenyl]urea | 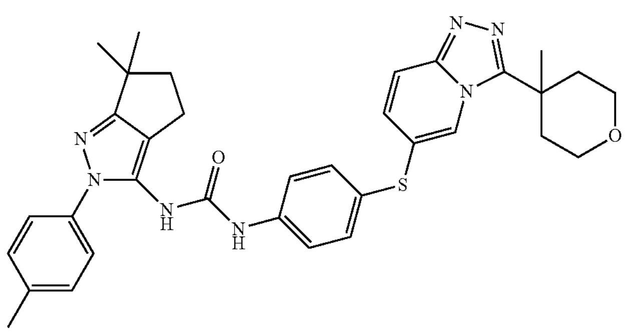 [SMILES: Cc1ccc(-n2nc3c(c2NC(=O)Nc2ccc(Sc4ccc5nnc(C6(C)CCOCC6)n5c4)cc2)CCC3(C)C)cc1] |
| 217 | 1-[5-(4-methyltetrahydropyran-4-yl)-2-(p-tolyl)pyrazol-3-yl]-3-[4-(4-pyridyloxy)phenyl]urea | 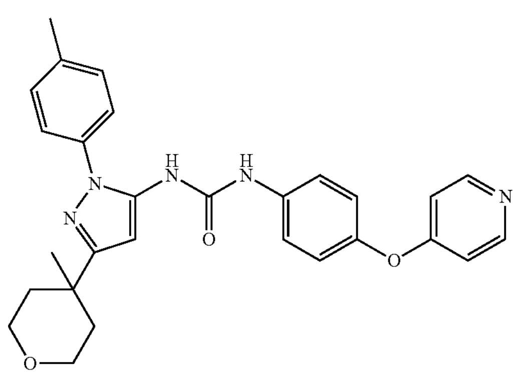 [SMILES: Cc1ccc(-n2nc(C3(C)CCOCC3)cc2NC(=O)Nc2ccc(Oc3ccncc3)cc2)cc1] |

TABLE II-continued

Compounds of the present teachings.

| Analog # | Compound name |
|---|---|
| 218 | 1-[5-(4-methyltetrahydropyran-4-yl)-2-(p-tolyl)pyrazol-3-yl]-3-[5-(2-morpholinoethyl)thiazol-2-yl]urea |
| 219 | 1-[5-(4-methyl-tetrahydropyran-4-yl)-2-(p-tolyl)pyrazol-3-yl]-3-[4-[(3-tetrahydropyran-4-yl-[1,2,4]triazolo[4,3-a]pyridin-6-yl)sulfanyl]phenyl]urea |
| 220 | 1-[5-(4-methyl-tetrahydropyran-4-yl)-2-(p-tolyl)pyrazol-3-yl]-3-[4-[[3-(4-methyltetrahydropyran-4-yl)-[1,2,4]triazolo[4,3-a]pyridin-6-yl]sulfanyl]phenyl]urea |
| 227 | 1-[5-tert-butyl-2-(3-chloro-4-hydroxy-phenyl)pyrazol-3-yl]-3-[5-(2-morpholino-ethyl)thiazol-2-yl]urea |

TABLE II-continued

Compounds of the present teachings.

| Analog # | Compound name | Structure |
|---|---|---|
| 230 | 1-[2-(3-chloro-4-hydroxyphenyl)-5-(3-methyloxetan-3-yl)pyrazol-3-yl]-3-[5-(2-morpholinoethyl)thiazol-2-yl]urea | 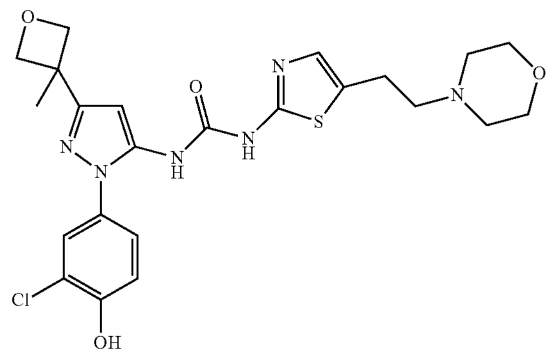 [SMILES: CC1(c2cc(NC(=O)Nc3ncc(CCN4CCOCC4)s3)n(-c3ccc(O)c(Cl)c3)n2)COC1] |
| 231 | 1-[2-(3-chloro-4-hydroxyphenyl)-5-(4-methyltetrahydropyran-4-yl)pyrazol-3-yl]-3-[4-(4-pyridyloxy)phenyl]urea | 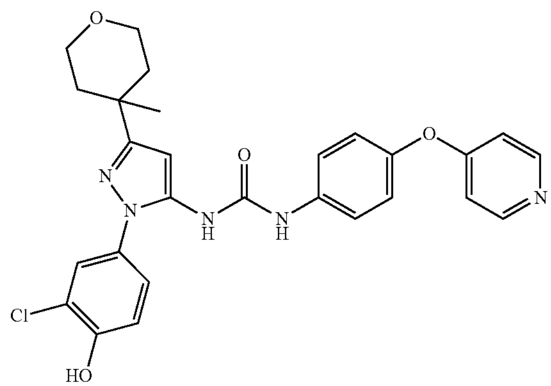 [SMILES: CC1(c2cc(NC(=O)Nc3ccc(Oc4ccncc4)cc3)n(-c3ccc(O)c(Cl)c3)n2)CCOCC1] |
| 232 | 1-[2-(3-chloro-4-hydroxyphenyl)-5-(4-methyltetrahydropyran-4-yl)pyrazol-3-yl]-3-[5-(2-morpholinoethyl)thiazol-2-yl]urea | 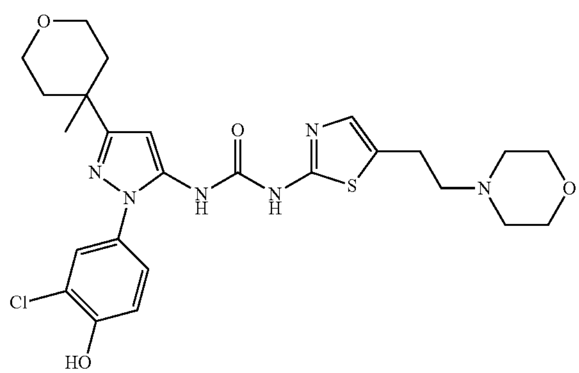 [SMILES: CC1(c2cc(NC(=O)Nc3ncc(CCN4CCOCC4)s3)n(-c3ccc(O)c(Cl)c3)n2)CCOCC1] |
| 233 | 1-[2-(4-hydroxyphenyl)-5-(4-methyltetrahydropyran-4-yl)pyrazol-3-yl]-3-[4-(4-pyridyloxy)phenyl]urea | 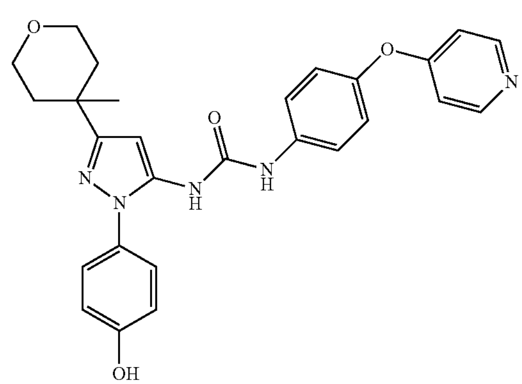 [SMILES: CC1(c2cc(NC(=O)Nc3ccc(Oc4ccncc4)cc3)n(-c3ccc(O)cc3)n2)CCOCC1] |

TABLE II-continued

Compounds of the present teachings.

| Analog # | Compound name | Structure |
|---|---|---|
| 237 | N-[5-tert-butyl-2-(4-hydroxyphenyl)pyrazol-3-yl]-2-[2-fluoro-4-(4-pyridyloxy)phenyl]acetamide | 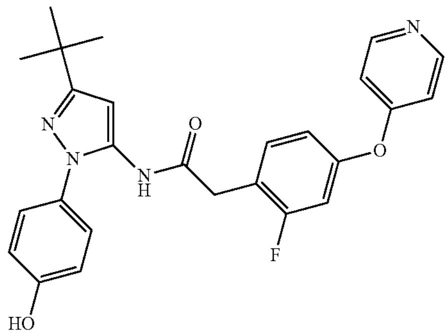 [SMILES: CC(C)(C)c1cc(NC(=O)Cc2ccc(Oc3ccncc3)cc2F)n(-c2ccc(O)cc2)n1] |
| 238 | N-[5-tert-butyl-2-(4-hydroxyphenyl)pyrazol-3-yl]-2-[3-fluoro-4-(4-pyridyloxy)phenyl]acetamide | 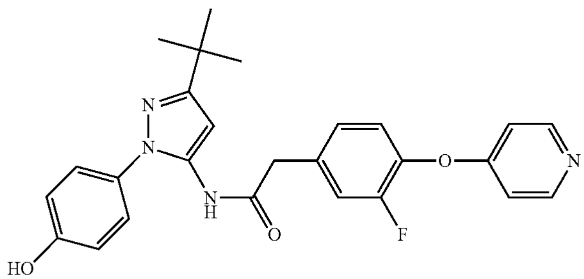 [SMILES: CC(C)(C)c1cc(NC(=O)Cc2ccc(Oc3ccncc3)c(F)c2)n(-c2ccc(O)cc2)n1] |
| 239 | N-[5-tert-butyl-2-(4-hydroxyphenyl)pyrazol-3-yl]-2-[3-chloro-4-(4-pyridyloxy)phenyl]acetamide | 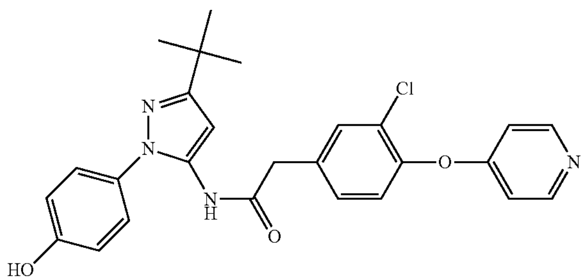 [SMILES: CC(C)(C)c1cc(NC(=O)Cc2ccc(Oc3ccncc3)c(Cl)c2)n(-c2ccc(O)cc2)n1] |
| 109 | N-[4-(4-pyridyloxy)phenyl]-2-pyrrolidin-1-yl-pyridine-4-carboxamide | 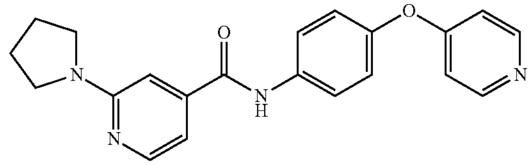 [SMILES: O=C(Nc1ccc(Oc2ccncc2)cc1)c1ccnc(N2CCCC2)c1] |
| 110 | N-[4-(4-pyridyloxy)phenyl]-3-pyrrolidin-1-yl-benzamide | 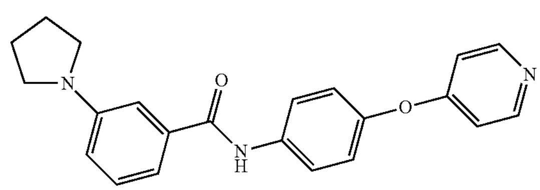 [SMILES: O=C(Nc1ccc(Oc2ccncc2)cc1)c1cccc(N2CCCC2)c1] |

Methods

The methods and compositions described herein utilize laboratory techniques well known to skilled artisans, and can be found in laboratory manuals such as Sambrook and Russel (2006), Condensed Protocols from Molecular Cloning: A Laboratory Manual, Cold Spring Harbor Laboratory Press, ISBN 0879697717; Sambrook J., et al., Molecular Cloning: A Laboratory Manual. 3rd ed. Cold Spring Harbor Laboratory Press, Cold Spring Harbor, N.Y., 2001; Spector, D. L. et al., Cells: A Laboratory Manual, Cold Spring Harbor Laboratory Press. Cold Spring Harbor, N.Y., 1998; Ausubel, F. M., et al., ed., Current Protocols in Molecular Biology, Wiley Interscience, 2003; Nagy, A., et al., Manipulating the Mouse Embryo: A Laboratory Manual (Third Edition). Cold Spring Harbor Laboratory Press, Cold Spring Harbor, N.Y., 2003; Hedrickson et al., Organic Chemistry 3rd edition, McGraw Hill, New York, 1970; Carruthers, W., and Coldham. I., Modern Methods of Organic Synthesis (4th Edition), Cambridge University Press. Cambridge. U.K., 2004; Graham Solomons T. W., et al., Organic Chemistry 9th edition, Wiley, John & Sons, Incorporated, 2007.

As used herein, the singular forms "a", "an" and "the" are intended to include the plural forms as well, unless the context indicates otherwise. Methods of administration of pharmaceuticals and dosage regimes can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition. McGraw-Hill, 1996; and Rowe, R. C., et al., Handbook of Pharmaceutical Excipients, Fourth Edition, Pharmaceutical Press, 2003.

Primary cell culture. Human tracheal epithelial cells (hTECs) were isolated and placed into culture in growth factor enriched medium as described previously (Tyner, J. W., et al. J. Clin. Invest. 116:309-21, 2006). For the present experiments, cells were seeded at $2 \times 10^5$ cells per well (24-well Transwell, Corning, Corning, N.Y.) and cultured under submerged conditions until confluent. Cultures were then maintained in DMEM-Ham's F12 medium with 2% NuSerum (BD, Franklin, N.J.), Primocin (100 µg/ml, InvivoGen, San Diego, Calif.), and retinoic acid ($1 \times 10^{-8}$ M. Sigma) with or without IL-13 (50 ng/ml, Peprotech. Rocky Hill, N.J.) for 2 days, and finally were switched to air-liquid interface conditions with or without IL-13 added twice per week for 3 weeks. Cells were also cultured in the presence or absence of a range of concentrations of chemical inhibitors. All inhibitors were added 1 day before addition of IL-13 and were re-added with each IL-13 treatment. Transepithelial electrical resistance (TEER) of cell cultures was monitored as described previously (Thavagnanam, S., et al. Ped. Res. 69:95-100, 2011).

Chemical inhibitors. BIRB-796 (Doramapimod) was obtained from American Custom Chemicals (San Diego Calif.). SB-203580 was obtained from EMD Chemicals (Gibbstown, N.J.). These compounds and all analogs were also synthesized in our laboratories and purified to >99% purity using silica gel column chromatography and recrystallization. Purity analysis was determined using a ZORBAX XDB-C8 column (Agilent) on an Agilent Series 1100 LC-MS instrument with UV detection at 215 and 254 nM. $^1$H NMR spectra were obtained using a Varian 400 MHz NMR instrument (Varian Medical Systems Inc., Palo Alto, Calif., USA). Instant JChem (version 5.9.3, 2012 release) was used for structure database management and search (http://www.chemaxon.com). Compounds were stored in the dark at 10 mM in DMSO before use in biological or biochemical assays.

Gene expression microarray analysis. Gene expression analysis was performed using ILLUMINA Human HT-12 BEADCHIP (Illumina, San Diego, Calif., USA). Total RNA was isolated from hTECs using the QIAGEN RNEasy kit (Qiagen) and was amplified and biotinylated using the Ambion Illumina TotalPrep Kit. Hybridization and scanning, including background correction, of Human HT-12 BeadChip arrays was performed according to the manufacturer's instructions, using BEADSTUDIO 3.0 software (Illumina) at the Washington University School of Medicine Genome Sequencing Center Microarray Core Facility. Microarray normalization and statistical analysis was performed using packages from the Bioconductor project executed in the R programming environment (Gentleman, R. C., et al. Genome Biol. 5:R80, 2004). Raw image data were imported into Bioconductor using read Illumina as implemented in the beadarray package with background subtraction and image sharpening. The resulting bead-level data was then normalized for intensity at the bead level using the HULK algorithm, to adjust for local spatial effects (i.e. cross-array gradients) (Dunning, M. J., et al. Bioinformatics. 23:2183-4, 2007; Cairns, J. M., et al. Bioinformatics. 24:2921-2, 2008; Lynch, A. G., et al., Stat. Methods Med. Res. 18:437-52, 2009). The data were then summarized for each bead type. A model-based variance stabilizing transformation, which generates values on a log 2 scale for compatibility with downstream analyses was applied to the bead-type summaries, followed by quantile normalization across the experiment using functions in the beadarray package. Bead-types not detected on at least 1 array (detection p<0.01) were then filtered to improve power to detect differentially expressed genes (Lin, S. M., et al. Nucleic Acids Res. 36:e11, 2008; Bolstad. B., et al. Bioinformatics. 19: 185-93, 2003; Hackstadt, A. J. and Hess, A. M. Bioinformatics. 10:11, 2009). Differential expression after 21 days of IL-13 treatment was assessed (IL-13 versus control) using linear models and empirical Bayes moderated F statistics as implemented in the LIMMA package (Smyth, G. K. Stat. Appl. Genet. Mol. Biol. 2004). Differences in gene expression were considered significant if P values were <0.05 after adjustment for multiple testing as described previously, so that false discovery rate was <5% (Benjamini, Y, and Hochberg, Y. J. R. Stat. Soc. B57: 289-300, 1995). Bead-types were annotated to genes using a combination of the manufacturer's annotation, transcript level annotations obtained from AceView, and annotations from the University of Cambridge Computational Biology Group in order to optimize interpretation of the gene expression data (Thierry-Mieg, D, and Thierry-Mieg, J. Genome Biol. 7 Suppl. 1. S12:11-4, 2006; Barbosa-Morais, N. L., et al. Nucleic Acids Res. 38:e17, 2010; Yin, J., et al. BMC Genomics. 11:50, 2010). Visualization and plotting was performed using TIBCO Spotfire DecisionSite for Functional Genomics (TIBCO Spotfire, Somerville, Mass., USA). Raw and processed microarray data were deposited in the National Center for Biotechnology Information Gene Expression Omnibus and are accessible through GEO Series accession number GSE37693 (Edgar, R., et al. Nucl. Acids Res. 30:207-10, 2002).

Real-time quantitative PCR assay. RNA was purified using the RNEASY kit (Qiagen, Valencia, Calif.) and reverse transcribed using High-Capacity cDNA Archive kit (Life Technologies, Carlsbad, Calif.). Target mRNA levels were quantified with real-time PCR using fluorogenic probe/primer combinations specific for CLCA1, CLCA2. CLCA4. MUC5AC, MAPK13, MAPK14, and GAPDH and TAQMAN FAST Universal master mix (Life Technologies). All PCR assays were quantitative and utilized plasmids containing the target gene sequences as standards. Sequences of the forward and reverse primers and probes were: 5'-AGTGTCA-CAGCCCTGATTGAATCAGTGAAT (SEQ ID NO: 1), 5'-AGTTGTGAAATACCTTGAGTAGACACCGT (SEQ ID NO: 2), and 5'-TAATGGAGCAGGTGCTGATGCTACTAA (SEQ ID NO: 3) for CLCA1; 5'-ACCCTATCTTGGACAG-CACC-TGGAGAA (SEQ ID NO: 4), 5'-CTTGGATATTCT-GTAGACTTTTACTCA (SEQ ID NO: 5) and 5'-TTTGAT-CAGGGCCAGGCTA-CAAGCTATGAA (SEQ ID NO: 6) for CLCA2; 5'TGGACATACAGAAGTTTTGGAACT (SEQ ID NO: 7), 5'-GCTGTA-AAATACCTGGAGTAGACT (SEQ ID NO: 8), and 5'-GATAATGGTGCAGGCGCTGAT-TCTTTCAAGAA (SEQ ID NO: 9) for CLCA4; 5'-AGGC-CAGCTACCGGGCCGGCCAGACCAT (SEQ ID NO: 10), 5'-GTCCCCGTACACGGCGCAGGTGGCCAGGCA (SEQ ID NO: 11), and 5'-TGCAACACCTGCACCTGTGACAG- CAGGAT (SEQ ID NO: 12) for MUC5AC; and 5'-CAGC-CGAGCCACA-TCCCTCAGACACCAT (SEQ ID NO: 13), 5'-CTTTACCAGAGTTAAAAGCAGCCCTGGTGACCA (SEQ ID NO: 14), and 5'-AGGTC-GGAGTCAAC-CGATTTGGTCGTATTG (SEQ ID NO: 15) for GAPDH. All probes were designed to span an intron and did not react with genomic DNA. Copy numbers of MAPK13 and MAPK14 mRNA were determined using pre-designed TAQMAN assays (Life Technologies). The cDNAs for CLCA1, CLCA2, GAPDH and a portion of MUC5AC were amplified by PCR from the RNA purified from hTECs and reversed transcribed to cDNA. The resulting PCR products were blunt cloned into PCR-Blunt vector (Invitrogen) and used as standards for the determination of the copy numbers of these genes. The plasmids encoding CLCA4, MAPK13 and MAPK14 were obtained from Thermo Scientific Open Biosystems (Huntsville, Ala.). All real-time PCR data was normalized to the level of GAPDH ($1 \times 10^7$ copies).

Immunostaining. Mouse anti-human MUC5AC biotin-conjugated mAb clone 45M1 was obtained from Thermo Lab Vision (Kalamazoo, Mich.). Rabbit anti-human CLCA1 antibody (designated #1228) was generated by peptide inoculation and peptide-based affinity purification using amino acids 681-693 as described previously (Gibson, A., et al. J. Biol. Chem. 280:27205-12, 2005). For immunocytochemistry, cells were fixed in 0.4% paraformaldehyde, permeabilized in PBS with 1% Tween-20), subjected to heat-induced epitope retrieval in 10 mM sodium citrate buffer (pH 6), blocked with Inage-It FX signal enhancer, with 2% fish gelatin (Sigma), and then incubated with anti-MUC5AC biotin-conjugated mAb and rabbit anti-CLCA1 antibody followed by ALEXA 488- or 555-conjugated streptavidin or ALEXA 555- or 633-conjugated goat anti-rabbit secondary Ab (Life Technologies), counterstained with SYTOX Green (Life Technologies) or DAPI (Life Technologies) and then imaged by conventional (Leica) or confocal (Zeiss LSM-510 META laser scanning confocal microscope) fluorescence microscopy. For immunohistochemistry, lung sections were incubated with citrate-based Antigen Unmasking Solution (Vector Labs, Burlingame, Calif.) for 10 min at 90° C. for antigen retrieval and then with biotinylated anti-MUC5AC mAb (2 µg/ml) and rabbit anti-CLCA1 Ab (10 µg/ml) in 70 mM NaCl, 30 mM HEPES, 2 mM $CaCl_2$, pH 7.4 with 1% BSA, 1% goat serum, and 0.1% cold water fish gelatin followed by 10 µg/ml ALEXA-488 conjugated streptavidin and 10 µg/ml Alexa-555 conjugated goat anti-rabbit IgG (Life Technologies) in the same buffer overnight at 4° C.

Generation of shRNA-expressing cells. Lentiviral vectors expressing small interfering RNA (siRNA) from short hairpin RNA (shRNA) were from the MISSION shRNA library (Sigma). A set of shRNA clones (constructed within the lentivirus plasmid pLKO.1-Puro) was obtained for each of the following mRNA targets: CLCA1 (NM_001285), MAPK13 (NM_002754) and MAPK14 (NM_001315). Lentiviral particles for each of the clones were generated by transfecting HEK 293T cells with shRNAi-pLKO.1-Puro plasmid, pHR'8.2deltaR packaging plasmid, and pCMV-VSV-G envelope plasmid using Fugene6 (Roche Applied Science, Indianapolis, Ind.) as the transfection agent (Stewart, S. A., et al. RNA. 9:493-501, 2003). The shRNA lentiviral particles were added to the apical and basal sides of hTEC cultures for 24 h at multiplicity of infection (MOI) 1 and then replaced with fresh media. Ten days later, cells were treated with or without IL13 as described above. Transduction efficiencies were 50-60% as determined using the MISSION Turbo-GFP control vector (SHC003, Sigma).

Cell-based ELISA for MUC5AC. Cells were fixed with 4% formaldehyde, rinsed with wash buffer (PBS with 0.1% Triton), incubated with blocking buffer containing 1× milk (BioFX Company, Owings Mills, Md.) for 1 h at 25° C., rinsed again, and incubated with mouse anti-human MUC5AC biotin-conjugated mAb clone 45M1 at 1:500 final dilution for 18 h at 4° C. Cells were then rinsed and incubated with neutravidin-horseradish peroxidase (Pierce Biotechnology, Rockford, Ill.) at a final dilution of 1:2000 for 1 h at 25° C. followed by developing solution (R&D Systems, Minneapolis, Minn.). The reaction was terminated using stop solution (R&D Systems) and absorbance measured at 450 nm. To normalize MUC5AC measurements for cell number per well, cells were washed again, incubated with 0.5% crystal violet solution for 30 min at 25° C., washed, incubated with 1% SDS (100 µl/well) for 1 h at 25° C., and assessed for absorbance at 595 nm. Values for MUC5AC levels were expressed as ratio of absorbance at 450 nm to absorbance at 595 nm.

Quantitative MUC5AC ELISA. To determine the level of MUC5AC in lung samples from COPD and control donors a quantitative MUC5AC ELISA was set up. The plasmid encoding the 45M1 epitope of MUC5AC was obtained from Dr. G. C. Hansson (Goteburg University, Gothenburg, Sweden). The recombinant protein was expressed in 293F cells and purified as described previously (Lidell, M. E., et al. FEBS J. 275:481-9, 2008). COPD and donor tissue was lysed in the mammalian protein extraction reagent (M-PER, Thermo Pierce Biotechnology) supplemented with Halt Protease & Phosphatase Inhibitor Cocktail (Thermo Pierce Biotechnology) and 5 mM EDTA. Protein concentration was determined using the BCA protein assay kit (Thermo Pierce Biotechnology). Protein cell lysates were plated on high binding Nunc Maxisorp ELISA plates (Thermo Nalge Nunc, Rochester, N.Y.) in carbonate-bicarbonate buffer pH 9.4 and incubated at 37° C. overnight. The recombinant standard of 45M1 was incubated at 4° C. The plates were washed with PBS-0.05% Tween-20 (Sigma) and blocked overnight with Sea Block blocking buffer (Thermo Pierce Biotechnology). The reaction was developed using the 45M1 biotin conjugated monoclonal antibody and Avidin-HRP using the I-Step UltraTMB-Elisa substrate (Thermo Pierce Biotechnology).

CLCA1 ELISA for cell culture samples. To determine CLCA1 level in cell lysates, a CLCA1 ELISA was developed using rabbit anti-N-CLCA1 antibody for detection and a purified recombinant CLCA1-3×FLAG containing amino acids 681-693 as a standard. The recombinant protein was expressed in 293 Tcells using the pCDNA3.1 vector (Life Technologies) and purified using anti-3×FLAG antibody (Sigma). ELISA plates (Thermo Scientific Nagle Nunc) were coated with 50-µl sample aliquots (1 µg/well total protein) or with varying concentrations of standard overnight at 4° C., washed, blocked with 3% fish gel in PBS for 2 h at 25° C., washed again, and anti-CLCA1 antibody was added at a final dilution of 1:100 for 1 h at 25° C. The plates were washed, and HRP-conjugated goat anti-rabbit secondary antibody (Santa Cruz) was added at 1:2000 dilution for 1 h at 25° C. Ab-binding was detected using color developing solutions (R&D Systems) with absorbance at 450 nm on a Spectra Max Plus plate reader (Molecular Devices, Sunnyvale, Calif.).

CLCA1 ELISA for lung tissue samples. To determine CLCA1 level in lung samples, a CLCA1 ELISA was developed based on anti-CLCA1 mAb (clone 8D3) for detection and purified recombinant CLCA1 as a standard. To generate the standard, a plasmid encoding the N-terminal portion of CLCA1 (amino acids 22-694) with a 6-His tag was expressed in 293F cells and purified by affinity chromatography. Lung tissue samples were lysed in M-PER reagent (Thermo Pierce Biotechnology) and cell lysates (10 μg/well) were plated in carbonate-bicarbonate buffer pH 9.4 overnight at 4° C. The plates were washed, blocked overnight with SEA BLOCK blocking buffer (Thermo Pierce Biotechnology), washed again, and anti-CLCA1 8D3 mAb was added at 1 μg/ml for 3 h. The plates were washed and HRP-conjugated Fab fragment of goat anti mouse IgG (H+L chains) antibody (Life Technologies) at 1:2000 was added for 1 h. After washing, Ab binding was detected using the I-Step Ultra TMB-ELISA substrate (Thermo Pierce Biotechnology) with absorbance at 450 nm on the Spectra Max Plus plate reader.

Generation of anti-CLCA1 mAb. To generate immunogen, N-CLCA1 was purified from baculovirus-infected insect cells (Hi5) in a customized pFastBac Dual vector in frame with an N-terminal honey bee mellitin signal sequence and C-terminal thrombin cleavage site followed by a 6-His tag. Recombinant baculovirus was generated in Sf9 insect cells. Recombinant N-CLCA1 was produced by infecting Hi5 cells cultured in serum-free ExCell 405 media. Culture supernatants were collected 72 hours post-infection and the proteins were purified to homogeneity using Ni-affinity chromatography followed by ion-exchange chromatography. Protein identity was verified by Western blot against the 6-His tag and purity was assessed by Coumassie-stained SDS-PAGE. For generation of mAbs. BALB/cJ mice were primed and boosted at 3-wk intervals with purified N-CLCA1 (50 μg) complexed with adjuvant. Approximately one month after the last boost, serum was harvested and tested for immunoreactivity against plate-immobilized N-CLCA1 purified from 293T cells. Mice with highest titers were boosted intravenously with N-CLCA1 (50 μg) and splenocytes were harvested 3 days later. Hybridomas were produced by fusion with P3X63Ag8.653 myeloma cells. Screening for positive clones was performed with ELISA using the pure insect-cell-generated N-CLCA1. Protein A/G chromatography was used to purify the mAbs. To screen hybridomas for anti-CLCA1 mAb production, ELISA plates (Thermo Scientific Nagle Nunc) were coated with recombinant purified N-CLCA1 overnight at 4° C., washed twice with 0.1% Triton in PBS, and then blocked with 3% fish gel in PBS for 2 h at 25° C. The plates were washed twice and hybridoma supernatants were added. The plates were washed, and HRP-conjugated goat anti-rabbit secondary antibody (Santa Cruz) was added at 1:2000 dilution for 1 h at 25° C. Plates were washed, and Ab-binding was detected using color developing solutions (R&D Systems) for absorbance at 450 nm on a Spectra Max Plus plate reader (Molecular Devices, Sunnyvale, Calif.).

Generation of CLCA1-expressing cell lines. To generate lung cell lines that stably expressed CLCA1 driven by the tetracycline-inducible gene promoter system, human lung mucoepidermoid carcinoma NCI-H292 cells were first transfected with pCMV-rtTA (rTetR-VP 16) (Clonetech, Mountain View, Calif.), and clones were selected with G418 (200 μg/ml). Clones with low background and high induction of luciferase gene expression when transfected with pTRE-Tight-luciferase (Clonetech) and treated with doxycycline (10 μg/ml) were selected for a second transfection with a TRE-driven CLCA1-expressing plasmid. Cell lines (NCI-H292-rtTA-CLCA1) with stable expression of pCMV-rtTA and pTRE-CMV-CLCA1 were selected with G418 and hygromycin (20 μg/ml). The CLCA1 gene (including Kozak sequence) was cloned from hTEC RNA using PCR and was inserted into pTRE-Tight using 5'-NotI and 3'-EcoRV restriction enzyme sites. All constructs were verified by DNA sequencing.

MAPK phospho-arrays. MAPK activation was assessed using a human phospho-MAPK antibody array (Proteome Profiler MAPK Array, R&D Systems) according to the manufacturer's instructions. The chemiluminescent signal from the arrays was captured on film, digitized with a UMAX PowerLook 1120 scanner and SilverFast Ai software, and quantified with ArrayVision 8.0 software (GE Healthcare Biosciences, Pittsburgh, Pa.).

Gene knockdown with siRNA. MAPK13 or MAPK14 STEALTH RNAi (Life Technologies) was transfected into NCI-H292-rtTA-CLCA1 cells using Lipofectamine RNAiMax (Life Technologies). For transfection, lipofectamine (2.5 μl) was mixed in RPMI-serum free media (200 μl) with RNAi (25 nM) by shaking for 30 min at 25° C. Cells were then incubated in the RNAi-Lipofectamine mixture for 24 h at 37° C., and then treated with doxycycline for an additional 24 h. Cellular RNA was isolated and reversed transcribed using the High Capacity cDNA Archive kit (Life Technologies), and target mRNA levels were determined by quantitative RT-PCR.

Human subjects. Lung tissue was obtained from the explanted lungs of 9 patients with very severe (GOLD Stage IV) COPD at the time of lung transplantation as described previously (Tyner, J. W., et al. J. Clin. Invest. 116:309-21, 2006; Kim, E. Y., et al. Nat. Med. 14:633-40, 2008; Agapov, E., et al. Am. J. Respir. Cell Mol. Biol. 41:379-84, 2009). Excess lung tissue from four lung transplant donors without COPD was used as a control. The University Human Studies Committee approved all protocols, and all subjects provided informed consent for participation in the study.

MAPK inhibitor assay. The MAPK13 blocking activity of test compounds was determined using an immobilized metal affinity polarization (IMAP) assay containing activated MAPK13, FITC-labeled substrate, and test compound. Full-length 6-His-tagged MAPK13 and constitutively active GST-MKK6 were prepared as described below. Activated MAPK13 was generated in 50 mM Hepes, 10 mM $MgCl_2$ and 1 mM DTT, containing 1 μM MAPK13, 2 μM MKK6 and 50 μM ATP for 1 h at 25° C. MKK6 was removed by incubation with glutathione SEPHAROSE 4B beads (GE Healthcare Biosciences). MAPK13 activation was confirmed by Western blot using anti-phospho-p38-MAPK (T180/Y182) antibody (R& D Systems, Minneapolis, Minn.). IMAP assays were performed in 96-well non-treated half-area black plates or 384-well black plates (Corning Inc., Corning, N.Y.) in a final reaction volume of 20 μl using the linear phase of the rate kinetics. Assay reactions contained 0-100 μM test compound, 5-35 nM ($EC_{80}$) activated MAPK13, 3 μM ($K_{m.app}$) ATP, and 100 nM FITC-labeled EGFR peptide substrate (FITC-KRELVERLTPSGEAPNQALLR-$NH_2$), which was a kind gift from John Schindler (Washington University). The reaction proceeded for 20 min at 25° C. in 10 mM Tris-HCl, 10 mM $MgCl_2$, 0.1% BSA, 0.05% $NaN_3$, 1 mM DT, pH 7.2 after which 60 μl of tri-valent metal nanoparticles containing IMAP binding reagent (Molecular Devices, Sunnyvale, Calif.) was added for 80 min at 25° C. The IMAP binding reagent was optimized at 1:600 (vol/vol) based on the number of acidic residues in the peptide substrate. Fluorescence polarization was measured with a Biotek Synergy 4 multi-mode plate reader (Biotek, Winooski, Vt.) with excitation at 485 nm and emission at 528 nm. The $IC_{50}$ values for each compound were determined from the compound concentration versus fluorescence polarization (mP) plot using nonlinear curve fitting with GraphPad Prism software (Graphpad Software, La Jolla, Calif.).

MAPK purification for biochemical assays and crystallization. Full-length human MAPK13 (1-365) and MAPK13 crystallization construct (1-352) were cloned into pET28a as N-terminal 6-His-tagged constructs. A constitutively active mutant MKK6-GST fusion construct (GST-MKK6 Glu) was a gift from Peiqing Sun (Scripps, La Jolla, Calif.). A pET28a construct of λ-phosphatase was a gift from Dima Klenchin (University of Wisconsin, Madison, Wis.). All constructs were confirmed by sequencing and transformed into Rosetta2 (DE3) *E. coli* (EMD Millipore, Billerica, Mass.) and expressed as soluble proteins that were purified using the specific affinity tags followed by gel filtration chromatography. The MAPK13 proteins expressed in *E. coli* displayed a high degree of auto-phosphorylation, so they were dephosphorylated with λ-phosphatase prior to final purification by ion exchange (Mono Q). All buffers used during purification (lysis, column, and storage) of MAPK13 required addition of 10% glycerol and 1-5 mM reducing agent (either β-mercaptoethanol or DTT) to prevent precipitation of the recombinant protein. The final purified MAPK13 for crystallization was stored in buffer containing 20 mM Hepes pH 7.5, 150 mM NaCl, 10% glycerol, and 1 mM DTT.

Figure 9:
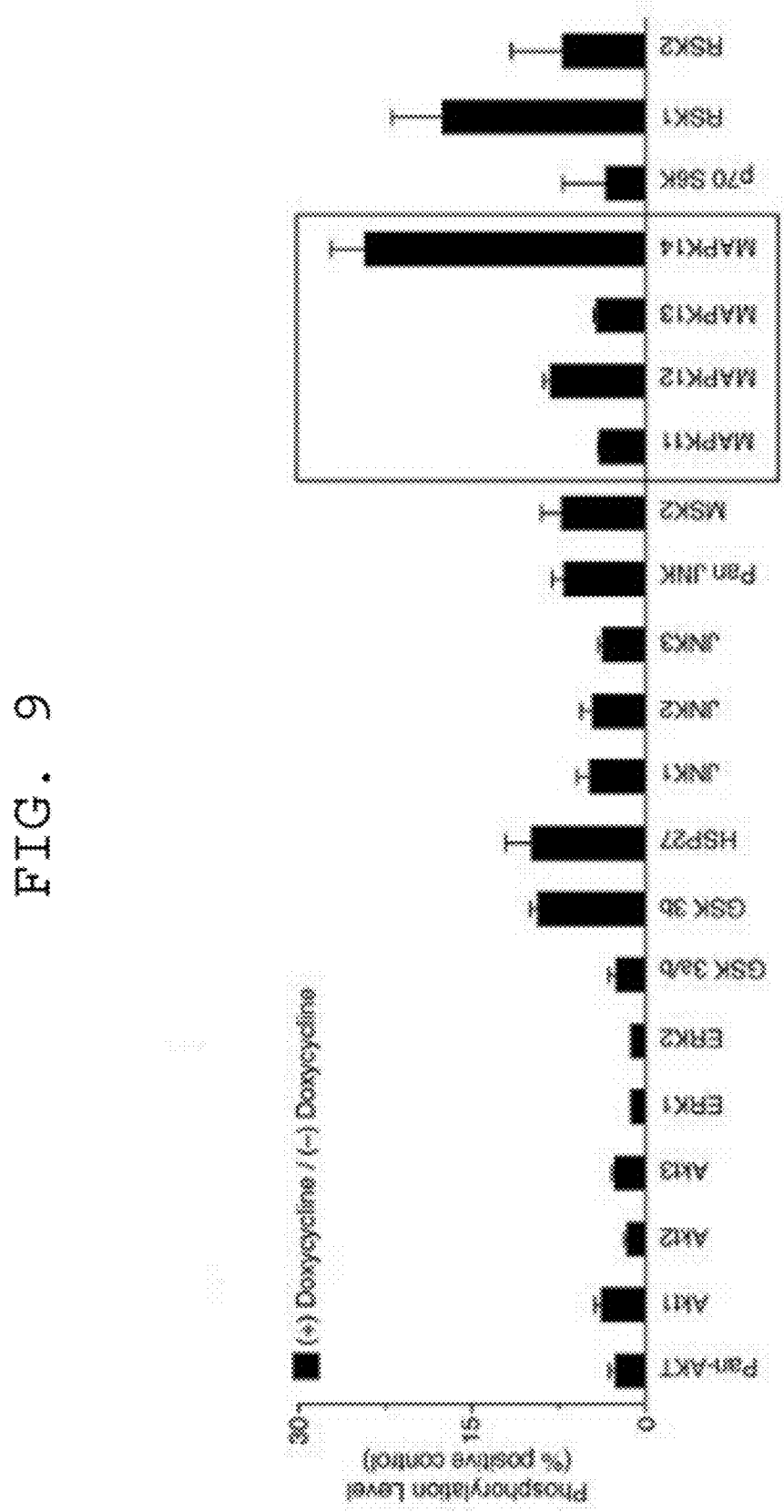
FIG. 9 illustrates the effect of CLCA1 induction on MAPK activation.

MAPK crystallization, x-ray diffraction data collection, and structure determination. Crystals of non-phosphorylated MAPK13 were obtained by mixing protein solution (at 10 mg/ml) with reservoir solution (50 mM ammonium tartrate, 18% PEG 3350) in a 4:1 (protein:reservoir) ratio. The non-phosphorylated MAPK13 crystals were used to obtain structures of MAPK13 in complex with compounds by soaking. Briefly, compounds dissolved in DMSO at a concentration of 100 mM were added to crystallization drops at one-tenth volume for a final concentration of 10 mM compound in the drop. Crystals were allowed to soak for 3-5 hours. Crystals were cryoprotected by addition of 25% glycerol and stream-frozen at 100° K. X-ray diffraction data were collected at Advanced Photon Source beamline 19ID (non-phosphorylated) and Advanced Light Source beamline 4.2.2 (Compound 61 and 124). Data were processed using HKL-2000 software (Otwinowski, Z, and Minor, W. Methods in Enzymology: Macromolecular Crystallography. Vol. 276 (eds. Carter. C. W. J. & Sweet, R. M.) 307-326 (Academic Press, New York, 1997). The phase problem was solved by molecular replacement using Phaser crystallographic software (McCoy, A. J., et al. J. Appl. Crystallogr. 40:658-74, 2007). For non-phosphorylated MAPK13 the probe structure was a deposited structure of MAPK13 from a structural genomics project (PDB code: 3COI). Although our structure displayed similar crystal packing to the previously deposited one, there were noticeable large differences in the C-terminal region revealed in our high-resolution structure (FIG. 9). The structures of MAPK13 with compounds were isomorphous to the non-phosphorylated structure, so they were determined by rigid body refinement. Compounds were clearly visible in Fo–Fc difference maps following rigid body refinement (FIG. 1). Compounds were fit to electron density maps manually using Coot software and refinement carried out in PIHENIX software (Emsley. P., et al. Acta. Crystallogr. D. Biol. Crystallogr. 66:486-501, 2010; Adams, P. D., et al. Acta. Crystallogr. D. Biol. Crystallogr. 66:213-21, 2010). Ramachandran analysis was as follows (% favored/% percent outliers): non-phosphorylated, 95.6/0.6; compound 61, 96.1/0.3; compound 124, 95.5/0.9. Final coordinates and experimental structure factors were deposited in the RCSB Protein Data Bank with following codes: 4EXU, 4EYJ, and 4EYM. Data collection and refinement statistics are provided in Table 3. All molecular graphics figures were produced using PyMOL.

MAPK13/small molecule binding assay. Kinetics of MAPK13 binding to small molecules was assessed using bio-layer interferometry with an Octet (ForteBio, Menlo Park, Calif.). Super-streptavidin-coated biosensors from ForteBio were used to capture biotinylated MAPK13 onto the surface of the sensor. After reaching baseline, sensors were moved to association step containing 2500, 1250, 625, 312.5, or 156.3 nM inhibitor for 300 s and then dissociated for 300 s. Curves were corrected by a double-referencing technique using both biotin-coated pins dipped into the experimental wells and a buffer-only reference. The running buffer consisted of 10 mM Hepes pH 7.5, 150 mM NaCl, 0.05% Tween, and 5% DMSO. Half-lives were calculated from dissociation constants determined from global kinetic analysis.

Statistical analysis. Values for gene expression were analyzed using a one- or two-way analysis of variance (ANOVA) as appropriate for a factorial experimental design. PCR data was compared by unpaired Student's t-test with Welch's correction for unequal variances when appropriate. Inhibitor effects were analyzed using two-way ANOVA. Significance level for all analyses was 0.05.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates that hCLCA1 controls mucin gene expression.

Figure 8:
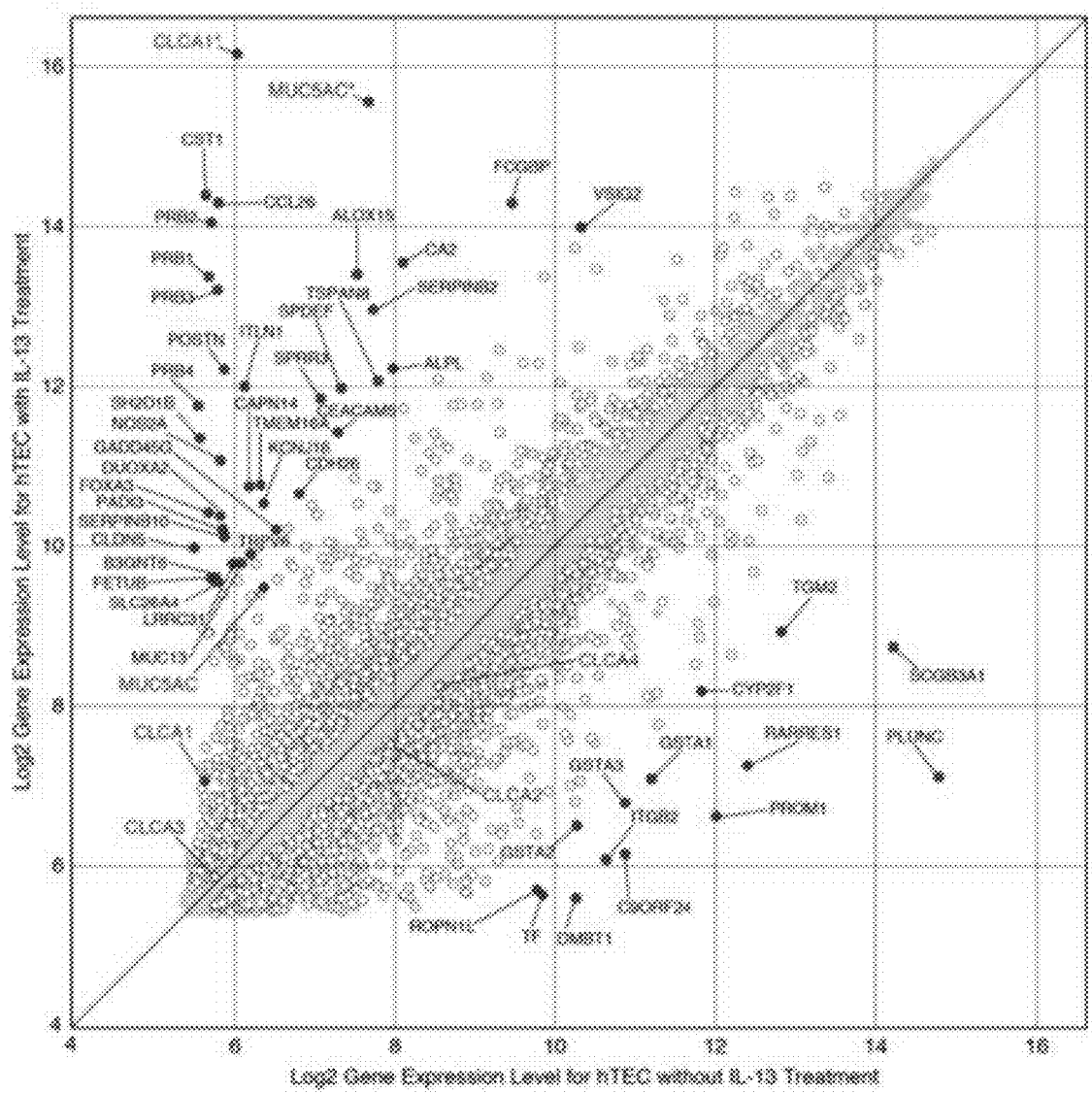
FIG. 8 illustrates IL-13-driven gene expression in human airway epithelial cells.

Human tracheal epithelial cells (hTECs) were incubated with IL-13 (50 ng/ml) under submerged conditions for 2 d and then air-liquid interface conditions for up to 21 d, and cell lysates were analyzed for hCLCA1, hCLCA2, and hCLCA4 mRNA levels by real-time quantitative PCR (qPCR) assay. Human CLCA1 but not CLCA2, CLCA3, or CLCA4 gene expression was increased in concert with IL-13 induction of mucous cell metaplasia (signified by increased MUC5AC mRNA) in well-differentiated human airway epithelial cells (FIG. 1*a,b*). Levels of CLCA2 and CLCA4 were detectable and were increased during differentiation under air-liquid interface conditions, but neither was increased by IL-13 treatment. Levels of CLCA3 mRNA were undetectable under these conditions. Whole genome microarray analysis of gene expression showed significant upregulation of CLCA1 and MULC5AC mRNA levels relative to all other genes (FIG. 8). The increases in CLCA and MUC5AC mRNA resulted in corresponding increases in CLCA1 and MUC5AC protein levels (FIG. 1*c,d,e*). FIG. 1*c* shows corresponding levels of CLCA1 in cell lysate and apical cell supernatant determined by ELISA. FIG. 1*d* shows corresponding levels of MUC5AC determined by cell-based ELISA. FIG. 1*e* shows corresponding immunocytochemistry for DAPI, CLCA1, and MUC5AC using confocal microscopy. Scale bar: 50 μm. FIG. 1*f* shows corresponding immunocytochemistry at a more apical (high z axis) and subjacent (low z axis) cellular location. Arrows indicate the same reference cells for high and low z axis. Scale bar: 50 μm.

FIGS. 1*c* and *d* show that increases in CLCA1 and MUC5AC mRNA resulted in corresponding increases in CLCA1 and MUC5AC protein levels, with significant detection of these proteins in cell lysate and apical cell supernatant.

FIG. 1e and f show confocal microscopy of IL-13-stimulated hTECs immunostained for CLCA1 and MUC5AC. These figures show colocalization in a spatial pattern of apical MUC5AC coupled with subjacent CLCA1.

Next, levels of hCLCA1 and MUC5AC mRNA in hTECs, which were transduced with lentivirus encoding hCLCA1 or control shRNA, were determined. Specific siRNA-mediated knockdown of CLCA1 expression caused quantitative inhibition of IL-13-driven mucous cell metaplasia (FIG. 1g,h). Corresponding hCLCA1 and MUC5AC protein levels were determined by ELISA. All values represent mean±SEM, and (*) indicates a significant increase from corresponding no IL-13 treatment control or decrease from no shRNA treatment.

The degree of siRNA-mediated inhibition was similar to transfection efficiencies achieved with shRNA-encoding lentivirus in this primary cell-culture system for human tracheal epithelial cells (hTECs). These results show that CLCA1 can be a master regulator of the IL-13 to mucin gene expression signaling pathway, and in contrast to the mouse system, appears to function without redundancy from other CLCA gene products.

Example 2

This example illustrates that CLCA1 induces mucin gene expression through MAPK13.

To determine the signaling mechanism for CLCA1-dependent induction of mucin gene expression, NCI-H292 cells were used (derived from a lung mucoepidermoid carcinoma) to establish a cell line with stable expression of the CLCA1 gene under the control of a doxycycline-inducible promoter system (as diagrammed in FIG. 2a).

Figure 2B:
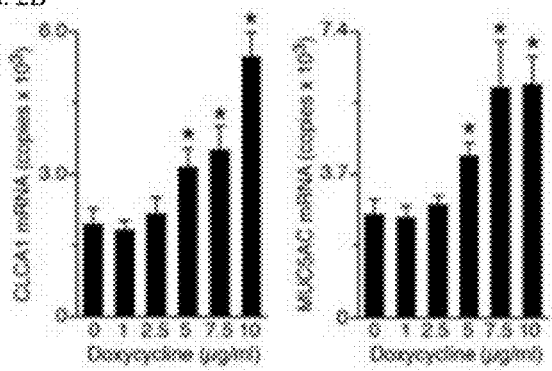
Figure 2C:
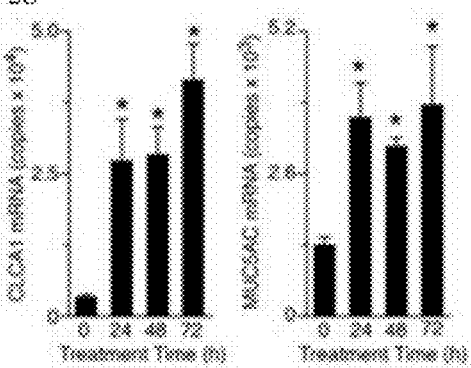
Figure 2D:
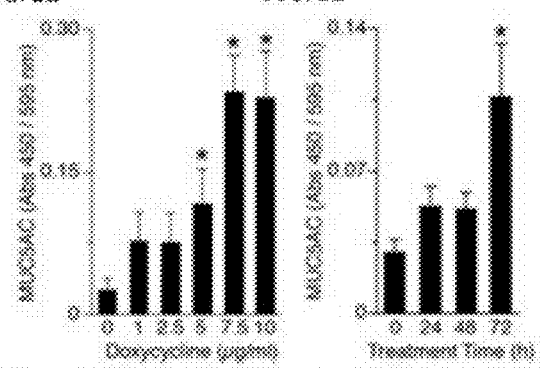
Figure 2E:
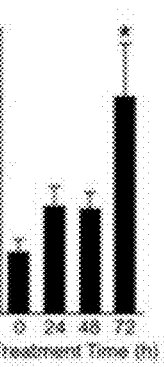
Figure 2F:
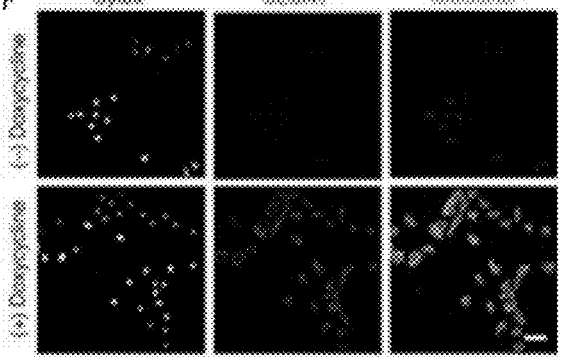

To show this cell line with stably expressed CLCA1 gene behaved similarly to hTECs, cells were treated with doxycyline (0-10 µg/ml) for 48 h, and hCLCA1 and MUC5AC mRNA levels were determined by real-time qPCR assay. Analysis of NCI-H292-rtTA-CLCA1 cells indicated that expression of CLCA1 was sufficient for mucin gene expression based on time- and dose-dependent induction of CLCA1 and MUC5AC gene expression (FIG. 2b,c). Time course for mucin gene expression in NCI-Ht92-rrTA-hCLCA1 cells seen in FIG. 2c was determined by treating cells with doxycycline (7.5 µg/ml) for 0-72 h. Dose-response for mucus protein levels in NCI-H292-rtTA-hCLCA1 cells was determined by treating cells with doxycycline for 48 h and MUC5AC level was determined by cell-based ELISA. Time course for mucus protein levels in NCI-H92-rrTA-hCLCA1 cells was determined by treating cells with doxycycline (7.5 µg/ml for 0-72 h), and MUC5AC level was determined by ELISA. As similar to primary hTECs in Example 1, the increases in CLCA1 and MUC5AC mRNA levels were accompanied by concomitant increases in hCLCA1 and MUC5AC protein (FIG. 2d,e,f).

To determine the downstream signaling from the CLCA1 gene product using phospho-MAPK antibody arrays to screen for any possible MAPK activation subsequent to doxycycline-activation of CLCA1 expression, NCI-H292-rtTA-hCLCA1 cells were treated with doxycycline (7.5 µg/ml for 18 h) with or without BIRB-796 (10 µM), and cell lysates were analyzed by phospho-MAPK antibody array. Doxycycline treatment of NCI-H292-rtTA-CLCA1 cells caused time-dependent activation of twelve MAPKs (FIG. 3a). Box indicates results for MAPK values. Values represent percent of positive control (mean±SEM), and (*) indicates a significant increase from corresponding no doxycycline control. The largest doxycycline-induced increase in MAPK phosphorylation (doxycline treatment versus no treatment) was found for MAPK14 (also known as p38α-MAPK) (FIG. 3a and FIG. 9), consistent with MAPK14 inhibitor blockade of cytokine-induced MUC5AC gene expression in airway epithelial cells (Atherton, H. C., et al. Am. J. Physiol. Lung Cell Mol. Physiol. 285:L730-9, 2003; Song, K. S., et al. J. Biol. Chem. 278:23243-50, 2003). However, blockade was only achieved at high concentrations of inhibitor that may no longer be specific for MAPK14. Moreover, others found no effect of MAPK14 inhibitors on PMA-induced MUC5AC expression in NCI-H292 cells or airway epithelial cells (Hewson, C. A., et al. J. Mol. Biol. 344:683-95, 2004; Yuan-chen Wu, D., et al. Am. J. Pathol. 170:20-32, 2007). Unexpectedly, a similarly large increase in phosphorylation of MAPK13 (p38δ-MAPK) was observed, which has no certain function in this cell system or others, especially relative to other MAPK family members.

Next, NCI-H292-rtTA-hCLCA1 cells were treated with doxycycline (7.5 µg/ml for 18 h) with other concentrations of BIRB-796, SB203580, and vehicle control, and levels of hCLCA1 and MUC5AC mRNA were determined by real-time qPCR assay. Corresponding MUC5AC level were determined by cell-based ELISA. BIRB-796, which blocks MAPK11-14, inhibited doxycyline-induced MUC5AC mRNA and protein production, whereas SB203580, which blocks only MAPK11 and MAPK14 (Kuma, Y., et al. J. Biol. Chem. 280:19472-9, 2005), did not inhibit MUC5AC synthesis (FIG. 3b,c).

To determine the role of MAPK13 in the regulation of mucin gene expression, MAPK13 RNAi was used to suppress expression. Cells were transfected with or without control or MAPK13 or MAPK14 siRNA, (25 nM), treated with or without doxycycline (7.5 µg/ml for 48 h), and levels of MAPK13, MAPK14, MUC5AC and hCLCA1 mRNA were determined by real-time qPCR. Corresponding MUC5AC protein levels were determined by cell-based ELISA. Suppression of MAPK13 expression (using two different RNAi sequences) did not influence doxycyline-induced expression of CLCA1 but completely blocked expression of MUC5AC gene expression (FIG. 3d,e). Treatment with MAPK14 RNAi did not block doxycycline-induced MUC5AC synthesis or affect CLCA1 mRNA levels (FIG. 3d,e). Blockade of MUC5AC mRNA induction was reflected in inhibition of corresponding MUC5AC protein levels (FIG. 3f). These results placed MAPK13 downstream of CLCA1 and upstream of MUC5AC gene expression in NCI-H292 cells.

A similar influence of MAPK13 over mucin gene expression was found in primary-culture hTECs. hTECs were incubated with IL-13 (50 ng/ml) under submerged conditions for 2 d and then air-liquid interface conditions for up to 21 d with or without BIRB-796 or SB203580, and levels of hCLCA1 and MUC5AC mRNA were determined by real-time qPCR assay. Corresponding MUC5AC protein levels were determined by cell-based ELISA. MAPK blockade with BIRB-796 markedly suppressed IL-13-induced MUC5AC gene expression without affecting corresponding CLCA1 levels whereas treatment with SB203580 had no significant effect on CLCA1 or MUC5AC gene expression (FIG. 4a,b). hTECs were then transduced with lentivirus encoding MAPK13, MAPK14, or control shRNA and then were treated with IL-13 (50 ng/ml) under submerged conditions for 2 d and then air-liquid interface conditions for up to 21 d. Cell lysates were analyzed for hCLCA1, MUC5AC, MAPK13, and MAPK14 mRNA levels using real-time PCR. Corresponding levels of MUC5AC protein was determined by cell-based ELISA. Suppression of MAPK13 expression (using two different shRNA sequences delivered with a lentiviral vector) did not influence IL-13-induced expression of CLCA1 but significantly blocked the expected increase in MUC5AC mRNA and protein levels (FIG. 4c,d). In this system, lentiviral transfection efficiencies of 40-50% resulted in a similar quantitative decrease in MAPK13 and MUC5AC mRNA and protein levels. Transduction of airway epithelial cells with lentivirus encoding MAPK14 shRNA achieved a similar selective decrease in target mRNA but showed less influence on IL-13-induced MUC5AC gene expression or CLCA1 mRNA levels. Blockade of MUC5AC mRNA induction was reflected in inhibition of corresponding MUC5AC protein levels (FIG. 4e).

Example 3

This example illustrates that IL-13 activation of CLCA1-MAPK13 signaling pathway for mucin genes found in human airway epithelial cells in culture can be activated in human lungs in vivo during chronic obstructive lung disease.

In these experiments, the status of CLCA1 expression and signaling in humans with mucus overproduction and mucous cell metaplasia was analyzed. For these experiments, whole lung explants from lung transplant recipients with very severe COPD (GOLD Stage IV) as well as control tissue from lung donors who did not have COPD (see Table 2 below) were obtained.

This approach avoids the acute effects of cigarette smoke, since transplant recipients and lung donors were not current cigarette smokers. RNA from lungs of COPD) and non-COPD control patients was assayed for IL-13, hCLCA1, MAPK13, and MUC5AC mRNA levels using real-time qPCR. All values represent mean±SEM (n=9 COPD patients and 4 non-COPD controls). Under these conditions, the lung tissue obtained from subjects with COPD contained significant increases in IL-13 and MUC5AC gene expression (as noted previously) as well as increased CLCA1 and MAPK13 gene expression (FIG. 5a). Levels of hCLCA1 and MUC5AC were determined by ELISA. The increases in CLCA1 and MUC5AC mRNA were also reflected in increased levels of the corresponding proteins (FIG. 5b). Immunostaining of lung tissue samples demonstrated co-localization of CLCA1 and MUC5AC in mucosal mucous cells (FIG. Sc). Next, cell lysates from lungs of COPD and non-COPD patients were subjected to phospho-MAPK antibody array. Increases in CLCA1 and MAPK13 gene expression are accompanied by significant increases in MAPK13 activation that are relatively prominent compared to other MAPKs (FIG. 5d). Thus, IL-13 activation of CLCA1-MAPK13 signaling pathway for mucin genes found in human airway epithelial cells in culture can be activated in human lungs in vivo during chronic obstructive lung disease.

TABLE 2

Clinical characteristics of COPD subjects used for analysis of lung tissue. Values represent mean ± SD.

| Characteristic | Value |
|---|---|
| N (female/male) | 9 (4/5) |
| Age (years) | 59.1 ± 5.3 |
| FEV$_1$ (L) | 0.63 ± 0.11 |
| FEV$_1$ (% predicted) | 20.1 ± 4.8 |
| FVC (L) | 2.39 ± 0.88 |
| FVC (% predicted) | 59.2 ± 17.1 |
| FEV$_1$/FVC | 0.30 ± 0.11 |
| DLCO | 6.88 ± 3.10 |
| DLCO (% predicted) | 28.1 ± 6.8 |

TABLE 2-continued

Clinical characteristics of COPD subjects used for analysis of lung tissue. Values represent mean ± SD.

| Characteristic | Value |
|---|---|
| Smoking history | |
| Packs per day | 1.31 ± 0.33 |
| Years smoked | 28.1 ± 10.5 |
| Pack-years | 41.7 ± 27.4 |
| Years quit | 6.7 ± 5.8 |

Example 4

This example illustrates a potent and effective action of rationally designed MAPK13 inhibitors in blocking IL-13-induced mucus production in a high-fidelity system of primary-culture human airway epithelial cells.

Figure 10:
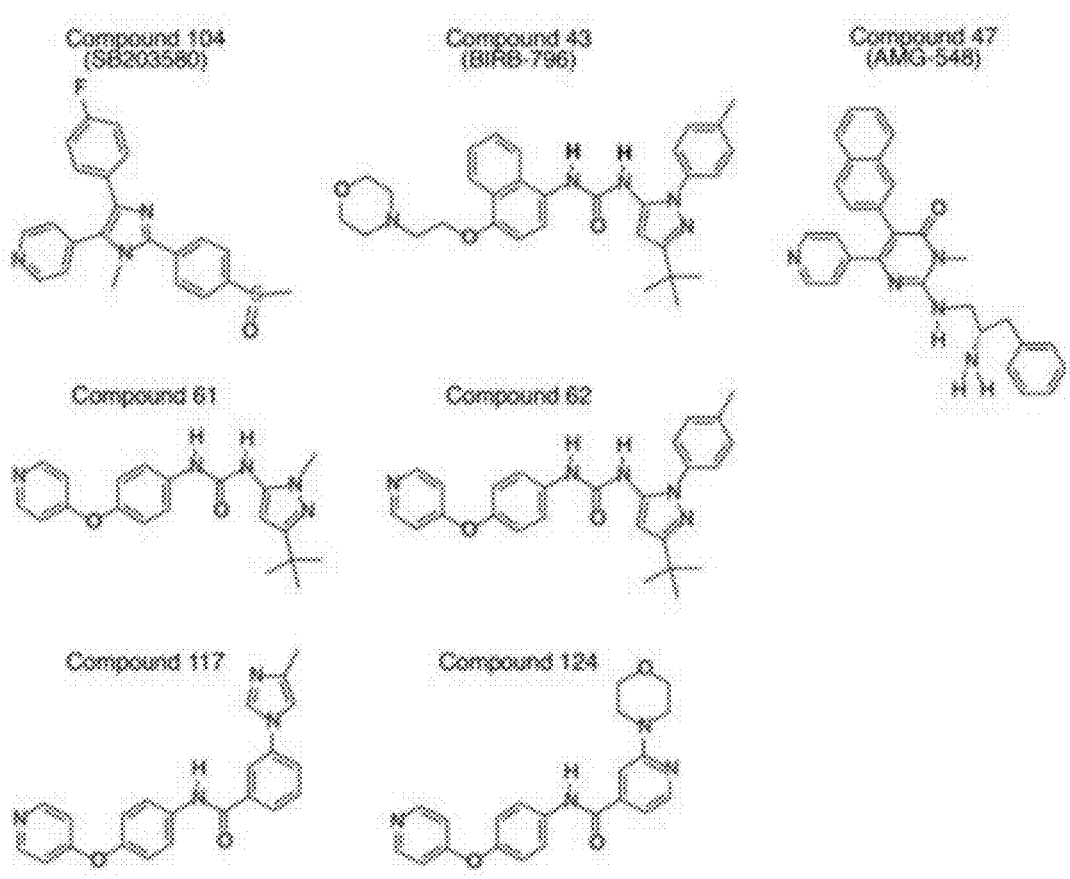
FIG. 10 illustrates the chemical structures of known and newly-generated inhibitor for MAPK3 and MAPK14.
Figure 11:
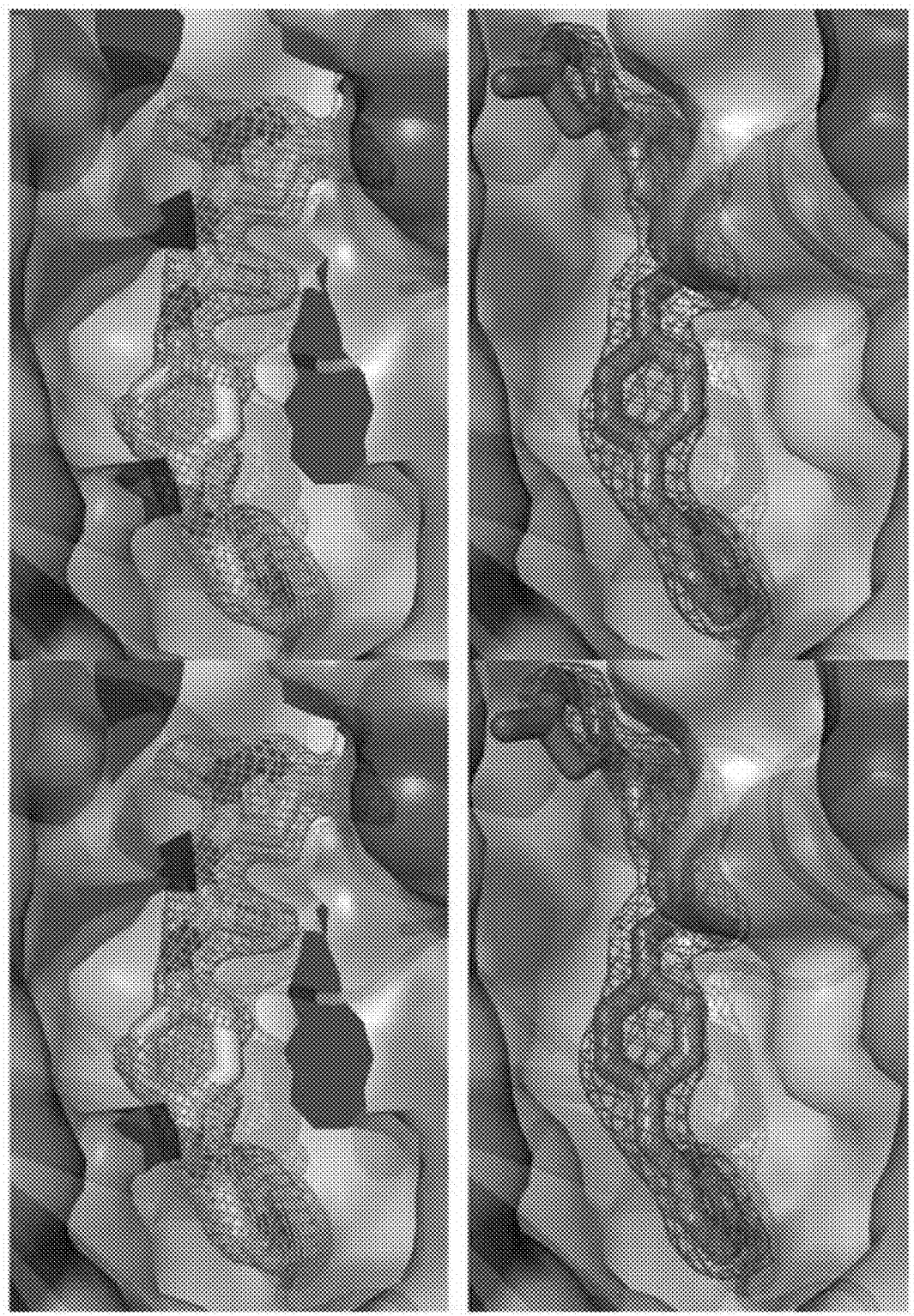
FIG. 11 illustrates the side-by-side stereo view of compound 61 and compound 117 co-crystal structures with MAPK13.

To develop a potent MAPK13 inhibitor, a ligand hopping strategy was utilized which took advantage of MAPK13 and MAPK14 homology (60% sequence identity) and thereby design new analogs of MAPK14 inhibitors with improved affinity for MAPK13. BIRB-796 exhibited potent inhibition of MAPK14 (the original target for this compound), but relatively weak activity for MAPK13 (Kuma, Y., et al. J. Biol. Chem. 280:19472-9, 2005). The selectivity of BIRB-796 for MAPK14 is based largely on incorporating a bulky moiety that readily occupies a distinct pocket in MAPK14 that is not present in MAPK13. Access to this pocket is controlled by an adjacent gatekeeper residue, which is a small threonine in MAPK14 compared to a large methionine in MAPK3. To initiate the structure-based drug design approach, inactive apo-MAPK13 was crystallized and the structure was determined to high resolution. Overlay was created by superposition of MAPK14 backbone coordinates from the MAPK4/BIRB-796 co-crystal structure (PDB ID: 1KV2 [REF PMID 11896401]) onto MAPK13. Indeed, superposition of the MAPK14-BIRB-796 co-crystal structure onto MAPK13 revealed steric interference between the inhibitor and the gatekeeper methionine (FIG. 6a, FIG. 10, and FIG. 11). In FIG. 6a, position of the gatekeeper methionine (Met 107) is highlighted and shown in CPK while regions encompassing the ATP binding pocket and Phe pocket are circled. Therefore, BIRB-796 was used as a starting compound to build slimmer analogs that might exhibit greater potency for MAPK13 by eliminating the steric clash while maintaining other beneficial structural features. Of particular interest is BIRB-796 because it binds to MAPK14 in the Asp-Phe-Gly (DFG)-out mode (Pargellis, C., et al. Nat. Struct. Biol. 9:268-72, 2002). This mechanism results in rotation of the conserved DFG motif out of the Phe-binding pocket (i.e., DFG-out) and thereby produces a prolonged off-rate (Pargellis, C., et al. Nat. Struct. Biol. 9:268-72, 2002; Kuglstatter, A., et al. Bioorg. Med. Chem. Lett. 20:5217-20, 2010).

With the aid of protein structure modeling, analogs were designed and synthesized that incorporated a smaller monoaryl ring in place of BIRB-796's bulky naphthalene to prevent clashing with the gatekeeper methionine (FIG. 12). Further, a structure-based drug design strategy was incorporated by producing co-crystals of new analogs bound with MAPK13 to aid in analog design (FIG. 6b,c and Table 3). Slimmer analogs were found to bind to MAPK13 in the expected manner (FIG. 6b,c). Moreover, analogs with DFG-out binding (e.g., Compound 61) exhibited slow-off binding kinetics while those exhibiting DFG-in binding (e.g., Compound 117) did not (FIG. 6d,e).

TABLE 3

Data collection and refinement statistics for MAPK13 complexes with inhibitor compounds.

| Compound | None | 61 | 117 |
|---|---|---|---|
| Data collection statistics | | | |
| Space group | $P2_12_12_1$ | $P2_12_12_1$ | $P2_12_12_1$ |
| Cell dimensions | | | |
| a, b, c (Å) | 60.9, 69.4, 92.5 | 60.9, 69.9, 92.8 | 61.3, 69.7, 93.1 |
| α, β, γ (°) | 90, 90, 90 | 90, 90, 90 | 90, 90, 90 |
| Resolution (Å) | 50.0-1.70(1.76-)* | 50.0-2.10(2.18-) | 50.0-2.00(2.07-) |
| $R_{sym}$ or $R_{merge}$ | 0.065(0.504) | 0.068(0.360) | 0.055(0.369) |
| I/σI | 29.6(4.1) | 25.9(4.7) | 21.6(2.5) |
| Completeness (%) | 99.3(99.7) | 90.4(98.9) | 81.2(87.8) |
| Redundancy | 6.7(6.9) | 6.4(6.0) | 4.6(4.4) |
| Refinement statistics | | | |
| Resolution (Å) | 35.0-1.70 | 35.0-2.10 | 35.0-2.00 |
| No. reflections | 43514 | 21034 | 22378 |
| $R_{work}/R_{free}$ | 0.201/0.220 | 0.242/0.275 | 0.218/0.262 |
| No. atoms | | | |
| Protein | 2781 | 2753 | 2776 |
| Ligand/ion | 0 | 27 | 28 |
| Water | 319 | 277 | 171 |
| B-factors | | | |
| Protein | 32.4 | 37.1 | 54.5 |
| Ligand/ion | N.A. | 26.9 | 34.9 |
| Water | 42.3 | 40.6 | 44.3 |
| R.m.s. deviations | | | |
| Bond lengths (Å) | 0.003 | 0.004 | 0.002 |
| Bond angles (°) | 0.739 | 0.844 | 0.792 |

*Values in parentheses are for highest-resolution shell.

In concert with this structural analysis, analogs for MAPK13 inhibitory activity were tested using an immobilized metal affinity polarization (IMAP) assay that detected fluorescence polarization as a function of remaining MAPK13 activity. Among the compounds with determination of co-crystal structure, those with the most potent MAPK13 inhibition (e.g., Compounds 61 and 62) were those with the DFG-out mode of MAPK engagement (FIG. 6f). AMG-548 exhibited weak inhibitory activity consistent with lower affinity for MAPK13 compared to MAPK14. More detailed 16-point inhibitor concentration-response curves were performed for the highest potency compounds. This analysis also showed that the most active DFG-out compounds (i.e., 61 and 62) were more potent than DFG-in compounds (i.e., 117 and 124) and compared favorably with less selective inhibitors designed to inhibit MAPK14 (i.e., AMG-548 and SB203580) (FIG. 6g and Table 4).

Figure 13:
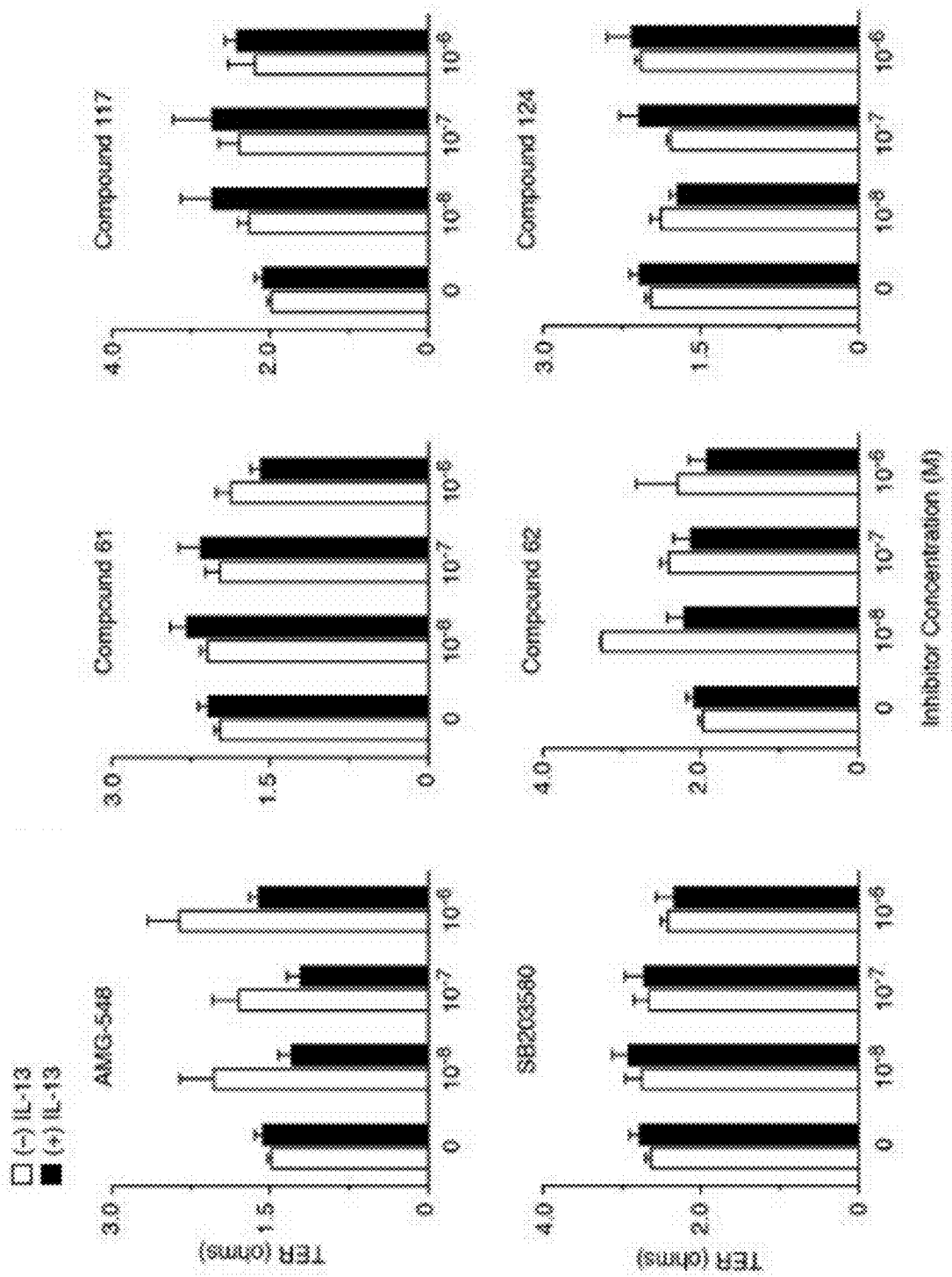
FIG. 13 illustrates the effect of tool compounds on transepithelial resistance.

Next, each of the tool compounds were tested for the effect on mucus production relative to the compounds designed and reported to inhibit MAPK14. Treatment with Compounds 61 and 62 markedly suppressed IL-13-induced MUC5AC production in primary-culture human airway epithelial cells whereas treatment with SB203580 had no significant effect in this system (FIG. 6h). The concentrations and relative compound potencies for blockade of mucus production correlated closely with the comparable values for MAPK13 inhibition (as presented in FIG. 6f, g and Table 4). The most effective compound (#62) achieved an IC50 for blockade of mucus production at less than $10^{-8}$ M. Moreover, none of the tested compounds caused any significant change in transepithelial resistance even at $10^{-6}$ M, indicating the lack of any cytotoxic effect despite treatment for 14 days (FIG. 13). The findings therefore revealed a potent and effective action of rationally designed MAPK13 inhibitors in blocking IL-13-induced mucus production in a high-fidelity system of primary-culture human airway epithelial cells.

TABLE 4

$IC_{50}$ values for MAPK13 inhibition.

| Compound | IC50 | 95% Confidence | $R^2$ |
|---|---|---|---|
| 58 | | | |
| 62 | 280.5 | 209.8-374.9 | 0.983 |
| 61 | 619.5 | 530.1-723.9 | 0.9941 |
| 43 (BIRB-796) | 1968 | 1547-2503 | 0.9879 |
| 47 (AMG-548) | 7736 | 6467-9253 | 0.9889 |
| 117 | 15785 | 12530-19885 | 0.9931 |
| 124 | 98747 | 28862-337855 | 0.9811 |
| 104 (SB203580) | $8.755 \times 10^7$ | | 0.9037 |
| DMSO (vehicle) | 18952 | | 0.3036 |

| compound | MAPK13 $IC_{50}$ (nM) | MAPK13 co-crystal | $t_{1/2}$ (s) | Relative Dissociation kinetics |
|---|---|---|---|---|
| 58 | 16.47 | DFG-out | 137 | slow |
| 61 | 82.72 | DFG-out | 111 | slow |
| 89 | 27.54 | DFG-out | 1200 | slow |
| 115 | 8,650 | | 204 | slow |
| 117 | 10,200 | DFG-in | 2.8 | fast |
| 124 | 14,884 | DFG-in | 1.2 | fast |

Figure 7:
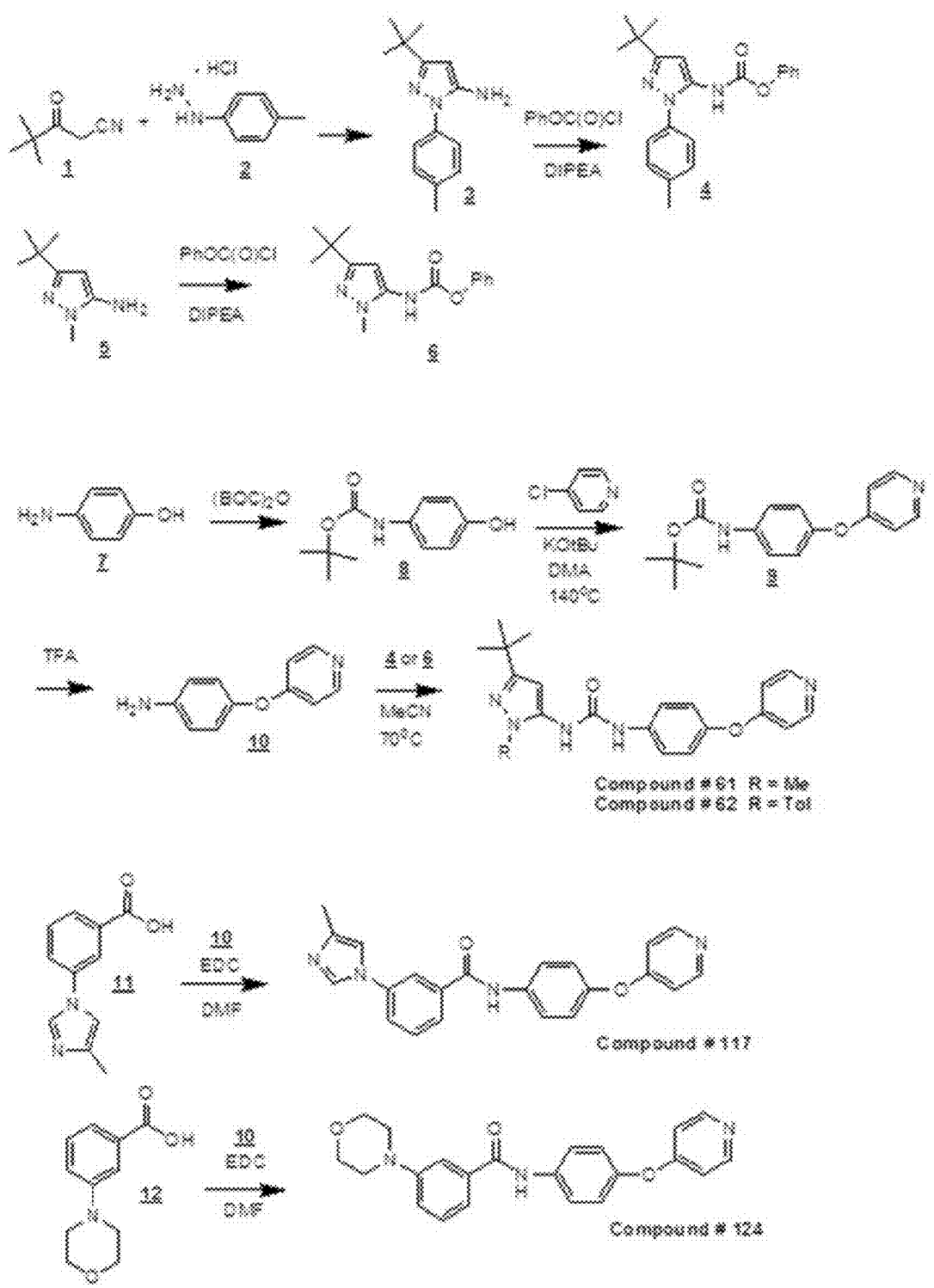
FIG. 7 illustrates the synthesis of compounds 61, 62, 117, 124.

MAPK13 $IC_{50}$ determined using IMAP-based biochemical assay $t_{1/2}$ determined using BLI Examples 5-14 refer to FIG. 7.

Example 5

This example illustrates the synthesis of pyrazole (3).

Pivaloylacetonitrile (1) (1.9 g, 15.1 mMol) was placed in a flask with tolyl hydrazine hydrochloride (2) (2.4 g, 15.1 mMol) in ethanol (19 mL) and the solution was heated to reflux for 1.5 hr. The solution was concentrated in vacuo until only a small amount of ethanol remained whereupon it was triturated with hexane, allowing it to stir for 1 hr before filtration of the white solid. Pyrazole 3 was isolated as it hydrochloride salt (3.6 g. 1.35 mMol) and was determined to be pure by LC-MS analysis (M+H=230.1).

Example 6

This example illustrates the synthesis of activated pyrazole (4).

Pyrazole 3 (1.0 g, 4.4 mM), diisopropylethylamine (684 mg, 5.3 mMol, 1.2 eq.), and DCM (9 mL) were cooled to −10° C. and phenyl chloroformate (750 mg, 4.8 mMol, 1.1 eq.) was added in a single portion. The solution was allowed to warm to 0° C. and stir for 30 min. The solution was partitioned between ether and aqueous sodium bicarbonate and the ether layer was washed with brine. The organic fraction was dried over anhydrous sodium sulfate and the solvent removed in vacuo and the residue purified using silica gel chromatography eluting with ethyl acetate (5%-50%)/hexane. Solvent removal afforded the product (4) as brittle foam (1.46 g, 4.2 mMol, 95% yield), which provided a single peak by LC-MS analysis (M+H=350.3). $^1$H NMR (400 MHz, CDCl$_3$) δ: 7.40-7.38 (m, 3H), 7.34 (dd, J=8.4, Hz, 2H). 7.25 (tt, J=7.6 Hz, 2H), 7.12 (d, J=6.6 Hz, 2H) 6.95 (br s, 1H). 6.5 (s, 1H), 2.43 (s, 3H), 1.36 (s, 9H).

Example 7

This example illustrates the synthesis of activated pyrazole (6).

Pyrazole 5 (673 mg, 4.4 mMol), diisopropylethylamine (684 mg, 5.3 mMol, 1.2 eq.), and DCM (9 mL) were cooled to −10° C. and phenyl chloroformate (750 mg, 4.8 mMol, 1.1 eq.) was added in a single portion. The solution was allowed to warm to 0° C. and stir for 30 min. The solution was partitioned between ether and aqueous sodium bicarbonate and the ether layer was washed with brine. The organic fraction was dried over anhydrous sodium sulfate and the solvent removed in vacuo and the residue purified using silica gel chromatography eluting with ethyl acetate (5%-50%)/hexane. Solvent removal afforded the product (6) as brittle foam (1.0 g, 3.9 mMol, 90% yield), which provided a single peak by LC-MS analysis (M+H=274.1). $^1$H NMR (400 MHz, CDCl$_3$) δ: 7.4 (dd, J=8.0, 7.6 Hz, 2H), 7.25 (tt, J=7.6 Hz, 1H), 7.18 (d, J=8.0 Hz, 2H), 6.95 (brs, 1H), 6.15 (s, 1H), 3.79 (s, 3H), 1.29 (s, 9H).

Example 8

This example illustrates the synthesis of BOC-protected phenol (8).

4-Aminophenol 7 (10 g, 91 mMol) was dissolved in THF (200 mL) and cooled in an ice bath. BOC carbonate (20 g, 91 mMol) was added and the cooling bath was removed and the solution was stirred overnight. The reaction was partitioned between ether and aqueous 1N hydrochloric acid, followed by washing the organic layer with water and aqueous sodium bicarbonate. Drying over anhydrous sodium sulfate and solvent removal in vacuo afforded 8 as a solid (18.3 g, 85 mMol). Analysis by TLC and LC-MS indicated that the product was pure (M+H=210.6). $^1$H NMR (400 MHz, CDCl$_3$) δ: 7.18 (d, J=8.8 Hz, 2H), 6.74 (d, J=8.8 Hz, 2H), 6.32 (s, 1H), 1.50 (s, 9H).

Example 9

This example illustrates the synthesis of pyridine ether (9).

Phenol 8 (6.0 g, 28.6 mMol), 4-chloropyridine hydrochloride (3.57 g, 23.8 mMol), and potassium t-butoxide (5.86 g, 52.3 mMol) were placed in a flask that was then flushed with nitrogen. DMA (60 mL) was added via cannula and the reaction heated to 90° C. for 2 hr. The reaction was cooled and partitioned between ether and aqueous 0.5 N sodium hydroxide, and the organic layer was washed with water (4×) and brine. Drying over anhydrous sodium sulfate and solvent removal in vacuo afforded a viscous oil that crystallized upon standing (4.15 g). This material was purified using silica gel column chromatography, eluting with ethyl acetate (30%-75%) in hexane. Solvent removal afforded 9 as a white solid (3.0 g, 10.4 mMol). LC-MS analysis showed the product to be 95% pure (M+H=287.4). $^1$H NMR (400 MHz, CDCl$_3$) δ: 8.5 (d, J=6.4 Hz, 2H), 7.48 (d, J=8.8 Hz, 2H). 7.05 (d, J=9.2 Hz, 2H), 7.01 (d, J=6.8 Hz, 2H), 6.62 (s, 1H), 1.53 (s, 9H).

Example 10

This example illustrates the synthesis of aniline (10).

To BOC protected ether 9 (2.9 g, 10.1 mMol) was added TFA (20 mL) and the solution was stirred for 1 hr. The volatile liquids were removed in vacuo and the residue was partitioned between ethyl acetate and aqueous sodium bicarbonate. The organic layer was washed with brine, dried over anhydrous sodium sulfate, and the solvent removed in vacuo to afford 10 as a white solid (1.76 g. 94.5 mMol). LC-MS analysis showed the product to be >95% pure (M+H=187.2). $^1$H NMR (400 MHz, CDCl$_3$) δ: 8.43 (d, J=6.8 Hz, 2H), 6.9 (d, J=8.4 Hz. 2H), 6.85 (d, =6.4 Hz, 2H). 6.72 (d, J=9.2 Hz, 2H), 4.26 (br s, 2H).

Example 11

This example illustrates the synthesis of compound #61.

Aniline 10 (100 mg, 0.53 mMol) was combined with activated pyrazole 6 (144 mg, 0.53 mMol) in acetonitrile (1 mL) and heated to 70° C. for 1.5 hr. The reaction was partitioned between ether and aqueous 0.5 N sodium hydroxide and the organic layer was washed with water (4×) followed by brine. Drying over anhydrous sodium sulfate and solvent removal in vacuo afforded an oil which was purified using silica gel chromatography, eluting with methanol (0%-5%) in DCM. Solvent removal afforded Compound #61 as a brittle foam (157 mg, 0.48 mMol). The sample was >98% pure by LC-MS analysis (M+H=366.5). $^1$H NMR (400 MHz, CDCl$_3$) δ: 8.88 (br s, 1H), 8.55 (br s, 1H), 8.44 (d, J=6.4 Hz, 2H), 7.57 (d, J=8.8 Hz, 2H), 7.03 (d, J=6.8 Hz, 2H), 6.99 (d, J=9.2 Hz, 2H), 6.27 (s, 1H), 3.82 (s, 3H), 1.28 (s, 9H).

Example 12

This example illustrates the synthesis of compound #62.

Aniline 10 (100 mg, 0.53 mMol) was combined with activated pyrazole 4 (185 mg, 0.53 mMol) in DMF (1 mL) and heated to 70° C. for 1.5 hr. The reaction was partitioned between ether and aqueous 0.5 N sodium hydroxide and the organic layer was washed with water (4×) followed by brine. Drying over anhydrous sodium sulfate and solvent removal in vacuo afforded an oil which was purified using silica gel chromatography, eluting with methanol (0%-5%) in DCM. Solvent removal afforded Compound #62 as a brittle foam (220 mg, 0.50 mMol). The sample was >99% pure by LC-MS analysis (M+H=442.3). $^1$H NMR (400 MHz, CDCl$_3$) δ: 8.69 (s, 1H), 8.31 (d, J=6.4 Hz, 2H), 7.65 (s, 1H), 7.45 (d, J=9.2 Hz, 2H), 7.29 (d, J=8.0 Hz, 2H), 7.11 (d, J=8.0 Hz. 2H), 6.94 (d, J=2.4 Hz, 2H). 6.92 (s, 2H), 6.37 (s, 11H), 2.26 (s, 3H), 1.30 (s, 9H).

Example 13

This example illustrates the synthesis of compound #117.

Acid 11 (190 mg, 1 mMol) was placed in a dried flask with aniline 10 (175 mg, 1 mMol) and EDC (191 mg, 1 mMol). DMF (3 mL) was added and the solution stirred 5 hr. The solution was extracted with water and ethyl acetate and the organic layer, washed with water (4×) and aqueous sodium bicarbonate, and dried over anhydrous sodium sulfate. Solvent removal afforded Compound #117 as a solid which was purified using silica gel column chromatography, eluting with ethyl acetate (15%-90%) in hexane. Solvent removal afforded a solid which was >98% pure by LC-MS. $^1$H NMR (400 MHz, DMSO) δ: 10.43 (s, 1H), 8.44 (m, 3H), 8.12 (m, 1H), 7.82-7.90 (m, 4H), 7.66 (dd, J=8.0 Hz, 1H), 7.61 (s, 1H), 7.19 (d, J=7.2 Hz, 2H), 6.91 (d, J=6.4 Hz, 2H), 2.19 (s, 3H).

Example 14

This example illustrates the synthesis of compound #124.

Acid 12 (196 mg, 1 mMol) was placed in a dried flask with aniline 10 (175 mg, 1 mMol) and EDC (191 mg, 1 mMol). DMF (3 mL) was added and the solution stirred 5 hr. The solution was extracted with water and ethyl acetate and the organic layer, washed with water (4×) and aqueous sodium bicarbonate, and dried over anhydrous sodium sulfate. Solvent removal afforded a solid which was purified using silica gel column chromatography, eluting with ethyl acetate (20%-90%) in hexane. Solvent removal afforded Compound #124 as a solid which was >99% pure by LC-MS. $^1$H NMR (400 MHz, CDCl$_3$) δ: 8.42 (d. J=6.4 Hz 2H), 8.2-8.5 (m, 2H), 7.72 (d, J=8.8 Hz, 2H), 7.38 (d, J=9.2, ½H), 7.0-7.1 (m, 3H), 6.94 (d, J=5.2 Hz, 1H), 6.88 (d, J=6.8 Hz, 2H), 6.80 (d, J=8.4 Hz, ½H), 3.77-3.81 (m, 4H), 3.54-3.58 (m, 4H).

Examples 15-25

In these Examples, reactions were followed and product identity and purity determined by proton NMR and LC-MS. The LC-MS was an AGILENT Series 1000 LC-MSD (Agilent Technologies, Inc., Santa Clara, Calif., USA) with UV detection at 215 nM and 254 nM, and a mass detector. It utilized an AGILENT ZORBAX XDB-C8 reverse phase analytical column (4.6×50 mm dimensions) and elution was performed using acetonitrile and distilled water (containing 0.1% v/v trifluoroacetic acid) with a 1 ml/min flow; the gradient was initiated at 5% acetonitrile and progressed in a linear fashion over 5 min to 95% acetonitrile and there maintained for 1 additional minute. For compounds listed as being analyzed using conditions selected for lipophilic compounds, the gradient was initiated at 50% acetonitrile and progressed in a linear fashion over 5 min to 95% acetonitrile and maintained for 1 additional minute. Thin layer chromatography (TLC) was performed using normal phase silica gel plates obtained from Analtech, Inc. (75 Blue Hen Drive, Newark, Del.): Silica Gel GF, 250 microns. Intermediates are numbered sequentially and can be referred to by underline in the text. Analogs use a database numbering which is distinct from intermediates and are can be referred to in bold in the text and in the schemes.

Example 15

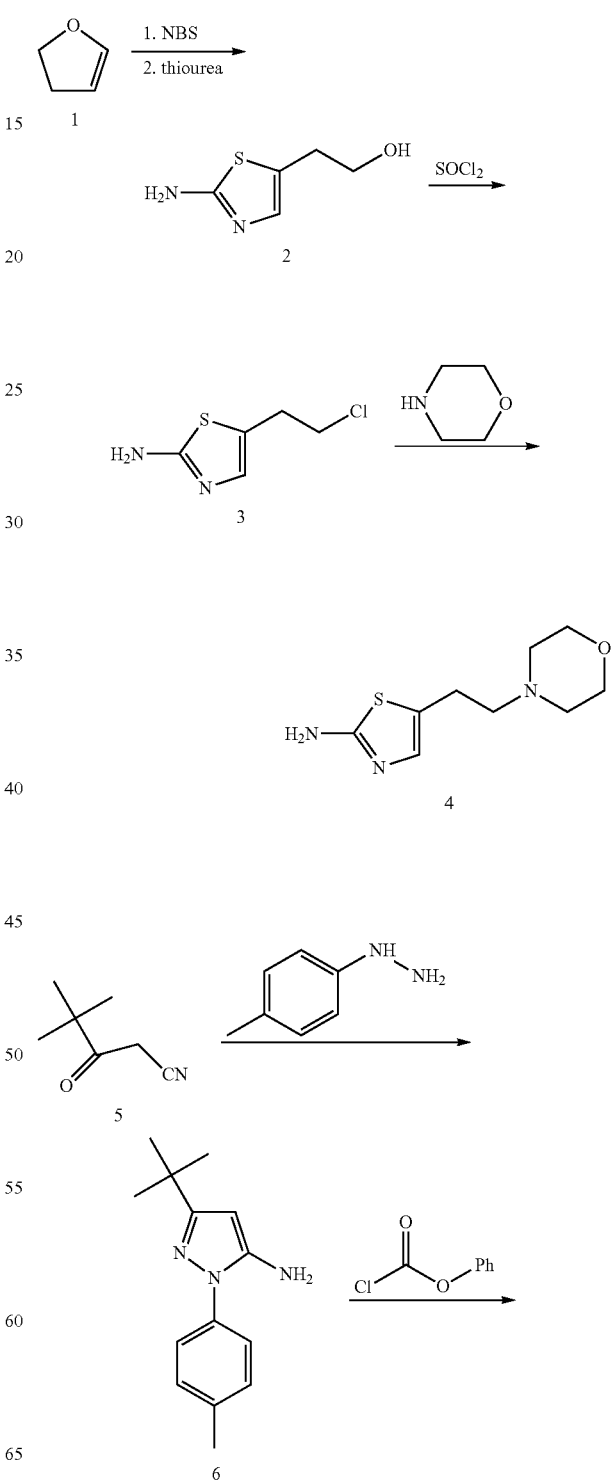

Scheme 1.

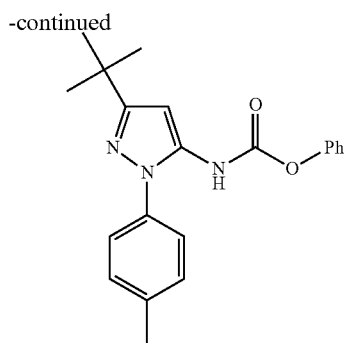

7 heat
4 + 7 ⟶

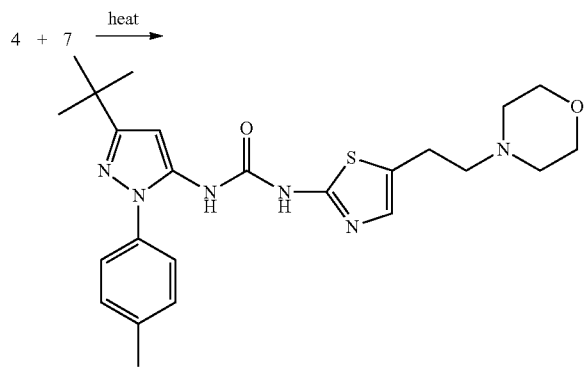

89

In these experiments as shown in Scheme 1, a suspension of NBS (59 g) in water (370 ml) was cooled in an ice bath and dihydrofuran (37 ml) was added drop-wise. The reaction was stirred for one additional hr at 0° C. and then thiourea (25 g) was added in portions, after which the solution was refluxed overnight. The cooled solution was extracted with ethyl acetate (2×) and the aqueous layer was treated with AMBERLYST 15 (Dow Chemical Co., Pevely, Mo. USA) strong acid resin (80 g) and filtered. The resin was washed with water and then product was collected by rinsing the resin with ammonia in methanol prepared by mixing concentrated ammonium hydroxide (80 ml) in methanol (700 ml). Solvent removal afforded thiazole 2 as a brown solid (26 g). The thiazole was dissolved in methanolic HCl, the volatiles were removed in vacuo, and the residue crystallized from methanol and ether to obtain 2 as the hydrochloride salt.

Thiazole 2 (10.3 g, as the hydrochloride) was mixed with chloroform (200 ml) and thionyl chloride (45 ml) was added slowly. The mixture was heated to reflux for 45 min and then cooled and the volatiles removed in vacuo. The dark solid was dissolved in hot ethanol and ether added to cause precipitation, after which the solids were filtered and washed with ether and cried in vacuo to afford 3 as its hydrochloride salt (7.2 g).

Thiazole 3 (19.4 g, as its hydrochloride salt) was mixed with sodium bicarbonate (8.21 g), sodium iodide (3.6 g), acetonitrile (250 ml), and morpholine (51.1 ml) and heated to 88° C. for 4 hr. To the cooled reaction was added ethyl acetate 400 ml) and 10% aq. sodium carbonate (250 ml) and the solution was extracted. The organic layer was washed with brine (2×) and dried over sodium sulfate. Solvent removal afforded 4 as a brown solid (19 g) that was dissolved in methanol/DCM (5:95) and filtered through a plug of silica gel to afford 4 of sufficient purity for use in the next step.

Pivaloylacetonitrile (19.0 g) was refluxed with tolylhydrazine hydrochloride (24.0 g) in ethanol (190 ml) for 1.5 hr. The solution was cooled and volatiles removed in vacuo. The residue was extracted with ethyl acetate and 10% aq. sodium carbonate, and the organic layer washed with water and brine. Drying over sodium sulfate and solvent removal afforded pyrazole 6 as an off-white solid (30 g).

Pyrazole 6 (12.7 g), saturated aq. sodium bicarbonate (338 ml), and THF (200 ml) were cooled in an ice-bath. The rapidly stirring mixture was added phenyl chloroformate (13.0 g) drop-wise. After one additional hr of stirring the mixture was extracted with ether and the organic layer washed with water. Drying over sodium sulfate and solvent removal in vacuo afforded a white solid that was dissolved in DCM (80-100 ml) and hexane (350 ml) added wile rapidly stirring. The solids were filtered, washed with hexane, and dried to afford pyrazole 7 as a white solid (16.9 g). LC-MS retention time=5.35 min.

Procedure 1. Preparation of 1-(5-tert-Butyl-2-p-tolyl-2H-pyrazol-3-yl)-3-[5-(2-morpholin-4-yl-ethyl)-thiazol-2-yl]-urea (Analog 89): Thiazole 4 (7.33 g) and pyrazole 7 (12.0 g) were mixed with acetonitrile (80 ml) and heated to 70° C. for 2.5 hr. After cooling a thick precipitate formed and to this water (200 ml) was added and stirring was continued for 20 min. The solids were filtered and washed with cold water (3×80 ml) and the white solid dried in vacuo. This was recrystallized using hot ethyl acetate with a little hexane, cooled, and filtered to obtain Analog 89 as a white solid (10.9 g). LC-MS retention time=3.70 min (M+H=469.2); TLC Rf=0.6 (methanol/DCM, 5:95).

Example 16

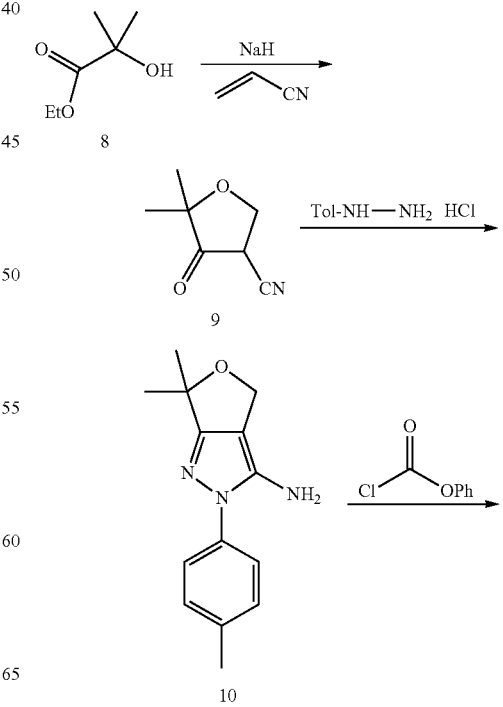

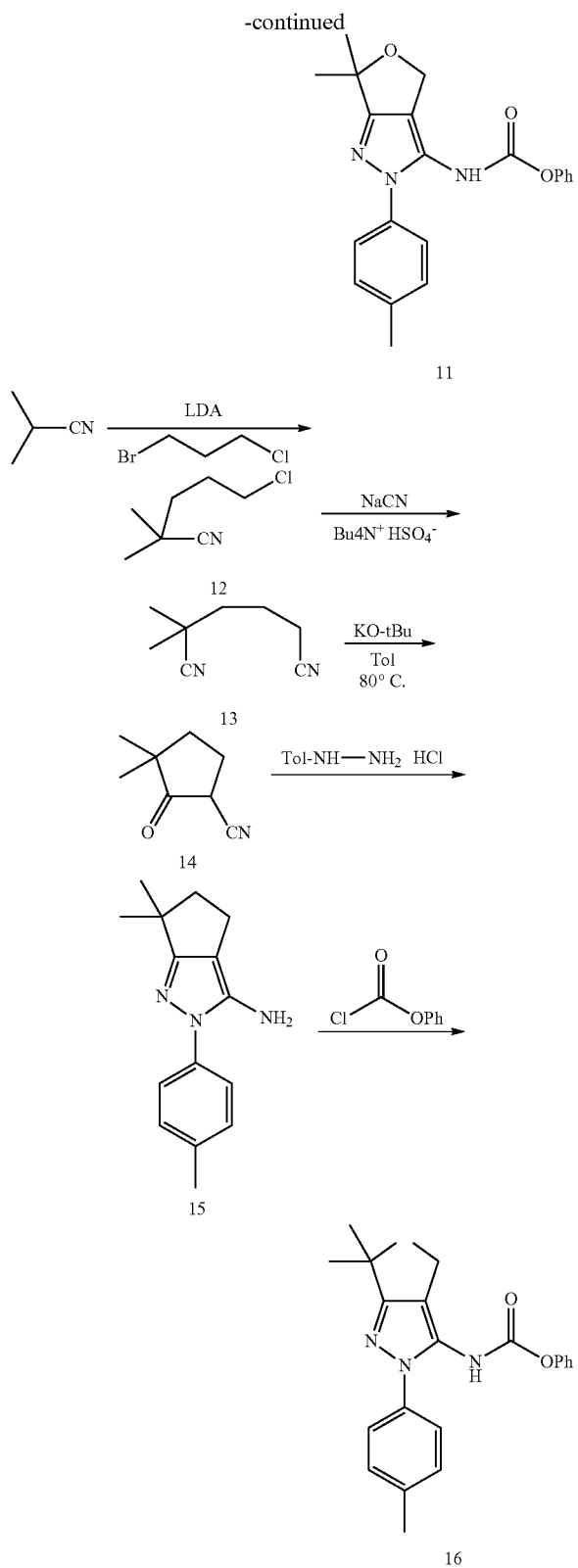

In these experiments as shown in Scheme 2, ester 8 (15 g) and acrylonitrile (6.5 ml) were placed in a flask with THF (200 ml) and cooled in an ice-bath. Sodium hydride (5.2 g, 60% in oil) was added in portions and the reaction was stirred for 1 hr. The solution was acidified with 2 N aqueous hydrochloric acid (1.5 eq.) and ether and water were added and the mixture extracted. The organic layer was washed with water and brine and dried over sodium sulfate. Solvent removal afforded a liquid that was purified using silica gel chromatography, eluting with a gradient of 10% to 60% ethyl acetate in hexane to provide 9 as a clear liquid (5.34 g). TLC Rf=0.2 (ethyl acetate/hexane, 15:85).

Ketone 9 (0.5 g) and tolylhydrazine hydrochloride (0.57 g) were refluxed in ethanol (7 ml) for one hr. After solvent removal in vacuo the residue was extracted with ethyl acetate and aq. 10% sodium carbonate and the organic layer was washed with water and brine. Drying over sodium sulfate and solvent removal afforded pyrazole 10 as a pure solid (0.72 g). LC-MS retention time=3.25 min (M+H=244.1). The pyrazole (10) (0.549 g) was dissolved in THF (6 ml) and saturated aqueous sodium bicarbonate (15 ml) and cooled in an ice-bath. Phenyl chloroformate (1.06 g) was added dropwise and the reaction stirred for 30 min and then partitioned between ethyl acetate and water. The organic layer was dried over sodium sulfate and solvent removed in vacuo. The residue was purified by silica gel chromatography, eluting with a gradient comprising 0% to 50% ethyl acetate in hexane. The pyrazole carbamate (11) was obtained as a white solid (0.68 g). LC-MS retention time=4.61 min (M+H=364.1).

Isobutronitrile (4.81 g) was added drop-wise to a slurry of LDA (69.6 mmol) in hexane (150 ml) at 0° C. The alkylating agent (12.0 g) was added in one portion and the reaction allowed to warm to 20° C., and stir for 2 hr. Water was added followed by ether and the solution was extracted and the organic layer washed with water (2×). The organic layer was dried over sodium sulfate and the solvent removed at 40 torr vacuum to afford 11 as a clear liquid (9.4 g). The nitrile product (12) (9.4 g) was mixed with sodium cyanide (6.3 g), tetrabutylammonium bisulfate (0.66 g), and water (180 ml) and refluxed for 2 hr. The solution was cooled and extracted with ether. The ether layer was washed 2× and dried over sodium sulfate and the ether removed in vacuo to afford dinitrile 13 as a clear liquid (4.9 g). The dinitrile (13) (4.8 g), potassium t-butoxide (2.37 g), and toluene (100 ml) were heated to 80° C. for 2 hr. The reaction became very thick. After cooling ether and 3N aq. hydrochloric acid was added and stirred for 7 min and the layers separated. The organic layer was washed with water and brine and dried over sodium sulfate and solvent removed in vacuo to afford a residue that was purified via silica gel chromatography eluting with ethyl acetate/hexane (1:4) which afforded keto nitrile (14) as a clear liquid. The crude product was heated as in ethyl acetate and triturated with hexane to afford a white solid (2.0 g). TLC Rf=0.25 (ethyl acetate/hexane, 15:85).

Keto-nitrile 14 (0.75 g) and toluylhydrazine hydrochloride (0.80 g) were refluxed in ethanol (10 ml) for 1.5 hr and then cooled. After solvent removal in vacuo the residue was extracted with ethyl acetate and 10% aq. sodium carbonate, washing the organic layer with water and brine. Drying over sodium sulfate and solvent removal in vacuo afforded pyrazole 15 (1.0 g) as a tan solid. LC-MS retention time=3.39 min (M+H=242.1); TLC Rf=0.15 (ethyl acetate/hexane (15:85).

The pyrazole (15) (0.487 g) was dissolved in THF (5 ml) and saturated aqueous sodium bicarbonate (13 ml) and cooled in an ice-bath. Phenyl chloroformate (0.475 g) was added dropwise and the reaction stirred for 30 min and then partitioned between ethyl acetate and water. The organic layer was dried over sodium sulfate and solvent removed in vacuo. The residue was purified by silica gel chromatography, eluting with a gradient comprised of 0% to 40% ethyl acetate in hexane. The pyrazole carbamate (16) was obtained as a white solid (0.69 g). LC-MS retention time=5.09 min (M+H=362.1).

Example 17

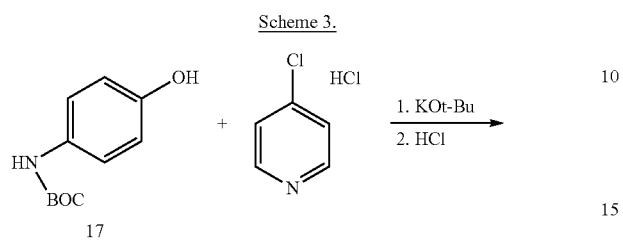
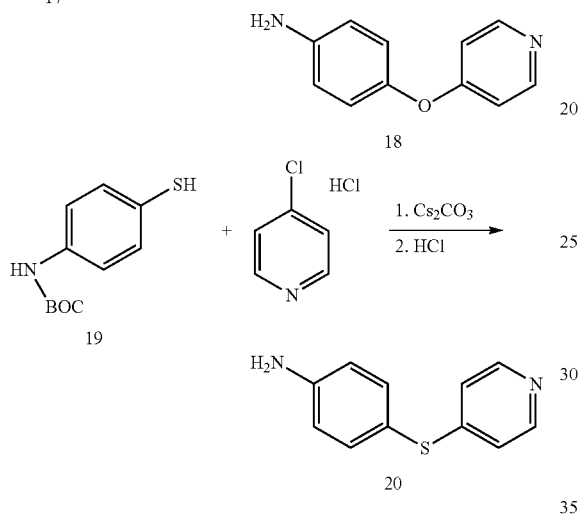

In these experiments as shown in Scheme 3, phenol 17 (17 g) and 4-chloropyridine hydrochloride (16 g) were placed in a flask with DMA (200 ml) and cooled in an ice-bath. Potassium t-butoxide (30.2 g) dissolved in DMA (100 ml) was added via cannula and the slurry was heated to 95° C. After 3.5 hr HPLC analysis showed the reaction was 50% complete and another 1.5 eq. of potassium t-butoxide was added to the reaction and it was heated for another 3 hr. The reaction was cooled and extracted with ethyl acetate and water, washing the organic layer with water (3×) and then with brine. Drying over sodium sulfate and solvent removal in vacuo afforded a solid residue that was purified using silica gel chromatography, eluting with ethyl acetate/DCM (gradient from 0% ethyl acetate to 50% ethyl acetate). Alternatively the crude produce could be purified by dissolving in the minimal volume of DCM while heating and then adding 1×-2× volume-equivalents of hexane while stirring. The ether product was obtained as a white solid (19.2 g). TLC Rf=0.25 (ethyl acetate/hexane, 25:75). The BOC group was removed by dissolving the ether (19.2 g) in 4M hydrogen chloride in dioxane (200 ml) and stirring for 3 hr. Solvent removal afforded a residue that was extracted with ether/DCM and 10% aq. sodium carbonate. The organic layer was washed with water and brine, drying over sodium sulfate. The residue was recrystallized with hot benzene/hexane (1:1) and solids were filtered and washed with DCM/hexane (1:3) to obtain aniline-ether 18 as a white solid (12 g). LC-MS retention time=arrives at solvent front.

Thiol 19 (3.0 g), 4-chloropyridine hydrochloride (1.8 g), and cesium carbonate (11.8 g) were placed in a flask with DMSO (30 ml) and heated to 90° C. for 1 hr. The slurry was cooled and partitioned between ethyl acetate and water, and the organic layer washed with water (3×) followed by brine. Drying over sodium sulfate and solvent removal afforded a pale oil (4.3 g) that was purified via silica gel chromatography, eluting with a gradient comprised of 10% to 60% ethyl acetate in hexane. The thioether was obtained as a pure white solid (3.0 g). TLC Rf=0.45 (ethyl acetate/hexane, 15:85). The BOC group was removed using 4M hydrogen chloride in dioxane, stirring for 3 hr. The volatiles were removed and the residue partitioned between DCM/ether and 10% aqueous sodium carbonate. The organic layer was washed with water and dried over sodium sulfate, removing solvent in vacuo to afford thioether 20 (1.7 g). LC-MS retention time=2.367 min (M+H=203.2).

Example 18

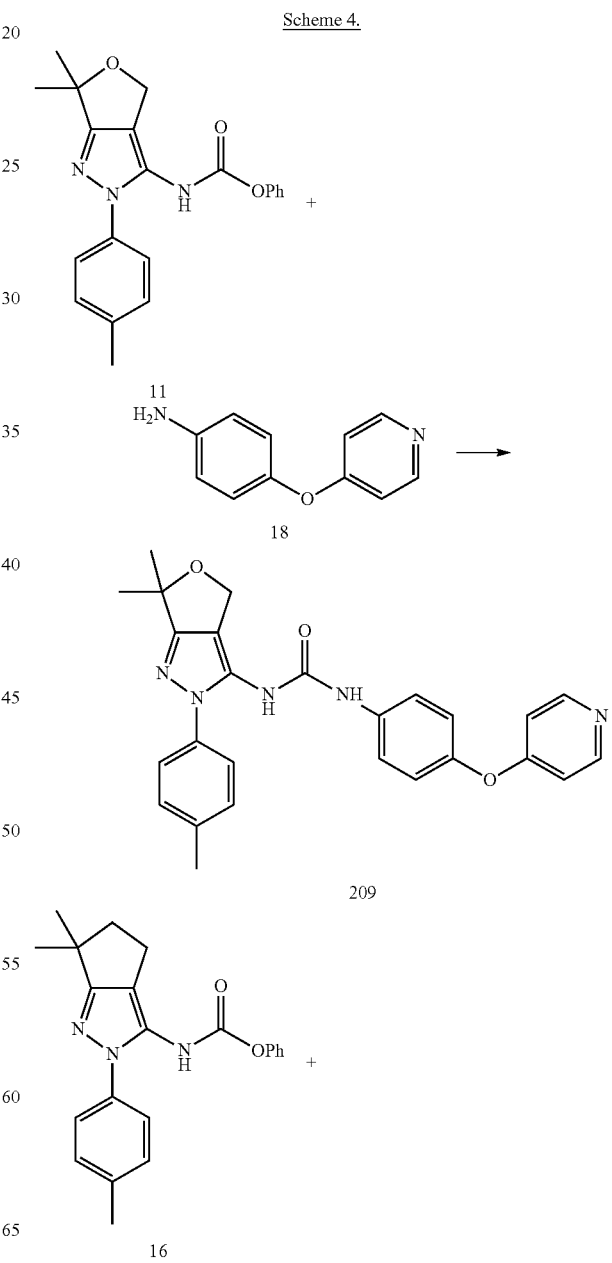

-continued

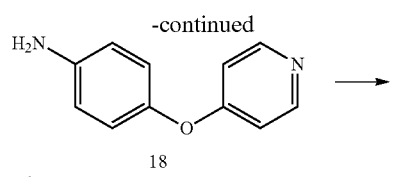

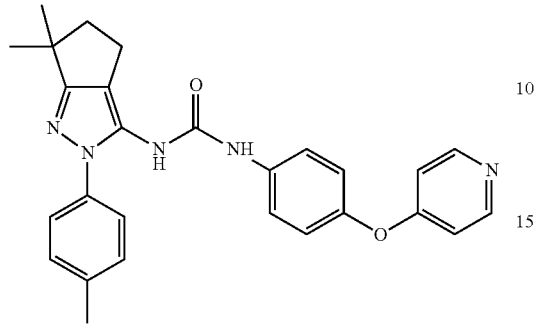

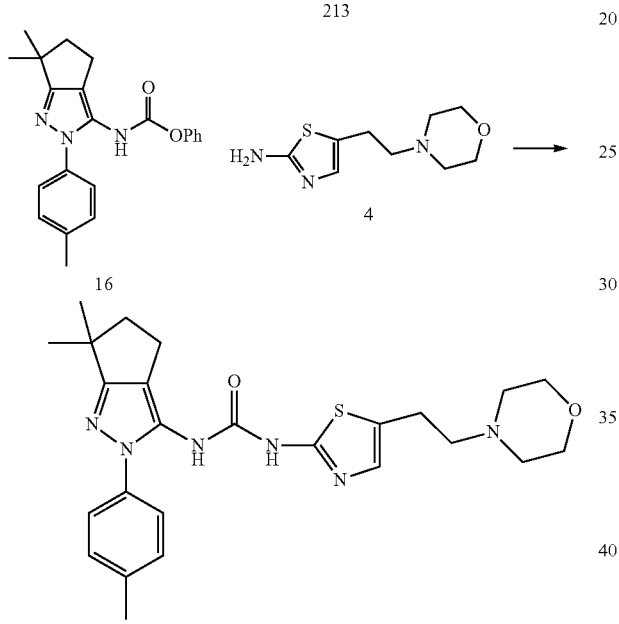

Experiments as shown in Scheme 4 include the following syntheses.

Preparation of 1-(6,6-Dimethyl-2-p-tolyl-2,6-dihydro-4H-furo[3,4-c]pyrazol-3-yl)-3-[4-(pyridin-4-yloxy)-phenyl]-urea (Analog 209). Carbamate 11 (20 mg) and aniline 18 (11 mg) were heated at 85° C. in acetonitrile (0.5 ml) for 3 hr. The solvent was removed in vacuo and the residue triturated with ether to obtain a white solid which was filtered and washed with ether to afford urea Analog 209 (20 mg) as a white solid. LC-MS retention time=3.40 min (M+H=456.1).

Preparation of 1-(6,6-Dimethyl-2-p-tolyl-2,4,5,6-tetrahydro-cyclopentapyrazol-3-yl)-3-[4-(pyridin-4-yloxy)-phenyl]-urea (Analog 213). Carbamate 16 (20 mg) and aniline 18 (11 mg) were heated at 85° C. in acetonitrile (0.5 ml) for 3 hr. The solvent was removed in vacuo and the residue purified using silica gel chromatography, eluting with a gradient comprising 0% to 10% methanol in DCM to afford 24 mg of pure urea Analog 213 as a white solid. LC-MS retention time=3.68 min (M+H=454.2).

Preparation of 1-(6,6-Dimethyl-2-p-tolyl-2,4,5,6-tetrahydro-cyclopentapyrazol-3-yl)-3-[5-(2-morpholin-4-yl-ethyl)-thiazol-2-yl]-urea (Analog 214). Carbamate 16 (20 mg) and thiazole 4 (12 mg) were heated at 85° C. in acetonitrile (0.5 ml) for 3 hr. The solvent was removed in vacuo and the residue purified using silica gel chromatography, eluting with a gradient comprising 0% to 10% methanol in DCM to afford 22 mg of pure urea Analog 214 as a white solid. LC-MS retention time=3.49 min (M+H=481.2).

Example 19

Scheme 5.

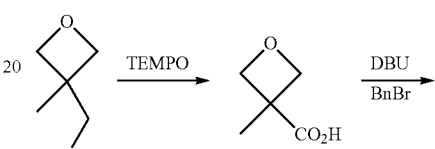

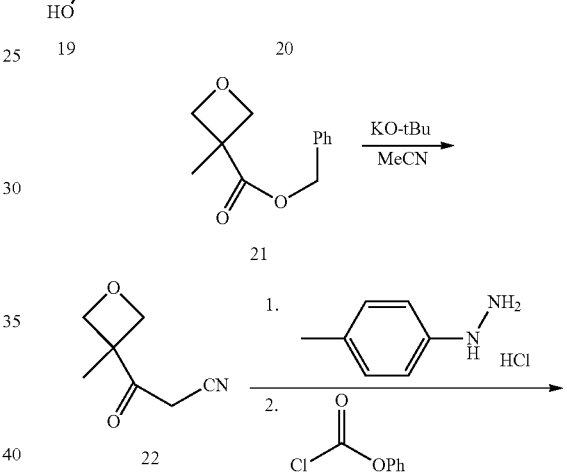

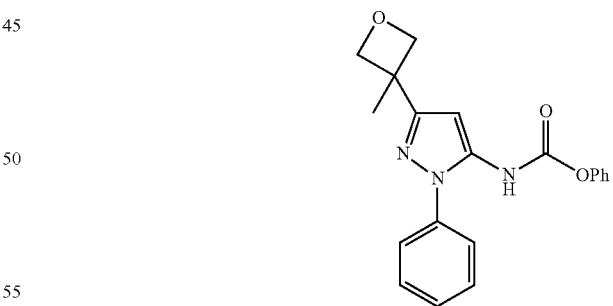

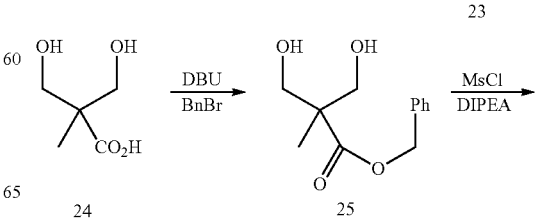

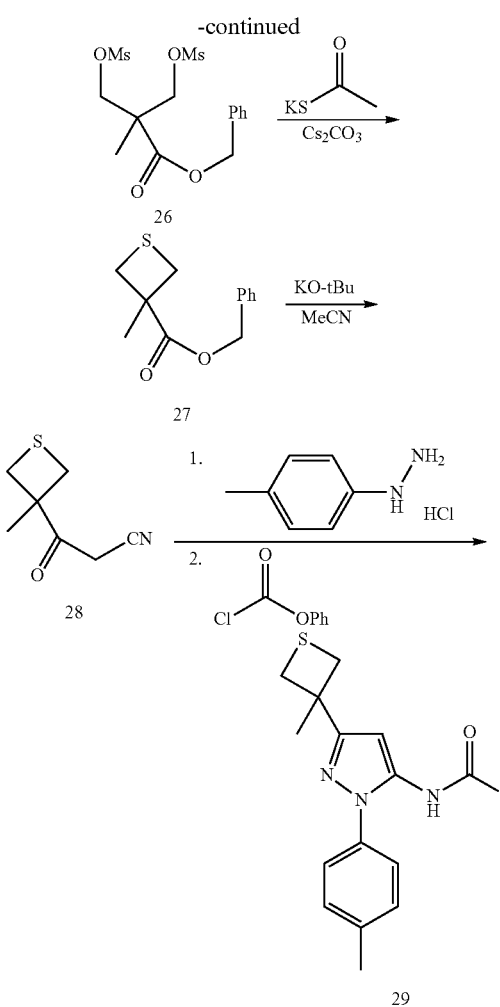

In these experiments, commercially available oxetane 19 (17.7 g), (bis)acetoxy)iodobenzene (111.7 g), acetonitrile (200 ml), and water (200 ml) were cooled in an ice-bath. TEMPO (5.42 g) was added and the solution was stirred overnight at room temperature. The solution was cooled and solid sodium hydroxide (38 g) was added and the reaction was washed with ether (2×). The aqueous layer was cooled in an ice-bath and acidified with 12 N hydrochloric acid to pH 3 and then extracted with ether (3×500 ml). The solvent was removed in vacuo to afford the carboxylic acid (20) as a liquid (14 g). Carboxylic acid 20 (9 g) was dissolved in acetonitrile (180 ml) and cooled in an ice-bath. DBU (13 g) was added followed by slow addition of benzyl bromide (14 g) and the solution stirred overnight at room temperature. Remove solvent in vacuo to reduce volume by one-half and then partition the residue between ether and aqueous 1N hydrochloric acid. Wash the organic layer with water (2×) and dry over sodium sulfate. Solvent removal afforded a brown oil (14.8 g) that was purified using silica gel chromatography, eluting with a gradient comprising 0% to 30% ethyl acetate in hexane. Benzyl ester 21 was obtained (9.7 g). LC-MS retention time=4.25 min (M+H not observed); TLC Rf=0.35 (ethyl acetate:hexane (1:9).

Solid potassium t-butoxide (7.9 g) was placed in a dry flask with THF (35 ml) and it was placed in an ice-bath. Dry acetonitrile (2.0 g) was added followed by benzyl ester 21 (9.7 g) in THF (15 ml). The reaction was followed using LC-MS to determine completion and then the flask was placed in an ice-bath and aqueous 2N hydrochloric acid was added. The reaction was extracted with DCM (2×150 ml) and the organic layer washed with water and then brine and dried over sodium sulfate. Solvent removal afforded 9.4 g or a pale yellow oil that was purified using silica gel chromatography, eluting with a gradient comprised of 5% to 90% ethyl acetate in hexane to obtain 22 as a pale yellow oil (4.68 g).

Keto-nitrile 22 (4.68 g) and toluylthydrazine hydrochloride (5.34 g) were mixed with ethanol (45 ml) and the warmed to 35° C. The reaction was complete in 3.5 hr and the reaction partitioned between DCM (200 ml) and saturated aqueous sodium bicarbonate, washing with water and brine. The organic layer was dried over sodium sulfate and the solvent removed at RT under vacuum to obtain 8.5 g of an orange wax. This was triturated with ether (200 ml), stirring 3 hr, and filtered, rinsing with ether to obtain a first fraction of the pyrazole as an off-white solid (3.4 g). The mother liquor was purified using silica gel chromatography, eluting with a gradient comprised of 0% to 50% ethyl acetate in hexane to obtain a second pure fraction of pyrazole (3.8 g). LC-MS retention time=2.89 min (M+H=244.1); TLC Rf=0.5 (ethyl acetate/hexane (1:1). The pyrazole (0.5 g) was placed in a flask with THF (5 mL) and saturated aqueous sodium bicarbonate (10 ml) and cooled in an ice-bath. Phenyl chloroformate (0.965 g) was added slowly and the reaction stirred for 20 min. The reaction was partitioned between ethyl acetate and water and the organic layer washed with water and then dried over sodium sulfate and the solvent removed in vacuo to afford 1.30 g of carbamate 23 as an oil that was purified using silica gel chromatography, eluting with a gradient comprised of 5% to 50% ethyl acetate in hexane. LC-MS retention time=4.55 min (M+H=364.1).

Commercially available diol 24 (50 g) was and acetonitrile (650 ml) were cooled in an ice-bath and DBU (56.75 g) added. Benzyl bromide (61.85 g) was added over 30 min and the solution was allowed to warm to room temperature and stir for 24 hr. The solvent was removed in vacuo and the residue diluted with water (600 ml) and stirred in an ice-bath to cause crystallization of the benzyl ester, which was filtered and washed with cold water and then dried by pulling air through the solid. This material was suspended in ether and filtered, washing with ether to obtain pure benzyl ester 25 (52.8 g). A second fraction of benzyl ester was obtained by combining the washings, adding DCM (600 ml) and aqueous 2N hydrochloric acid (100 ml) and extracting. The organic layer was washed with water and then saturated sodium bicarbonate and brine. After drying over sodium sulfate the solvent was removed in vacuo to afford benzyl ester 25 as a solid (25.6 g). LC-MS retention time=3.338 min (M+H=225.2).

Benzyl ester 25 (131 g) was placed in a flask with DCM (1000 ml) and DIPEA (170.5 g) and cooled in an ice-bath. Methane sulfonylchloride (140.7 g) was added slowly and the reaction stirred for 30 min. The solution was extracted with water, aqueous 2N hydrochloric acid, water (2×), saturated aqueous sodium bicarbonate, and brine. Drying over sodium sulfate and solvent removal in vacuo afforded 208.8 g of dimesylate 26 as a viscous liquid in greater than 95% purity. LC-MS retention time=4.486 min (no M+H peak); TLC Rf=0.55 (ethyl acetatehexane (1:1).

Dimesylate 26 (120.2 g) was placed in a flask fitted with an mechanical stirrer with DMF (1000 ml), cesium carbonate (154 g) and stirred while cooling in an ice-bath. Potassium thioacetate (36.1 g) was added in portions while k=maintaining a nitrogen atmosphere and the mixture heated to 60° C. The reaction was maintained overnight while monitoring using HPLC for completion. After 30 hr the reaction was complete and it was cooled in an ice-bath.

Ice water was added to the mixture followed by ether and the mixture was partitioned, and the organic layer was washed with water (5×) and then dried over sodium sulfate. Solvent removal afforded 73 g of a brown oil that was purified twice by silica gel chromatography, eluting with a gradient comprised of 2% to 8% ethyl acetate in hexane to obtain 24 g of thiooxetane 27. LC-MS retention time=5.08 min (M+H=223.0); TLC Rf=0.78 (ethyl acetate/hexane (1:9).

Potassium t-butoxide (3.78 g) and dry THF (15 ml) were placed into a flask and cooled in an ice-bath. Dry acetonitrile (1.01 g) was added and then thiooxetane 27 (5 g) dissolved in THF (10 ml) was rapidly added with efficient stirring. After 30 min the reaction was complete and, while still in ice-bath, aqueous 2N hydrochloric acid was added and the solution was extracted with ether. The layers were partitioned and the organic layer dried over sodium sulfate and the solvent removed at 50 torr to obtain 5.5 g of a yellow oil which was purified using silica gel chromatography, eluting with a gradient comprised of 0% to 50% ethyl acetate in hexane. The keto-nitrile was obtained as an oil (3.41 g). TLC Rf=0.8 (ethyl acetate/hexane (1:1).

The keto-nitrile (3.41 g) was mixed with toluylhydrazine hydrochloride (3.48 g) in ethanol (35 ml) and heated to 50° C. for 45 min. Upon cooling a precipitate forms and is found to be toluylhydrazine hydrochloride and removed by filtration (1.5 g). The mother liquors are partitioned between ether/ DCM and aqueous sodium bicarbonate, and the organic layer is washed with water and brine. Drying over sodium sulfate and solvent removal in vacuo afforded a solid that was triturated with ether and filtered to obtain 2.05 g of pure pyrazole as a white solid. The mother liquors were purified using silica gel chromatography to obtain an additional 0.17 g of pyrazole product. LC-MS retention time=3.58 min (M+H=260.1); TLC Rf=0.55 (ethyl acetate/hexane (1:3). The pyrazole (2.5 g) was placed in a flask with THF (35 ml) and saturated aqueous bicarbonate (60 ml) and cooled in an ice-bath. Phenyl chloroformate (2.1 g) was added and the mixture stirred for 1 hr and then partitioned between ethyl acetate and water. The organic layer was dried over sodium sulfate and the solvent removed to afford 4.8 g of an oil which was purified using silica gel chromatography eluting with a gradient comprised of 0% to 35% ethyl acetate in hexane. Carbamate 28 was obtained as a white solid (3.47 g). LC-MS retention time=5.25 min (M4-H=380.1); TLC Rf=0.7 (ethyl acetate/ hexane (1:3).

Example 19

Scheme 6.

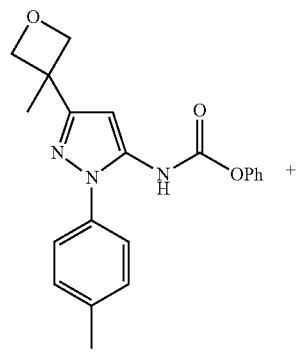

23

+

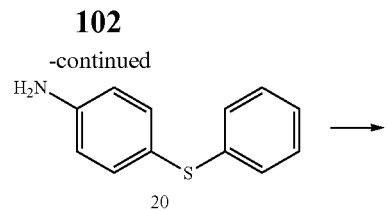

20

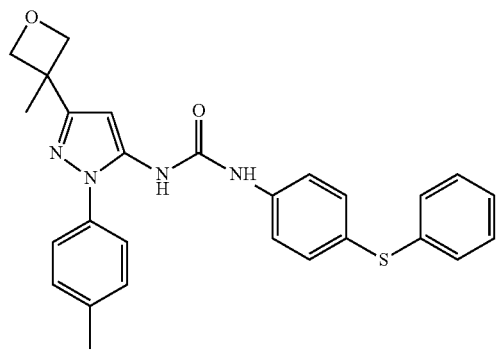

204

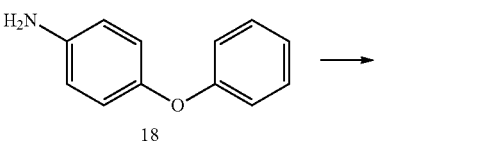

18

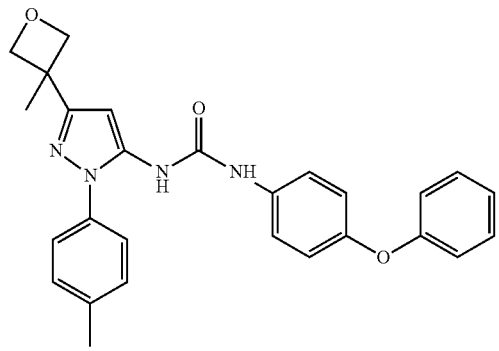

186

23 +

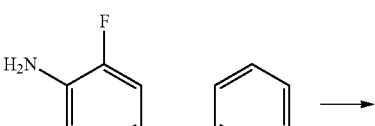

30

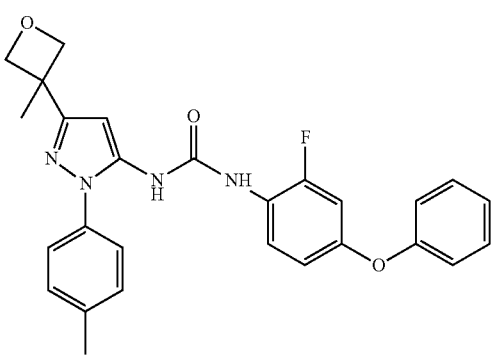

192

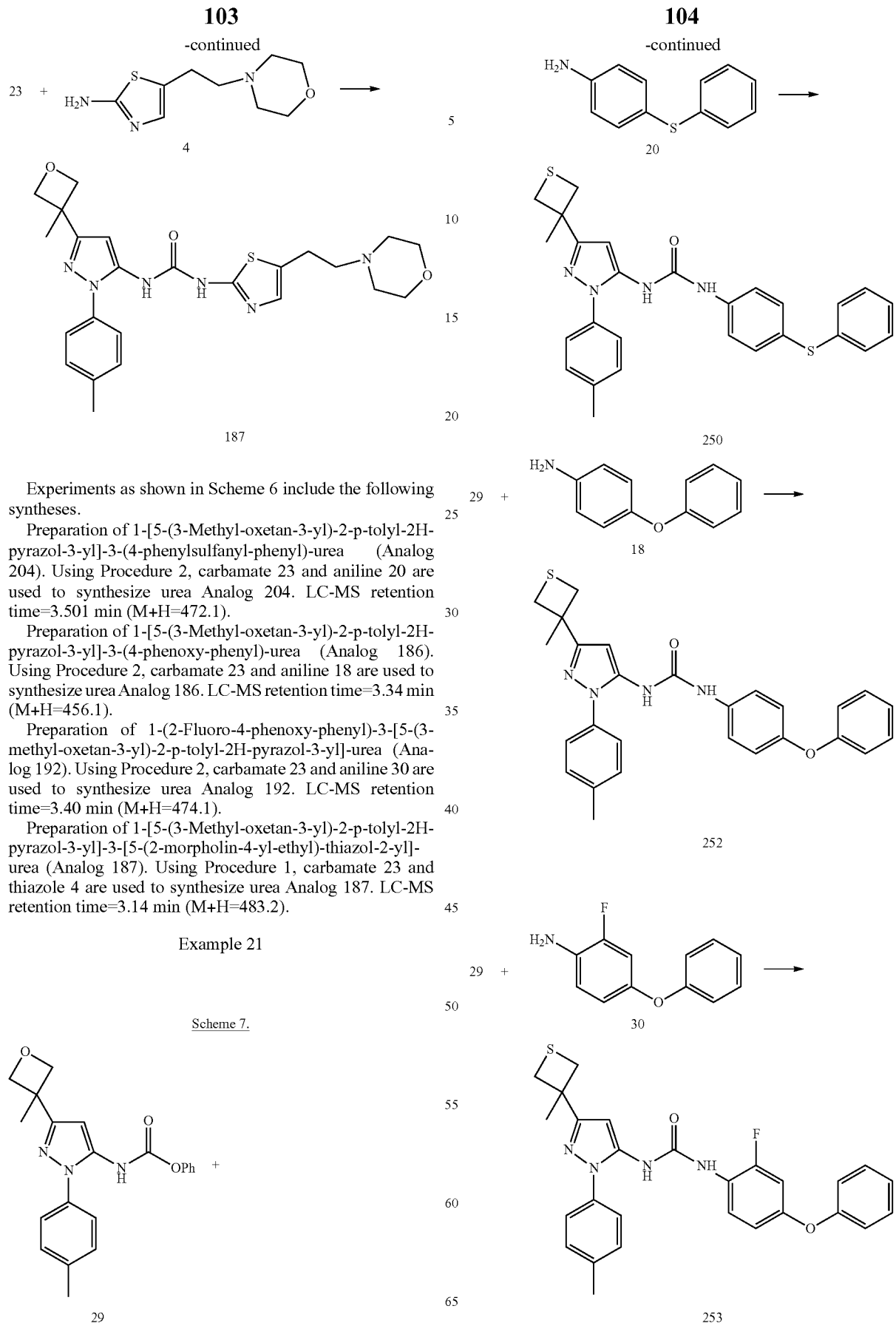

Experiments as shown in Scheme 6 include the following syntheses.

Preparation of 1-[5-(3-Methyl-oxetan-3-yl)-2-p-tolyl-2H-pyrazol-3-yl]-3-(4-phenylsulfanyl-phenyl)-urea (Analog 204). Using Procedure 2, carbamate 23 and aniline 20 are used to synthesize urea Analog 204. LC-MS retention time=3.501 min (M+H=472.1).

Preparation of 1-[5-(3-Methyl-oxetan-3-yl)-2-p-tolyl-2H-pyrazol-3-yl]-3-(4-phenoxy-phenyl)-urea (Analog 186). Using Procedure 2, carbamate 23 and aniline 18 are used to synthesize urea Analog 186. LC-MS retention time=3.34 min (M+H=456.1).

Preparation of 1-(2-Fluoro-4-phenoxy-phenyl)-3-[5-(3-methyl-oxetan-3-yl)-2-p-tolyl-2H-pyrazol-3-yl]-urea (Analog 192). Using Procedure 2, carbamate 23 and aniline 30 are used to synthesize urea Analog 192. LC-MS retention time=3.40 min (M+H=474.1).

Preparation of 1-[5-(3-Methyl-oxetan-3-yl)-2-p-tolyl-2H-pyrazol-3-yl]-3-[5-(2-morpholin-4-yl-ethyl)-thiazol-2-yl]-urea (Analog 187). Using Procedure 1, carbamate 23 and thiazole 4 are used to synthesize urea Analog 187. LC-MS retention time=3.14 min (M+H=483.2).

Example 21

Scheme 7.

105

-continued

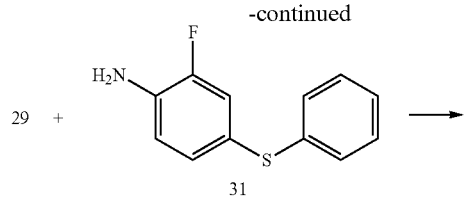
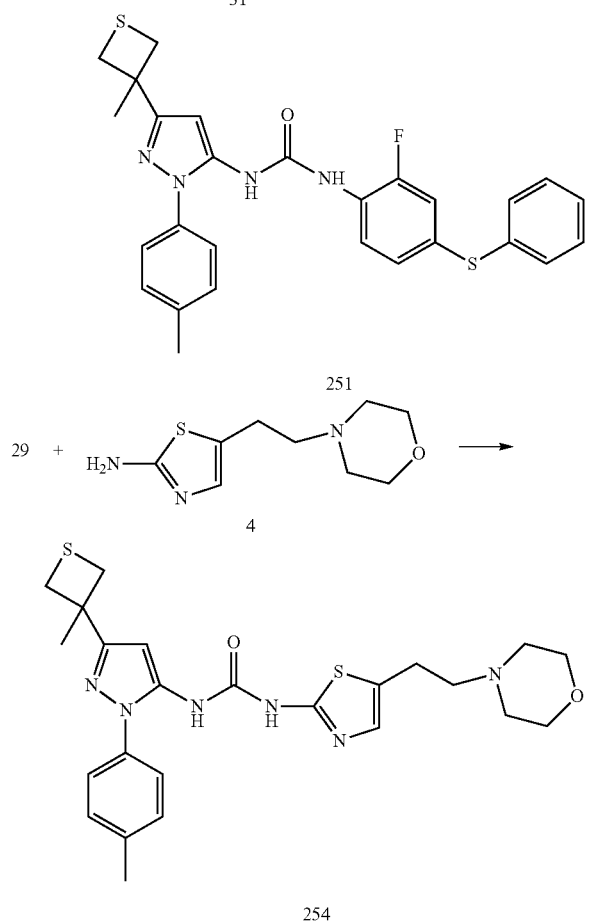

Experiments as shown in Scheme 7 include the following syntheses.

Preparation of 1-[5-(3-Methyl-thietan-3-yl)-2-p-tolyl-2H-pyrazol-3-yl]-3-(4-phenylsulfanyl-phenyl)-urea (Analog 250). Using Procedure 2, carbamate 29 and aniline 20 are used to synthesize urea Analog 250. LC-MS retention time=4.070 min (M+H=488.5); TLC Rf=0.1 (ethyl acetate/hexane (1:1)).

Preparation of 1-[5-(3-Methyl-thietan-3-yl)-2-p-tolyl-2H-pyrazol-3-yl]-3-(4-phenoxy-phenyl)-urea (Analog 252). Using Procedure 2, carbamate 29 and aniline 18 are used to synthesize urea Analog 252. LC-MS retention time=3.957 min (M+H=472.5); TLC Rf=0.1 (ethyl acetate).

Preparation of 1-(2-Fluoro-4-phenoxy-phenyl)-3-([5-(3-methyl-thietan-3-yl)-2-p-tolyl-2H-pyrazol-3-yl]-urea (Analog 253). Using Procedure 2, carbamate 29 and aniline 30 are used to synthesize urea Analog 253. LC-MS retention time=3.995 min (M+H=490.4).

Preparation of 1-(2-Fluoro-4-phenylsulfanyl-phenyl)-3-[5-(3-methyl-thietan-3-yl)-2-p-tolyl-2H-pyrazol-3-yl]-urea (Analog 251). Using Procedure 2, carbamate 29 and aniline 31 are used to synthesize urea Analog 251. LC-MS retention time=4.24 min (M+H=506.4).

106

Preparation of 1-[5-(3-Methyl-thietan-3-yl)-2-p-tolyl-2H-pyrazol-3-yl]-3-[5-(2-morpholin-4-yl-ethyl)-thiazol-2-yl]-urea (Analog 254). Using Procedure 1, carbamate 29 and thiazole 4 are used to synthesize urea Analog 254.

Example 22

Scheme 8.

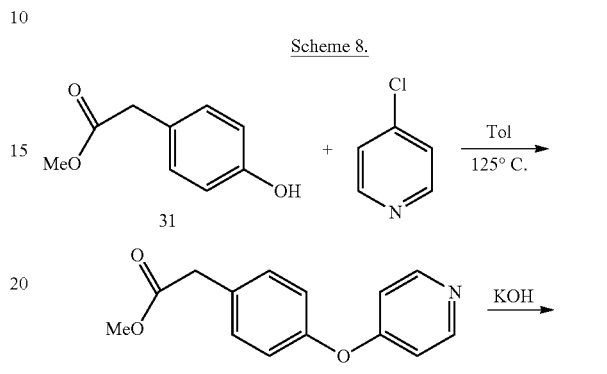
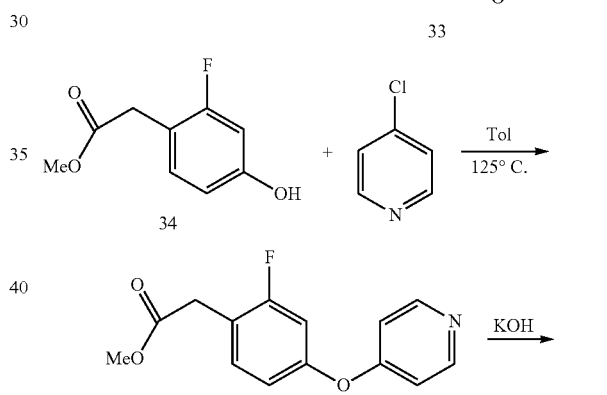
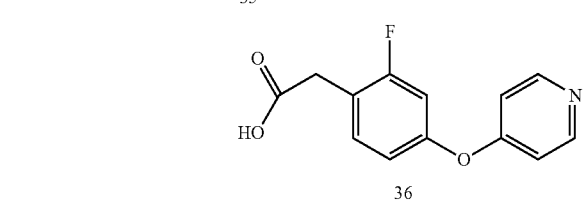
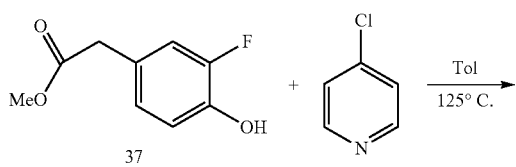
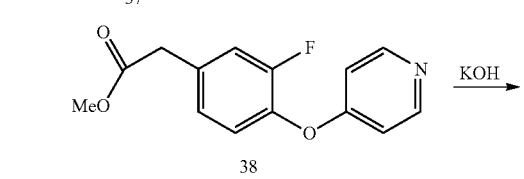

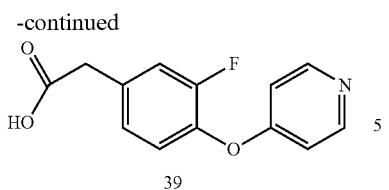

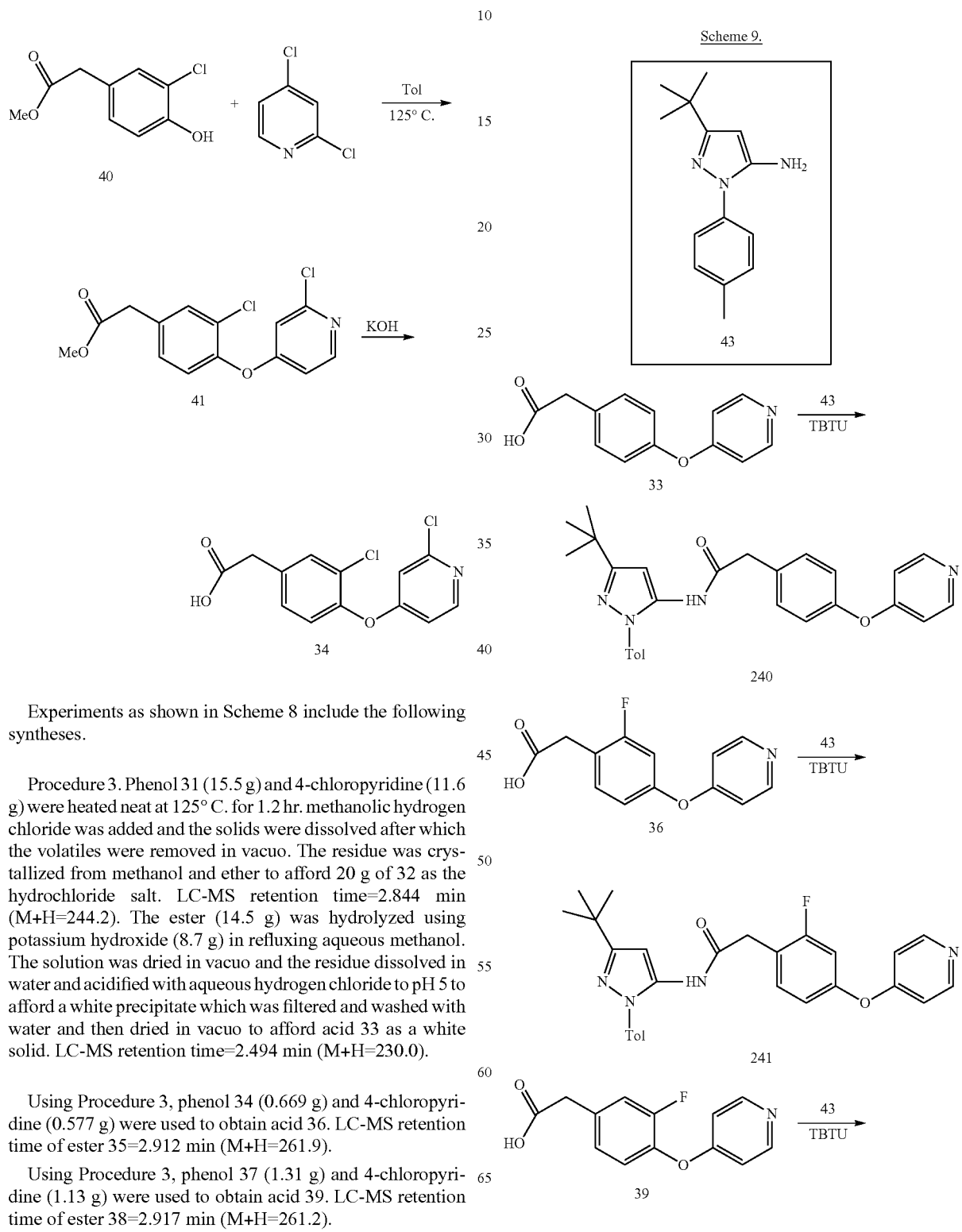

Experiments as shown in Scheme 8 include the following syntheses.

Procedure 3. Phenol 31 (15.5 g) and 4-chloropyridine (11.6 g) were heated neat at 125° C. for 1.2 hr. methanolic hydrogen chloride was added and the solids were dissolved after which the volatiles were removed in vacuo. The residue was crystallized from methanol and ether to afford 20 g of 32 as the hydrochloride salt. LC-MS retention time=2.844 min (M+H=244.2). The ester (14.5 g) was hydrolyzed using potassium hydroxide (8.7 g) in refluxing aqueous methanol. The solution was dried in vacuo and the residue dissolved in water and acidified with aqueous hydrogen chloride to pH 5 to afford a white precipitate which was filtered and washed with water and then dried in vacuo to afford acid 33 as a white solid. LC-MS retention time=2.494 min (M+H=230.0).

Using Procedure 3, phenol 34 (0.669 g) and 4-chloropyridine (0.577 g) were used to obtain acid 36. LC-MS retention time of ester 35=2.912 min (M+H=261.9).

Using Procedure 3, phenol 37 (1.31 g) and 4-chloropyridine (1.13 g) were used to obtain acid 39. LC-MS retention time of ester 38=2.917 min (M+H=261.2).

Using Procedure 3, except heating at 150° C., phenol 40 (6.0 g) and 2,4-dichloropyridine (6.68 g) were used to obtain acid 42. LC-MS retention time of ester 41-4.82 min (M+H=278.3).

Example 23

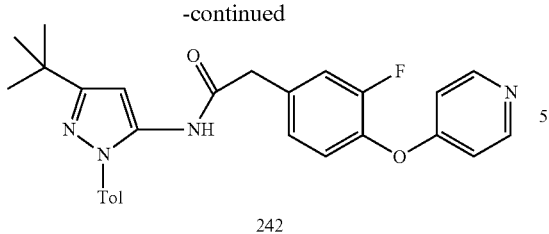

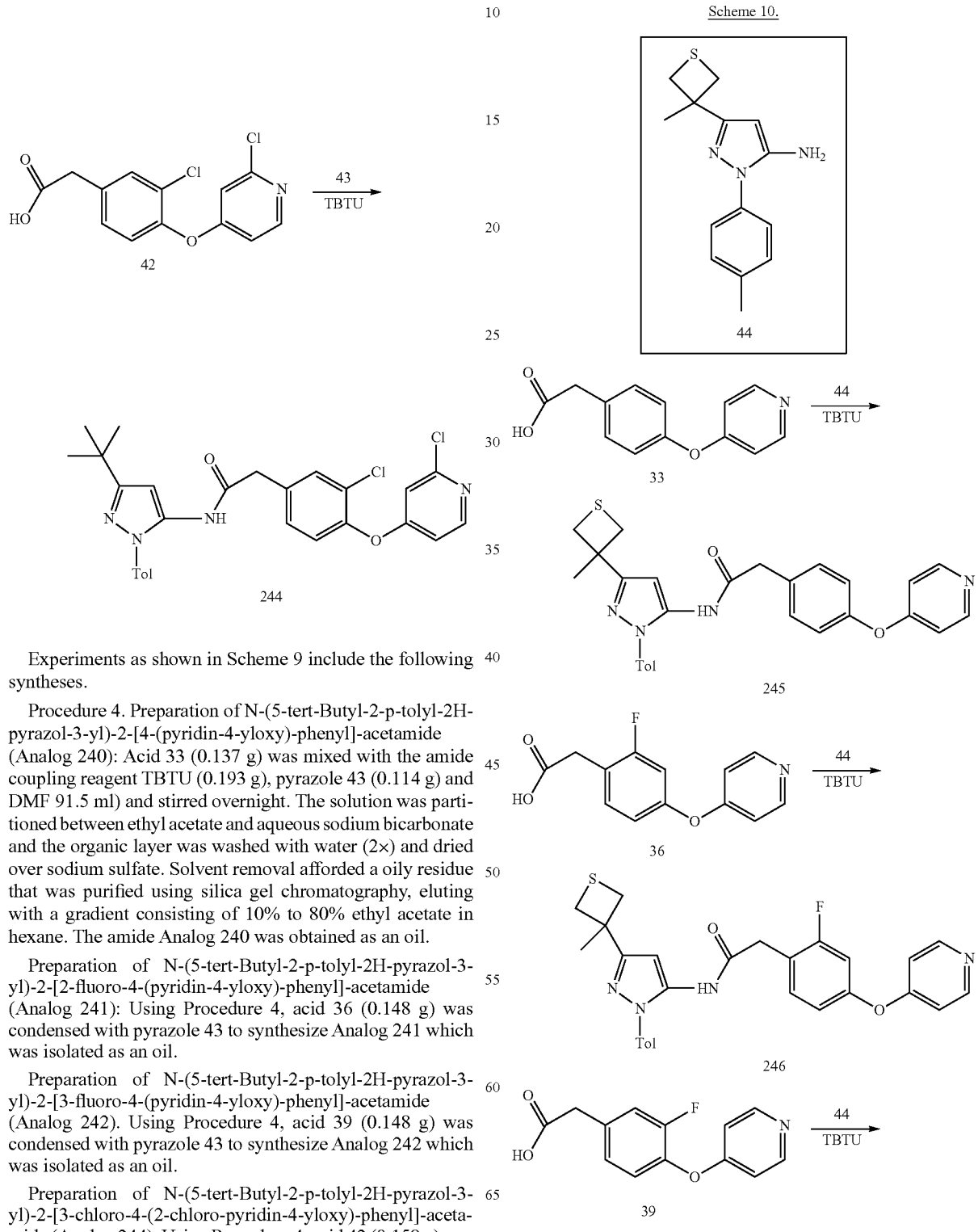

Experiments as shown in Scheme 9 include the following syntheses.

Procedure 4. Preparation of N-(5-tert-Butyl-2-p-tolyl-2H-pyrazol-3-yl)-2-[4-(pyridin-4-yloxy)-phenyl]-acetamide (Analog 240): Acid 33 (0.137 g) was mixed with the amide coupling reagent TBTU (0.193 g), pyrazole 43 (0.114 g) and DMF 91.5 ml) and stirred overnight. The solution was partitioned between ethyl acetate and aqueous sodium bicarbonate and the organic layer was washed with water (2×) and dried over sodium sulfate. Solvent removal afforded a oily residue that was purified using silica gel chromatography, eluting with a gradient consisting of 10% to 80% ethyl acetate in hexane. The amide Analog 240 was obtained as an oil.

Preparation of N-(5-tert-Butyl-2-p-tolyl-2H-pyrazol-3-yl)-2-[2-fluoro-4-(pyridin-4-yloxy)-phenyl]-acetamide (Analog 241): Using Procedure 4, acid 36 (0.148 g) was condensed with pyrazole 43 to synthesize Analog 241 which was isolated as an oil.

Preparation of N-(5-tert-Butyl-2-p-tolyl-2H-pyrazol-3-yl)-2-[3-fluoro-4-(pyridin-4-yloxy)-phenyl]-acetamide (Analog 242). Using Procedure 4, acid 39 (0.148 g) was condensed with pyrazole 43 to synthesize Analog 242 which was isolated as an oil.

Preparation of N-(5-tert-Butyl-2-p-tolyl-2H-pyrazol-3-yl)-2-[3-chloro-4-(2-chloro-pyridin-4-yloxy)-phenyl]-acetamide (Analog 244). Using Procedure 4, acid 42 (0.158 g) was condensed with pyrazole 43 to synthesize Analog 244 which was isolated as an oil. LC-MS retention time=5.728 min (M+H=510.2).

Example 23 log 249 which was isolated as an oil. LC-MS retention time=5.702 min (M+H=540.2).

Example 24

Scheme 11.

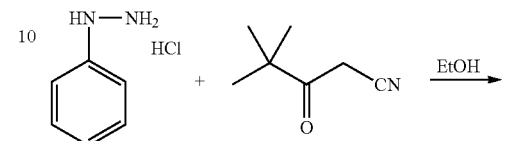

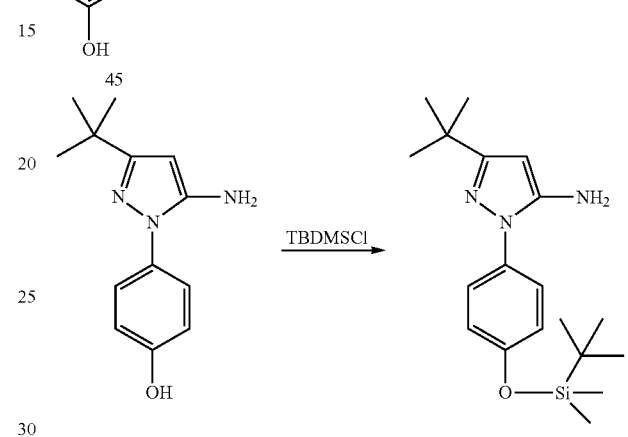

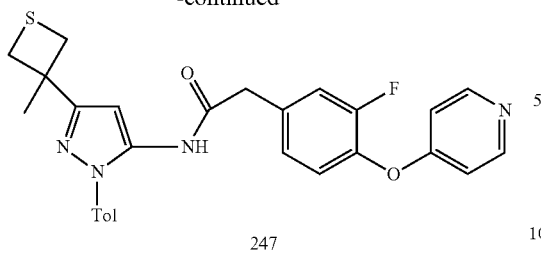

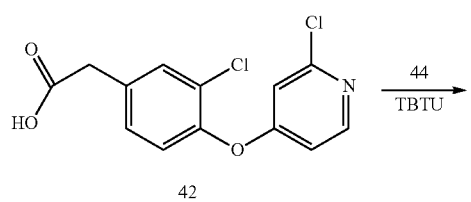

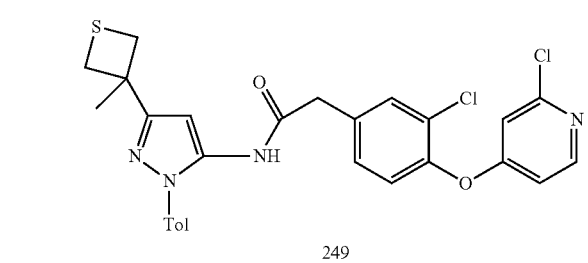

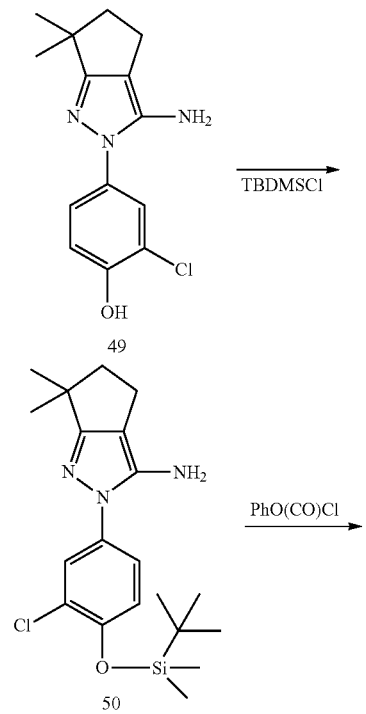

Experiments as shown in Scheme 10 include the following syntheses.

Preparation of N-[5-(3-Methyl-thietan-3-yl)-2-p-tolyl-2H-pyrazol-3-yl]-2-[4-(pyridin-4-yloxy)-phenyl]-acetamide (Analog 245). Using Procedure 4, acid 33 (0.137 g) was condensed with pyrazole 44 to synthesize Analog 245 which was isolated as an oil. LC-MS retention time=3.803 min (M+H=471.4).

Preparation of 2-[2-Fluoro-4-(pyridin-4-yloxy)-phenyl]-N-[5-(3-methyl-thietan-3-yl)-2-p-tolyl-2H-pyrazol-3-yl]-acetamide (Analog 246). Using Procedure 4, acid 36 (0.148 g) was condensed with pyrazole 44 to synthesize Analog 246 which was isolated as an oil. LC-MS retention time=3.83 min (M+H=489.5).

Preparation of 2-[3-Fluoro-4-(pyridin-4-yloxy)-phenyl]-N-[5-(3-methyl-thietan-3-yl)-2-p-tolyl-2H-pyrazol-3-yl]-acetamide (Analog 247). Using Procedure 4, acid 39 (0.148 g) was condensed with pyrazole 44 to synthesize Analog 247 which was isolated as an oil. LC-MS retention time=3.81 min (M+4=489.5).

Preparation of 2-[3-Chloro-4-(2-chloro-pyridin-4-yloxy)-phenyl]-N-[5-(3-methyl-thietan-3-yl)-2-p-tolyl-2H-pyrazol-3-yl]-acetamide (Analog 249). Using Procedure 4, acid 42 (0.158 g) was condensed with pyrazole 44 to synthesize Ana- -continued

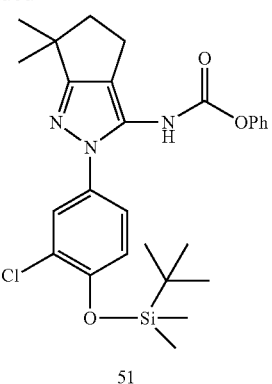

51

-continued

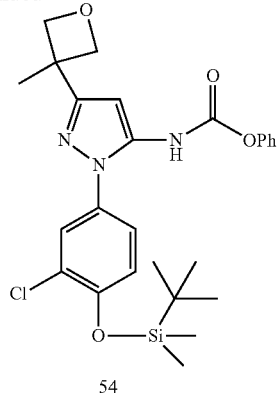

54

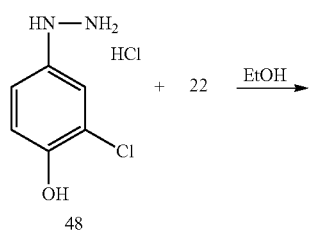

+ 22 →(EtOH)

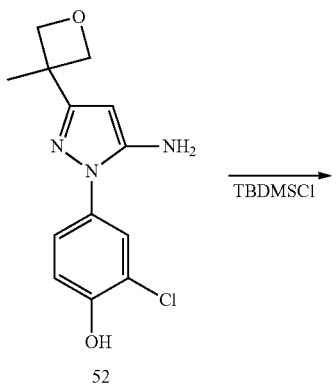

52 →(TBDMSCl)

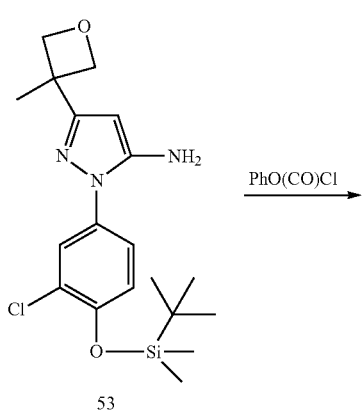

53 →(PhO(CO)Cl)

Experiments as shown in Scheme 11 include the following syntheses.

4-Hydroxyphenylhydrazine hydrochloride (2.5 g) was mixed with pivaloylacetonitrile (1.98 g) in Ethanol (25 ml) and refluxed for 1 hr. The solvent was removed and the residue partitioned between ethyl acetate and aq. sodium bicarbonate and the organic layer washed with water, dried over sodium sulfate, and solvent removed to afford 3.5 g of pyrazole 46 in pure form. LC-MS retention time=2.96 min (M+H=232.1). In a flask cooled in an ice-bath, the pyrazole was placed in DCM (35 ml) with t-butyldimethylchlorosilane (2.56 g), triethyl amine (2.57 ml), and DMAP (0.1 g) and allowed to stir overnight. The solution was partitioned between ether and aqueous sodium bicarbonate and the organic layer washed with water and brine, and then dried over sodium sulfate. Solvent removal afforded an oil that was purified by silica gel chromatography, eluting with ethyl acetate in hexane to obtain pure 47. LC-MS retention time=5.563 min (M+H=356.3); TLC Rf=0.3 (ethyl acetate-hexane (1:9)). 3-Chloro-4-hydroxyphenylhydrazine hydrochloride (1.75 g) was mixed with keto-nitrile 14 (1.23 g) in ethanol (15 ml) and refluxed for 1 hr. The solvent was removed and the residue partitioned between ethyl acetate and aq. sodium bicarbonate and the organic layer washed with water, dried over sodium sulfate, and solvent removed to afford a residue that was purified using silica gel chromatography, eluting with a gradient comprised of 5% to 75% ethyl acetate in hexane to afford pyrazole 49 (0.92 g). LC-MS retention time=3.32 min (M+H=278.1). In a flask cooled in an ice-bath, the pyrazole was placed in DMF (3 ml) with t-butyldimethylchlorosilane (0.53 g) and imidazole (0.26 g) and allowed to stir for 3 hr. The solution was partitioned between ether and aqueous sodium bicarbonate and the organic layer washed with water and brine, and then dried over sodium sulfate to afford an oil which was purified using silica gel chromatography, eluting with ethyl acetate/hexane (15:85) to obtain pure 50. LC-MS retention time=4.84 min (M+H=392.1). The pyrazole (1.06 g) was mixed with THF (8 ml) and aqueous sodium bicarbonate (15 ml) and cooled in an ice-bath. Phenyl chloroformate (0.635 g) was added and the mixture stirred for 1 hr and then extracted with ether, dried over sodium sulfate, and the solvent removed to obtain 1.67 g of an oil. This was purified using silica gel chromatography, eluting with ethyl acetate/hexane (2:8) carbamate 51 as a solid foam (0.9 g). LC-MS retention time using gradient method for lipophilic compounds=5.56 min (M+H=512.2).

3-Chloro-4-hydroxyphenylhydrazine hydrochloride (1.75 g) was mixed with keto-nitrile 22 (1.25 g) in ethanol (8 ml) and heated at 35° C. for 2 hr. The solvent was removed and the residue partitioned between ethyl acetate and aq. sodium bicarbonate and the organic layer washed with water, dried over sodium sulfate, and solvent removed to afford a residue that was purified using silica gel chromatography, eluting with a gradient comprised of 5% to 75% ethyl acetate in hexane to afford pyrazole 52 (0.20 g) as a solid. LC-MS retention time=2.78 min (M+H=280.5). In a flask cooled in an ice-bath, the pyrazole was placed in DMF (0.6 ml) with t-butyldimethylchlorosilane (0.11 g) and imidazole (0.06 g) and allowed to stir for 2 hr. The solution was partitioned between ether and aqueous sodium bicarbonate and the organic layer washed with water and brine, and then dried over sodium sulfate to afford an oil which was purified using silica gel chromatography, eluting with ethyl acetate/hexane (3:7) to obtain pure 53 (0.23 g). LC-MS retention time=5.03 min (M+H=394.1). The pyrazole was mixed with THF (4 ml) and aqueous sodium bicarbonate (8 ml) and cooled in an ice-bath. Phenyl chloroformate (0.137 g) was added, the mixture stirred for 30 min, and then extracted with ether followed by drying over sodium sulfate. Solvent removal provided 0.21 g of an oil which was purified using silica gel chromatography, eluting with ethyl acetate/hexane (2:8) to afford carbamate 54 as a solid (0.12 g). LC-MS retention time using gradient method for lipophilic compounds=4.80 min (M+H=514.1).

Example 25

Scheme 12.

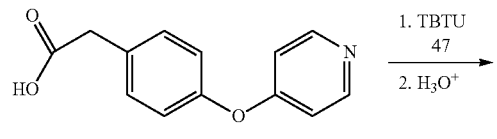

33

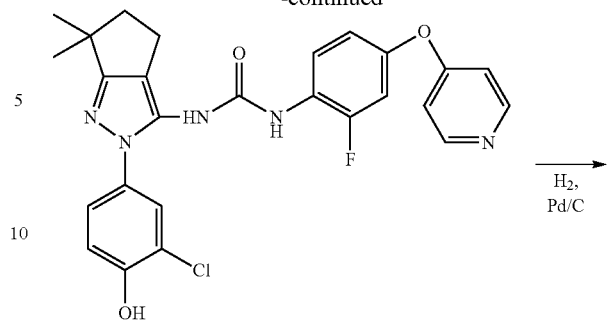

234

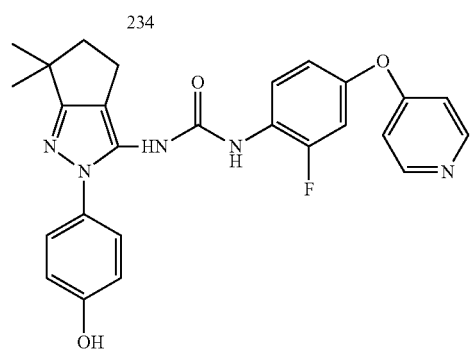

235

18 + 54 →

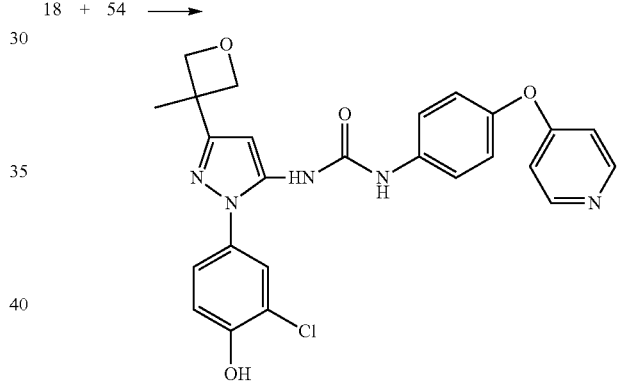

229

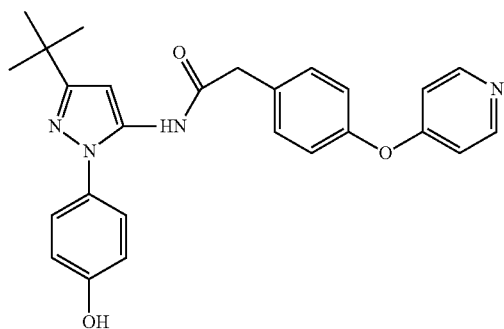

236

30 + 51 →

Experiments as shown in Scheme 12 include the following syntheses.

Preparation of N-[5-tert-Butyl-2-(4-hydroxy-phenyl)-2H-pyrazol-3-yl]-2-[4-(pyridin-4-yloxy)-phenyl]-acetamide (Analog 236). Using Procedure 4, acid 33 (0.137 g) was condensed with pyrazole 47 to prepare the silyl-protected amide intermediate which was deprotected by stirring with acetic acid/THF/water (3:1:1) for 1 hr. Solvent removal and purification using silica gel chromatography, eluting with ethyl acetate/hexane afforded Analog 236 as a waxy oil. LC-MS retention time=4.855 min (M+H=442.3).

Preparation of 1-[2-(3-Chloro-4-hydroxy-phenyl)-6,6-dimethyl-2,4,5,6-tetrahydro-cyclopentapyrazol-3-yl]-3-[2-fluoro-4-(pyridin-4-yloxy)-phenyl]-urea (Analog 234). Using Procedure 2, carbamate 30 (0.137 g) was condensed with pyrazole 51 to prepare the silyl-protected urea intermediate which was deprotected by stirring with acetic acid/THF/water (3:1:1) overnight. Solvent removal and purification by trituration with ether afforded 0.09 g of Analog 234 as a solid foam. LC-MS retention time=3.61 min (M+H=508.1).

Preparation of 1-[2-Fluoro-4-(pyridin-4-yloxy)-phenyl]-3-[2-(4-hydroxy-phenyl)-6,6-dimethyl-2,4,5,6-tetrahydrocyclopentapyrazol-3-yl]-urea (Analog 235). Analog 234 (0.11 g) was hydrogenated at 50 p.s.i. hydrogen pressure using Pd/C catalyst in THF containing triethylamine (0.11 g). The reduction was completed in 2 hr and the mixture was filtered and partitioned between ethyl acetate and aqueous sodium bicarbonate. The organic layer was washed with water and dried over sodium sulfate. Solvent removal afforded a glassy solid which was triturated with ether. The white solid was filtered and dried to afford urea Analog 235 (0.067 g). LC-MS retention time=3.36 min (M+H=474.1).

Preparation of 1-[2-(3-Chloro-4-hydroxy-phenyl)-5-(3-methyl-oxetan-3-yl)-2H-pyrazol-3-yl]-3-phenyl-urea; compound with pyridine (Analog 229). Using Procedure 2, carbamate 54 (0.06 g) was condensed with aniline 18 (0.028 g) to prepare the silyl-protected urea intermediate which was purified using silica gel chromatography, eluting with a gradient comprised of 0% to 10% methanol in DCM to afford 0.058 g of pure silyl-protected urea intermediate (0.058 g). LC-MS retention time=4.51 min (M+H=606.1). This was deprotected by stirring with acetic acid/THF/water (3:1:1) overnight. Solvent removal and trituration with ether afforded 0.4 g of Analog 229 as a white solid. LC-MS retention time=3.17 min (M+H=492.1).

All references cited herein are incorporated by reference, each in its entirety. Applicant reserves the right to challenge any conclusions presented by the authors of any reference.

SEQUENCE LISTING

```
<110> Washington University

<120> ANTI-MUCUS DRUGS AND USES THEREFOR

<130> 1001-0650

<150> PCT/US13/050921

<151> 2013-07-17

<150> US 61/672378

<151> 2012-07-17

<160> 15

<170> PatentIn version 3.5

<210> 1
<211> 30
<212> DNA
<213> Homo sapiens
<400> 1
agtgtcacag ccctgattga atcagtgaat                     30

<210> 2
<211> 29
<212> DNA
<213> Homo sapiens
<400> 2
agttgtgaaa taccttgagt agacaccgt                      29

<210> 3
<211> 27
<212> DNA
<213> Homo sapiens
<400> 3
taatggagca ggtgctgatg ctactaa                        27

<210> 4
<211> 27
<212> DNA
<213> Homo sapiens
<400> 4
accctatctt ggacagcacc tggagaa                        27

<210> 5
<211> 27
<212> DNA
<213> Homo sapiens
<400> 5
cttggatatt ctgtagactt ttactca                        27

<210> 6
<211> 30
<212> DNA
<213> Homo sapiens
<400> 6
tttgatcagg gccaggctac aagctatgaa                     30

<210> 7
<211> 24
<212> DNA
<213> Homo sapiens
<400> 7
tggacataca gaagttttgg aact                           24

<210> 8
<211> 24
<212> DNA
<213> Homo sapiens
<400> 8
gctgtaaaat acctggagta gact                           24

<210> 9
<211> 32
<212> DNA
```

SEQUENCE LISTING

<400> 9
gataatggtg caggcgctga ttctttcaag aa    32

<210> 10
<211> 28
<212> DNA
<213> Homo sapiens

<400> 10
aggccagcta ccgggccggc cagaccat    28

<210> 11
<211> 30
<212> DNA
<213> Homo sapiens

<400> 11
gtccccgtac acggcgcagg tggccaggca    30

<210> 12
<211> 29
<212> DNA
<213> Homo sapiens

<400> 12
tgcaacacct gcacctgtga cagcaggat    29

<210> 13
<211> 28
<212> DNA
<213> Homo sapiens

<400> 13
cagccgagcc acatccctca gacaccat    28

<210> 14
<211> 33
<212> DNA
<213> Homo sapiens

<400> 14
ctttaccaga gttaaaagca gccctggtga cca    33

<210> 15
<211> 30
<212> DNA
<213> Homo sapiens

<400> 15
aggtcggagt caaccgattt ggtcgtattg    30

---

SEQUENCE LISTING

<160> NUMBER OF SEQ ID NOS: 15

<210> SEQ ID NO 1
<211> LENGTH: 30
<212> TYPE: DNA
<213> ORGANISM: Homo sapiens

<400> SEQUENCE: 1
agtgtcacag ccctgattga atcagtgaat    30

<210> SEQ ID NO 2
<211> LENGTH: 29
<212> TYPE: DNA
<213> ORGANISM: Homo sapiens

<400> SEQUENCE: 2
agttgtgaaa taccttgagt agacaccgt    29

<210> SEQ ID NO 3
<211> LENGTH: 27
<212> TYPE: DNA
<213> ORGANISM: Homo sapiens

<400> SEQUENCE: 3
taatggagca ggtgctgatg ctactaa    27

```
<210> SEQ ID NO 4
<211> LENGTH: 27
<212> TYPE: DNA
<213> ORGANISM: Homo sapiens

<400> SEQUENCE: 4
accctatctt ggacagcacc tggagaa                                    27

<210> SEQ ID NO 5
<211> LENGTH: 27
<212> TYPE: DNA
<213> ORGANISM: Homo sapiens

<400> SEQUENCE: 5
cttggatatt ctgtagactt ttactca                                    27

<210> SEQ ID NO 6
<211> LENGTH: 30
<212> TYPE: DNA
<213> ORGANISM: Homo sapiens

<400> SEQUENCE: 6
tttgatcagg gccaggctac aagctatgaa                                 30

<210> SEQ ID NO 7
<211> LENGTH: 24
<212> TYPE: DNA
<213> ORGANISM: Homo sapiens

<400> SEQUENCE: 7
tggacataca gaagttttgg aact                                       24

<210> SEQ ID NO 8
<211> LENGTH: 24
<212> TYPE: DNA
<213> ORGANISM: Homo sapiens

<400> SEQUENCE: 8
gctgtaaaat acctggagta gact                                       24

<210> SEQ ID NO 9
<211> LENGTH: 32
<212> TYPE: DNA
<213> ORGANISM: Homo sapiens

<400> SEQUENCE: 9
gataatggtg caggcgctga ttctttcaag aa                              32

<210> SEQ ID NO 10
<211> LENGTH: 28
<212> TYPE: DNA
<213> ORGANISM: Homo sapiens

<400> SEQUENCE: 10
aggccagcta ccgggccggc cagaccat                                   28

<210> SEQ ID NO 11
<211> LENGTH: 30
<212> TYPE: DNA
<213> ORGANISM: Homo sapiens

<400> SEQUENCE: 11
gtccccgtac acggcgcagg tggccaggca                                 30
```

```
<210> SEQ ID NO 12
<211> LENGTH: 29
<212> TYPE: DNA
<213> ORGANISM: Homo sapiens

<400> SEQUENCE: 12
tgcaacacct gcacctgtga cagcaggat                                          29

<210> SEQ ID NO 13
<211> LENGTH: 28
<212> TYPE: DNA
<213> ORGANISM: Homo sapiens

<400> SEQUENCE: 13
cagccgagcc acatccctca gacaccat                                           28

<210> SEQ ID NO 14
<211> LENGTH: 33
<212> TYPE: DNA
<213> ORGANISM: Homo sapiens

<400> SEQUENCE: 14
ctttaccaga gttaaaagca gccctggtga cca                                     33

<210> SEQ ID NO 15
<211> LENGTH: 30
<212> TYPE: DNA
<213> ORGANISM: Homo sapiens

<400> SEQUENCE: 15
aggtcggagt caaccgattt ggtcgtattg                                         30
```

What is claimed is:

1. A compound, or a pharmaceutically acceptable salt thereof, of Formula I

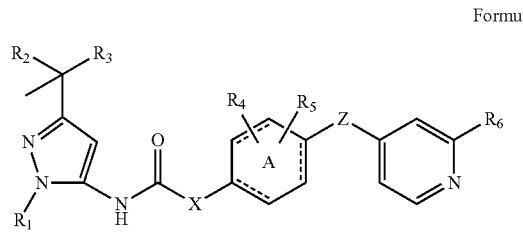

Formula I wherein $R_1$ is selected from the group consisting of H, lower alkyl and aryl;

$R_2$ and $R_3$ together are a 4-6 member heterocylic ring with 1 or 2 heteroatoms, each heteroatom selected from the group consisting of N, O and S.

X is selected from the group consisting of $CH_2$, NH, O, and S;

ring A is a 6-membered aliphatic, aromatic, or heteroaromatic ring, wherein each $R_4$ and $R_5$ is independently selected from the group consisting of H, a halogen, lower alkyl, $-CF_3$, $-OR_8$ and $-SR_9$;

each of $R_8$ and $R_9$ is independently selected from the group consisting of H, lower alkyl, cycloalkyl, cycloalkylalkyl, heterocyclyl, heterocycloalkyl, aryl, and arylaklyl;

Z is selected from the group consisting of $CH_2$, NH, O and S; and $R_6$ is selected from the group consisting of H, amine, lower alkyl, cycloalkyl, cycloalkylalkyl, heterocyclyl, heterocyloalkyl, aryl, arylalkyl, $-OR_{12}$, $-SR_{13}$, $-NR_{14}R_{15}$, $-C(O)NR_{16}R_{17}$, $-NR_{18}C(O)R_{19}$, $-C(O)OR_{20}$, $-NR_{21}C(O)OR_{22}$, and $-NR_{23}C(O)NR_{24}R_{25}$;

wherein each of $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ and $R_{25}$ is independently selected from the group consisting of H, lower alkyl, cycloalkyl, cycloalkylalkyl, heterocyclyl, heterocycloalkyl, aryl, and arylaklyt;

and wherein lower alkyl is $C_1$-$C_{10}$ linear alkyl, $C_3$-$C_{10}$ cyclic alkyl and 0, 1, 2 or 3 carbons of a lower alkyl are replaced with a heteroatom, each heteroatom selected from the group consisting of N, O, and S.

2. A compound or a pharmaceutically acceptable salt thereof in accordance with claim 1, wherein the compound is selected from the group consisting of

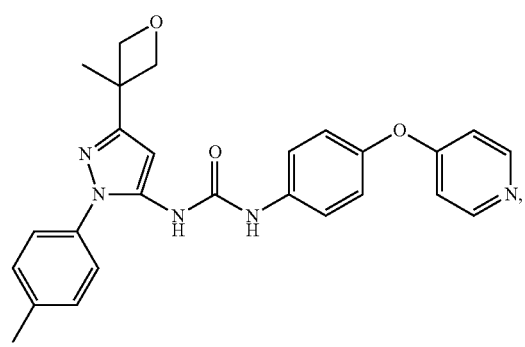
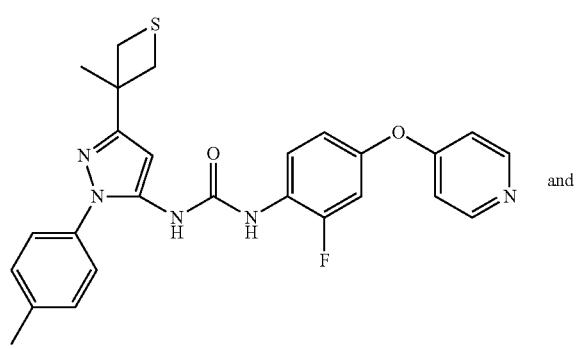
and
3. A compound or a pharmaceutically acceptable salt thereof in accordance
  with claim 1, of structure
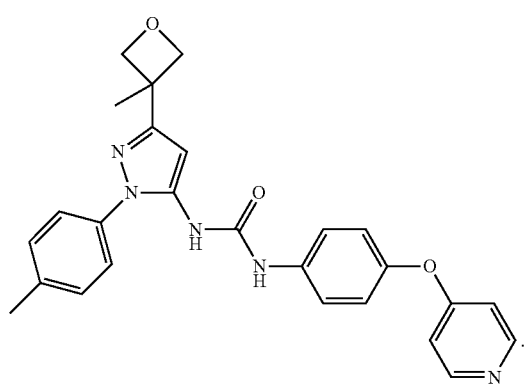 [SMILES: Cc1ccc(-n2nc(C3(C)COC3)cc2NC(=O)Nc2ccc(Oc3ccncc3)cc2)cc1]
4. A compound Or a pharmaceutically acceptable salt thereof in accordance
  with claim 1, of structure.
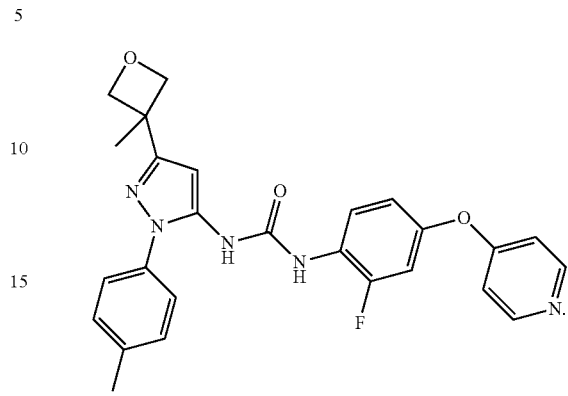
5. A compound or a pharmaceutically acceptable salt thereof in accordance with claim 1, wherein the compound is selected from the group consisting of
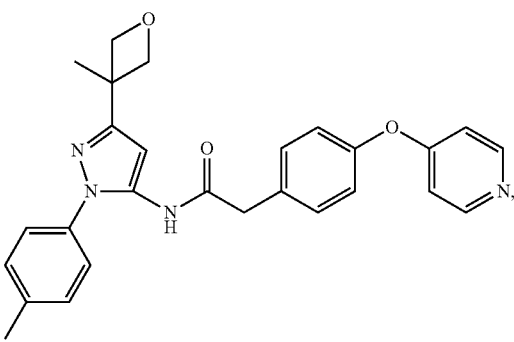
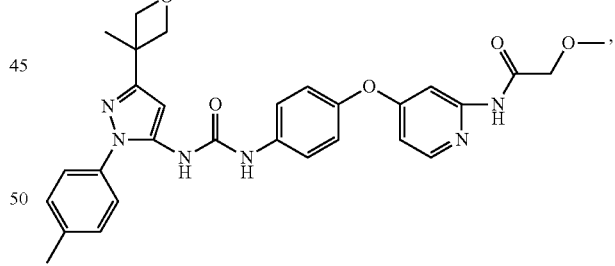
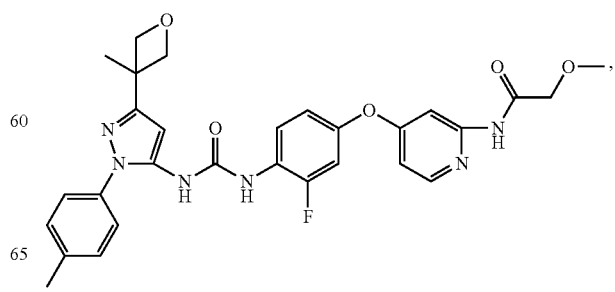

-continued

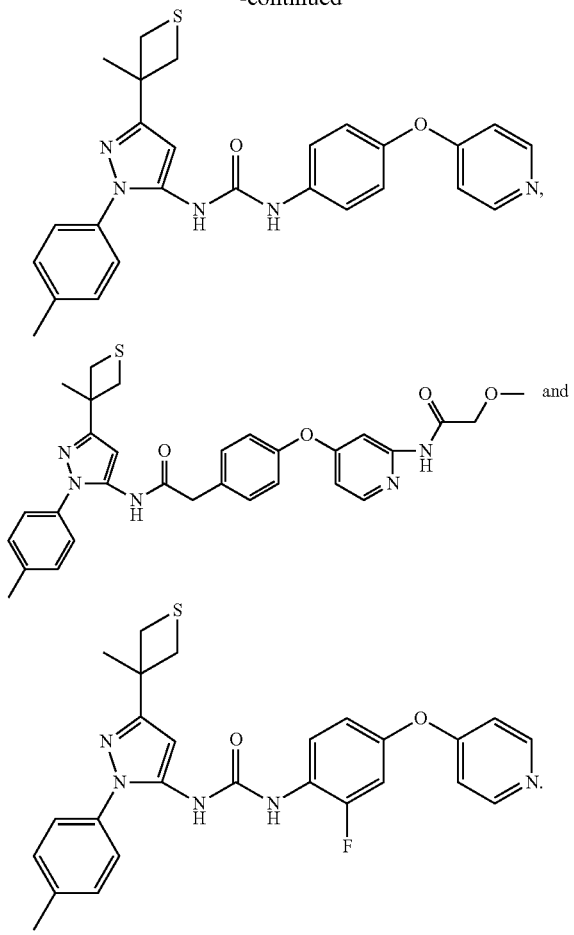

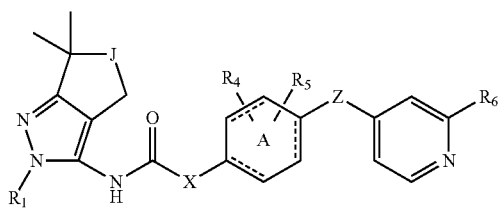

6. A compound, or a pharmaceutically acceptable salt thereof, of Formula II

Formula II wherein $R_1$ is selected from the group consisting of H, lower alkyl, and aryl:,
J is selected from the group consisting of $CH_2$, O, and S;
X is selected from the group consisting of $CH_2$, HN, O, and S;
ring A is a 6-membered aliphatic, aromatic, or heteroaromatic ring, wherein each $R_4$ and $R_5$ is independently selected from the group consisting of H, a halogen, lower alkyl, $-CF_3$, $-OR_8$ and $-SR_9$;
each of $R_8$ and $R_9$ is selected from the group consisting of H, lower alkyl, cycloalkyl, cycloalkylalkyl, heterocyclyl, heterocycloalkyl, aryl, and arylaklyl;
Z is selected from the group consisting of $CH_2$, NH, O, and S; and $R_6$ is selected from the group consisting of H, amine, lower alkyl, cycloalkyl, cycloalkylalkyl, heterocyclyl, heterocyloalkyl, aryl, aylalkyl, $-OR_{12}$, $-SR_{13}$, $-NR_{14}R_{15}$, $-C(O)NR_{16}R_{17}$, $-NR_{18}C(O)R_{19}$, $-C(O)OR_{20}$, $-NR_{21}C(O)OR_{22}$, and $-NR_{23}C(O)NR_{24}R_{25}$;

wherein each of $R_{12}$, $R_{13}$, $R_{14}$, $R_{15}$, $R_{16}$, $R_{18}$, $R_{19}$, $R_{20}$, $R_{21}$, $R_{22}$, $R_{23}$, $R_{24}$ and $R_{25}$ is independently selected from the group consisting of H, lower alkyl, cycloalkyl, cycloalkylalkyl, heterocyclyl, heterocycloalkyl, aryl, and alylaklyl; and wherein lower alkyl is $C_1$-$C_{10}$ linear alkyl, $C_3$-$C_{10}$ branched alkyl, or $C_3$-$C_{10}$ cyclic alkyl and 0, 1, 2 or 3 carbons of a lower alkyl are replaced with a heteroatom, each heteroatom selected from the group consisting of N, O, and S.

7. A compound or a pharmaceutically acceptable salt thereof in accordance with claim 6, wherein the compound is selected from the group consisting, of

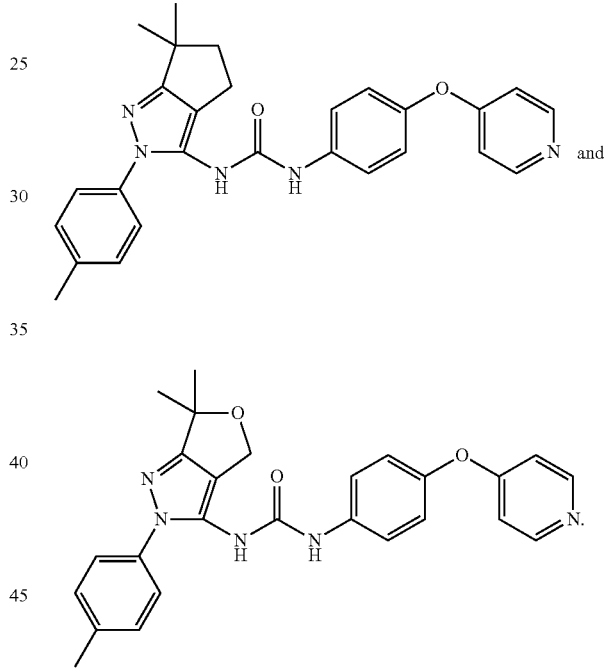

8. A compound or a pharmaceutically acceptable salt thereof in accordance with claim 6, wherein the compound is selected from the group consisting of

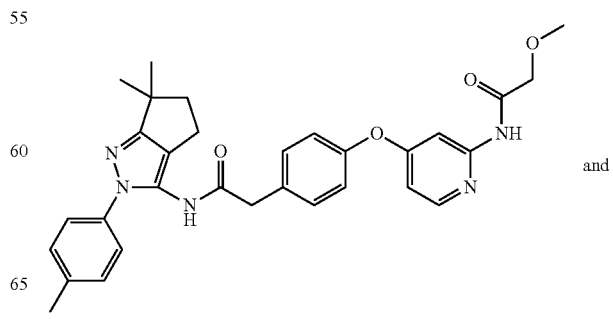

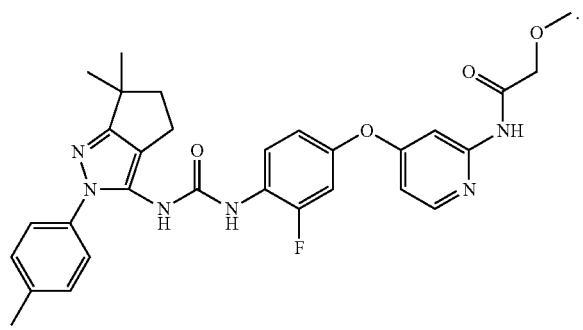

9. A compound, or a pharmaceutically acceptable salt thereof, of Formula VI:

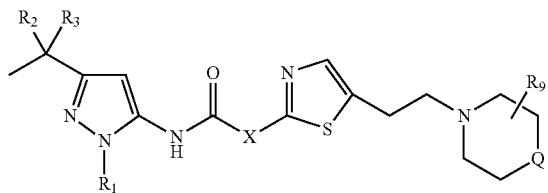

Formula VI wherein $R_1$ is selected from the group consisting of H, lower alkyl, and aryl;

$R_2$ and $R_3$ are each independently selected form the group consisting of H or lower alkyl, or together are a 4-6 member aliphatic, carbocyclic, or heterocyclic ring with 0, 1, or 2 heteroatoms, each heteroatom selected from the group consisting of N, O, and S;

Q is selected from the group consisting of O and S;

X is selected from the group consisting of $CH_2$ and NH;

$R_9$ is selected from the group consisting of H, lower alkyl, cycloalkyl, cycloalkylalkyl, heterocycyl, hetemcycylalkyl, aryl, arylalkyl, —NHC(O)$R_8$, —NHC(O)NR$_{10}$R$_{11}$, —CH$_2$NHC(O)R$_{12}$, —CH$_{2NHC(O)NR13}$R$_{14}$, —C(O)NR$_{15}$R$_{16}$, and —C(O)OR$_{17}$;

wherein each of $R_8$, $R_{10}$, $R_{11}$, $R_{12}$, $R_{13}$, $R_{14}$, $R_{15}$, $R_{16}$ and $R_{17}$ is independently selected from the group consisting of H, lower alkyl, cycloalkyl, cycloalkylalkyl, heterocyclyl, heterocycloalkyl, aryl, and arylaklyl; and wherein lower alkyl is $C_1$-$C_{10}$ linear alkyl, $C_3$-$C_{10}$ branched alkyl, or $C_3$-$C_{10}$ cyclic alkyl and 0, 1, 2 or 3 carbons of a lower alkyl are replaced with a heteroatom, each heteroatom selected from the group consisting of N, O, and S.

10. A compound or a pharmaceutically acceptable salt thereof in accordance with claim 9, wherein X is NH.

11. A compound or a pharmaceutically acceptable salt thereof in accordance with claim 10, wherein the compound is

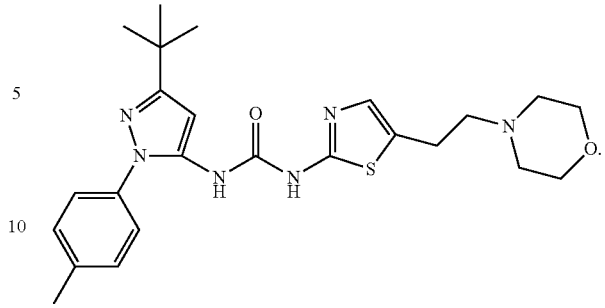

12. A compound or a pharmaceutically acceptable salt thereof in accordance with claim 9, wherein X is $CH_2$.

13. A compound or a pharmaceutically acceptable salt thereof in accordance with claim 12, wherein the compound is

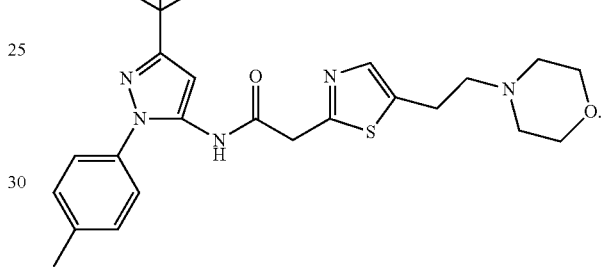

14. A compound, or a pharmaceutically acceptable salt thereof, of Formula VII

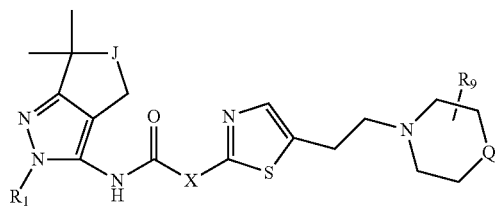

Formula VII wherein $R_1$ is selected from the group consisting of H, lower alkyl, and aryl;

J is selected from the group consisting of $CH_2$, O, and S;

X is selected from the group consisting of $CH_2$ and NH;

Q is selected from the group consisting of O and S; and $R_9$ is selected from the group consisting of H, lower alkyl, cycloalkyl, cycloalkylalkyl, heterocyclyl, heterocyclylalkyl, aryl, arylalkyl, —C(O)NR$_{18}$R$_9$, and —C(O)OR$_{20}$;

wherein each $R_{18}$, $R_{19}$ and $R_{20}$ is independently selected from the group consisting of H, lower alkyl, cycloalkyl, cycloalkylalkyl, heterocyclyl, heterocyeloalkyl, aryl, and arylalkyl; and wherein lower alkyl is linear alkyl, $C_1$-$C_{10}$ branched alkyl, or $C_3$-$C_{10}$ cyclic alkyl and 0, 1, 2 or 3 carbons of a lower alkyl are replaced with a heteroatom, each heteroatom selected from the group consisting of N, O, and S.

15. A compound or a pharmaceutically acceptable salt thereof in accordance with claim 14, wherein the compound is selected from the group consisting of
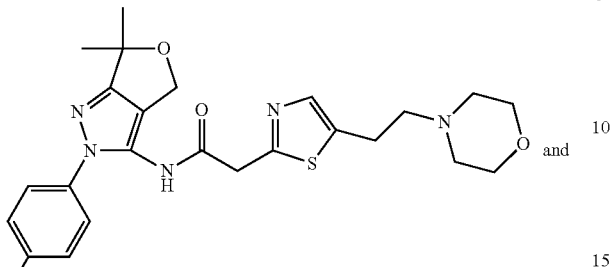 and
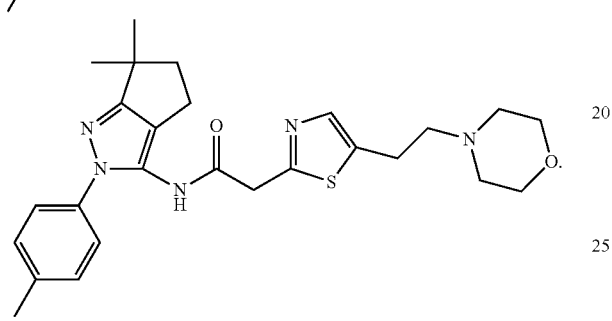

UNITED STATES PATENT AND TRADEMARK OFFICE
CERTIFICATE OF CORRECTION

| | | |
|---|---|---|
| PATENT NO. | : 9,187,470 B2 | Page 1 of 3 |
| APPLICATION NO. | : 14/599427 | |
| DATED | : November 17, 2015 | |
| INVENTOR(S) | : Michael Holtzman et al. | |

It is certified that error appears in the above-identified patent and that said Letters Patent is hereby corrected as shown below:

Column 15, the fourth structure (line 34) is incorrectly drawn. The correct structure is:

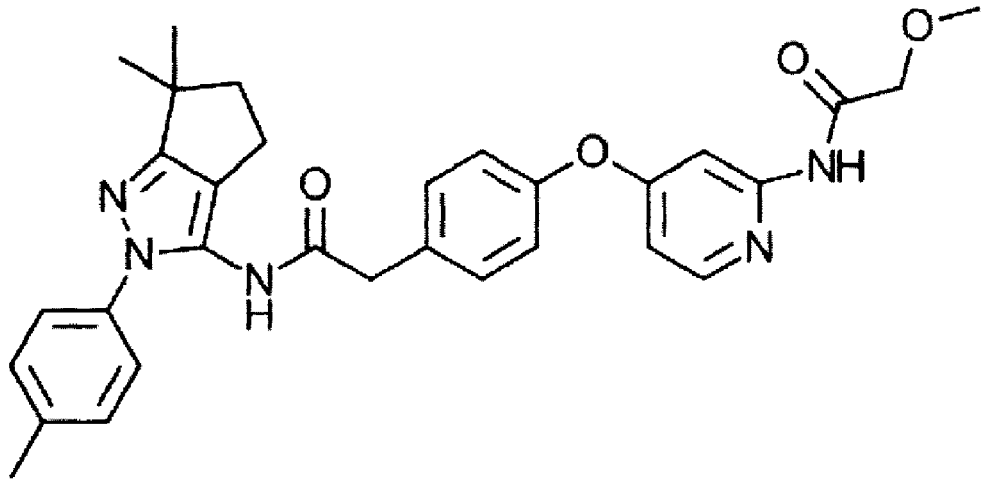

Column 16, line 7 the structure is incorrectly drawn. The correct structure is:

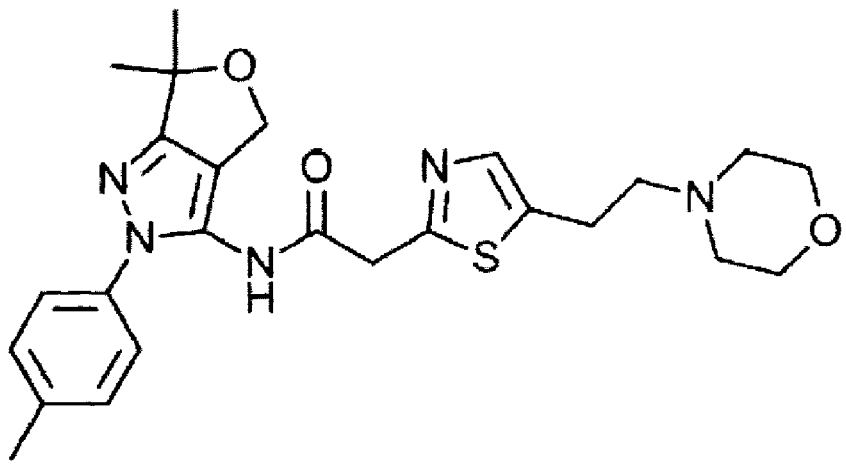

Signed and Sealed this
First Day of March, 2016

Michelle K. Lee
*Director of the United States Patent and Trademark Office*

CERTIFICATE OF CORRECTION (continued)
U.S. Pat. No. 9,187,470 B2

Column 16, line 48 the structure is incorrectly drawn. The structure should be:

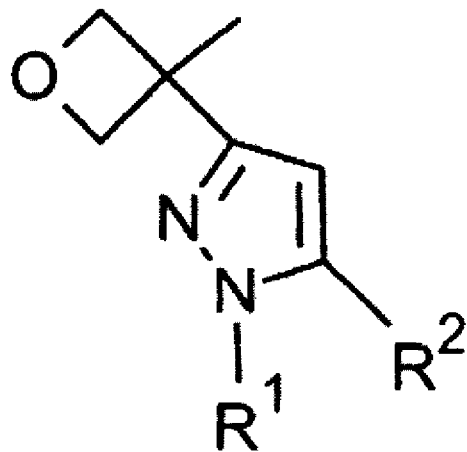

Column 23, line 20 replace: $COR_{11}$ with $-CO_2R_{11}$,

Column 25, line 21 replace: $-CH_2NHC(O)NR_{11}R_{14}$, with $-CH_2NHC(O)NR_{13}R_{14}$ Column 45, line 18 replace: pyraxol with pyrazol Column 103, line 58 is incorrectly drawn. The structure should be:

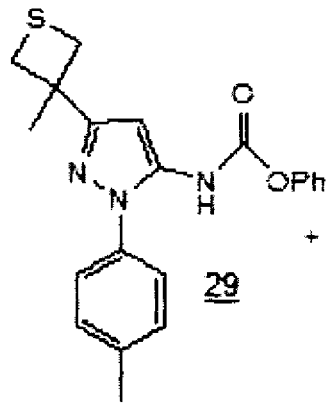

Column 105, line 58 replace: -3-([5 with -3[5.

Column 123, lines 66 replace: $Ch_2$ with $CH_2$

CERTIFICATE OF CORRECTION (continued)
U.S. Pat. No. 9,187,470 B2

Column 125, line 20 the structure is drawn incorrectly. The structure should be:

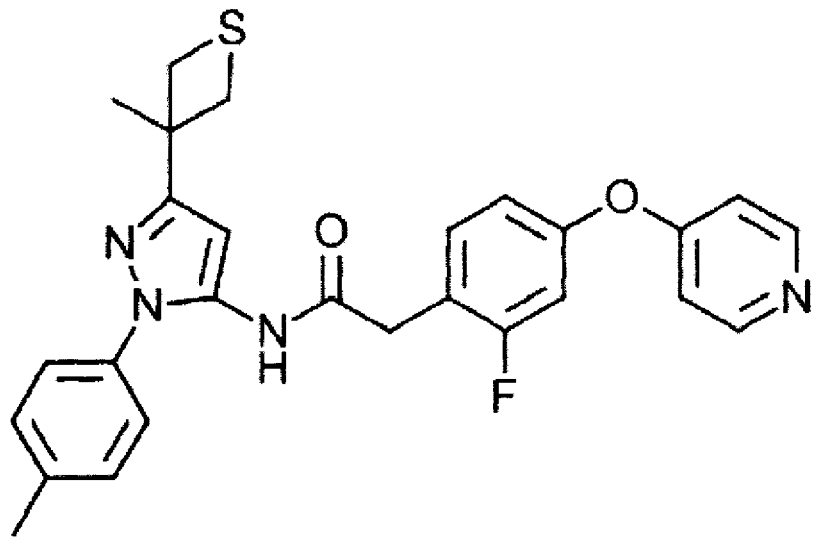

Column 129, line 51 replace: $CH_2\text{-}CH_{2NHC(O)NR13}R_{14}$, with $-CH_2NHC(O)NR_{13}R_{14}$, Column 130, line 58 replace: $-C(O)NR_{18}R_9$, with $-C(O)NR_{18}R_{19}$,

UNITED STATES PATENT AND TRADEMARK OFFICE
CERTIFICATE OF CORRECTION

PATENT NO. : 9,187,470 B2  
APPLICATION NO. : 14/599427  
DATED : November 17, 2015  
INVENTOR(S) : Michael Holtzman et al.

Page 1 of 1

It is certified that error appears in the above-identified patent and that said Letters Patent is hereby corrected as shown below:

In The Specification

Column 19, line 50, replace R4 and R5 are H with:     $R_4$ and $R_5$ are H

The structure on Column 38 lines 40-54 is a duplicate of structure immediately above it and should be deleted.

Column 93, line 52, structure #16 should be:

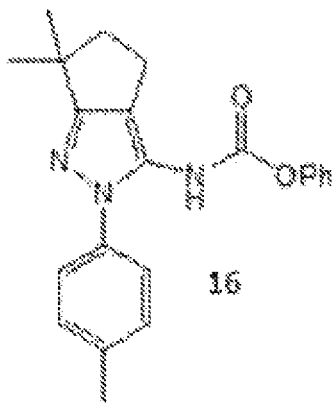

Signed and Sealed this  
Sixteenth Day of August, 2016

Michelle K. Lee  
*Director of the United States Patent and Trademark Office*